US005872212A

United States Patent [19]
Warren et al.

[11] Patent Number: 5,872,212
[45] Date of Patent: Feb. 16, 1999

[54] PESTICIDAL PROTEINS AND STRAINS

[75] Inventors: Gregory W. Warren; Michael G. Koziel, both of Cary; Martha A. Mullins, Raleigh; Gordon J. Nye, Apex; Brian Carr; Nalini M. Desai, both of Cary; Kristy Kostichka, Durham, all of N.C.

[73] Assignee: Novartis Finance Corporation, New York, N.Y.

[21] Appl. No.: 470,566

[22] Filed: Jun. 6, 1995

Related U.S. Application Data

[60] Division of Ser. No. 463,483, Jun. 5, 1995, which is a continuation-in-part of Ser. No. 314,594, Sep. 28, 1994, abandoned, which is a continuation-in-part of Ser. No. 218,018, Mar. 23, 1994, abandoned, which is a continuation-in-part of Ser. No. 37,057, Mar. 25, 1993, abandoned.

[51] Int. Cl.$^6$ .......................... C07K 2/00; C07K 14/195; C07K 14/32; C07K 14/355
[52] U.S. Cl. ............................................. 530/350; 530/825
[58] Field of Search ................... 514/2, 8, 12; 424/282.1, 424/94.2; 530/825, 350, 395

[56] References Cited

U.S. PATENT DOCUMENTS

| | | | |
|---|---|---|---|
| 3,632,747 | 1/1972 | Satohiro et al. | 424/93 |
| 3,651,215 | 3/1972 | Satohiro et al. | 424/93 |
| 4,996,155 | 2/1991 | Sick et al. | 435/252.3 |
| 5,011,685 | 4/1991 | Granados | 424/93 |
| 5,262,158 | 11/1993 | Payne et al. | 424/93 |
| 5,262,323 | 11/1993 | Baird et al. | 435/252.5 |

FOREIGN PATENT DOCUMENTS

| | | |
|---|---|---|
| 0498537A2 | 1/1992 | European Pat. Off. . |
| 0501650A2 | 2/1992 | European Pat. Off. . |
| WO88/08880 | 11/1988 | WIPO . |
| WO9013651 | 11/1990 | WIPO . |
| WO91/16432 | 10/1991 | WIPO . |
| WO91/16434 | 10/1991 | WIPO . |
| US94/03131 | 7/1994 | WIPO . |
| WO94/21795 | 9/1994 | WIPO . |

OTHER PUBLICATIONS

Arellano, A., et al., "Evidence of a New *Bacillus thuriengiensis* Toxin Active Against the Australian Sheep Blowfly *Lucilla cuprina*", *Proceedings and Abstracts of the 5th International Colloquium on Invertebrate Pathology and Microbial Control*, Adelaide, Austrailia, 20–24 Aug., 1990, p. 291.

Beecher, Douglas J., et al., "A Novel Bicomponent Hemolysin from *bacillus cereus*", *Infection and Immunity*, 58(7):2220–2227 (1990).

Faust, R.M., "Bacterial Diseases", In: *Insect Diseases*, G. Cantwell, ed., Marcel Dekker, NY 1974, pp. 90–102.

Faust R.M., et al., "Bacteria and Their Toxins as Insecticides", In:*Microbial and Viral Pesticides*, E. Kurstak, Ed., Marcel Dekker, NY, 1982, pp. 84–89, 108–120.

Gilmore, Michael S., et al., "A *Bacillus cereus* Cytolytic Determinant, Cereolysin AB, Which Comprises the Phospholipase C and Sphingomyelinase Genes: Nucleotide Sequence and Genetic Linkage", *Journal of Bacteriology*, 171(2):744–753 (1989).

Heimpel, A.M., "The pH in the Gut and Blood of the Larch Sawfly, *Pristiphora erichsonii*(HTG.), and Other Insects with Reference to the Pathogenicity of *Bacillus cereus* FR. and FR.", *Can. J. Zool.*, 33:99–106 (1955).

(List continued on next page.)

*Primary Examiner*—Jeffrey E. Russel
*Attorney, Agent, or Firm*—J. Timothy Meigs; Gary M. Pace

[57] ABSTRACT

The present invention is drawn to pesticidal strains and proteins. Bacillus strains which are capable of producing pesticidal proteins and auxiliary proteins during vegetative growth are provided. Also provided are the purified proteins, nucleotide sequences encoding the proteins and methods for using the strains, proteins and genes for controlling pests.

9 Claims, 1 Drawing Sheet

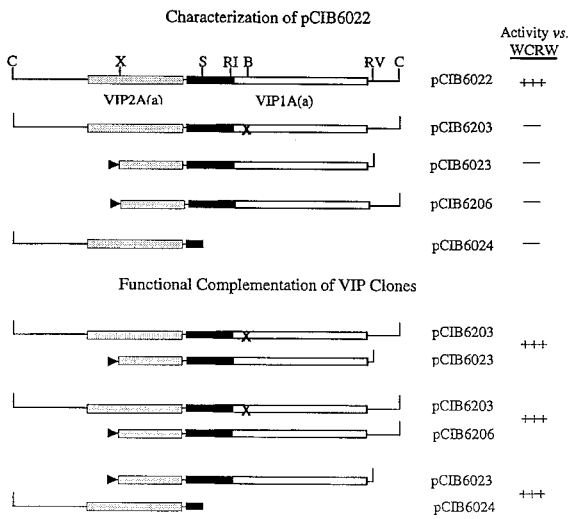

OTHER PUBLICATIONS

Heimpel, A.M., "Investigations of the Mode of Action of Strains of *Bacillus cereus* FR. and FR. Pathogenic for the Larch Sawfly, *Pristiphora erichsonii*(HTG.)", *Can. J. Zool.,* 33:311–326 (1995).

Hofte, H., et al., "Insecticidal Crystal Proteins of *Bacillus thuringiensis*", *Microbiological Reviews*, 53(2):242–255 (1989).

Koziel, M.G., et al., "Field Performance of Elite Tansgenic Maize Plants Expressing an Insecticidal Protein Derived from *Bacillus thuringiensis*", *Bio/Technology,* 11:194–200 (1993).

Krieg, A., "Thuricin, a Bacteriocin Produced by *Bacillus thuringiensis*", *J. Invert. Path.,* 15:291 (1970).

Krieg, A., "Concerning Alpha–exotoxin Produced by Vegetative Cells of *Bacillus thuringiensis* and *Bacillus cereus*", *J. Invert. Path.,* 17:134–135 (1971).

Kushner, D.J., et al., "Lecithinase Production by Strains of *Bacillus cereus* FR. and FR. Pathogenic for the Larch Sawfly, *Pristiphora erichsonii* (HTG.)", *Can. J. Microbiol.,* 3:547–551 (1957).

Luthy, P., et al., "*Bacillus thuringiensis* as a Bacterial Insecticide: Basic Consideration and Application", In: *Microbial and Viral Pesticides*, E. Kurstak, Ed., Marcel Dekker, NY 1982, pp. 37–39, 54–56.

Myers, P.S., et al., "Localization of a Mosquito–Larval Toxin of *Bacillus sphaericus* 1593", *Appl. Environ. Microbiol.,* 39(1):1205–1211 (1980).

Porter, A.G., et al., "Mosquitocidal Toxins of Bacilli and Their Genetic Manipulation for Effective Biological Control of Mosquitoes", *Microbiological Reviews*, 57(4):838–861 (1993).

Sekar, V., "The Insecticidal Crystal Protein Gene is Expressed in Vegetative Cells of *Bacillus thuringiensis* var. *temebropmos*", *Current Microbiology*, 17:347–349 (1988).

Shivakumar, A.G., et al., Abstract, :Cloned Crystal Protein Genes Express Vegetatively in *Bacillus subtilis, Plasmid,* 16(3):230 (1986).

Thanabalu, T., et al., "Proteolytic Processing of the Mosquitocidal Toxin from *Bacillus sphaericus* SSII–1", *J. Bacteriol.,* 174(15):5051–5056 (1992).

European International Search Report dated May 3, 1996.

Bernier et al., "*Bacillus thuringiensis* Strains A20 and A29 and Insecticidal Compounds Therefrom, and Compositions Containing These Compounds", Abstract No. 227249, *New Zealand Patent Office Journal*, 80(6):798, (1988).

Jellis et al., "*Bacillus thuringiensis* δ–Endotoxin Variants and Insecticidal Compositions", Abstract No. 228108, *New Zealand Patent Office Journal* , 81(3):359, (1992).

Schurter et al., "Genetic Manifpulation of *B. thuringiensis* and *B. cereus* Vectors and Insecticidal Composition", Abstract No. 229191, *New Zealand Patent Office Journal*, 81(3):363, (1992).

Tayabali et al., "Semiautomated Quantification of Cytotoxic Damage Induced in Cultered Insect Cells Exposed to Commercial *Bacillus thuringiensis* Biopesticides", *Journal of Applied Toxicology*, 15(5): 365–373 (1995).

Thanabalu et al., "Cytotoxicity and ADP–Ribosylating Activity of the Mosquitocidal Toxin from *Bacillus sphaericus* SSII–1: Possible Roles of the 27–and 70–Kilodalton Peptides", *Journal of Bacteriology*, 175(8): 2314–2320 (1993).

Vaithlingam et al., "Anti–Coleopteran Toxin and Gene", Abstract No. 226442, *New Zealand Patent Office Journal*, 80(7):931, (1991).

Wahisaka et al., "Bacillus thuringiensis *Mutant and Bacterial Insecticide*", Abstract No. 199725, *New Zealand Patent Office Journal*, (1982).

Walther et al., "Analysis of Mosquito Larvicidal Potential Exhibited by Vegetative Cells of *Bacillus thuringiensis* subsp. *israelensis*", *Applied and Environmental Microbiology*, 52(4): 650–653 (1986).

Ward et al., "*Bacillus thuringiensis* var. *israelensis* δ–Endotoxin Cloning and Expression of the Toxin in Sporogenic and Asporogenic Strains of *Bacillus subtilis*", *Journal of Molecular Biology*, 191(1): 13–22 (1986).

Broadwell et al, The 42–and 51–Kilodalton Mosquitocidal . . . J. Bacter., pp. 2217–2223, vol. 172, No. 5. May, 1990.

Luthy et al, Presence of Endotoxin in Vegetative Cells . . . Can. J. Microb., vol. 16, pp. 905–906. 1970.

Myers et al, Toxic Activity of *Bacillus sphaericus* . . . Infection and Immunity. vol. 19, No. 3, pp. 1047–1053. Mar. 1978.

Yoshisue et al. Effects of *Bacillus thuringiensis* var. *israelensis* 20–kDa Protein. Biosci. Biotech. Biochem. 1992, vol. 56, No. 9, pp. 1429–1433.

Figure 1

Characterization of pCIB6022

| | Activity vs. WCRW |
|---|---|
| pCIB6022 | +++ |
| pCIB6203 | — |
| pCIB6023 | — |
| pCIB6206 | — |
| pCIB6024 | — |

Functional Complementation of VIP Clones

| | Activity vs. WCRW |
|---|---|
| pCIB6203 / pCIB6023 | +++ |
| pCIB6203 / pCIB6206 | +++ |
| pCIB6023 / pCIB6024 | +++ |

PESTICIDAL PROTEINS AND STRAINS

This is a divisional application of Ser. No. 08/463,483, filed Jun. 5, 1995 which is a continuation-in-part of Ser. No. 08/314,594 filed Sep. 28, 1994, now abandoned, which is a continuation-in-part of Ser. No. 08/218,018, filed Mar. 23, 1994, now abandoned, which is a continuation-in-part of Ser. No. 08/037,057, filed Mar. 25, 1993, now abandoned.

FIELD OF THE INVENTION

The present invention is drawn to methods and compositions for controlling plant and non-plant pests.

BACKGROUND OF THE INVENTION

Insect pests are a major factor in the loss of the world's commercially important agricultural crops. Broad spectrum chemical pesticides have been used extensively to control or eradicate pests of agricultural importance. There is, however, substantial interest in developing effective alternative pesticides.

Microbial pesticides have played an important role as alternatives to chemical pest control. The most extensively used microbial product is based on the bacterium *Bacillus thuringiensis* (Bt). Bt is a gram-positive spore forming Bacillus which produces an insecticidal crystal protein (ICP) during sporulation.

Numerous varieties of Bt are known that produce more than 25 different but related ICP's. The majority of ICP's made by Bt are toxic to larvae of certain insects in the orders Lepidoptera, Diptera and Coleoptera. In general, when an ICP is ingested by a susceptible insect the crystal is solubilized and transformed into a toxic moiety by the insect gut proteases. None of the ICP's active against coleopteran larvae such as Colorado potato beetle (*Leptinotarsa decemlineata*) or Yellow mealworm (*Tenebrio molitor*) have demonstrated significant effects on members of the genus Diabrotica particularly *Diabrotica virgifera virgifera*, the western corn rootworm (WCRW) or *Diabrotica longicornis barberi*, the northern corn rootworm.

*Bacillus cereus* (Bc) is closely related to Bt. A major distinguishing characteristic is the absence of a parasporal crystal in Bc. Bc is a widely distributed bacterium that is commonly found in soil and has been isolated from a variety of foods and drugs. The organism has been implicated in the spoilage of food.

Although Bt has been very useful in controlling insect pests, there is a need to expand the number of potential biological control agents.

BRIEF DESCRIPTION OF THE FIGURE

FIG. 1: Characterization of pCIB6022. Boxed regions represent the extent of VIP1A(*a*) and VIP2A(*a*). White box represents the portion of VIP1 encoding the 80 kDa peptide observed in Bacillus. Dark box represents the N-terminal 'propeptide' of VIP1A(*a*) predicted by DNA sequence analysis. Stippled box represents the VIP2A(*a*) coding region. Large 'X' represents the location of the frameshift mutation introduced into VIP1A(*a*). Arrows represent constructs transcribed by the beta-galactosidase promoter. Restriction Sites: C-Cla I; X-Xba I; S-Sca I; RI-Eco RI; B-Bgl II; RV-Eco RV.

SUMMARY OF THE INVENTION

The present invention is drawn to compositions and methods for controlling plant and non-plant pests. Particularly, new pesticidal proteins are disclosed which are isolatable from the vegetative growth stage of Bacillus. Bacillus strains, proteins, and genes encoding the proteins are provided.

The methods and compositions of the invention may be used in a variety of systems for controlling plant and non-plant pests.

DETAILED DESCRIPTION OF THE INVENTION

Compositions and methods for controlling plant pests are provided. In particular, novel pesticidal proteins are provided which are produced during vegetative growth of Bacillus strains. The proteins are useful as pesticidal agents.

The present invention recognizes that pesticidal proteins are produced during vegetative growth of Bacillus strains. To date, all of the identified pesticidal proteins of the invention are secreted from the cell. Prior to the present invention, there was no recognition in the art that a class or classes of pesticidal proteins are produced during vegetative growth of Bacillus. The only report was of a single mosquitocidal toxin from *Bacillus sphaericus* SSII-1 by Myers and Yousten in *Infect. Immun.*, 19:1047–1053 (1978). Having recognized that such a class exists, the present invention embraces all vegetative insecticidal proteins, hereinafter referred to as VIPs, except for the mosquitocidal toxin from *B. sphaericus*.

The present VIPs are not abundant after sporulation and are particularly expressed during log phase growth before stationary phase. For the purpose of the present invention vegetative growth is defined as that period of time before the onset of sporulation. Genes encoding such VIPs can be isolated, cloned and transformed into various delivery vehicles for use in pest management programs.

For purposes of the present invention, pests include but are not limited to insects, fungi, bacteria, nematodes, mites, ticks, protozoan pathogens, animal-parasitic liver flukes, and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera and Lepidoptera.

Tables 1–10 gives a list of pests associated with major crop plants and pests of human and veterinary importance. Such pests are included within the scope of the present invention.

TABLE 1

Lepidoptera (Butterflies and Moths)

Maize

*Ostrinia nubilalis*, European corn borer
*Agrotis ipsilon*, black cutworm
*Helicoverpa zea*, corn earworm
*Spodoptera frugiperda*, fall armyworm
*Diatraea grandiosella*, southwestern corn borer
*Elasmopalpus lignosellus*, lesser cornstalk borer
*Diatraea saccharalis*, sugarcane borer Sorghum

*Chilo partellus*, sorghum borer
*Spodoptera frugiperda*, fall armyworm
*Helicoverpa zea*, corn earworm
*Elasmopalpus lignosellus*, lesser cornstalk borer
*Feltia subterranea*, granulate cutworm

TABLE 1-continued

Lepidoptera (Butterflies and Moths)

Wheat

*Pseudaletia unipunctata*, army worm
*Spodoptera frugiperda*, fall armyworm
*Elasmopalpus lignosellus*, lesser cornstalk borer
*Agrotis orthogonia*, pale western cutworm
*Elasmopalpus lignosellus*, lesser cornstalk borer Sunflower

*Suleima helianthana*, sunflower bud moth
*Homoeosoma electellum*, sunflower moth Cotton

*Heliothis virescens*, cotton boll worm
*Helicoverpa zea*, cotton bollworm
*Spodoptera exigua*, beet armyworm
*Pectinophora gossypiella*, pink bollworm Rice

*Diatraea saccharalis*, sugarcane borer
*Spodoptera frugiperda*, fall armyworm
*Helicoverpa zea*, corn earworm Soybean

*Pseudoplusia includens*, soybean looper
*Anticarsia gemmatalis*, velvetbean caterpillar
*Plathypena scabra*, green cloverworm
*Ostrinia nubilalis*, European corn borer
*Agrotis ipsilon*, black cutworm
*Spodoptera exigua*, beet armyworm
*Heliothis virescens*, cotton boll worm
*Helicoverpa zea*, cotton bollworm Barley

*Ostrinia nubilalis*, European corn borer
*Agrotis ipsilon*, black cutworm

TABLE 2

Coleoptera (Beetles)

Maize

*Diabrotica virgifera virgifera*, western corn rootworm
*Diabrotica longicornis barberi*, northern corn rootworm
*Diabrotica undecimpunctata howardi*, southern corn rootworm
*Melanotus spp.*, wireworms
*Cyclocephala borealis*, northern masked chafer (white grub)
*Cyclocephala immaculata*, southern masked chafer (white grub)
*Popillia japonica*, Japanese beetle
*Chaetocnema pulicana*, corn flea beetle
*Sphenophorus maidis*, maize billbug Sorghum

*Phyllophaga crinita*, white grub
*Eleodes, Conoderus,* and *Aeolus spp.*, wireworms
*Oulema melanopus*, cereal leaf beetle
*Chaetocnema pulicaria*, corn flea beetle
*Sphenophorus maidis*, maize billbug Wheat

*Oulema melanopus*, cereal leaf beetle
*Hypera punctata*, clover leaf weevil
*Diabrotica undecimpunctata howardi*, southern corn rootworm Sunflower

*Zygogramma exclamationis*, sunflower beetle
*Bothyrus gibbosus*, carrot beetle

Cotton

*Anthonomus grandis*, boll weevil

Rice

*Colaspis brunnea*, grape colaspis

TABLE 2-continued

Coleoptera (Beetles)

*Lissorhoptrus oryzophilus*, rice water weevil
*Sitophilus oryzae*, rice weevil

Soybean

*Epilachna varivestis*, Mexican bean beetle

TABLE 3

Homoptera (Whiteflies Aphids etc. . .)

Maize

*Rhopalosiphum maidis*, corn leaf aphid
*Anuraphis maidiradicis*, corn root aphid Sorghum

*Rhopalosiphum maidis*, corn leaf aphid
*Sipha flava*, yellow sugarcane aphid

Wheat

Russian wheat aphid
*Schizaphis graminum*, greenbug
*Macrosiphum avenae*, English grain aphid Cotton

*Aphis gossypii*, cotton aphid
*Pseudatomoscelis seriatus*, cotton fleahopper
*Trialeurodes abutilonea*, bandedwinged whitefly Rice

*Nephotettix nigropictus*, rice leafhopper

Soybean

*Myzus persicae*, green peach aphid
*Empoasca fabae*, potato leafhopper

Barley

*Schizaphis graminum*, greenbug

Oil Seed Rape

*Brevicoryne brassicae*, cabbage aphid

TABLE 4

Hemiptera (Bugs)

Maize

*Blissus leucopterus leucopterus*, chinch bug

Sorghum

*Blissus leucopterus leucopterus*, chinch bug

Cotton

*Lygus lineolaris*, tarnished plant bug

Rice

*Blissus leucopterus leucopterus*, chinch bug
*Acrosternum hilare*, green stink bug Soybean

*Acrosternum hilare*, green stink bug

Barley

*Blissus leucopterus leucopterus*, chinch bug
*Acrosternum hilare*, green stink bug
*Euschistus servus*, brown stink bug

TABLE 5

Orthoptera (Grasshoppers, Crickets, and Cockroaches)

Maize

*Melanoplus femurrubrum*, redlegged grasshopper
*Melanoplus sanguinipes*, migratory grasshopper
Wheat

*Melanoplus femurrubrum*, redlegged grasshopper
*Melanoplus differentialis*, differential grasshopper
*Melanoplus sanguinipes*, migratory grasshopper
Cotton

*Melanoplus femurrubrum*, redlegged grasshopper
*Melanoplus differentialis*, differential grasshopper
Soybean

*Melanoplus femurrubrum*, redlegged grasshopper
*Melanoplus differentialis*, differential grasshopper
Structural/Household

*Periplaneta americana*, American cockroach
*Blattella germanica*, German cockroach
*Blatta orientalis*, oriental cockroach

TABLE 6

Diptera (Flies and Mosquitoes)

Maize

*Hylemya platura*, seedcorn maggot
*Agromyza parvicornis*, corn blotch leafminer
Sorghum

*Contarinia sorghicola*, sorghum midge
Wheat

*Mayetiola destructor*, Hessian fly
*Sitodiplosis mosellana*, wheat midge
*Meromyza americana*, wheat stem maggot
*Hylemya coarctata*, wheat bulb fly
Sunflower

*Neolasioptera murtfeldtiana*, sunflower seed midge
Soybean

*Hylemya platura*, seedcorn maggot
Barley

*Hylemya platura*, seedcorn maggot
*Mayetiola destructor*, Hessian fly
Insects attacking humans and animals and disease carriers

*Aedes aegypti*, yellowfever mosquito
*Aedes albopictus*, forest day mosquito
*Phlebotomus papatasii*, sand fly
*Musca domestica*, house fly
*Tabanus atratus*, black horse fly
*Cochliomyia hominivorax*, screwworm fly

TABLE 7

Thysanoptera (Thrips)

Maize

*Anaphothrips obscurus*, grass thrips
Wheat

*Frankliniella fusca*, tobacco thrips
Cotton

*Thrips tabaci*, onion thrips

TABLE 7-continued

Thysanoptera (Thrips)

*Frankliniella fusca*, tobacco thrips
Soybean

*Sericothrips variabilis*, soybean thrips
*Thrips tabaci*, onion thrips

TABLE 8

Hymenoptera (Sawflies, Ants, Wasps, etc.)

Maize

*Solenopsis milesta*, thief ant
Wheat

*Cephus cinctus*, wheat stem sawfly

TABLE 9

Other Orders and Representative Species

Dermaptera (Earwigs)

*Forficula auricularia*, European earwig
Isoptera (Termites)

*Reticulitermes flavipes*, eastern subterranean termite
Mallophaga (Chewing Lice)

*Cuclotogaster heterographa*, chicken head louse
*Bovicola bovis*, cattle biting louse
Anoplura (Sucking Lice)

*Pediculus humanus*, head and body louse
Siphonaptera (Fleas)

*Ctenocephalides felis*, cat flea

TABLE 10

Acari (Mites and Ticks)

Maize

*Tetranychus urticae*, twospotted spider mite
Sorghum

*Tetranychus cinnabarinus*, carmine spider mite
*Tetranychus urticae*, twospotted spider mite
Wheat

*Aceria tulipae*, wheat curl mite
Cotton

*Tetranychus cinnabarinus*, carmine spider mite
*Tetranychus urticae*, twospotted spider mite
Soybean

*Tetranychus turkestani*, strawberry spider mite
*Tetranychus urticae*, twospotted spider mite
Barley

*Petrobia latens*, brown wheat mite
Important human and animal *Acari*

*Demacentor variabilis*, American dog tick
*Argas persicus*, fowl tick
*Dermatophagoides farinae*, American house dust mite
*Dermatophagoides pteronyssinus*, European house dust mite Now that it has been recognized that pesticidal proteins can be isolated from the vegetative growth phase of Bacillus, other strains can be isolated by standard techniques and tested for activity against particular plant and non-plant pests. Generally Bacillus strains can be isolated from any environmental sample, including soil, plant, insect, grain elevator dust, and other sample material, etc., by methods known in the art. See, for example, Travers et al. (1987) Appl. Environ. Microbiol. 53:1263–1266; Saleh et al. (1969) Can J. Microbiol. 15:1101–1104; DeLucca et al. (1981) Can. J. Microbiol. 27:865–870; and Norris, et al. (1981) "The genera Bacillus and Sporolactobacillus," In Starr et al. (eds.), The Prokaryotes: A Handbook on Habitats, Isolation, and Identification of Bacteria, Vol. II, Springer-Verlog Berlin Heidelberg. After isolation, strains can be tested for pesticidal activity during vegetative growth. In this manner, new pesticidal proteins and strains can be identified.

Such Bacillus microorganisms which find use in the invention include *Bacillus cereus* and *Bacillus thuringiensis*, as well as those Bacillus species listed in Table 11.

TABLE 11

| List of Bacillus species |
|---|
| Morphological Group 1 |
| *B. megaterium* |
| *B. cereus** |
| *B. cereus* var. *mycoides* |
| *B. thuringiensis** |
| *B. licheniformis* |
| *B. subtilis** |
| *B. pumilus* |
| *B. firmus** |
| *B. coagulans* |
| Morphological Group 2 |
| *B. polymyxa* |
| *B. macerans* |
| *B. circulans* |
| *B. stearothermophilus* |
| *B. alvei** |
| *B. laterosporus** |
| *B. brevis* |
| *B. pulvifaciens* |
| *B. popilliae** |
| *B. lentimorbus** |
| *B. larvae** |
| Morphological Group 3 |
| *B. sphaericus** |
| *B. pasteurii* |
| Unassigned Strains |
| Subgroup A |
| *B. apiarus** |
| *B. filicolonicus* |
| *B. thiaminolyticus* |
| *B. alcalophilus* |
| Subgroup B |
| *B. cirroflagellosus* |
| *B. chitinosporus* |
| *B. lentus* |
| Subgroup C |
| *B. badius* |
| *B. aneurinolyticus* |
| *B. macroides* |
| *B. freundenreichii* |
| Subgroup D |
| *B. pantothenticus* |

TABLE 11-continued

| List of Bacillus species |
|---|
| *B. epiphytus* |
| Subgroup E1 |
| *B. aminovorans* |
| *B. globisporus* |
| *B. insolitus* |
| *B. psychrophilus* |
| Subgroup E2 |
| *B. psychrosaccharolyticus* |
| *B. macquariensis* |

* = Those *Bacillus* strains that have been previously found associated with insects
Grouping according to Parry, J. M. *et al.* (1983) Color Atlas of *Bacillus* species, Wolfe Medical Publications, London.

In accordance with the present invention, the pesticidal proteins produced during vegetative growth can be isolated from Bacillus. In one embodiment, insecticidal proteins produced during vegetative growth, can be isolated. Methods for protein isolation are known in the art. Generally, proteins can be purified by conventional chromatography, including gel-filtration, ion-exchange, and immunoaffinity chromatography, by high-performance liquid chromatography, such as reversed-phase high-performance liquid chromatography, ion-exchange high-performance liquid chromatography, size-exclusion high-performance liquid chromatography, high-performance chromatofocusing and hydrophobic interaction chromatography, etc., by electrophoretic separation, such as one-dimensional gel electrophoresis, two-dimensional gel electrophoresis, etc. Such methods are known in the art. See for example *Current Protocols in Molecular Biology*, Vols. 1 and 2, Ausubel et al. (eds.), John Wiley & Sons, N.Y. (1988). Additionally, antibodies can be prepared against substantially pure preparations of the protein. See, for example, Radka et al. (1983) *J. Immunol.* 128:2804; and Radka et al. (1984) *Immunogenetics* 19:63. Any combination of methods may be utilized to purify protein having pesticidal properties. As the protocol is being formulated, pesticidal activity is determined after each purification step.

Such purification steps will result in a substantially purified protein fraction. By "substantially purified" or "substantially pure" is intended protein which is substantially free of any compound normally associated with the protein in its natural state. "Substantially pure" preparations of protein can be assessed by the absence of other detectable protein bands following SDS-PAGE as determined visually or by densitometry scanning. Alternatively, the absence of other amino-terminal sequences or N-terminal residues in a purified preparation can indicate the level of purity. Purity can be verified by rechromatography of "pure" preparations showing the absence of other peaks by ion exchange, reverse phase or capillary electrophoresis. The terms "substantially pure" or "substantially purified" are not meant to exclude artificial or synthetic mixtures of the proteins with other compounds. The terms are also not meant to exclude the presence of minor impurities which do not interfere with the biological activity of the protein, and which may be present, for example, due to incomplete purification.

Once purified protein is isolated, the protein, or the polypeptides of which it is comprised, can be characterized and sequenced by standard methods known in the art. For example, the purified protein, or the polypeptides of which it is comprised, may be fragmented as with cyanogen bromide, or with proteases such as papain, chymotrypsin, trypsin, lysyl-C endopeptidase, etc. (Oike et al. (1982) *J. Biol. Chem.* 257:9751–9758; Liu et al. (1983) *Int. J. Pept. Protein Res.* 21:209–215). The resulting peptides are separated, preferably by HPLC, or by resolution of gels and electroblotting onto PVDF membranes, and subjected to amino acid sequencing. To accomplish this task, the peptides are preferably analyzed by automated sequenators. It is recognized that N-terminal, C-terminal, or internal amino acid sequences can be determined. From the amino acid sequence of the purified protein, a nucleotide sequence can be synthesized which can be used as a probe to aid in the isolation of the gene encoding the pesticidal protein.

It is recognized that the pesticidal proteins may be oligomeric and will vary in molecular weight, number of protomers, component peptides, activity against particular pests, and in other characteristics. However, by the methods set forth herein, proteins active against a variety of pests may be isolated and characterized.

Once the purified protein has been isolated and characterized it is recognized that it may be altered in various ways including amino acid substitutions, deletions, truncations, and insertions. Methods for such manipulations are generally known in the art. For example, amino acid sequence variants of the pesticidal proteins can be prepared by mutations in the DNA. Such variants will possess the desired pesticidal activity. Obviously, the mutations that will be made in the DNA encoding the variant must not place the sequence out of reading frame and preferably will not create complementary regions that could produce secondary mRNA structure. See, EP Patent Application Publication No. 75,444.

In this manner, the present invention encompasses the pesticidal proteins as well as components and fragments thereof. That is, it is recognized that component protomers, polypeptides or fragments of the proteins may be produced which retain pesticidal activity. These fragments include truncated sequences, as well as N-terminal, C-terminal, internal and internally deleted amino acid sequences of the proteins.

Most deletions, insertions, and substitutions of the protein sequence are not expected to produce radical changes in the characteristics of the pesticidal protein. However, when it is difficult to predict the exact effect of the substitution, deletion, or insertion in advance of doing so, one skilled in the art will appreciate that the effect will be evaluated by routine screening assays.

The proteins or other component polypeptides described herein may be used alone or in combination. That is, several proteins may be used to control different insect pests.

Some proteins are single polypeptide chains while many proteins consist of more than one polypeptide chain, i.e., they are oligomeric. Additionally, some VIPs are pesticidally active as oligomers. In these instances, additional protomers are utilized to enhance the pesticidal activity or to activate pesticidal proteins. Those protomers which enhance or activate are referred to as auxiliary proteins. Auxiliary proteins activate or enhance a pesticidal protein by interacting with the pesticidal protein to form an oligomeric protein having increased pesticidal activity compared to that observed in the absence of the auxiliary protein.

Auxiliary proteins activate or increase the activity of pesticidal proteins such as the VIP1 protein from AB78. Such auxiliary proteins are exemplified by, but not limited to, the VIP2 protein from AB78. As demonstrated in the Experimental section of the application, auxiliary proteins can activate a number of pesticidal proteins. Thus, in one embodiment of the invention, a plant, Parent 1, can be transformed with an auxiliary protein. This Parent 1 can be crossed with a number of Parent 2 plants transformed with one or more pesticidal proteins whose pesticidal activities are activated by the auxiliary protein.

The pesticidal proteins of the invention can be used in combination with Bt endotoxins or other insecticidal proteins to increase insect target range. Furthermore, the use of the VIPs of the present invention in combination with Bt δ-endotoxins or other insecticidal principles of a distinct nature has particular utility for the prevention and/or management of insect resistance. Other insecticidal principles include protease inhibitors (both serine and cysteine types), lectins, α-amylase and peroxidase. In one preferred embodiment, expression of VIPs in a transgenic plant is accompanied by the expression of one or more Bt δ-endotoxins. This co-expression of more than one insecticidal principle in the same transgenic plant can be achieved by genetically engineering a plant to contain and express all the genes necessary. Alternatively, a plant, Parent 1, can be genetically engineered for the expression of VIPs. A second plant, Parent 2, can be genetically engineered for the expression of Bt δ-endotoxin. By crossing Parent 1 with Parent 2, progeny plants are obtained which express all the genes introduced into Parents 1 and 2. Particularly preferred Bt δ-endotoxins are those disclosed in U.S. Pat. No. 5,625,136, herein incorporated by reference.

A substantial number of cytotoxic proteins, though not all, are binary in action. Binary toxins typically consist of two protein domains, one called the A domain and the other called the B domain (see *Sourcebook of Bacterial Protein Toxins*. J. E. Alouf and J. H. Freer eds.(1991) Academic Press). The A domain possesses a potent cytotoxic activity. The B domain binds an external cell surface receptor before being internalized. Typically, the cytotoxic A domain must be escorted to the cytoplasm by a translocation domain. Often the A and B domains are separate polypeptides or protomers, which are associated by a protein-protein interaction or a di-sulfide bond. However, the toxin can be a single polypeptide which is proteolytically processed within the cell into two domains as in the case for Pseudomonas exotoxin A. In summary binary toxins typically have three important domains, a cytotoxic A domain, a receptor binding B domain and a translocation domain. The A and B domain are often associated by protein-protein interacting domains.

The receptor binding domains of the present invention are useful for delivering any protein, toxin, enzyme, transcription factor, nucleic acid, chemical or any other factor into target insects having a receptor recognized by the receptor binding domain of the binary toxins described in this patent. Similarly, since binary toxins have translocation domains which penetrate phosopholipid bilayer membranes and escort cytotoxins across those membranes, such translocation domains may be useful in escorting any protein, toxin, enzyme, transcription factor, nucleic acid, chemical or any other factor across a phospholipid bilayer such as the plasma membrane or a vesicle membrane. The translocation domain may itself perforate membranes, thus having toxic or insecticidal properties. Further, all binary toxins have cytotoxic domains; such a cytotoxic domain may be useful as a lethal protein, either alone or when delivered into any target cell(s) by any means.

Finally, since binary toxins comprised of two polypeptides often form a complex, it is likely that there are protein-protein interacting regions within the components of the binary toxins of the invention. These protein-protein interacting domains may be useful in forming associations between any combination of toxins, enzymes, transcription factors, nucleic acids, antibodies, cell binding moieties, or any other chemicals, factors, proteins or protein domains.

Toxins, enzymes, transcription factors, antibodies, cell binding moieties or other protein domains can be fused to pesticidal or auxiliary proteins by producing in frame genetic fusions which, when translated by ribosomes, would produce a fusion protein with the combined attributes of the VIP and the other component used in the fusion. Furthermore, if the protein domain fused to the VIP has an affinity for another protein, nucleic acid, carbohydrate, lipid, or other chemical or factor, then a three-component complex can be formed. This complex will have the attributes of all of its components. A similar rationale can be used for producing four or more component complexes. These complexes are useful as insecticidal toxins, pharmaceuticals, laboratory reagents, and diagnostic reagents, etc. Examples where such complexes are currently used are fusion toxins for potential cancer therapies, reagents in ELISA assays and immunoblot analysis.

One strategy of altering pesticidal or auxiliary proteins is to fuse a 15-amino-acid "S-tag" to the protein without destroying the insect cell binding domain(s), translocation domains or protein-protein interacting domains of the proteins. The S-tag has a high affinity ($K_d=10^{-9}M$) for a ribonuclease S-protein, which, when bound to the S-tag, forms an active ribonuclease (See F. M. Richards and H. W. Wyckoff (1971) in "The Enzymes", Vol. IV (Boyer, P. D. ed.). pp. 647–806. Academic Press, New York). The fusion can be made in such a way as to destroy or remove the cytotoxic activity of the pesticidal or auxiliary protein, thereby replacing the VIP cytotoxic activity with a new cytotoxic ribonuclease activity. The final toxin would be comprised of the S-protein, a pesticidal protein and an auxiliary protein, where either the pesticidal protein or the auxiliary protein is produced as translational fusions with the S-tag. Similar strategies can be used to fuse other potential cytotoxins to pesticidal or auxiliary proteins including (but not limited to) ribosome inactivating proteins, insect hormones, hormone receptors, transcription factors, proteases, phosphatases, Pseudomonas exotoxin A, or any other protein or chemical factor that is lethal when delivered into cells. Similarly, proteins can be delivered into cells which are not lethal, but might alter cellular biochemistry or physiology.

The spectrum of toxicity toward different species can be altered by fusing domains to pesticidal or auxiliary proteins which recognize cell surface receptors from other species. Such domains might include (but are not limited to) antibodies, transferrin, hormones, or peptide sequences isolated from phage displayed affinity selectable libraries. Also, peptide sequences which are bound to nutrients, vitamins, hormones, or other chemicals that are transported into cells could be used to alter the spectrum of toxicity. Similarly, any other protein or chemical which binds a cell surface receptor or the membrane and could be internalized might be used to alter the spectrum of activity of VIP1 and VIP2.

The pesticidal proteins of the present invention are those proteins which confer a specific pesticidal property. Such proteins may vary in molecular weight, having component polypeptides at least a molecular weight of 30 kDa or greater, preferably about 50 kDa or greater.

The auxiliary proteins of the invention may vary in molecular weight, having at least a molecular weight of about 15 kDa or greater, preferably about 20 kDa or greater; more preferably, about 30 kDa or greater. The auxiliary proteins themselves may have component polypeptides.

It is possible that the pesticidal protein and the auxiliary protein may be components of a multimeric, insecticidal protein. Such a insecticidal protein which includes the auxiliary proteins as one or more of its component polypeptides may vary in molecular weight, having at least a molecular weight of 50 kDa up to at least 200 kDa, preferably about 100 kDa to 150 kDa.

An auxiliary protein may be used in combination with the pesticidal proteins of the invention to enhance activity or to activate the pesticidal protein. To determine whether the auxiliary protein will affect activity, the pesticidal protein can be expressed alone and in combination with the auxiliary protein and the respective activities compared in feeding assays for pesticidal activity.

It may be beneficial to screen strains for potential pesticidal activity by testing activity of the strain alone and in combination with the auxiliary protein. In some instances an auxiliary protein in combination with the native proteins of the strains yields pesticidal activity where none is seen in the absence of an auxiliary protein.

The auxiliary protein can be modified, as described above, by various methods known in the art. Therefore, for purposes of the invention, the term "Vegetative Insecticidal Protein" (VIP) encompasses those proteins produced during vegetative growth which alone or in combination can be used for pesticidal activity. This includes pesticidal proteins, auxiliary proteins and those proteins which demonstrate activity only in the presence of the auxiliary protein or the polypeptide components of these proteins.

It is recognized that there are alternative methods available to obtain the nucleotide and amino acid sequences of the present proteins. For example, to obtain the nucleotide sequence encoding the pesticidal protein, cosmid clones, which express the pesticidal protein, can be isolated from a genomic library. From larger active cosmid clones, smaller subclones can be made and tested for activity. In this manner, clones which express an active pesticidal protein can be sequenced to determine the nucleotide sequence of the gene. Then, an amino acid sequence can be deduced for the protein. For general molecular methods, see, for example, Molecular Cloning, A Laboratory Manual, Second Edition, Vols. 1–3, Sambrook et al. (eds.) Cold Spring Harbor Laboratory Press, Cold Spring Harbor, N.Y. (1989), and the references cited therein.

The present invention also encompasses nucleotide sequences from organisms other than Bacillus, where the nucleotide sequences are isolatable by hybridization with the Bacillus nucleotide sequences of the invention. Proteins encoded by such nucleotide sequences can be tested for pesticidal activity. The invention also encompasses the proteins encoded by the nucleotide sequences. Furthermore, the invention encompasses proteins obtained from organisms other than Bacillus wherein the protein cross-reacts with antibodies raised against the proteins of the invention. Again the isolated proteins can be assayed for pesticidal activity by the methods disclosed herein or others well-known in the art.

Once the nucleotide sequences encoding the pesticidal proteins of the invention have been isolated, they can be manipulated and used to express the protein in a variety of hosts including other organisms, including microorganisms and plants.

The pesticidal genes of the invention can be optimized for enhanced expression in plants. See, for example U.S. Pat. No. 5,625,136; EPA 0359472; EPA 0385962; WO 91/16432;

Perlak et al. (1991) *Proc. Natl. Acad. Sci. USA* 88:3324–3328; and Murray et al. (1989) *Nucleic Acids Research* 17:477–498. In this manner, the genes can be synthesized utilizing plant preferred codons. That is the preferred codon for a particular host is the single codon which most frequently encodes that amino acid in that host. The maize preferred codon, for example, for a particular amino acid may be derived from known gene sequences from maize. Maize codon usage for 28 genes from maize plants is found in Murray et al. (1989), *Nucleic Acids Research* 17:477–498, the disclosure of which is incorporated herein by reference. Synthetic genes can also be made based on the distribution of codons a particular host uses for a particular amino acid.

In this manner, the nucleotide sequences can be optimized for expression in any plant. It is recognized that all or any part of the gene sequence may be optimized or synthetic. That is, synthetic or partially optimized sequences may also be used.

In like manner, the nucleotide sequences can be optimized for expression in any microorganism. For Bacillus preferred codon usage, see, for example U.S. Pat. No. 5,024,837 and Johansen et al. (1988) *Gene* 65:293–304.

Methodologies for the construction of plant expression cassettes as well as the introduction of foreign DNA into plants are described in the art. Such expression cassettes may include promoters, terminators, enhancers, leader sequences, introns and other regulatory sequences operably linked to the pesticidal protein coding sequence. It is further recognized that promoters or terminators of the VIP genes can be used in expression cassettes.

Generally, for the introduction of foreign DNA into plants Ti plasmid vectors have been utilized for the delivery of foreign DNA as well as direct DNA uptake, liposomes, electroporation, micro-injection, and the use of microprojectiles. Such methods had been published in the art. See, for example, Guerche et al., (1987) *Plant Science* 52:111–116; Neuhause et al., (1987) *Theor. Appl. Genet.* 75:30–36; Klein et al., (1987) *Nature* 327:70–73; Howell et al., (1980) *Science* 208:1265; Horsch et al., (1985) *Science* 227:1229–1231; DeBlock et al., (1989) *Plant Physiology* 91:694–701; *Methods for Plant Molecular Biology* (Weissbach and Weissbach, eds.) Academic Press, Inc. (1988); and *Methods in Plant Molecular Biology* (Schuler and Zielinski, eds.) Academic Press, Inc. (1989). See also abandoned U.S. application Ser. No. 08/008,374 herein incorporated by reference. See also, EPA 0193259 and EPA 0451878A1. It is understood that the method of transformation will depend upon the plant cell to be transformed.

It is further recognized that the components of the expression cassette may be modified to increase expression. For example, truncated sequences, nucleotide substitutions or other modifications maybe employed. See, for example Perlak et al. (1991) *Proc. Natl. Acad. Sci. USA* 88:3324–3328; Murray et al., (1989) *Nucleic Acids Research* 17:477–498; and WO 91/16432.

The construct may also include any other necessary regulators such as terminators, (Guerineau et al., (1991), *Mol. Gen. Genet.*, 226:141–144; Proudfoot, (1991), *Cell*, 64:671–674; Sanfacon et al., (1991), *Genes Dev.*, 5:141–149; Mogen et al., (1990), *Plant Cell*, 2:1261–1272; Munroe et al., (1990), *Gene*, 91:151–158; Ballas et al et al., (1989), *Nucleic Acids Res.*, 17:7891–7903; Joshi et al., (1987), *Nucleic Acid Res.*, 15:9627–9639); plant translational consensus sequences (Joshi, C. P., (1987), *Nucleic Acids Research*, 15:6643–6653), introns (Luehrsen and Walbot, (1991), *Mol. Gen. Genet.*, 225:81–93) and the like, operably linked to the nucleotide sequence. It may be beneficial to include 5' leader sequences in the expression cassette construct. Such leader sequences can act to enhance translation. Translational leaders are known in the art and include:

Picornavirus leaders, for example, EMCV leader (encephalomyocarditis 5' noncoding region) (Elroy-Stein, O., Fuerst, T. R., and Moss, B. (1989) *PNAS USA* 86:6126–6130);

Potyvirus leaders, for example, TEV lgeader (Tobacco Etch Virus) (Allison et al., (1986); MDMV leader (Maize Dwarf Mosaic Virus); *Virology*, 154:9–20), and Human immunoglobulin heavy-chain binding protein (BiP), (Macejak, D. G., and Sarnow, P., (1991), *Nature*, 353:90–94;

Untranslated leader from the coat protein mRNA of alfalfa mosaic virus (AMV RNA 4), (Jobling, S. A., and Gehrke, L., (1987), *Nature*, 325:622–625;

Tobacco mosaic virus leader (TMV), (Gallie, D. R. et al., (1989), *Molecular Biology of RNA*, pages 237–256; and Maize Chlorotic Mottle Virus leader (MCMV) (Lommel, S. A. et al., (1991), *Virology*, 81:382–385. See also, Della-Cioppa et al., (1987), *Plant Physiology*, 84:965–968.

A plant terminator may be utilized in the expression cassette. See, Rosenberg et al., (1987), *Gene*, 56:125; Guerineau et al., (1991), *Mol. Gen. Genet.*, 226:141–144; Proudfoot, (1991), *Cell*, 64:671–674; Sanfacon et al., (1991), *Genes Dev.*, 5:141–149; Mogen et al., (1990), *Plant Cell*, 2:1261–1272; Munroe et al., (1990), *Gene*, 91:151–158; Ballas et al., (1989), *Nucleic Acids Res.*, 17:7891–7903; Joshi et al., (1987), *Nucleic Acid Res.*, 15:9627–9639.

For tissue specific expression, the nucleotide sequences of the invention can be operably linked to tissue specific promoters. See, for example, U.S. Pat. No. 5,625,136 herein incorporated by reference.

It is recognized that the genes encoding the pesticidal proteins can be used to transform insect pathogenic organisms. Such organisms include Baculoviruses, fungi, protozoa, bacteria and nematodes.

The Bacillus strains of the invention may be used for protecting agricultural crops and products from pests. Alternatively, a gene encoding the pesticide may be introduced via a suitable vector into a microbial host, and said host applied to the environment or plants or animals. Microorganism hosts may be selected which are known to occupy the "phytosphere" (phylloplane, phyllosphere, rhizosphere, and/or rhizoplana) of one or more crops of interest. These microorganisms are selected so as to be capable of successfully competing in the particular environment with the wild-type microorganisms, provide for stable maintenance and expression of the gene expressing the polypeptide pesticide, and, desirably, provide for improved protection of the pesticide from environmental degradation and inactivation.

Such microorganisms include bacteria, algae, and fungi. Of particular interest are microorganisms, such as bacteria, e.g., Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc, and Alcaligenes; fungi, particularly yeast, e.g., Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum*, Agrobacteria, *Rhodopseudomonas spheroides, Xanthomonas campestris, Rhizobium melioti, Alcaligenes entrophus, Clavibacter xyli* and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae,* and *Aureobasidium pollulans*. Of particular interest are the pigmented microorganisms.

A number of ways are available for introducing a gene expressing the pesticidal protein into the microorganism host under conditions which allow for stable maintenance and expression of the gene. For example, expression cassettes can be constructed which include the DNA constructs of interest operably linked with the transcriptional and translational regulatory signals for expression of the DNA constructs, and a DNA sequence homologous with a sequence in the host organism, whereby integration will occur, and/or a replication system which is functional in the host, whereby integration or stable maintenance will occur.

Transcriptional and translational regulatory signals include but are not limited to promoter, transcriptional initiation start site, operators, activators, enhancers, other regulatory elements, ribosomal binding sites, an initiation codon, termination signals, and the like. See, for example, U.S. Pat. No. 5,039,523; U.S. Pat. No. 4,853,331; EPO 0480762A2; Sambrook et al. supra; Molecular Cloning, a Laboratory Manual, Maniatis et al. (eds) Cold Spring Harbor Laboratory, Cold Spring Harbor, N.Y. (1982); Advanced Bacterial Genetics, Davis et al. (eds.) Cold Spring Harbor Laboratory, Cold Spring Harbor, N.Y. (1980); and the references cited therein.

Suitable host cells, where the pesticide-containing cells will be treated to prolong the activity of the toxin in the cell when the then treated cell is applied to the environment of the target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such a Saccharomyces and Schizosaccharromyces; and Basidiomycetes yeast, such as Rhodotorula, Aureobasidium, Sporobolomyces, and the like.

Characteristics of particular interest in selecting a host cell for purposes of production include ease of introducing the protein gene into the host, availability of expression systems, efficiency of expression, stability of the protein in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as *Rhodotorula sp., Aureobasidium sp., Saccharomyces sp.,* and *Sporobolomyces sp.*; phylloplane organisms such as *Pseudomonas sp., Erwinia sp.*, and *Flavobacterium sp.*; or such other organisms as Escherichia, *LactoBacillus sp., Bacillus sp.*, and the like. Specific organisms include *Pseudomonas aeurginosa, Pseudomonas fluorescens, Saccharomyces cerevisiae, Bacillus thuringiensis, Escherichia coli, Bacillus subtilis*, and the like.

VIP genes can be introduced into micro-organisms that multiply on plants (epiphytes) to deliver VIP proteins to potential target pests. Epiphytes can be gram-positive or gram-negative bacteria for example.

Root colonizing bacteria, for example, can be isolated from the plant of interest by methods known in the art. Specifically, a *Bacillus cereus* strain which colonizes roots could be isolated from roots of a plant (for example see J. Handelsman, S. Raffel, E. Mester, L. Wunderlich and C. Grau, *Appl. Environ. Microbiol.* 56:713–718, (1990)). VIP1 and/or VIP2 could be introduced into a root colonizing *Bacillus cereus* by standard methods known in the art.

Specifically, VIP1 and/or VIP2 derived from *Bacillus cereus* strain AB78 can be introduced into a root colonizing *Bacillus cereus* by means of conjugation using standard methods (J. Gonzalez, B. Brown and B. Carlton, *Proc. Natl. Acad. Sci.* 79:6951–6955, (1982)).

Also, VIP1 and/or VIP2 or other VIPs of the invention can be introduced into the root colonizing Bacillus by means of electro-transformation. Specifically, VIPs can be cloned into a shuttle vector, for example, pHT3101 (D. Lereclus et al., *FEMS Microbiol. Letts.*, 60:211–218 (1989)) as described in Example 10. The shuttle vector pHT3101 containing the coding sequence for the particular VIP can then be transformed into the root colonizing Bacillus by means of electroporation (D. Lereclus et al. 1989, *FEMS Microbiol. Letts.* 60:211–218).

Expression systems can be designed so that VIP proteins are secreted outside the cytoplasm of gram negative bacteria, *E. coli*, for example. Advantages of having VIP proteins secreted are (1) it avoids potential toxic effects of VIP proteins expressed within the cytoplasm and (2) it can increase the level of VIP protein expressed and (3) can aid in efficient purification of VIP protein.

VIP proteins can be made to be secreted in *E. coli*, for example, by fusing an appropriate *E. coli* signal peptide to the amino-terminal end of the VIP signal peptide or replacing the VIP signal peptide with the *E. coli* signal peptide. Signal peptides recognized by *E. coli* can be found in proteins already known to be secreted in *E. coli*, for example the OmpA protein (J. Ghrayeb, H. Kimura, M. Takahara, Y. Masui and M. Inouye, *EMBO J.*, 3:2437–2442 (1984)). OmpA is a major protein of the *E. coli* outer membrane and thus its signal peptide is thought to be efficient in the translocation process. Also, the OmpA signal peptide does not need to be modified before processing as may be the case for other signal peptides, for example lipoprotein signal peptide (G. Duffaud, P. March and M. Inouye, *Methods in Enzymology.* 153:492 (1987)).

Specifically, unique BamHI restriction sites can be introduced at the amino-terminal and carboxy-terminal ends of the VIP coding sequences using standard methods known in the art. These BamHI fragments can be cloned, in frame, into the vector pIN-III-ompA1, A2 or A3 (J. Ghrayeb, H. Kimura, M. Takahara, H. Hsiung, Y. Masui and M. Inouye, *EMBO J.*, 3:2437–2442 (1984)) thereby creating ompA:VIP fusion gene which is secreted into the periplasmic space. The other restriction sites in the polylinker of pIN-III-ompA can be eliminated by standard methods known in the art so that the VIP amino-terminal amino acid coding sequence is directly after the ompA signal peptide cleavage site. Thus, the secreted VIP sequence in *E. coli* would then be identical to the native VIP sequence.

When the VIP native signal peptide is not needed for proper folding of the mature protein, such signal sequences can be removed and replaced with the ompA signal sequence. Unique BamnHI restriction sites can be introduced at the amino-termini of the proprotein coding sequences directly after the signal peptide coding sequences of VIP and at the carboxy-termini of VIP coding sequence. These BamHI fragments can then be cloned into the pIN-III-ompA vectors as described above.

General methods for employing the strains of the invention in pesticide control or in engineering other organisms as pesticidal agents are known in the art. See, for example U.S. Pat. No. 5,039,523 and EP 0480762A2.

VIPs can be fermented in a bacterial host and the resulting bacteria processed and used as a microbial spray in the same manner that *Bacillus thuringiensis* strains have been used as insecticidal sprays. In the case of a VIP(s) which is secreted from Bacillus, the secretion signal is removed or mutated using procedures known in the art. Such mutations and/or deletions prevent secretion of the VIP protein(s) into the growth medium during the fermentation process. The VIPs are retained within the cell and the cells are then processed to yield the encapsulated VIPs. Any suitable microorganism can be used for this purpose. Psuedomonas has been used to express *Bacillus thuringiensis* endotoxins as encapsulated proteins and the resulting cells processed and sprayed as an insecticide. (H. Gaertner et al. 1993, In Advanced Engineered Pesticides, L. Kim ed.)

Various strains of *Bacillus thuringiensis* are used in this manner. Such Bt strains produce endotoxin protein(s) as well as VIPs. Alternatively, such strains can produce only VIPs. A sporulation deficient strain of *Bacillus subtilis* has been shown to produce high levels of the CryIIIA endotoxin from *Bacillus thuringiensis* (Agaisse, H. and Lereclus, D., "Expression in *Bacillus subtilis* of the *Bacillus thuringiensis* CryIIIA toxin gene is not dependent on a sporulation-specific sigma factor and is increased in a spoOA mutant", *J. Bacteriol.*, 176:4734–4741 (1994)). A similar spoOA mutant can be prepared in *Bacillus thuringiensis* and used to produce encapsulated VIPs which are not secreted into the medium but are retained within the cell.

To have VIPs maintained within the Bacillus cell the signal peptide can be disarmed so that it no longer functions as a secretion signal. Specifically, the putative signal peptide for VIP1 encompasses the first 31 amino acids of the protein with the putative consensus cleavage site, Ala-X-Ala, at the C-terminal portion of this sequence (G. von Heijne, *J. Mol. Biol.* 184:99–105 (1989)) and the putative signal peptide for VIP2 encompasses the first 40 amino acids of the protein with the putative cleavage site after Ala40. The cleavage sites in either VIP1 or VIP2 can be mutated with methods known in the art to replace the cleavage site consensus sequence with alternative amino acids that are not recognized by the signal peptidases.

Alternatively, the signal peptides of VIP1, VIP2 and/or other VIPs of the invention can be eliminated from the sequence thereby making them unrecognizable as secretion proteins in Bacillus. Specifically, a methionine start site can be engineered in front of the proprotein sequence in VIP1, starting at Asp32, or the proprotein sequence in VIP2, starting at Glu41 using methods known in the art.

VIP genes can be introduced into micro-organisms that mutiply on plants (epiphytes) to deliver VIP proteins to potential target pests. Epiphytes can be gram-positive or gram-negative bacteria for example.

The Bacillus strains of the invention or the microorganisms which have been genetically altered to contain the pesticidal gene and protein may be used for protecting agricultural crops and products from pests. In one aspect of the invention, whole, i.e., unlysed, cells of a toxin (pesticide)-producing organism are treated with reagents that prolong the activity of the toxin produced in the cell when the cell is applied to the environment of target pest(s).

Alternatively, the pesticides are produced by introducing a heterologous gene into a cellular host. Expression of the heterologous gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These naturally encapsulated pesticides may then be formulated in accordance with conventional techniques for application to the environment hosting a target pest, e.g., soil, water, and foliage of plants. See, for example EPA 0192319, and the references cited therein.

The active ingredients of the present invention are normally applied in the form of compositions and can be applied to the crop area or plant to be treated, simultaneously or in succession, with other compounds. These compounds can be both fertilizers or micronutrient donors or other preparations that influence plant growth. They can also be selective herbicides, insecticides, fungicides, bactericides, nematicides, mollusicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers.

Preferred methods of applying an active ingredient of the present invention or an agrochemical composition of the present invention which contains at least one of the pesticidal proteins produced by the bacterial strains of the present invention are leaf application, seed coating and soil application. The number of applications and the rate of application depend on the intensity of infestation by the corresponding pest.

In one embodiment of the invention a *Bacillus cereus* microorganism has been isolated which is capable of killing *Diabrotica virgifera virgifera*, and *Diabrotica longicornis barberi*. The novel *B. cereus* strain AB78 has been deposited in the Agricultural Research Service, Patent Culture Collection (NRRL), Northern Regional Research Center, 1815 North University Street, Peoria, Ill. 61604, USA and given Accession No. NRRL B-21058.

A fraction protein has been substantially purified from the *B. cereus* strain. This purification of the protein has been verified by SDS-PAGE and biological activity. The protein has a molecular weight of about 60 to about 100 kDa, particularly about 70 to about 90 kDa, more particularly about 80 kDa, hereinafter VIP.

Amino-terminal sequencing has revealed the N-terminal amino-acid sequence to be: NH$_2$-Lys-Arg-Glu-Ile-Asp-Glu-Asp-Thr-Asp-Thr-Asx-Gly-Asp-Ser-Ile-Pro- (SEQ ID NO:8) where Asx represents either Asp or Asn. The entire amino acid sequence is given in SEQ ID NO:7. The DNA sequence which encodes the amino acid sequence of SEQ ID NO:7 is disclosed in SEQ ID NO:6.

An oligonucleotide probe for the region of the gene encoding amino acids 3–9 of the NH$_2$-terminus has been generated. The probe was synthesized based on the codon usage of a *Bacillus thuringiensis* (Bt) δ-endotoxin gene. The nucleotide sequence of the oligonucleotide probe used for Southern hybridizations was as follows:

5'-GAA ATT GAT CAA GAT ACN GAT-3' (SEQ ID NO:9) where N represents any base.

In addition, the DNA probe for the Bc AB78 VIP1 gene described herein, permits the screening of any Bacillus strain or other organisms to determine whether the VIP1 gene (or related gene) is naturally present or whether a particular transformed organism includes the VIP1 gene.

The invention now being generally described, the same will be better understood by reference to the following detailed examples that are provided for the purpose of illustration and are not to be considered limiting of the invention unless so specified.

A standard nomenclature has been developed based on the sequence identity of the proteins encompassed by the present invention. The gene and protein names for the detailed examples which follow and their relationship to the names used in the parent application are shown below.

| Gene/Protein Name under Standard Nomenclature | Gene/Protein Name in Parent | Description of Protein |
|---|---|---|
| VIP1A(a) | VIP1 | VIP1 from strain AB78 as disclosed in SEQ ID NO:5. |
| VIP2A(a) | VIP2 | VIP2 from strain AB78 as disclosed in SEQ ID NO:2. |
| VIP1A(b) | VIP1 homolog | VIP1 from *Bacillus thuringiensis* var. *tenebrionis* as disclosed in SEQ ID NO:21. |
| VIP2A(b) | VIP2 homolog | VIP2 from *Bacillus thuringiensis* var. *tenebrionis* as disclosed in SEQ ID NO:20. |
| VIP3A(a) | — | VIP from strain AB88 as disclosed in SEQ ID NO:28 of the present application |
| VIP3A(b) | — | VIP from strain AB424 as disclosed in SEQ ID NO:31 of the present application |

EXPERIMENTAL

EXAMPLE 1

AB78 ISOLATION AND CHARACTERIZATION

*Bacillus cereus* strain AB78 was isolated as a plate contaminant in the laboratory on T3 media (per liter: 3 g tryptone, 2 g tryptose, 1.5 g yeast extract, 0.05M sodium phosphate (pH 6.8), and 0.005 g MnCl$_2$; Travers, R. S. 1983). During log phase growth, AB78 gave significant activity against western corn rootworm. Antibiotic activity against gram-positive *Bacillus spp*. was also demonstrated (Table 12).

TABLE 12

Antibiotic activity of AB78 culture supernatant

| | Zone of inhibition(cm) | |
|---|---|---|
| Bacteria tested | AB78 | Streptomycin |
| E. coli | 0.0 | 3.0 |
| B. megaterium | 1.1 | 2.2 |
| B. mycoides | 1.3 | 2.1 |
| B. cereus CB | 1.0 | 2.0 |
| B. cereus 11950 | 1.3 | 2.1 |
| B. cereus 14579 | 1.0 | 2.4 |
| B. cereus AB78 | 0.0 | 2.2 |
| Bt var. israelensis | 1.1 | 2.2 |
| Bt var. tenebrionis | 0.9 | 2.3 |

Morphological characteristics of AB78 are as follows: Vegetative rods straight, 3.1–5.0 mm long and 0.5–2.0 mm wide. Cells with rounded ends, single in short chains. Single subterminal, cylindrical-oval, endospore formed per cell. No parasporal crystal formed. Colonies opaque, erose, lobate and flat. No pigments produced. Cells motile. Flagella present.

Growth characteristics of AB78 are as follows:

Facultative anaerobe with optimum growth temperature of 21°–30° C. Will grow at 15°, 20°, 25°, 30° and 37° C. Will not grow above 40° C. Grows in 5–7% NaCl.

Table 13 provides the biochemical profile of AB78.

TABLE 13

Biochemical characteristics of *B. cereus* strain AB78.

| Acid from L-arabinose | – | Methylene blue reoxidized | + |
|---|---|---|---|
| Gas from L-arabinose | – | Nitrate reduced | + |
| Acid from D-xylose | – | NO$_3$ reduced to NO$_2$ | + |
| Gas from D-xylose | – | VP | + |
| Acid from D-glucose | + | H$_2$O$_2$ decomposed | + |
| Gas from D-glucose | – | Indole | – |
| Acid from lactose | – | Tyrosine decomposed | + |
| Gas from lactose | – | Dihydroxiacetone | – |
| Acid from sucrose | – | Litmus milk acid | – |
| Gas from sucrose | – | Litmus milk coagulated | – |
| Acid from D-mannitol | – | Litmus milk alkaline | – |
| Gas from D-mannitol | – | Litmus milk peptonized | – |
| Proprionate utilization | + | Litmus milk reduced | – |
| Citrate utilization | + | Casein hydrolyzed | + |
| Hippurate hydrolysis | w | Starch hydrolyzed | + |
| Methylene blue reduced | + | Gelatin liquidified | + |
| | | Lecithinase produced | w | w = weak reaction

EXAMPLE 2

BACTERIAL CULTURE

A subculture of Bc strain AB78 was used to inoculate the following medium, known as TB broth:

| Tryptone | 12 | g/l |
|---|---|---|
| Yeast Extract | 24 | g/l |
| Glycerol | 4 | ml/l |
| KH$_2$PO$_4$ | 2.1 | g/l |
| K$_2$HPO$_4$ | 14.7 | g/l |
| pH 7.4 | | |

The potassium phosphate was added to the autoclaved broth after cooling. Flasks were incubated at 30° C. on a rotary shaker at 250 rpm for 24 h.–36 h, which represents an early to mid-log growth phase.

The above procedure can be readily scaled up to large fermentors by procedures well known in the art.

During vegetative growth, usually 24–36 h. after starting the culture, which represents an early to mid-log growth phase, AB78 bacteria were centrifuged from the culture supernatant. The culture supernatant containing the active protein was used in bioassays.

EXAMPLE 3
INSECT BIOASSAYS

B. cereus strain AB78 was tested against various insects as described below.

Western, Northern and Southern corn rootworm, *Diabrotica virgifera virgifera, D. longcornis barberi* and *D. undecempunctata howardi*, respectively: dilutions were made of AB78 culture supernatant grown 24–36 h., mixed with molten artificial diet (Marrone et al. (1985) *J. of Economic Entomology* 78:290–293) and allowed to solidify. Solidified diet was cut and placed in dishes. Neonate larvae were placed on the diet and held at 30° C. Mortality was recorded after 6 days.

*E. coli* clone bioassay: *E. coli* cells were grown overnight in broth containing 100 μg/ml ampicillin at 37° C. Ten ml culture was sonicated 3X for 20 sec each. 500 μl of sonicated culture was added to molten western corn rootworm diet.

Colorado potato beetle, *Leptinotarsa decemlineata*: dilutions in Triton X-100 (to give final concentration of 0.1% TX-100) were made of AB78 culture supernatant grown 24–36 h. Five cm² potato leaf pieces were dipped into these dilutions, air dried, and placed on moistened filter paper in plastic dishes. Neonate larvae were placed on the leaf pieces and held at 30° C. Mortality was recorded after 3–5 days.

Yellow mealworm, *Tenebrio molitor*: dilutions were made of AB78 culture supernatant grown 24–36 h., mixed with molten artificial diet (Bioserv #F9240) and allowed to solidify. Solidified diet was cut and placed in plastic dishes. Neonate larvae were placed on the diet and held at 30° C. Mortality was recorded after 6–8 days.

European corn borer, black cutworm, tobacco budworm, tobacco hornworm and beet armyworm; *Ostrinia nubilalis, Agrotis ipsilon, Heliothis virescens, Manduca sexta* and *Spodoptera exigua*, respectively: dilutions, in TX-100 (to give final concentration of 0.1% TX-100), were made of AB78 culture supernatant grown 24–36 hrs. 100 μl was pipetted onto the surface of 18 cm² of solidified artificial diet (Bioserv #F9240) and allowed to air dry. Neonate larvae were then placed onto the surface of the diet and held at 30° C. Mortality was recorded after 3–6 days.

Northern house mosquito, *Culex pipiens*:-dilutions were made of AB78 culture supernatant grown 24–36 h. 100 μl was pipetted into 10 ml water in a 30 ml plastic cup. Third instar larvae were added to the water and held at room temperature. Mortality was recorded after 24–48 hours. The spectrum of entomocidal activity of AB78 is given in Table 14.

TABLE 14

Activity of AB78 culture supernatant against various insect species

| Insect species tested to date | Order | Activity |
|---|---|---|
| Western corn rootworm (*Diabrotica virgifera vigifera*) | Col | +++ |
| Northern corn rootworm (*Diabrotica longicornis barberi*) | Col | +++ |
| Southern corn rootworm | Col | − |

TABLE 14-continued

Activity of AB78 culture supernatant against various insect species

| Insect species tested to date | Order | Activity |
|---|---|---|
| (*Diabrotica undecimpunctata howardi*) | | |
| Colorado potato beetle (*Leptinotarsa decemlineata*) | Col | − |
| Yellow mealworm (*Tenebrio molitor*) | Col | − |
| European corn borer (*Ostrinia nubilalis*) | Lep | − |
| Tobacco budworm (*Heliothis virescens*) | Lep | − |
| Tobacco hornworm (*Manduca sexta*) | Lep | − |
| Beet armyworm (*Spodoptera exigua*) | Lep | − |
| Black cutworm (*Agrotis ipsilon*) | Lep | − |
| Northern house mosquito (*Culex pipiens*) | Dip | − |

The newly discovered *B. cereus* strain AB78 showed a significantly different spectrum of insecticidal activity as compared to known coleopteran active δ-endotoxins from Bt. In particular, AB78 showed more selective activity against beetles than known coleopteran-active Bt strains in that it was specifically active against *Diabrotica spp.* More specifically, it was most active against *D. virgifera virgifera* and *D. longicornis barberi* but not *D. undecimpunctata howardi*.

A number of Bacillus strains were bioassayed for activity during vegetative growth (Table 15) against western corn rootworm. The results demonstrate that AB78 is unique in that activity against western corn rootworm is not a general phenomenon.

TABLE 15

| Bacillus strain | Percent WCRW mortality |
|---|---|
| *B. cereus* AB78 (Bat.1) | 100 |
| *B. cereus* AB78 (Bat.2) | 100 |
| *B. cereus* (Carolina Bio.) | 12 |
| *B. cereus* ATCC 11950 | 12 |
| *B. cereus* ATCC 14579 | 8 |
| *B. mycoides* (Carolina Bio.) | 30 |
| *B. popilliae* | 28 |
| *B. thuringiensis* HD135 | 41 |
| *B. thuringiensis* HD191 | 9 |
| *B. thuringiensis* GC91 | 4 |
| *B. thuringiensis* isrealensis | 24 |
| Water Control | 4 |

Specific activity of AB78 against western corn rootworm is provided in Table 16.

TABLE 16

Activity of AB78 culture supernatant against neonate western corn rootworm

| Culture supernatant concentration (μl/ml) | Percent WCRW mortality |
|---|---|
| 100 | 100 |
| 25 | 87 |
| 10 | 80 |
| 5 | 40 |

TABLE 16-continued

Activity of AB78 culture supernatant against neonate western corn rootworm

| Culture supernatant concentration (μl/ml) | Percent WCRW mortality |
|---|---|
| 2.5 | 20 |
| 1 | 6 |
| 0 | 0 |

The $LC_{50}$ was calculated to be 6.2 μl of culture supernatant per ml of western corn rootworm diet.

The cell pellet was also bioassayed and had no activity against WCRW. Thus, the presence of activity only in the supernatant indicates that this VIP is an exotoxin.

EXAMPLE 4

ISOLATION AND PURIFICATION OF CORN ROOTWORM ACTIVE PROTEINS FROM AB78

Culture media free of cells and debris was made to 70% saturation by the addition of solid ammonium sulfate (472 g/L). Dissolution was at room temperature followed by cooling in an ice bath and centrifugation at 10,000×g for thirty minutes to pellet the precipitated proteins. The supernatant was discarded and the pellet was dissolved in 1/10 the original volume of 20 mM TRIS-HCl at pH 7.5. The dissolved pellet was desalted either by dialysis in 20 mM TRIS-HCl pH 7.5, or passing through a desalting column.

The desalted material was titrated to pH 3.5 using 20 mM sodium citrate pH 2.5. Following a thirty minute room temperature incubation the solution was centrifuged at 3000×g for ten minutes. The supernatant at this stage contained the greatest amount of active protein.

Following neutralization of the pH to 7.0 the supernatant was applied to a Mono-Q, anion exchange, column equilibrated with 20 mM TRIS pH 7.5 at a flow rate of 300 mL/min. The column was developed with a stepwise and linear gradient employing 400 mM NaCl in 20 mM TRIS pH 7.5.

Bioassay of the column fractions and SDS-PAGE analysis were used to confirm the active fractions. SDS-PAGE analysis identified the biologically active protein as having components of a molecular weight in the range of about 80 kDa and 50 kDa.

EXAMPLE 5

SEQUENCE ANALYSIS OF THE CORN ROOTWORM ACTIVE PROTEIN

The 80 kDa component isolated by SDS-PAGE was transferred to PVDF membrane and was subjected to amino-terminal sequencing as performed by repetitive Edman cycles on an ABI 470 pulsed-liquid sequencer. Transfer was carried out in 10 mM CAPS buffer with 10% methanol pH 11.0 as follows:

Incubation of the gel following electrophoresis was done in transfer buffer for five minutes. ProBlott PVDF membrane was wetted with 100% MeOH briefly then equilibrated in transfer buffer. The sandwich was arranged between foam sponges and filter paper squares with the configuration of cathode-gel-membrane-anode.

Transfer was performed at 70 V constant voltage for 1 hour.

Following transfer, the membrane was rinsed with water and stained for two minutes with 0.25% Coomassie Blue R-250 in 50% MeOH.

Destaining was done with several rinses with 50% MeOH 40% water 10% acetic acid.

Following destaining the membrane was air dried prior to excision of the bands for sequence analysis. A BlottCartridge and appropriate cycles were utilized to achieve maximum efficiency and yield. Data analysis was performed using model 610 Sequence Analysis software for identifying and quantifying the PTH-amino acid derivatives for each sequential cycle.

The N-terminal sequence was determined to be:

NH2-Lys-Arg-Glu-Ile-Asp-Glu-Asp-Thr-Asp-Thr-Asx-Gly-Asp-Ser-Ile-Pro-(SEQ ID NO:8) where Asx represents Asp or Asn. The complete amino acid sequence for the 80 kDa component is disclosed in SEQ ID NO:7. The DNA sequence which encodes SEQ ID NO:7 is disclosed in SEQ ID NO:6.

EXAMPLE 6

CONSTRUCTION OF DNA PROBE

An oligonucleotide probe for the region of the gene encoding amino acids 3–9 of the N-terminal sequence (Example 5) was generated. The probe was synthesized based on the codon usage of a *Bacillus thuringiensis* (Bt) δ-endotoxin gene. The nucleotide sequence

5'-GAA ATT GAT CAA GAT ACN GAT-3' (SEQ ID NO:9)

was used as a probe in Southern hybridizations. The oligonucleotide was synthesized using standard procedures and equipment.

EXAMPLE 7

ISOELECTRIC POINT DETERMINATION OF THE CORN ROOTWORM ACTIVE PROTEIN

Purified protein from step 5 of the purification process was analyzed on a 3–9 pI isoelectric focusing gel using the Phastgel electrophoresis system (Pharmacia). Standard operating procedures for the unit were followed for both the separation and silver staining development procedures. The pI was approximated at about 4.9.

EXAMPLE 8

PCR DATA ON AB78

PCR analysis (See, for example U.S. patent application Ser. No. 08/008,006; and, Carozzi et al. (1991) *Appl Environ. Microbiol.* 57(11):3057–3061, herein incorporated by reference.) was used to verify that the *B. cereus* strain AB78 did not contain any insecticidal crystal protein genes of *B. thuringiensis* or *B. sphaericus* (Table 17).

TABLE 17

Bacillus insecticidal crystal protein gene primers tested by PCR against AB78 DNA.

| Primers Tested | Product Produced |
|---|---|
| 2 sets specific for CryIIIA | Negative |
| CryIIIB | Negative |
| 2 sets specific for CryIA | Negative |
| CryIA(a) | Negative |
| CryIA(b) specific | Negative |
| CryIB | Negative |
| CryIC specific | Negative |
| CryIE specific | Negative |
| 2 sets specific for *B. sphaericus* | Negative |
| 2 sets specific for CryIV | Negative |
| Bacillus control (PI-PLC) | Positive |

EXAMPLE 9

COSMID CLONING OF TOTAL DNA FROM *B. CEREUS* STRAIN AB78

The VIP1A(*a*) gene was cloned from total DNA prepared from strain AB78 as follows:

Isolation of AB78 DNA was as follows:
1. Grow bacteria in 10 ml L-broth overnight. (Use 50 ml sterile centrifuge tube)
2. Add 25 ml of fresh L-broth and ampicillin (30 μg/ml).
3. Grow cells 2–6 h. at 30° C. with shaking.
4. Spin cells in a 50 ml polypropylene orange cap tube in IEC benchtop clinical centrifuge at ¾ speed.
5. Resuspend cell pellet in 10 ml TES (TES=50 mM TRIS pH 8.0, 100 mM EDTA, 15 mM NaCl).
6. Add 30 mg lysozyme and incubate 2 hrs at 37° C.
7. Add 200 μl 20% SDS and 400 μl Proteinase K stock (20 mg/ml). Incubate at 37° C.
8. Add 200 μl fresh Proteinase K. Incubate 1 hr. at 55° C. Add 5 ml TES to make 15 ml final volume.
9. Phenol extract twice (10 ml phenol, spin at room temperature at ¾ speed in an IEC benchtop clinical centrifuge). Transfer supernatant (upper phase) to a clean tube using a wide bore pipette.
10. Extract once with 1:1 vol. phenol:chloroform/isoamyl alcohol (24:1 ratio).
11. Precipitate DNA with an equal volume of cold isopropanol; Centrifuge to pellet DNA.
12. Resuspend pellet in 5 ml TE.
13. Precipitate DNA with 0.5 ml 3M NaOAc pH 5.2 and 11 ml 95% ethanol. Place at −20° C. for 2 h.
14. "Hook" DNA from tube with a plastic loop, transfer to a microfage tube, spin, pipette off excess ethanol, dry in vacuo.
15. Resuspend in 0.5 ml TE. Incubate 90 min. at 65° C. to help get DNA back into solution.
16. Determine concentration using standard procedures.

Cosmid Cloning of AB78

All procedures, unless indicated otherwise, were performed according to Stratagene Protocol, Supercos 1 Instruction Manual, Cat. No. 251301.

Generally, the steps were as follows:
A. Sau 3A partial digestion of the AB78 DNA.
B. Preparation of vector DNA
C. Ligation and packaging of DNA
D. Tittering the cosmid library
  1. Start a culture of HB101 cells by placing 50 ml of an overnight culture in 5 mls of TB with 0.2% maltose. Incubate 3.5 hrs. at 37° C.
  2. Spin out cells and resuspend in 0.5 ml 10 mM MgSO$_4$
  3. Add together: 100 μl cells 100 μl diluted packaging mixture 100 μl 10 mM MgSO$_4$ 30 μl TB
  4. Adsorb at room temperature for 30 minutes with no shaking.
  5. Add 1 ml TB and mix gently. Incubate 30 minutes at 37° C.
  6. Plate 200 μl onto L-amp plates. Incubate at 37° C. overnight.

At least 400 cosmid clones were selected at random and screened for activity against western corn rootworm as described in Example 3. DNA from 5 active clones and 5 non-active clones were used in Southern hybridizations. Results demonstrated that hybridization using the above described oligonucleotide probe correlated with western corn rootworm activity (Table 18).

Cosmid clones P3-12 and P5-4 have been deposited with the Agricultural Research Service Patent Culture Collection (NRRL) and given Accession Nos. NRRL B-21061 and NRRL B-21059 respectively.

TABLE 18

Activity of AB78 cosmid clones against western corn rootworm.

| Clone | Mean percent mortality (N = 4) |
|---|---|
| Clones which hybridize with probe | |
| P1-73 | 47 |
| P1-83 | 64 |
| P2-2 | 69 |
| P3-12 | 85 |
| P5-4 | 97 |
| Clones which do not hybridize with probe | |
| P1-2 | 5 |
| P3-8 | 4 |
| P3-9 | 12 |
| P3-18 | 0 |
| P4-6 | 9 |

EXAMPLE 10

IDENTIFICATION OF A 6 KB REGION ACTIVE AGAINST WESTERN CORN ROOTWORM

DNA from P3-12 was partially digested with restriction enzyme Sau 3A, and ligated into the E. coli vector pUC19 and transformed into E. coli. A DNA probe specific for the 80 kDa VIP1A(a) protein was synthesized by PCR amplification of a portion of P3-12 DNA. Oligonucleotides MK113 and MK117, which hybridize to portions of VIP1A (a), were synthesized using the partial amino acid sequence of the 80 kDa protein. Plasmid subclones were identified by colony hybridization to the PCR-generated probe, and tested for activity against western corn rootworm. One such clone, PL2, hybridized to the PCR-generated fragment, and was active against western corn rootworm in the assay previously described.

A 6 kb Cla I restriction fragment from pL2 was cloned into the Sma I site of the E. coli-Bacillus shuttle vector pHT 3101 (Lereclus, D. etal., *FEMS Microbiology Letters* 60:211–218 (1989)) to yield pCIB6201. This construct confers anti-western corn rootworm activity upon both Bacillus and E.coli strains, in either orientation. pCIB6022 contains this same 6 kb Cla I fragment in pBluescript SK(+) (Stratagene), produces equivalent VIP1A(a) protein (by western blot), and is also active against western corn rootworm.

The nucleotide sequence of pCIB6022 was determined by the dideoxy termination method of Sanger et al., *Proc. Natl. Acad. Sci.* USA, 74:5463–5467 (1977), using PRISM Ready Reaction Dye Deoxy Terminator Cycle Sequencing Kits and PRISM Sequenase® Terminator Double-Stranded DNA Sequencing Kit and analyzed on an ABI 373 automatic sequencer. The sequence is given in SEQ ID NO:1. The 6 kb fragment encodes both VIP1A(a) and VIP2A(a), as indicated by the open reading frames described in SEQ ID NO:1. The sequence encoding VIP1A(a) is further disclosed in SEQ ID NO:4. The relationship between. VIP1A(a) and VIP2A(a) within the 6 kb fragment found in pCIB6022 is depicted in FIG. 1. pCIB6022 was deposited with the Agricultural Research Service, Patent Culture Collection, (NRRL), Northern Regional Research Center, 1815 North University Street, Peoria, Ill. 61604, USA, and given the Accession No. NRRL B-21222.

EXAMPLE 11
FUNCTIONAL DISSECTION OF THE VIP1A(a) DNA REGION

To confirm that the VIP1A(a) open reading frame (ORF) is necessary for insecticidal activity a translational frameshift mutation was created in the gene. The restriction enzyme Bgl II recognizes a unique site located 857 bp into the coding region of VIP1A(a). pCIB6201 was digested with Bgl II, and the single-stranded ends filled-in with DNA polymerase (Klenow fragment) and dNTPS. The plasmid was religated and transformed into E. coli. The resulting plasmid, pCIB6203, contains a four nucleotide insertion in the coding region of VIP1A(a). pCIB6203 does not confer WCRW insecticidal activity, confirming that VIP1A(a) is an essential component of western corn rootworm activity.

To further define the region necessary to encode VIP1A (a), subclones of the VIP1A(a) and VIP2A(a) (auxiliary protein) region were constructed and tested for their ability to complement the mutation in pCIB6203. pCIB6023 contains the 3.7 kb Xba I-EcoRV fragment in pBluescript SK(+) (Stratagene). Western blot analysis indicates that pCIB6023 produces VIP1A(a) protein of equal size and quantity as clones PL2 and pCIB6022. pCIB6023 contains the entire gene encoding the 80 kD protein. pCIB6023 was deposited with the Agricultural Research Service, Patent Culture Collection, (NRRL), Northern Regional Research Center, 1815 North University Street, Peoria, Ill. 61604, USA, and given the Accession No. NRRL B-21223N. pCIB6206 contains the 4.3 kb Xba I-Cla I fragment from pCIB6022 in pBluescript SK(+) (Stratagene). pCIB6206 was also deposited with the Agricultural Research Service, Patent Culture Collection, (NRRL), Northern Regional Research Center, 1815 North University Street, Peoria, Ill. 61604, USA, and given the Accession No. NRRL B-21321.

pCIB6023, pCIB6206, and pCIB6203 do not produce detectable western corn rootworm activity when tested individually. However, a mixture of cells containing pCIB6203 (VIP1A(a)-mutated, plus VIP2A(a)) and cells containing pCIB6023 (only VIP1A(a)) shows high activity against western corn rootworm. Similarly, a mixture of cells containing pCIB6206 and cells containing pCIB6203 shows high activity against western corn rootworm.

To further define the limits of VIP2A(a), we constructed pCIB6024, which contains the entirety of VIP2A(a), but lacks most of the VIP1A(a) coding region. pCIB6024 was constructed by gel purifying the 2.2 kb Cla I-Sca I restriction fragment from pCIB6022, filling in the single-stranded ends with DNA polymerase (Klenow fragment) and dNTPs, and ligating this fragment into pBluescript SK(+) vector (Stratagene) digested with the enzyme Eco RV. Cells containing pCIB6024 exhibit no activity against western corn rootworm. However, a mixture of cells containing pCIB6024 and cells containing pCIB6023 shows high activity against western corn rootworm .(See FIG. 1).

Thus, pCIB6023 and pCIB6206 must produce a functional VIP1A(a) gene product, while pCIB6203 and pCIB6024 must produce a functional VIP2A(a) gene product. These results suggest a requirement for a gene product (s) from the VIP2A(a) region, in combination with VIP1A (a), to confer maximal western corn rootworm activity. (See FIG. 1.)

EXAMPLE 12
AB78 ANTIBODY PRODUCTION

Antibody production was initiated in 2 Lewis rats to allow for both the possibility of moving to production of hybridoma cell lines and also to produce enough serum for limited screening of genomic DNA library. Another factor was the very limited amount of antigen available and the fact that it could only be produced to purity by PAGE and subsequent electrotransfer to nitrocellulose.

Due to the limited availability of antigen on nitrocellulose, the nitrocellulose was emulsified in DMSO and injected into the hind footpads of the animals to elicit B-cell production in the popliteal lymph nodes just upstream. A strong reacting serum was produced as judged by western blot analysis with the first production bleed. Several subsequent injections and bleeds produced enough serum to accomplish all of the screening required.

Hybridoma production with one of the rats was then initiated. The popliteal lymph node was excised, macerated, and the resulting cells fused with mouse myeloma P3×63Ag8.653. Subsequent cell screening was accomplished as described below. Four initial wells were selected which gave the highest emulsified antigen reaction to be moved to limited dilution cloning. An additional 10 wells were chosen for expansion and cryoperservation.

Procedure to Emulsify AB78 on nitrocellulose in DMSO for ELISA screening:

After electrotransfer of AB78 samples run on PAGE to nitrocellulose, the reversible strain Ponceau S is used to visualize all protein transferred. The band corresponding to AB78 toxin, previously identified and N-terminal sequenced, was identified and excised from nitrocellulose. Each band is approximately 1 mm×5 mm in size to minimize the amount of nitrocellulose emulsified. A single band is placed in a microfuge tube with 250 $\mu$l of DMSO and macerated using a plastic pestle (Kontes, Vineland, N.J.). To aid in emulsification, the DMSO mixture is heated for 2–3 minutes at 37° C.–45° C. Some further maceration might be necessary following heating; however, all of the nitrocellulose should be emulsified. Once the AB78 sample is emulsified, it is placed on ice. In preparation for microtiter plate coating with the emulsified antigen, the sample must be diluted in borate buffered saline as follows: 1:5, 1:10, 1:15, 1:20, 1:30, 1:50, 1:100, and 0. The coating antigen must be prepared fresh immediately prior to use.

ELISA protocol:
1. Coat with AB78/DMSO in BBS. Incubate overnight at 4° C.
2. Wash plate 3× with 1× ELISA wash buffer.
3. Block (1% BSA & 0.05% Tween 20 in PBS) for 30 minutes at Room Temperature.
4. Wash plate 3× with 1× ELISA wash buffer.
5. Add rat serum. Incubate 1.5 hours at 37° C.
6. Wash plate 3× with 1× ELISA wash buffer.
7. Add goat anti-rat at a concentration of 2 $\mu$g/ml in ELISA diluent. Incubate 1 hr. at 37° C.
8. Wash plate 3× with 1× ELISA wash buffer.
9. Add rabbit anti-goat alkaline phosphatase at 2 $\mu$g/ml in ELISA diluent. Incubate 1 hr. at 37° C.
10. Wash 3× with 1× ELISA wash buffer.
11. Add Substrate. Incubate 30 minutes at room temperature.
12. Stop with 3N NaOH after 30 minutes.

Preparation of VIP2A(a) Antisera

A partially purified AB78 culture supernatant was separated by discontinuous SDS PAGE (Novex) following manufacturer's instructions. Separated proteins were electrophoresed to nitrocellulose (S&S #21640) as described by Towbin et al., (1979). The nitrocellulose was stained with Ponceau S and the VIP2A(a) band identified. The VIP2A(a) band was excised and emulsified in DMSO immediately prior to injection. A rabbit was initially immunized with emulsified VIP2A(a) mixed approximately 1:1 with Freund's Complete adjuvant by intramuscular injection at four different sites. Subsequent immunizations occurred at four week intervals and were identical to the first, except for the use of Freund' Incomplete adjuvant. The first serum harvested following immunization reacted with VIP2A(a) protein. Western blot analysis of AB78 culture supernatant using this antisera identifies predominately fall length VIP2A(a) protein.

EXAMPLE 13
ACTIVATION OF INSECTICIDAL ACTIVITY OF NON-ACTIVE BT STRAINS WITH AB78 VIP CLONES

Adding pCIB6203 together with a 24 h culture (early to mid-log phase) supernatant from Bt strain GC91 produces 100% mortality in Diabrotica virgifera virgifera. Neither pCIB6203 nor GC91 is active on Diabrotica virgifera virgifera by itself. Data are shown below:

| Test material | Percent Diabrotica mortality |
|---|---|
| pCIB6203 | 0 |
| GC91 | 16 |
| pCIB6203 + GC91 | 100 |
| Control | 0 |

EXAMPLE 14
ISOLATION AND BIOLOGICAL ACTIVITY OF B. CEREUS AB81

A second B. cereus strain, designated AB81, was isolated from grain bin dust samples by standard methodologies. A subculture of AB81 was grown and prepared for bioassay as described in Example 2. Biological activity was evaluated as described in Example 3. The results are as follows:

| Insect species tested | Percent Mortality |
|---|---|
| Ostrinia nubilalis | 0 |
| Agrotis ipsilon | 0 |
| Diabrotica virgifera virgifera | 55 |

EXAMPLE 15
ISOLATION AND BIOLOGICAL ACTIVITY OF B. THURINGIENSIS AB6

A B. thuringiensis strain, designated AB6, was isolated from grain bin dust samples by standard methods known in the art. A subculture of AB6 was grown and prepared for bioassay as described in Example 2. Half of the sample was autoclaved 15 minutes to test for the presence of β-exotoxin.

Biological activity was evaluated as described in Example 3. The results are as follows:

| Insect species tested | Percent Mortality |
|---|---|
| Ostrinia nubilalis | 0 |
| Agrotis ipsilon | 100 |
| Agrotis ipsilon (autoclaved sample) | 0 |
| Diabrotica virgifera virgifera | 0 |

The reduction of insecticidal acitivity of the culture supernatant to insignificant levels by autoclaving indicates that the active principle is not β-exotoxin.

Strain AB6 has been deposited in the Agricultural Research Service, Patent Culture Collection (NRRL), Northern Regional Research Center, 1815 North University Street, Peoria, Ill. 61604, USA, and given Accession No. NRRL B-21060.

EXAMPLE 16
ISOLATION AND BIOLOGICAL CHARACTERIZATION OF B. THURINGIENSIS AB88

A Bt strain, designated AB88, was isolated from grain bin dust samples by standard methodologies. A subculture of AB88 was grown and prepared for bioassay as described in Example 2. Half of the sample was autoclaved 15 minutes to test for the presence of β-exotoxin. Biological activity was evaluated against a number of insect species as described in Example 3. The results are as follows:

| Insect species tested | Order | Percent mortality of culture supernatant | |
|---|---|---|---|
| | | Non-autoclaved | Autoclaved |
| Agrotis ipsilon | Lepidoptera | 100 | 5 |
| Ostrinia nubilalis | Lepidoptera | 100 | 0 |
| Spodoptera frugiperda | Lepidoptera | 100 | 4 |
| Helicoverpa zea | Lepidoptera | 100 | 12 |
| Heliothis virescens | Lepidoptera | 100 | 12 |
| Leptinotarsa decemlineata | Coleoptera | 0 | 0 |
| Diabrotica virgifera virgifera | Coleoptera | 0 | 5 |

The reduction of insecticidal acitivity of the culture supernatant to insignificant levels by autoclaving indicates that the active principle is not β-exotoxin.

Delta-endotoxin crystals were purified from strain AB88 by standard methodologies. No activity from pure crystals was observed when bioassayed against Agrotis ipsilon.

EXAMPLE 17
PURIFICATION OF VIPS FROM STRAIN AB88

Bacterial liquid culture was grown overnight at 30° C. in TB media. Cells were spun out and the supernatant retained. Proteins were precipitated with ammonium sulfate (70% saturation), centrifuged and the pellet retained. The pellet was resuspended in the original volume of 20 mM Tris pH 7.5 and dialyzed against the same buffer. AB88 dialysate was more turbid than comparable material from AB78. AB88 proteins have been separated by several different methods following clarification including isoelectric focusing (Rotofor, BioRad, Hercules, Calif.), precipitation at pH 4.5, ion-exchange chromotography, size exclusion chromatography and ultrafiltration.

European corn borer (ECB)-active protein remained in the pellet obtained by pH 4.5 precipitation of dialysate. When preparative IEF was done on the dialysate using pH 3–10 ampholytes, ECB insecticidal activity was found in all fractions with pH of 7 or greater. SDS-PAGE analysis of these fractions showed protein bands of MW~60 kDa and ~80 kDa. The 60 kDa and 80 kDa bands were separated by anion exchange HPLC on a Poros-Q column (PerSeptive Biosystems, Cambridge, Mass.). N-terminal sequence was obtained from two fractions containing proteins of slightly differing MW, but both of approximately 60 kDa in size. The sequences obtained were similar to each other and to some δ-endotoxins. anion exchange fraction 23 (smaller) :xEPFVSAxxxQxxx (SEQ ID NO:10) anion exchange fraction 28 (larger):xEYENVEPFVSAx (SEQ ID NO:11)

When the ECB-active pH 4.5 pellet was further separated by anion exchange on a Poros-Q column, activity was found only in fractions containing a major band of ~60 kDa.

Black cutworm-active protein also remained in the pellet when AB88 dialysate was brought down to pH 4.5. In preparative IEF using pH 3–10 ampholytes, activity was not found in the ECB-active IEF fractions; instead, it was highest in a fraction of pH 4.5–5.0. Its major components have molecular weights of ~35 and ~80 kDa.

The pH 4.5 pellet was separated by anion exchange HPLC to yield fractions containing only the 35 kDa material and fractions containing both 35 kDa and 80 kDa bands.

EXAMPLE 18
CHARACTERIZATION OF AB88 VIP

Fractions containing the various lepidopteran active vegetative proteins were generated as described in Example 17. Biological analysis of fractions demonstrated that different VIPs were responsible for the different lepidopteran species activity.

The *Agrotis ipsilon* activity is due to an 80 kDa and/or a 35 kDa protein, either delivered singly or in combination. These proteins are not related to any δ-endotoxins from Bt as evidenced by the lack of sequence homology of known Bt δ-endotoxin sequences. Also, these proteins are not found in the AB88 δ-endotoxin crystal. N-terminal sequences of the major δ-endotoxin proteins were compared with the N-terminal sequences of the 80 kDa and 35 kDa VIP and revealed no sequence homology. A summary of the results follows:

| Agrotis VIP N-terminal sequences | N-terminal sequence of major δ-endotoxin proteins |
|---|---|
| | 130 kDa |
| | MDNNPNINE (SEQ ID NO:14) |
| 80 kDa | 80 kDa |
| MNKNNTKLPTRALP | MDNNPNINE (SEQ ID NO:15) |
| (SEQ ID NO:12) | |
| | 60 kDa |
| | MNVLNSGRTTI (SEQ ID NO:16) |
| 35 kDa | |
| ALSENTGKDGGYIVP | |
| (SEQ ID NO:13) | |

The *Ostrinia nubilalis* activity is due to a 60 kDa VIP and the *Spodoptera frugiperda* activity is due to a VIP of unknown size.

*Bacillus thuringiensis* strain AB88 has been deposited in the Agricultural Research Service, Patent Culture Collection (NRRL), Northern Regional Research Center, 1815 North University Street, Peoria, Ill. 61604, USA and given the Accession No. NRRL B-21225.

EXAMPLE 18A
ISOLATION AND BIOLOGICAL ACTIVITY OF *B. THURINGIENSIS* AB424

A *B. thuringiensis* strain, designated AB424, was isolated from a moss covered pine cone sample by standard methods known in the art. A subculture of AB424 was grown and prepared for bioassay as described in Example 2.

Biological activity was evaluated as described in Example 3. The results are as follows:

| Insect species tested | Percent mortality |
|---|---|
| *Ostrinia nubilalis* | 100 |
| *Agrotis ipsilon* | 100 |
| *Diabrotica virgifera virgifera* | 0 |

Strain AB424 has been deposited in the Agricultural Research Service, Patent Culture Collection (NRRL), Northern Regional Research Center, 1815 North University Street, Peoria, Ill. 61604, USA, and given Accession No. NRRL B-21439.

EXAMPLE 18B
CLONING OF THE VIP3A(*a*) and VIP3A(*b*) GENES WHICH ENCODE PROTEINS ACTIVE AGAINST BLACK CUTWORM DNA from isolates AB88 and AB424 was digested with the restriction enzymes XbaI and EcoRI respectively, ligated into pBluescript vector previously linearized with the same enzymes and dephosphorylated, and transformed into *E. coli* DH5α strain. Recombinant clones were blotted onto nitrocellulose filters which were subsequently probed with a 33-bases long oligonucleotide corresponding to the 11-N terminal amino acids of the 80 kDa protein active against *Agrotis ipsilon* (black cutworm). Four out of 400 recombinant clones were positive. Insect bioassays of the positive recombinants exhibited toxicity to black cutworm larvae comparable to that of AB88 or AB424 supernantants.

The nucleotide sequence of pCIB7104, a positive recombinant clone from AB88, and of pCIB7107, a positive recombinant clone from AB424, was determined by the dideoxy termination method of Sanger et al., *Proc. Natl. Acad. Sci.* USA, 74:5463–5467 (1977), using PRISM Ready Reaction Dye Deoxy Terminator Cycle Sequencing Kits and PRISM Sequenase® Terminator Double-Stranded DNA Sequencing Kit and analysed on an ABI 373 automatic sequencer.

The clone pCIB7104 contains the VIP3A(*a*) gene whose coding region is disclosed in SEQ ID NO:28 and the encoded protein sequence is disclosed in SEQ ID NO:29. A synthetic version of the coding region designed to be highly expressed in maize is given in SEQ ID NO:30. Any number of synthetic genes can be designed based on the amino acid sequence given in SEQ ID NO:29.

The clone pCIB7107 contains the VIP3A(*b*) gene whose coding region is disclosed in SEQ ID NO:31 and the encoded protein is disclosed in SEQ ID NO:32. Both pCIB7104 and pCIB7107 have been deposited with the Agricultural Research Service Patent Culture Collection (NRRL) and given Accession Nos. NRRL B-21422 and B-21423, respectively.

EXAMPLE 18C
IDENTIFICATION OF NOVEL VIP3-LIKE GENES BY HYBRIDIZATION

To identify Bacillus containing genes related to the VIP3A(*a*) from isolate AB88, a collection of Bacillus isolates was screened by hybridization. Cultures of 463 Bacillus strains were grown in microtiter wells until sporulation. A 96-pin colony stampel was used to transfer the cultures to 150 mm plates containing L-agar. Inoculated plates were kept at 30° C. for 10 hours, then at 4° C. overnight. Colonies were blotted onto nylon filters and probed with a 1.2 Kb HindIII VIP3A(*a*) derived fragment. Hybridization was performed overnight at 62° C. using hybridization conditions of Maniatis et al *Molecular Cloning: A Laboratory Manual* (1982). Filters were washed with 2×SSC/0.1% SDS at 62° C. and exposed to X-ray film.

Of the 463 Bacillus strains screened, 60 contain VIP3-like genes that could detected by hybridization.

EXAMPLE 18D
CHARACTERIZATION OF A *B. thuringiensis* STRAIN M2194 CONTAINING A CRYPTIC VIP3-LIKE GENE A *B. thuringiensis* strain, designated M2194, was shown to contain VIP3-like gene(s) by colony hybridization as described in Example 18C. The M2194 VIP3 like gene is considered cryptic since no expression can be detected throughout the bacterial growth phases either by immunoblot analysis using polyclonal antibodies raised against the VIP3A(a) protein isolated from AB88 or by bioassay as described in Example 3.

The M2194 VIP3-like gene was cloned into pKS by following the protocol described in Example 9, which created pCIB7108. *E. coli* containing pCIB7108 which comprises the M2194 VIP3 gene were active against black cutworm demonstrating that the gene encodes a functional protein with insecticidal activity. The plasmid pCIB7108 has been deposited with the Agricultural Research Service Patent Culture Collection (NRRL) and given Accession No. NRRL B-21438.

EXAMPLE 19
ISOLATION AND BIOLOGICAL ACTIVITY OF OTHER *BACILLUS SP.*

Other Bacillus species have been isolated which produce proteins with insecticidal activity during vegetative growth. These strains were isolated from environmental samples by standard methodologies. Isolates were prepared for bioassay and assayed as described in Examples 2 and 3 respectively. Isolates which produced insecticidal proteins during vegetative growth with activity against *Agrotis epsilon* in the bioassay are tabulated below. No correlation was observed between the presence of a δ-endotoxin crystal and vegetative insecticidal protein production.

| Bacillus isolate | Presence of δ-endotoxin crystal | Percent mortality |
| --- | --- | --- |
| AB6 | + | 100 |
| AB53 | − | 80 |
| AB88 | + | 100 |
| AB195 | − | 60 |
| AB211 | − | 70 |
| AB217 | − | 83 |
| AB272 | − | 80 |
| AB279 | − | 70 |
| AB289 | + | 100 |
| AB292 | + | 80 |
| AB294 | − | 100 |
| AB300 | − | 80 |
| AB359 | − | 100 |

Isolates AB289, AB294 and AB359 have been deposited in the Agricultural Research Service, Patent Culture Collection (NRRL), Northern Regional Research Center, 1815 North University Street, Peoria Ill. 61604, USA and given the Accession Numbers NRRL B-21227, NRRL B-21229, and NRRL B-21226 respectively.

Bacillus isolates which produce insecticidal proteins during vegetative growth with activity against *Diabrotica virgifera virgifera* are tabulated below.

| Bacillus isolate | Presence of δ-endotoxin crystal | Percent mortality |
| --- | --- | --- |
| AB52 | − | 50 |
| AB59 | − | 71 |
| AB68 | + | 60 |
| AB78 | − | 100 |
| AB122 | − | 57 |
| AB218 | − | 64 |
| AB256 | − | 64 |

Isolates AB59 and AB256 have been deposited in the Agricultural Research Service, Patent Culture Collection (NRRL), Northern Regional Research Center, 1815 North University Street, Peoria Ill. 61604, USA, and given the Accession Numbers NRRL B-21228 and NRRL B-21230, respectively.

EXAMPLE 20
IDENTIFICATION OF NOVEL VIP1/VIP2 LIKE GENES BY HYBRIDIZATION

To identify strains containing genes related to those found in the VIP1A(a)/VIP2A(a) region of AB78, a collection of Bacillus strains was screened by hybridization. Independent cultures of 463 Bacillus strains were grown in wells of 96 well microtiter dishes (five plates total) until the cultures sporulated. Of the strains tested, 288 were categorized as *Bacillus thuringiensis*, and 175 were categorized as other Bacillus species based on the presence or absence of δ-endotoxin crystals. For each microtiter dish, a 96-pin colony stamper was used to transfer approximately 10 μl of spore culture to two 150 mm plates containing L-agar. Inoculated plates were grown 4–8 hours at 30° C., then chilled to 4° C. Colonies were transferred to nylon filters, and the cells lysed by standard methods known in the art. The filters were hybridized to a DNA probe generated from DNA fragments containing both VIP1A(a) and VIP2A(a) DNA sequences. Hybridization was performed overnight at 65° C. using the hybridization conditions of Church and Gilbert (Church, G. M., and W. Gilbert, PNAS, 81:1991–1995 (1984)). Filters were washed with 2×SSC containing 0.1% SDS at 65° C. and exposed to X-Ray film.

Of the 463 Bacillus strains screened, 55 strains were identified that hybridized to the VIP1A(a)/VIP2A(a) probe. DNA was isolated from 22 of these strains, and analyzed using a Southern blot with VIP1A(a)/VIP2A(a) DNA as probes. These strains were grouped into 8 classes based on their Southern blot pattern. Each class differed in Southern blot pattern from AB78. One class had a pattern identical to that of the VIP1A(a)/VIP2A(a) homologs from *Bacillus thuringiensis* var tenebrionis (see below). Each of the 22 strains was tested for activity against western corn rootworm (WCRW). Three strains, AB433, AB434, and AB435 were found to be active on WCRW. Western blot analysis using VIP2A(a) antisera revealed that strains AB6, AB433, AB434, AB435, AB444, and AB445 produce a protein(s) of equivalent size to VIP2A(a).

Notable among the strains identified was *Bacillus thuringiensis* strain AB6, (NRRL B-21060) which produced a VIP active against black cutworm (*Agrotis ipsilon*) as described in Example 15. Western blot analysis with polyclonal antisera to VIP2A(a) and polyclonal antisera to VIP1A(a) suggests that AB6 produces proteins similar to VIP2A(a) and VIP1A(a). Thus, AB6 may contain VIPs similar to VIP1A(a) and VIP2A(a), but with a different spectrum of insecticidal activity.

EXAMPLE 21
CLONING OF A VIP1A(a)/VIP2A(a) HOMOLOG FROM *BACILLUS THURINGIENSIS* VAR. TENEBRIONIS

Several previously characterized Bacillus strains were tested for presence of DNA similar to VIP1A(a)/VIP2A(a) by Southern blot analysis. DNA from Bacillus strains AB78, AB88, GC91, HD-1 and ATCC 10876 was analyzed for presence of VIP1A(a)/VIP2A(a) like sequences. DNA from Bt strains GC91 and HD-1, and the Bc strain ATCC 10876 did not hybridize to VIP2A(a)/VIP1A(a) DNA, indicating they lack DNA sequences similar to VIP1A(a)/VIP2A(a) genes. Similarly, DNA from the insecticidal strain AB88 (Example 16) did not hybridize to VIP1A(a)/VIP2A(a) DNA region, suggesting that the VIP activity produced by this strain does not result from VIP1A(a)/VIP2A(a)

homologs. In contrast, *Bacillus thuringiensis* var. tenebrionis (Btt) contained sequences that hybridized to the VIP1A(a)/VIP2A(a) region. Further analysis confirmed that Btt contains VIP1A(a)/VIP2A(a) like sequences.

To characterize the Btt homologs of VIP2A(a) and VIP1A(a), the genes encoding these proteins were cloned. Southern blot analysis identified a 9.5 kb Eco RI restriction fragment likely to contain the coding regions for the homologs. Genomic DNA was digested with Eco RI, and DNA fragments of approximately 9.5 kb in length were gel-purified. This DNA was ligated into pBluescript SK(+) digested with Eco RI, and transformed into *E. coli* to generate a plasmid library. Approximately 10,000 colonies were screened by colony hybridization for the presence of VIP2A(a) homologous sequences. Twenty eight positive colonies were identified. All twenty eight clones are identical, and contain VIP1A(a)/VIP2A(a) homologs. Clone pCIB7100 has been deposited in the Agricultural Research Service, Patent Culture Collection (NRRL), Northern Regional Research Center, 1815 North University Street, Peoria Ill. 61604, USA, and given the Accession Number B-21322. Several subclones were constructed from pCIB7100. A 3.8 kb Xba I fragment from pCIB7100 was cloned into pBluescript SK(+) to yield pCIB7101. A 1.8 kb Hind III fragment and a 1.4 kb Hind III fragment from pCIB7100 were cloned into pBluescript SK(+) to yield pCIB7102 and pCIB7103, respectively. Subclones pCIB7101, pCIB7102 and pCIB7103 have been deposited in the Agricultural Research Service, Patent Culture Collection (NRRL), Northern Regional Research Center, 1815 North University Street, Peoria Ill. 61604, USA, and given the Accession Numbers B-21323, B-21324 and B-21325 respectively.

The DNA sequence of the region of pCIB7100 containing the VIP2A(a)/VIP1A(a) homologs was determined by the dideoxy chain termination method (Sanger et al., 1977, *Proc. Natl. Acad. Sci.* USA 74:5463–5467). Reactions were performed using PRISM Ready Reaction Dye Deoxy Terminator Cycle Sequencing Kits and PRISM Sequenase® Terminator Double-Stranded DNA Sequencing Kits, and analyzed on an ABI model 373 automated sequencer. Custom oligonucleotides were used as primers to determine the DNA sequence in certain regions. The DNA sequence of this region is shown in SEQ ID NO:19.

The 4 kb region shown in SEQ ID NO:19 contains two open readings frames (ORFs), which encode proteins with a high degree of similarity to VIP1A(a) and VIP2A(a) proteins from strain AB78. The amino acid sequence of the VIP2A(a) homolog, designated as VIP2A(b) using the standardized nomenclature, is found at SEQ ID NO:20 and the amino acid sequence of the VIP1A(a) homolog, designated as VIP1A(b) using the standardized nomenclature, is disclosed at SEQ ID NO:21. The VIP2A(b) protein exhibits 91% amino acid identity to VIP2A(a) from AB78. An alignment of the amino acid sequences of the two VIP2 proteins is provided in Table 19. The VIP1A(b) protein exhibits 77% amino acid identity to VIP1A(a) from AB78. An alignment of these two VIP1 proteins is provided in Table 21. The alignment shown in Table 20 discloses the similarity between VIP1A(b) and VIP1A(a) from AB78. This alignment reveals that the amino terminal regions of the two VIP1 proteins share higher amino acid identity in the amino-terminal region than in the carboxy terminal region. In fact, the amino terminal two thirds (up to aa 618 of the VIP1A(b) sequence shown in Table 20) of the two proteins exhibit 91% identity, while the carboxy-terminal third (from aa 619-833 of VIP1A(b)) exhibit only 35% identity.

Western blot analysis indicated that *Bacillus thuringiensis* var. tenebrionis (Btt) produces both VIP1A(a) like and VIP2A(a) like proteins. However, these proteins do not appear to have activity against western corn rootworm. Bioassay for activity against western corn rootworm was performed using either a 24 h culture supernatant from Btt or *E. coli* clone pCIB7100 (which contains the entire region of the VIP1A(a)/VIP2A(a) homologs). No activity against western corn rootworm was detected in either case.

Given the similarity between the VIP2 proteins from Btt and AB78, the ability of VIP2A(b) from Btt to substitute for VIP2A(a) from AB78 was tested. Cells containing pCIB6206 (which produces AB78 VIP1A(a) but not VIP2A(a) protein) were mixed with Btt culture supernatant, and tested for activity against western corn rootworm. While neither Btt culture supernatant nor cells containing pCIB6206 had activity on WCRW, the mixture of Btt and pCIB6206 gave high activity against WCRW. Furthermore, additional bioassay showed that the Btt clone pCIB7100, which contains the Btt VIP1A(b)/VIP2A(b) genes in *E. coli*, also confers activity against WCRW when mixed with pCIB6206. Thus, the VIP2A(b) protein produced by Btt is functionally equivalent to the VIP2A(a) protein produced by AB78.

Thus, the ability to identify new strains with insecticidal activity by using VIP DNA as hybridization probes has been demonstrated. Furthermore, Bacillus strains that contain VIP1A(a)/VIP2A(a) like sequences, produce VIP1A(a)/VIP2A(a) like protein, yet demonstrate toxicity toward different insect pests. Similar methods can identify many more members of the VIP1/VIP2 family. Furthermore, use of similar methods can identify homologs of other varieties of VIPs (for example, the VIPs from AB88).

TABLE 19

Alignment of VIP2 Amino Acid Sequences from *Bacillus thuringiensis* var. *tenebrionis*
(VIP2A(b)) vs. AB78 (VIP2A(a))

```
Btt    1 MQMEGKLFV VSKT LQVVTR TVLLSTV YSI T LLNN VVIKA DQ LNINSQSK    50 SEQ ID NO:20
         | . | | | | | | | : | | | . | | | | | : | | | | | | | : | | . | | | |   | | | | : | | | | | | | | |
AB78   1 MKMEGKLFM VSKKLQVVTK TVLLSTVFSISLLNNEVIKAEQLNINSQSK        50 SEQ ID NO:2

51 YTNLQNLKIP DNA EDFKEDKGKAKEWGKEKGE EWRPPATEKGE MNNFLDN 100
         | | | | | | | | | . | . . | | | | | | | | : | | | | | | | | | : . | |  :   . | | | | | . | | | | | | |
      51 YTNLQNLKITDKVEDFKEDKEKAKEWGKEKEKEWKLTATEKGKMNNFLDN 100
```

TABLE 19-continued

Alignment of VIP2 Amino Acid Sequences from *Bacillus thuringiensis* var. *tenebrionis*
(VIP2A(b)) vs. AB78 (VIP2A(a))

```
101 KNDIKTNYKEITFSMAGSCEDEIKDLEEIDKI FDKANLSS SIITYKNVEP       150
    ||||:||||||||||||| ||| ||||||||.||||:|||.|||.||||||||
101 KNDIXTNYKEITFSMAGSFEDEIKDLKEIDKMFDKTNLSNSIITYKNVEP        150

151 ATIGFNKSLTEGNTINSDAMAQFKEQFLGKDMKFDSYLDTHLTAQQVSSK         200
    .||||||||||||||||||||||||||||::|:||||||||||||||||||
151 TTIGFNKSLTEGNTINSDAMAQFKEQFLDRDI KFDSYLDTHLTAQQVSSK        200

201 KRVILKVTVPSGKGSTTPTKAGVILNNNEYKMLIDNGYV LHVDKVSKVVK         250
    .|||||||||||||||||||||||||||.|||||||||:::|||||||||
201 ERVILKVTVPSGKGSTTPTKAGVILNNSEYKMLIDNGYMVHVDKVSKVVK         250

251 KGMECLQVEGTLLKKSLDFKNDINAEAHSWGMKI YEDWAKNLTASQREALD        300
    ||:||||:|||||||||||||||||||||||||| ||:|||:||.||||||
251 KGVECLQIEGTLLKKSLDFKNDINAEAHSWGMKNYEEWAKDLTDSQREALD        300

301 GYARQDYKEINNYLRNQGGSGNEKLDAQIKNISDALGKKPIPENITVYRW         350
    ||||||||||||||||||||||||||||| :|||||||||||||||||||
301 GYARQDYKEINNYLRNQGGSGNEKLDAQIKNISDALGKKPIPENITVYRW         350

351 CGMPEFGYQISDPLPSLKDFEEQFLNTIKEDKGYMSTSLSSERLAAFGSR         400
    ||||||||||||||||||||||||||||||||||||||||||||||||||
351 CGMPEFGYQISDPLPSLKDFEEQFLNTIKEDKGYMSTSLSSERLAAFGSR         400

401 KIILRLQVPKGSTGAYLSAIGGFASEKEILLDKDSKYHIDKATEVIIKGV         450
    ||||||||||||||||||||||||||||||||||||||||||.||||||||
401 KIILRLQVPKGSTGAYLSAIGGFASEKEILLDKDSKYHIDKVTEVIIKGV         450
451 KRYVVDATLLTN
    ||||||||||||                                              462
451 KRYVVDATLLTN                                              462
```

TABLE 20

Alignment of VIP1 Amino Acid Sequences from *Bacillus thuringiensis* var. *tenebrionis*
(VIP1A(b)) vs. AB78 (VIP1A(a))

```
Btt   1 MQMEGKLFV VSKTLQVVTRTVLLSTVYSITLLNNVVIKADQLNINSQSK        50 SEQ ID NO:20
        |.||||||:|||.|||||:|||||||:||.||||  ||||:|||||||||
Ab78  1 MKMEGKLFMVSKKLQVVTKTVLLSTVFSISLLNNEVIKAEQLNINSQSK         50 SEQ ID NO:2

51 YTNLQNLKIPDNAEDFKEDKGKAKEWGKEKGEEWRPPATEKGEMNNFLDN        100
        ||||||||.|..||||||||:|||||||:||||||||:.||:.|||||.||||||
     51 YTNLQNLKITDKVEDFKEDKEKAKEWGKEKEKEWKLTATEKGKMNNFLDN        100

101 KNDIKTNYKEITFSMAGSCEDEIKDLEEIDKI FDKANLSS SIITYKNVEP       150
        ||||:||||||||||||| ||| ||||||||.||||:|||.|||.||||||||
    101 KNDIXTNYKEITFSMAGSFEDEIKDLKEIDKMFDKTNLSNSIITYKNVEP        150

151 ATIGFNKSLTEGNTINSDAMAQFKEQFLGKDMKFDSYLDTHLTAQQVSSK        200
        .||||||||||||||||||||||||||||::|:||||||||||||||||||
    151 TTIGFNKSLTEGNTINSDAMAQFKEQFLDRDI KFDSYLDTHLTAQQVSSK       200

201 KRVILKVTVPSGKGSTTPTKAGVILNNNEYKMLIDNGYV LHVDKVSKVVK        250
        .|||||||||||||||||||||||||||.|||||||||:::|||||||||
    201 ERVILKVTVPSGKGSTTPTKAGVILNNSEYKMLIDNGYMVHVDKVSKVVK        250

251 KGMECLQVEGTLLKKSLDFKNDINAEAHSWGMKI YEDWAKNLTASQREALD       300
        ||:||||:|||||||||||||||||||||||||| ||:|||:||.||||||
    251 KGVECLQIEGTLLKKSLDFKNDINAEAHSWGMKNYEEWAKDLTDSQREALD       300

301 GYARQDYKEINNYLRNQGGSGNEKLDAQIKNISDALGKKPIPENITVYRW        350
        ||||||||||||||||||||||||||||| :|||||||||||||||||||
    301 GYARQDYKEINNYLRNQGGSGNEKLDAQIKNISDALGKKPIPENITVYRW        350

351 CGMPEFGYQISDPLPSLKDFEEQFLNTIKEDKGYMSTSLSSERLAAFGSR        400
        ||||||||||||||||||||||||||||||||||||||||||||||||||
    351 CGMPEFGYQISDPLPSLKDFEEQFLNTIKEDKGYMSTSLSSERLAAFGSR        400

401 KIILRLQVPKGSTGAYLSAIGGFASEKEILLDKDSKYHIDKATEVIIKGV        450
        ||||||||||||||||||||||||||||||||||||||||||.|||||||
    401 KIILRLQVPKGSTGAYLSAIGGFASEKEILLDKDSKYHIDKVTEVIIKGV        450
    451 KRYVVDATLLTN
        ||||||||||||                                              462
    451 KRYVVDATLLTN                                              462
```

EXAMPLE 22
FUSION OF VIP PROTEINS TO MAKE A SINGLE POLYPEPTIDE

VIP proteins may occur in nature as single polypeptides, or as two or more interacting polypeptides. When an active VIP is comprised of two or more interacting protein chains, these protein chains can be produced as a single polypeptide chain from a gene resulting from the fusion of the two (or more) VIP coding regions. The genes encoding the two chains are fused by merging the coding regions of the genes to produce a single open reading frame encoding both VIP polypeptides. The composite polypeptides can be fused to produce the smaller polypeptide as the $NH_2$ terminus of the fusion protein, or they can be fused to produce the larger of the polypeptides as the $NH_2$ terminus of the fusion protein. A linker region can optionally be used between the two polypeptide domains. Such linkers are known in the art. This linker can optionally be designed to contain protease cleavage sites such that once the single fused polypeptide is ingested by the target insect it is cleaved in the linker region to liberate the two polypeptide components of the active VIP molecule.

VIP1A(*a*) and VIP2A(*a*) from *B. cereus* strain AB78 are fused to make a single polypeptide by fusing their coding regions. The resulting DNA has the sequence given in SEQ ID NO:22 with the encoded protein given in SEQ ID NO:23. In like manner, other fusion proteins may be produced.

The fusion of the genes encoding VIP1A(*a*) and VIP2A(*a*) is accomplished using standard techniques of molecular biology. The nucleotides deleted between the VIP1A(*a*) and VIP2A(*a*) coding regions are deleted using known mutagenesis techniques or, alternatively, the coding regions are fused using PCR techniques.

The fused VIP polypeptides can be expressed in other organisms using a synthetic gene, or partially synthetic gene, optimized for expression in the alternative host. For instance, to express the fused VIP polypeptide from above in maize, one makes a synthetic gene using the maize preferred codons for each amino acid, see for example patent application U.S. Pat. No. 5,625,136 herein incorporated by reference. Synthetic DNA sequences created according to these methods are disclosed in SEQ ID NO:17 (maize optimized version of the 100 kDa VIP1A(*a*) coding sequence), SEQ ID NO:18 (maize optimized version of the 80 kDa VIP1A(*a*) coding sequence) and SEQ ID NO:24 (maize optimized version of the VIP2A(*a*) coding sequence).

Synthetic VIP1 and VIP2 genes optimized for expression in maize can be fused using PCR techniques, or the synthetic genes can be designed to be fused at a common restriction site. Alternatively, the synthetic fusion gene can be designed to encode a single polypeptide comprised of both VIP1 and VIP2 domains.

Addition of a peptide linker between the VIP1 and VIP2 domains of the fusion protein can be accomplished by PCR mutagenesis, use of a synthetic DNA linker encoding the linker peptide, or other methods known in the art.

The fused VIP polypeptides can be comprised of one or more binding domains. If more than one binding domain is used in the fusion, multiple target pests are controlled using such a fusion. The other binding domains can be obtained by using all or part of other VIPs; *Bacillus thuringiensis* endotoxins, or parts thereof; or other proteins capable of binding to the target pest or appropriate biding domains derived from such binding proteins.

One example of a fusion construction comprising a maize optimized DNA sequence encoding a single polypeptide chain fusion having VIP2A(*a*) at the N-terminal end and VIP1A(*a*) at the C-terminal end is provided by pCIB553 1. A DNA sequence encoding a linker with the peptide sequence PSTPPTPSPSTPPTPS (SEQ ID NO:47) has been inserted between the two coding regions. The sequence encoding this linker and relevant cloning sites is 5'-CCC GGG CCT TCT ACT CCC CCA ACT CCC TCT CCT AGC ACG CCT CCG ACA CCT AGC GAT ATC GGA TCC-3' (SEQ ID NO:48). Oligonucleotides were synthesized to represent both the upper and lower strands and cloned into a pUC vector following hybridization and phosphorylation using standard procedures. The stop codon in VIP2A(*a*) was removed using PCR and replaced by the BglII restriction site with a SmaI site. A translation fusion was made by ligating the Bam HI/PstI fragment of the VIP2A(*a*) gene from pCIB5522 (see Example 24), a PCR fragment containing the PstI-end fragment of the VIP2A(*a*) gene (identical to that used to construct pCIB5522), a synthetic linker having ends that would ligate with a blunt site at the 5' end and with BamHI at the 3' end and the modified synthetic VIP1A(*a*) gene from pCIB5526 described below (See SEQ ID NO:35). The fusion was obtained by a four way ligation that resulted in a plasmid containing the VIP2A(*a*) gene without a translation stop codon, with a linker and the VIP1A(*a*) coding region without the Bacillus secretion signal. The DNA sequence for this construction is disclosed in SEQ ID NO:49, which encodes the fusion protein disclosed in SEQ ID NO:50. A single polypeptide fusion where VIP1A(*a*) is at the N-terminal end and VIP2A(*a*) is at the C-terminal end can be made in a similar fashion. Furthermore, either one or both genes can be linked in a translation fusion with or without a linker at either the 5' or the 3' end to other molecules like toxin encoding genes or reporter genes.

EXAMPLE 23
TARGETING OF VIP2 TO PLANT ORGANELLES

Various mechanisms for targeting gene products are known to exist in plants and the sequences controlling the functioning of these mechanisms have been characterized in some detail. For example, the targeting of gene products to the chloroplast is controlled by a signal sequence found at the amino-terminal end of various proteins. This signal is cleaved during chloroplast import, yielding the mature protein (e.g. Comai et al. J. Biol. Chem. 263:15104–15109 (1988)). These signal sequences can be fused to heterologous gene products such as VIP2 to effect the import of those products into the chloroplast (van den Broeck et al. Nature 313:358–363 (1985)). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized.

Other gene products are localized to other organelles such as the mitochondrion and the peroxisome (e.g. Unger et al. Plant Molec. Biol. 13:411–418 (1989)). The cDNAs encoding these products can also be manipulated to effect the targeting of heterologous gene products such as VIP2 to these organelles. Examples of such sequences are the nuclear-encoded ATPases and specific aspartate amino transferase isoforms for mitochondria. Similarly, targeting to cellular protein bodies has been described by Rogers et al. (Proc. Natl. Acad Sci. USA 82:6512–6516 (1985)).

By the fusion of the appropriate targeting sequences described above to coding sequences of interest such as VIP2 it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the amino-terminal ATG of the transgene. The signal sequence selected should include the known cleavage site and the fusion constructed should take into account any amino acids after the cleavage site which are required for cleavage. In some cases this requirement may be fulfilled by the addition of a small number of amino acids between the cleavage site and the start codon ATG, or alternatively replacement of some amino acids within the coding sequence. Fusions constructed for chloroplast import can be tested for efficacy of chloroplast uptake by in vitro translation of in vitro transcribed constructions followed by in vitro chloroplast uptake using techniques described by (Bartlett et al. In: Edelmann et al. (Eds.) Methods in Chloroplast Molecular Biology, Elsevier. pp 1081–1091 (1982); Wasmann et al. Mol. Gen. Genet. 205:446–453 (1986)). These construction techniques are well known in the art and are equally applicable to mitochondria and peroxisomes.

The above described mechanisms for cellular targeting can be utilized not only in conjunction with their cognate promoters, but also in conjunction with heterologous promoters so as to effect a specific cell targeting goal under the transcriptional regulation of a promoter which has an expression pattern different to that of the promoter from which the targeting signal derives.

A DNA sequence encoding a secretion signal is present in the native Bacillus VIP2 gene. This signal is not present in the mature protein which has the N-terminal sequence of LKITDKVEDF (amino acid residues 57 to 66 of SEQ ID NO:2). It is possible to engineer VIP2 to be secreted out of the plant cell or to be targeted to subcellular organelles such as the endoplasmic reticulum, vacuole, mitochondria or plastids including chloroplasts. Hybrid proteins made by fusion of a secretion signal peptide to a marker gene have been successfully targeted into the secretion pathway. (Itirriaga G. et al., *The Plant Cell*, 1:381–390 (1989), Denecke et al., *The Plant Cell*, 2:51–59 (1990). Amino-terminal sequences have been identified that are responsible for targeting to the ER, the apoplast, and extracellular secretion from aleurone cells (Koehler & Ho, Plant Cell 2:769–783 (1990)).

The presence of additional signals are required for the protein to be retained in the endoplasmic reticulum or the vacuole. The peptide sequence KDEL/HDEL (SEQ ID NOs:51 and 52) at the carboxy-terminal of a protein is required for its retention in the endoplasmic reticulum (reviewed by Pelham, *Annual Review Cell Biol.*, 5:1–23 (1989). The signals for retention of proteins in the vacuole have also been characterized. Vacuolar targeting signals may be present either at the amino-terminal portion, (Holwerda et al., *The Plant Cell*, 4:307–318 (1992), Nakamura et al., *Plant Physiol.*, 101:1–5 (1993)), carboxy-terminal portion, or in the internal sequence of the targeted protein. (Tague et al., *The Plant Cell*, 4:307–318 (1992), Saalbach et al., *The Plant Cell*, 3:695–708 (1991)). Additionally, amino-terminal sequences in conjunction with carboxy-terminal sequences are responsible for vacuolar targeting of gene products (Shinshi et al. Plant Molec. Biol. 14:357–368 (1990)). Similarly, proteins may be targeted to the mitochondria or plastids using specific carboxy terminal signal peptide fusions (Heijne et al., *Eur. J. Biochem.*, 180:535–545 (1989), Archer and Keegstra, *Plant Molecular Biology*, 23:1105–1115 (1993)).

In order to target VIP2, either for secretion or to the various subcellular organelles, a maize optimized DNA sequence encoding a known signal peptide(s) may be designed to be at the 5' or the 3' end of the gene as required. To secrete VIP2 out of the cell, a DNA sequence encoding the eukaryotic secretion signal peptide MGWSWIFLFLLS-GAAGVHCL (SEQ ID NO:25) from U.S. patent application Ser. No. 08/267,641 or any other described in the literature (Itirriaga et al., *The Plant Cell*, 1:381–390 (1989), Denecke, et al., *The Plant Cell*, 2:51–59 (1990)) may be added to the 5' end of either the complete VIP2 gene sequence or to the sequence truncated to encode the mature protein or the gene truncated to nucleotide 286 or encoding a protein to start at amino acid residue 94 (methionine). To target VIP2 to be retained in the endoplasmic reticulum, a DNA sequence encoding the ER signal peptide KDEL/HDEL (SEQ ID NOs:51 and 52) in addition to the secretion signal, can be added to the 3' end of the gene. For vacuolar targeting a DNA sequence encoding the signal peptide SSSSFADSN-PIRVTDRAAST (SEQ ID NO:3; Holwerda et al., *The Plant Cell*, 4:307–318 (1992)) can be designed to be adjacent to the secretion signal or a sequence encoding a carboxyl signal peptide as described by Dombrowski et al., *The Plant Cell*, 5:587–596 (1993) or a functional variation may be inserted at the 3' end of the gene. Similarly, VIP2 can be designed to be targeted to either the mitochondria or the plastids, including the chloroplasts, by inserting sequences in the VIP2 sequence described that would encode the required targeting signals. The bacterial secretion signal present in VIP2 may be retained or removed from the final construction.

One example of a construction which incorporates a eukaryotic secretion signal fused to a coding sequence for a VIP is provided by pCIB5528. Oligonucleotides corresponding to both the upper and lower strand of sequences encoding the secretion signal peptide of SEQ ID NO:25 was synthesized and has the sequence 5'-GGATCCACC ATG GGC TGG AGC TGG ATC TTC CTG TTC CTG CTG AGC GGC GCC GCG GGC GTG CAC TGC CTGCAG-3' (SEQ ID NO:41). When hybridized, the 5' end of the secretion signal resembled "sticky-ends" corresponding to restriction sites BamHI and PstI. The oligonucleotide was hybridized and phosphorylated and ligated into pCIB5527 (construction described in Example 23A) which had been digested with BamHI/PstI using standard procedures. The resulting maize optimized coding sequence is disclosed in SEQ ID NO:42 which encodes the protein disclosed in SEQ ID NO:43. This encoded protein comprises the eukaryotic secretion signal in place of the Bacillus secretion signal.

One example of a construction which incorporates a vacuolar targetting signal fused to a coding sequence for a VIP is provided by pCIB5533. Oligonucleotides corresponding to both the upper and lower strand of sequences encoding the vacuolar targetting peptide of SEQ ID NO:3 was synthesized and has the sequence 5'-CCG CGG GCG TGC ACT GCC TCA GCA GCA GCA GCT TCG CCG ACA GCA ACC CCA TCC GCG TGA CCG ACC GCG CCG CCA GCA CCC TGC AG-3' (SEQ ID NO:44). When hybridized, the 5' end of the vacuolar targetting signal resembled "sticky-ends" corresponding to restriction sites SacII and PstI. The oligonucleotide was hybridized and phosphorylated and ligated into pCIB5528 (construction described above) which had been digested with SacII/PstI using standard procedures. The resulting maize optimized coding sequence is disclosed in SEQ ID NO:45 which encodes the protein disclosed in SEQ ID NO:46. This encoded protein comprises the vacuolar targetting peptide in addition to the eukaryotic secretion signal.

The VIP1 gene can also be designed to be secreted or targeted to subcellular organelles by similar procedures.

EXAMPLE 23A
REMOVAL OF BACILLUS SECRETION SIGNAL FROM VIP1A(a) AND VIP2A(a)

VIP1A(a) and VIP2A(a) are secreted during the growth of strain AB78. The nature of peptide sequences that act as secretion signals has been described in the literature (Simonen and Palva, Microbiological reviews, pg. 109–137 (1993)). Following the information in the above publication, the putative secretion signal was identified in both genes. In VIP1A(a) this signal is composed of amino acids 1–33 (See SEQ ID NO:5). Processing of the secretion signal probably occurs after the serine at amino acid 33. The secretion signal in VIP2A(a) was identified as amino acids 1–49 (See SEQ ID NO:2). N-terminal peptide analysis of the secreted mature VIP2A(a) protein revealed the N-terminal sequence LKITDKVEDFKEDK. This sequence is found beginning at amino acid 57 in SEQ ID NO:2. The genes encoding these proteins have been modified by removal of the Bacillus secretion signals.

A maize optimized VIP1A(a) coding region was constructed which had the sequences encoding the first 33 amino acids, i.e., the secretion signal, removed from its 5' end. This modification was obtained by PCR using an forward primer that contained the sequence 5'-GGA TCC ACC ATG AAG ACC AAC CAG ATC AGC-3' (SEQ ID NO:33), which hybridizes with the maize optimized gene (SEQ ID NO:26) at nucleotide position 100, and added a BamHI restriction site and a eukaryotic translation start site consensus including a start codon. The reverse primer that contained the sequence 5'-AAG CTT CAG CTC CTT G-3' (SEQ ID NO:34) hybridizes on the complementary strand at nucleotide position 507. A 527 bp amplification product was obtained containing the restriction sites BamHI at the 5' end and HindIII site at the 3' end. The amplification product was cloned into a T-vector (described in Example 24, below) and sequenced to ensure the correct DNA sequence. The BamHI/HindIII fragment was then obtained by restriction digest and used to replace the BamHI/HindIII fragment of the maize optimized VIP1A(a) gene cloned in the root-preferred promoter cassette. The construct obtained was designated pCIB5526. The maize optimized coding region for VIP1A (a) with the Bacillus secretion signal removed is disclosed as SEQ ID NO:35 and the encoded protein is disclosed as SEQ ID NO:36.

The gene encoding the processed form of VIP2A(a), i.e., a coding region with the secretion signal removed, was constructed by a procedure similar to that described for that used to construct the processed form of VIP1A(a), above. The modification was obtained by PCR using the forward primer 5'-GGA TCC ACC ATG CTG CAG AAC CTG AAG ATC AC-3' (SEQ ID NO:37). This primer hybridizes at nucleotide position 150 of the maize optimized VIP2A(a) gene (SEQ ID NO:27). A silent mutation has been inserted at nucleotide position 15 of this primer to obtain a PstI restriction site. The reverse primer has the sequence 5'-AAG CTT CCA CTC CTT CTC-3' (SEQ ID NO:38). A 259 bp product was obtained with HindIII restriction site at the 3' end. The amplification product was cloned into a T-vector, sequenced and ligated to a BamHI/HindIII digested root-preferred promoter cassette containing the maize optimized VIP2A(a). The construct obtained was designated pCIB5527. The maize optimized coding region for VIP2A (a) with the Bacillus secretion signal removed is disclosed as SEQ ID NO:39 and the encoded protein is disclosed as SEQ ID NO:40.

EXAMPLE 24
CONSTRUCTION AND CLONING OF THE VIP1A(a) AND VIP2A(a) MAIZE OPTIMIZED GENES

Design: The maize optimized genes were designed by reverse translation of the native VIP1A(a) and VIP2A(a) protein sequences using codons that are used most often in maize (Murray et al., *Nucleic Acid Research*, 17:477–498 (1989)). To facilitate cloning, the DNA sequence was further modified to incorporate unique restriction sites at intervals of every 200–360 nucleotides. VIP1A(a) was designed to be cloned in 11 such fragments and VIP2A(a) was cloned in 5 fragments. Following cloning of the individual fragments, adjacent fragments were joined using the restriction sites common to both fragments, to obtain the complete gene. To clone each fragment, oligonucleotides (50–85 nucleotides) were designed to represent both the upper and the lower strand of the DNA. The upper oligo of the first oligo pair was designed to have a 15 bp single stranded region at the 3' end which was homologous to a similar single stranded region of the lower strand of the next oligo pair to direct the orientation and sequence of the various oligo pairs within a given fragment. The oligos are also designed such that when the all the oligos representing a fragment are hybridized, the ends have single stranded regions corresponding to the particular restriction site to be formed. The structure of each oligomer was examined for stable secondary structures such as hairpin loops using the OLIGO program from NBI Inc. Whenever neccesary, nucleotides were changed to decrease the stability of the secondary structure without changing the amino acid sequence of the protein. A plant ribosomal binding site consensus sequence, TAAACAATG (Joshi et al., *Nucleic Acid Res.*, 15:6643–6653 (1987)) or eukaryotic ribosomal binding site concensus sequence CCACCATG (Kozak, *Nucleic Acid Research*, 12:857–872 (1984)) was inserted at the translational start codon of the gene.

Cloning: Oligos were synthesized by IDT Inc., and were supplied as lyophilized powders. They were resuspended at a concentration of 200 μM. To 30 μl of each oligo formamide was added a final concentration of 25–50% and the sample was boiled for two minutes before separation on a premade 10% polyacryamide/urea gel obtained from Novex. After electrophoresis, the oligo was detected by UV shadowing by placing the gel on a TLC plate containing a fluorescent indicator and exposing it to UV light. The region containing DNA of the correct size was excised and extracted from the polyacryamide by an overnight incubation of the minced gel fragment in a buffer containing 0.4M LiCl, 0.1 mM EDTA. The DNA was separated from the gel residue by centrifugation through a Millipore UFMC filter. The extracted DNA was ethanol precipitated by the addition of 2 volumes of absolute alcohol. After centrifugation, the precipitate was resuspended in dH$_2$O at a concentration of 2.5 μM. Fragments were cloned either by hybridization of the oligos and ligation with the appropriate vector or by amplification of the hybridized fragment using a equimolar mixture of all the oligos for a particular fragment as a template and end-specific PCR primers.

Cloning by hybridization and ligation: Homologous double stranded oligo pairs were obtained by mixing 5 μl of the upper and of the lower oligo for each oligo pair with buffer containing 1× polynucleotide kinase (PNK) buffer (70 mM Tris-HCl (pH 7.6), 10 mM MgCl$_2$ 5 mM dithiothreitol (DTT)), 50 mM KCl, and 5% formamide in a final volume of 50 μl. The oligos were boiled for 10 minutes and slow cooled to 37° C. or room temperature. 10 μl was removed for analysis on a 4% agarose in a TAE buffer system (Metaphore®; FMC). Each hybridized oligo pair was kinased by the addition of ATP at a final concentration of 1 mM, BSA at a final concentration of 100 μg per ml and 200 units of polynucleotide kinase and 1 μl of 10× PNK buffer in a volume of 10 μl. Following hybridization and phosphorylation, the reaction was incubated at 37° C. for 2 hours to overnight. 10 μl of each of the oligo pairs for a particular fragment, were mixed in a final volume of 50 μl. The oligo pairs were hybridized by heating at 80° C. for 10 minutes and slow cooling to 37° C. 2 μl of oligos was mixed with about 100 ng of an appropriate vector and ligated using a buffer containing 50 mM Tris-HCl (pH 7.8), 10 mM MgCl$_2$, 10 mM DTT, 1 mM ATP. The reaction was incubated at room temp. for 2 hours to overnight and transformed into DH5α strain of E.coli, plated on L-plates containing ampicillin at a concentration of 100 μg/ml using standard procedures. Positive clones were further characterized and confirmed by PCR miniscreen described in detail in U.S. Pat. No. 5,625,136 using the universal primers "Reverse" and M13 "−20" as primers. Positive clones were identified by digestion of DNA with appropriate enzymes followed by sequencing. Recombinants that had the expected DNA sequence were then selected for further work.

PCR Amplification and cloning into T-vector

PCR amplification was carried out by using a mixture of all the oligomers that represented the upper and the lower strand of a particular fragment (final concentration 5 mM each) as template, specific end primers for the particular fragment (final concentration 2 μM) 200 μM of each dATP, dTTP, dCTP and dGTP, 10 mM Tris-HCl (pH 8.3), 50 mM KCl, 1.5 mM MgCl$_2$, 0.01% gelatin and 5 units of Taq polymerase in a final reaction volume of 50 μl. The amplification reaction was carried out in a Perkin Elmer thermocycler 9600 by incubation at 95° C. for 1 min (1 cycle), followed by 20 cycles of 95° C. for 45 sec., 50° C. for 45 sec., 72° C. for 30 sec. Finally the reaction was incubated for 5 min at 72° C. before analyzing the product. 10 μl of the reaction was analyzed on a 2.5% Nusieve (FMC) agarose gel in a TAE buffer system. The correct size fragment was gel purified and used for cloning into a PCR cloning vector or T-vector. T-vector construction was as described by Marchuk et al., *Nucleic Acid Research*. 19:1154 (1991). pBluescriptsk+ (Stratagene®, Ca.) was used as the parent vector. Transformation and identification of the correct clone was carried out as described above.

Fragments 1, 3, 4, 5, 6, 8, and 9 of VIP1A(*a*) and fragments 2 and 4 of VIP2A(*a*) were obtained by cloning of PCR amplification products; whereas, fragments 2, 7, 10 and 11 of VIP1A(*a*) and fragments 1, 3, and 5 of VIP2A(*a*) were obtained by hybridization/ligation.

Once fragments with the desired sequence were obtained, the complete gene was assembled by cloning together adjacent fragments. The complete gene was resequenced and tested for activity against WCRW before moving it into plant expression vectors containing the root preferred promoter (disclosed in U.S. Pat. No. 5,466,785, herein incorporated by reference) and the rice actin promoter.

One such plant expression vector is pCIB5521. The maize optimized VIP1A(*a*) coding region (SEQ ID NO:26) was cloned in a plant expression vector containing the root preferred promoter at the 5' of the gene with the PEP Carboxylase intron #9 followed by the 35S terminator at the 3' end. The plasmid also contains sequences for ampicillin resistance from the plasmid pUC 19. Another plant expression vector is pCIB5522, which contains the maize optimized VIP2A(*a*) coding region (SEQ ID NO:27) fused to the root preferred promoter at the 5' of the gene with the PEP Carboxylase intron #9 followed by the 35S terminator at the 3' end.

EXAMPLE 25

NAD AFFINITY CHROMATOGRAPHY

A purification strategy was used based on the affinity of VIP2 for the substrate NAD. The supernatant from the pH 3.5 sodium citrate buffer treatment described in Example 4 was dialyzed in 20 mM TRIS pH 7.5 overnight. The neutralized supernatant was added to an equal volume of washed NAD agarose and incubated with gentle rocking at 4° C. overnight. The resin and protein solution were added to a 10 ml disposable polypropylene column and the protein solution allowed to flow out. The column was washed with 5 column volumes of 20 mM TRIS pH 7.5 then washed with 2–5 column volumes of 20 mM TRIS pH 7.5, 100 mM NaCl, followed by 2–5 column volumes of 20 mM TRIS 7.5. The VIP proteins were eluted in 20 mM TRIS pH 7.5 supplemented with 5 mM NAD. Approximately 3 column volumes of the effluent were collected and concentrated in a Centricon -10. Yield is typically about 7–15 μg of protein per ml of resin.

When the purified proteins were analyzed by SDS-PAGE followed by silver staining, two polypeptides were visible, one with Mr of approximately 80,000 and one with Mr of approximately 45,000. N-terminal sequencing revealed that the Mr 80,000 protein corresponded to a proteolytically processed form of VIP1A(*a*) and the Mr 45,000 form corresponded to a proteolytically processed form of VIP2A (*a*). The co-purification of VIP1A(*a*) with VIP2A(*a*) indicates that the two proteins probably form a complex and have protein-protein interacting regions. VIP1A(*a*) and VIP2A(*a*) proteins purified in this manner were biologically active against western corn rootworm.

EXAMPLE 26

EXPRESSION OF MAIZE OPTIMIZED VIP1A(*a*) AND VIP2A(*a*)

*E. coli* strains containing different plasmids comprising VIP genes were assayed for expression of VIPs. *E. coli* strains harboring the individual plasmids were grown overnight in L-broth and expressed protein was extracted from the culture as described in Example 3, above. Protein expression was assayed by Western Blot analysis using antibodies developed using standard methods known in the art, similar to those described in Example 12, above. Also, insecticidal activity of the expressed proteins were tested against Western corn rootworm according to the method in Example 3, above. The results of the *E. coli* expression assays are described below.

Expression of VIPs in *E. coli*

| Extract of *E. coli* Strain Harboring Indicated Plasmid | Assay No. 1 % Mortality | Assay No. 2 | Protein Detected |
|---|---|---|---|
| Control | 0 | 0 | no |
| pCIB5521 (maize optimized VIP1A(a)) | 47 | 27 | yes |
| pCIB5522 (maize optimized VIP2A(a)) | 7 | 7 | yes |
| pCIB6024 (native VIP2A(a)) | 13 | 13 | yes |
| pCIB6206 (native VIP1A(a)) | 27 | 40 | yes |
| Extracts pCIB5521 + pCIB5522 combined | 87 | 47 | |
| Extracts pCIB5521 + pCIB6024 combined | 93 | 100 | |
| Extracts pCIB5522 + pCIB6206 combined | 100 | 100 | |
| Extracts pCIB6024 + pCIB6206 combined | 100 | 100 | |

The DNA from these plasmids was used to transiently express the VIPs in a maize protoplast expression system. Protoplasts were isolated from maize 2717 Line 6 suspension cultures by digestion of the cell walls using Cellulase RS and Macerase R10 in appropriate buffer. Protoplasts were recovered by sieving and centrifugation. Protoplasts were transformed by a standard direct gene transfer method using approximately 75 μg plasmid DNA and PEG-40. Treated protoplasts were incubated overnight in the dark at room temperature. Analysis of VIP expression was accomplished on protoplast explants by Western blot analysis and insecticidal activity against Western corn rootworm as described above for the expression in *E. coli*. The results of the maize protoplast expression assays are described below.

Expression of VIPs in Plant Protoplasts

| Extract Tested | Assay No. 1 % Mortality | Assay No. 2 | Protein Detected |
|---|---|---|---|
| No DNA control | 27 | 10 | no |
| pCIB5521 (p) (maize optimized VIP1A(a)) | 20 (0) | 30 | yes |
| pCIB5522 (p) (maize optimizied VIP2A(a)) | 20 (0) | 20 | yes |
| Extracts pCIB5521 (p) + pCIB5522 (e) combined | 87 (82) | 90 | |
| Extracts pCIB5521 (p) + pCIB5522 (e) combined | 100 | — | |
| Extracts pCIB5522 (p) + pCIB5521 (e) combined | 53 (36) | — | |
| Extracts pCIB5521 (p) + pCIB6024 (e) combined | 100 | — | |
| Extracts pCIB5522 (p) + pCIB6206 (e) combined | 100 | — | |
| pCIB6024(e) (native VIP2A(a)) | 0 | — | yes |
| pCIB6206(e) (native VIP1A(a)) | 20 | — | yes |
| pCIB5521 + pCIB5522 (plasmids delivered by cotransformation) | 100 | 100 | yes |

(p) = extract of protoplast culture transformed with indicated plasmid
(e) = extract of *E. coli* strain harboring indicated plasmid The expression data obtained with both *E. coli* and maize protoplasts show that the maize optimized VIP1A(*a*) and VIP2A(*a*) genes make the same protein as the native VIP1A (*a*) and VIP2A(*a*) genes, respectively, and that the proteins encoded by the maize optimized genes are functionally equivalent to the proteins encoded by the native genes.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The following deposits have been made at Agricultural Research Service, Patent Culture Collection (NRRL), Northern Regional Research Center, 1815 North University Street, Peoria, Ill. 61604, USA:

| | | |
|---|---|---|
| 1. | *E. coli* PL2 | Accession No. NRRL B-21221N |
| 2. | *E. coli* pCIB6022 | Accession No. NRRL B-21222 |
| 3. | *E. coli* pCIB6023 | Accession No. NRRL B-21223N |
| 4. | *Bacillus thuringiensis* HD73-78V1P | Accession No. NRRL B-21224 |
| 5. | *Bacillus thuringiensis* AB88 | Accession No. NRRL B-21225 |
| 6. | *Bacillus thuringiensis* AB359 | Accession No. NRRL B-21226 |
| 7. | *Bacillus thuringiensis* AB289 | Accession No. NRRL B-21227 |
| 8. | *Bacillus sp.* AB59 | Accession No. NRRL B-21228 |
| 9. | *Bacillus sp.* AB294 | Accession No. NRRL B-21229 |
| 10. | *Bacillus sp.* AB256 | Accession No. NRRL B-21230 |
| 11. | *E. coli* PS-4 | Accession No. NRRL B-21059 |
| 12. | *E. coli* P3-12 | Accession No. NRRL B-21061 |

-continued

| | | |
|---|---|---|
| 13. | *Bacillus cereus* AB78 | Accession No. NRRL B-21058 |
| 14. | *Bacillus thuringiensis* AB6 | Accession No. NRRL B-21060 |
| 15. | *E. coli* pCIB6202 | Accession No. NRRL B-21321 |
| 16. | *E. coli* pCIB7100 | Accession No. NRRL B-21322 |
| 17. | *E. coli* pCIB7101 | Accession No. NRRL B-21323 |
| 18. | *E. coli* pCIB7102 | Accession No. NRRL B-21324 |
| 19. | *E. coli* pCIB7102 | Accession No. NRRL B-21325 |
| 20. | *E. coli* pCIB7104 | Accession No. NRRL B-21422 |
| 21. | *E. coli* pCIB7107 | Accession No. NRRL B-21423 |
| 22. | *E. coli* pCIB7108 | Accession No. NRRL B-21438 |
| 23. | *Bacillus thuringiensis* AB424 | Accession No. NRRL B-21439 |

Although the foregoing invention has been described in some detail by way of illustration and example for purposes of clarity of understanding, it will be obvious that certain changes and modifications may be practiced within the scope of the appended claims.

SEQUENCE LISTING ( 1 ) GENERAL INFORMATION:

( i i i ) NUMBER OF SEQUENCES: 52

( 2 ) INFORMATION FOR SEQ ID NO:1:

( i ) SEQUENCE CHARACTERISTICS:
( A ) LENGTH: 6049 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Bacillus cereus
( B ) STRAIN: AB78
( C ) INDIVIDUAL ISOLATE: NRRL B- 21058

( i x ) FEATURE:
( A ) NAME/KEY: CDS
( B ) LOCATION: 1082..2467
( D ) OTHER INFORMATION: /product="VIP2A(a)"

( i x ) FEATURE:
( A ) NAME/KEY: misc_feature
( B ) LOCATION: 2475..5126
( D ) OTHER INFORMATION: /note= "Coding sequence for the 100 kd VIP1A(a) protein. This coding sequence is repeated in SEQ ID NO:4 and translated separately."

( x i ) SEQUENCE DESCRIPTION: SEQ ID NO:1:

```
ATCGATACAA TGTTGTTTTA CTTAGACCGG TAGTCTCTGT AATTTGTTTA ATGCTATATT      60

CTTTACTTTG ATACATTTTA ATAGCCATTT CAACCTTATC AGTATGTTTT TGTGGTCTTC     120

CTCCTTTTTT TCCACGAGCT CTAGCTGCGT TTAATCCTGT TTTGGTACGT TCGCTAATAA     180

TATCTCTTTC TAATTCTGCA ATACTTGCCA TCATTCGAAA GAAGAATTTC CCCATAGCAT     240

TAGAGGTATC AATGTTGTCA TGAATAGAAA TAAAATCTAC ACCTAGCTCT TTGAATTTTT     300

CACTTAACTC AATTAGGTGT TTTGTAGAGC GAGAAATTCG ATCAAGTTTG TAAACAACTA     360

TCTTATCGCC TTTACGTAAT ACTTTTAGCA ACTCTTCGAG TTGAGGGCGC TCTTTTTTTA     420

TTCCTGTTAT TTTCTCCTGA TATAGCCTTT CTACACCATA TTGTTGCAAA GCATCTATTT     480

GCATATCGAG ATTTTGTTCT TCTGTGCTGA CACGAGCATA ACCAAAAATC AAATTGGTTT     540

CACTTCCTAT CTAAATATAT CTATTAAAAT AGCACCAAAA ACCTTATTAA ATTAAAATAA     600

GGAACTTTGT TTTTGGATAT GGATTTTGGT ACTCAATATG GATGAGTTTT TAACGCTTTT     660

GTTAAAAAAC AAACAAGTGC CATAAACGGT CGTTTTTGGG ATGACATAAT AAATAATCTG     720

TTTGATTAAC CTAACCTTGT ATCCTTACAG CCCAGTTTTA TTTGTACTTC AACTGACTGA     780

ATATGAAAAC AACATGAAGG TTTCATAAAA TTTATATATT TTCCATAACG GATGCTCTAT     840

CTTTAGGTTA TAGTTAAATT ATAAGAAAAA AACAAACGGA GGGAGTGAAA AAAAGCATCT     900

TCTCTATAAT TTTACAGGCT CTTTAATAAG AAGGGGGGAG ATTAGATAAT AAATATGAAT     960

ATCTATCTAT AATTGTTTGC TTCTACAATA ACTTATCTAA CTTTCATATA CAACAACAAA    1020

ACAGACTAAA TCCAGATTGT ATATTCATTT TCAGTTGTTC CTTTATAAAA TAATTTCATA    1080

A ATG AAA AGA ATG GAG GGA AAG TTG TTT ATG GTG TCA AAA AAA TTA        1126
  Met Lys Arg Met Glu Gly Lys Leu Phe Met Val Ser Lys Lys Leu
    1               5                  10                  15

CAA GTA GTT ACT AAA ACT GTA TTG CTT AGT ACA GTT TTC TCT ATA TCT      1174
Gln Val Val Thr Lys Thr Val Leu Leu Ser Thr Val Phe Ser Ile Ser
                20                  25                  30
```

| | | | | | | | | | | | | | | | | |
|---|---|---|---|---|---|---|---|---|---|---|---|---|---|---|---|---|
| TTA | TTA | AAT | AAT | GAA | GTG | ATA | AAA | GCT | GAA | CAA | TTA | AAT | ATA | AAT | TCT | 1222 |
| Leu | Leu | Asn | Asn | Glu | Val | Ile | Lys | Ala | Glu | Gln | Leu | Asn | Ile | Asn | Ser | |
| | | | 35 | | | | 40 | | | | | 45 | | | | |
| CAA | AGT | AAA | TAT | ACT | AAC | TTG | CAA | AAT | CTA | AAA | ATC | ACT | GAC | AAG | GTA | 1270 |
| Gln | Ser | Lys | Tyr | Thr | Asn | Leu | Gln | Asn | Leu | Lys | Ile | Thr | Asp | Lys | Val | |
| | | 50 | | | | | 55 | | | | | 60 | | | | |
| GAG | GAT | TTT | AAA | GAA | GAT | AAG | GAA | AAA | GCG | AAA | GAA | TGG | GGG | AAA | GAA | 1318 |
| Glu | Asp | Phe | Lys | Glu | Asp | Lys | Glu | Lys | Ala | Lys | Glu | Trp | Gly | Lys | Glu | |
| | 65 | | | | | 70 | | | | | 75 | | | | | |
| AAA | GAA | AAA | GAG | TGG | AAA | CTA | ACT | GCT | ACT | GAA | AAA | GGA | AAA | ATG | AAT | 1366 |
| Lys | Glu | Lys | Glu | Trp | Lys | Leu | Thr | Ala | Thr | Glu | Lys | Gly | Lys | Met | Asn | |
| 80 | | | | | 85 | | | | | 90 | | | | | 95 | |
| AAT | TTT | TTA | GAT | AAT | AAA | AAT | GAT | ATA | AAG | ACA | AAT | TAT | AAA | GAA | ATT | 1414 |
| Asn | Phe | Leu | Asp | Asn | Lys | Asn | Asp | Ile | Lys | Thr | Asn | Tyr | Lys | Glu | Ile | |
| | | | | 100 | | | | | 105 | | | | | 110 | | |
| ACT | TTT | TCT | ATG | GCA | GGC | TCA | TTT | GAA | GAT | GAA | ATA | AAA | GAT | TTA | AAA | 1462 |
| Thr | Phe | Ser | Met | Ala | Gly | Ser | Phe | Glu | Asp | Glu | Ile | Lys | Asp | Leu | Lys | |
| | | | | 115 | | | | 120 | | | | | 125 | | | |
| GAA | ATT | GAT | AAG | ATG | TTT | GAT | AAA | ACC | AAT | CTA | TCA | AAT | TCT | ATT | ATC | 1510 |
| Glu | Ile | Asp | Lys | Met | Phe | Asp | Lys | Thr | Asn | Leu | Ser | Asn | Ser | Ile | Ile | |
| | | 130 | | | | | 135 | | | | | 140 | | | | |
| ACC | TAT | AAA | AAT | GTG | GAA | CCG | ACA | ACA | ATT | GGA | TTT | AAT | AAA | TCT | TTA | 1558 |
| Thr | Tyr | Lys | Asn | Val | Glu | Pro | Thr | Thr | Ile | Gly | Phe | Asn | Lys | Ser | Leu | |
| | 145 | | | | | 150 | | | | | 155 | | | | | |
| ACA | GAA | GGT | AAT | ACG | ATT | AAT | TCT | GAT | GCA | ATG | GCA | CAG | TTT | AAA | GAA | 1606 |
| Thr | Glu | Gly | Asn | Thr | Ile | Asn | Ser | Asp | Ala | Met | Ala | Gln | Phe | Lys | Glu | |
| 160 | | | | | 165 | | | | | 170 | | | | | 175 | |
| CAA | TTT | TTA | GAT | AGG | GAT | ATT | AAG | TTT | GAT | AGT | TAT | CTA | GAT | ACG | CAT | 1654 |
| Gln | Phe | Leu | Asp | Arg | Asp | Ile | Lys | Phe | Asp | Ser | Tyr | Leu | Asp | Thr | His | |
| | | | | 180 | | | | | 185 | | | | | 190 | | |
| TTA | ACT | GCT | CAA | CAA | GTT | TCC | AGT | AAA | GAA | AGA | GTT | ATT | TTG | AAG | GTT | 1702 |
| Leu | Thr | Ala | Gln | Gln | Val | Ser | Ser | Lys | Glu | Arg | Val | Ile | Leu | Lys | Val | |
| | | | 195 | | | | | 200 | | | | | 205 | | | |
| ACG | GTT | CCG | AGT | GGG | AAA | GGT | TCT | ACT | ACT | CCA | ACA | AAA | GCA | GGT | GTC | 1750 |
| Thr | Val | Pro | Ser | Gly | Lys | Gly | Ser | Thr | Thr | Pro | Thr | Lys | Ala | Gly | Val | |
| | | 210 | | | | | 215 | | | | | 220 | | | | |
| ATT | TTA | AAT | AAT | AGT | GAA | TAC | AAA | ATG | CTC | ATT | GAT | AAT | GGG | TAT | ATG | 1798 |
| Ile | Leu | Asn | Asn | Ser | Glu | Tyr | Lys | Met | Leu | Ile | Asp | Asn | Gly | Tyr | Met | |
| | 225 | | | | | 230 | | | | | 235 | | | | | |
| GTC | CAT | GTA | GAT | AAG | GTA | TCA | AAA | GTG | GTG | AAA | AAA | GGG | GTG | GAG | TGC | 1846 |
| Val | His | Val | Asp | Lys | Val | Ser | Lys | Val | Val | Lys | Lys | Gly | Val | Glu | Cys | |
| 240 | | | | | 245 | | | | | 250 | | | | | 255 | |
| TTA | CAA | ATT | GAA | GGG | ACT | TTA | AAA | AAG | AGT | CTT | GAC | TTT | AAA | AAT | GAT | 1894 |
| Leu | Gln | Ile | Glu | Gly | Thr | Leu | Lys | Lys | Ser | Leu | Asp | Phe | Lys | Asn | Asp | |
| | | | | 260 | | | | | 265 | | | | | 270 | | |
| ATA | AAT | GCT | GAA | GCG | CAT | AGC | TGG | GGT | ATG | AAG | AAT | TAT | GAA | GAG | TGG | 1942 |
| Ile | Asn | Ala | Glu | Ala | His | Ser | Trp | Gly | Met | Lys | Asn | Tyr | Glu | Glu | Trp | |
| | | | | 275 | | | | | 280 | | | | | 285 | | |
| GCT | AAA | GAT | TTA | ACC | GAT | TCG | CAA | AGG | GAA | GCT | TTA | GAT | GGG | TAT | GCT | 1990 |
| Ala | Lys | Asp | Leu | Thr | Asp | Ser | Gln | Arg | Glu | Ala | Leu | Asp | Gly | Tyr | Ala | |
| | | 290 | | | | | 295 | | | | | 300 | | | | |
| AGG | CAA | GAT | TAT | AAA | GAA | ATC | AAT | AAT | TAT | TTA | AGA | AAT | CAA | GGC | GGA | 2038 |
| Arg | Gln | Asp | Tyr | Lys | Glu | Ile | Asn | Asn | Tyr | Leu | Arg | Asn | Gln | Gly | Gly | |
| | 305 | | | | | 310 | | | | | 315 | | | | | |
| AGT | GGA | AAT | GAA | AAA | CTA | GAT | GCT | CAA | ATA | AAA | AAT | ATT | TCT | GAT | GCT | 2086 |
| Ser | Gly | Asn | Glu | Lys | Leu | Asp | Ala | Gln | Ile | Lys | Asn | Ile | Ser | Asp | Ala | |
| 320 | | | | | 325 | | | | | 330 | | | | | 335 | |
| TTA | GGG | AAG | AAA | CCA | ATA | CCG | GAA | AAT | ATT | ACT | GTG | TAT | AGA | TGG | TGT | 2134 |
| Leu | Gly | Lys | Lys | Pro | Ile | Pro | Glu | Asn | Ile | Thr | Val | Tyr | Arg | Trp | Cys | |
| | | | | 340 | | | | | 345 | | | | | 350 | | |

-continued

```
GGC ATG CCG GAA TTT GGT TAT CAA ATT AGT GAT CCG TTA CCT TCT TTA   2182
Gly Met Pro Glu Phe Gly Tyr Gln Ile Ser Asp Pro Leu Pro Ser Leu
        355                 360                 365

AAA GAT TTT GAA GAA CAA TTT TTA AAT ACA ATC AAA GAA GAC AAA GGA   2230
Lys Asp Phe Glu Glu Gln Phe Leu Asn Thr Ile Lys Glu Asp Lys Gly
        370                 375                 380

TAT ATG AGT ACA AGC TTA TCG AGT GAA CGT CTT GCA GCT TTT GGA TCT   2278
Tyr Met Ser Thr Ser Leu Ser Ser Glu Arg Leu Ala Ala Phe Gly Ser
        385                 390                 395

AGA AAA ATT ATA TTA CGA TTA CAA GTT CCG AAA GGA AGT ACG GGT GCG   2326
Arg Lys Ile Ile Leu Arg Leu Gln Val Pro Lys Gly Ser Thr Gly Ala
400                 405                 410                 415

TAT TTA AGT GCC ATT GGT GGA TTT GCA AGT GAA AAA GAG ATC CTA CTT   2374
Tyr Leu Ser Ala Ile Gly Gly Phe Ala Ser Glu Lys Glu Ile Leu Leu
                420                 425                 430

GAT AAA GAT AGT AAA TAT CAT ATT GAT AAA GTA ACA GAG GTA ATT ATT   2422
Asp Lys Asp Ser Lys Tyr His Ile Asp Lys Val Thr Glu Val Ile Ile
        435                 440                 445

AAA GGT GTT AAG CGA TAT GTA GTG GAT GCA ACA TTA TTA ACA AAT       2467
Lys Gly Val Lys Arg Tyr Val Val Asp Ala Thr Leu Leu Thr Asn
        450                 455                 460
```

```
TAAGGAGATG AAAAATATGA AGAAAAAGTT AGCAAGTGTT GTAACGTGTA CGTTATTAGC   2527
TCCTATGTTT TGAATGGAA  ATGTGAATGC TGTTTACGCA GACAGCAAAA CAAATCAAAT   2587
TTCTACAACA CAGAAAAATC AACAGAAAGA GATGGACCGA AAAGGATTAC TTGGGTATTA   2647
TTTCAAAGGA AAAGATTTTA GTAATCTTAC TATGTTTGCA CCGACACGTG ATAGTACTCT   2707
TATTTATGAT CAACAAACAG CAAATAAACT ATTAGATAAA AACAACAAG  AATATCAGTC   2767
TATTCGTTGG ATTGGTTTGA TTCAGAGTAA AGAAACGGGA GATTTCACAT TTAACTTATC   2827
TGAGGATGAA CAGGCAATTA TAGAAATCAA TGGGAAAATT ATTTCTAATA AGGGAAAGA    2887
AAAGCAAGTT GTCCATTTAG AAAAAGGAAA ATTAGTTCCA ATCAAAATAG AGTATCAATC   2947
AGATACAAAA TTTAATATTG ACAGTAAAAC ATTTAAAGAA CTTAAATTAT TTAAAATAGA   3007
TAGTCAAAAC CAACCCCAGC AAGTCCAGCA AGATGAACTG AGAAATCCTG AATTTAACAA   3067
GAAAGAATCA CAGGAATTCT TAGCGAAACC ATCGAAAATA AATCTTTTCA CTCAAAAAAT   3127
GAAAAGGGAA ATTGATGAAG ACACGGATAC GGATGGGGAC TCTATTCCTG ACCTTTGGGA   3187
AGAAAATGGG TATACGATTC ACAATAGAAT CGCTGTAAAG TGGGACGATT CTCTAGCAAG   3247
TAAAGGGTAT ACGAAATTTG TTTCAAATCC ACTAGAAAGT CACACAGTTG GTGATCCTTA   3307
TACAGATTAT GAAAAGGCAG CAAGAGATCT AGATTTGTCA AATGCAAAGG AAACGTTTAA   3367
CCCATTGGTA GCTGCTTTTC CAAGTGTGAA TGTTAGTATG GAAAAGGTGA TATTATCACC   3427
AAATGAAAAT TTATCCAATA GTGTAGAGTC TCATTCATCC ACGAATTGGT CTTATACAAA   3487
TACAGAAGGT GCTTCTGTTG AAGCGGGGAT TGGACCAAAA GGTATTTCGT TCGGAGTTAG   3547
CGTAAACTAT CAACACTCTG AAACAGTTGC ACAAGAATGG GAACATCTA  CAGGAAATAC   3607
TTCGCAATTC AATACGGCTT CAGCGGGATA TTTAAATGCA AATGTTCGAT ATAACAATGT   3667
AGGAACTGGT GCCATCTACG ATGTAAAACC TACAACAAGT TTTGTATTAA ATAACGATAC   3727
TATCGCAACT ATTACGGCGA AATCTAATTC TACAGCCTTA AATATATCTC CTGGAGAAAG   3787
TTACCCGAAA AAAGGACAAA ATGGAATCGC AATAACATCA ATGGATGATT TAATTCCCA    3847
TCCGATTACA TTAAATAAAA AACAAGTAGA TAATCTGCTA AATAATAAAC CTATGATGTT   3907
GGAAACAAAC CAAACAGATG GTGTTTATAA GATAAAAGAT ACACATGGAA ATATAGTAAC   3967
TGGCGGAGAA TGGAATGGTG TCATACAACA AATCAAGGCT AAAACAGCGT CTATTATTGT   4027
```

```
GGATGATGGG  GAACGTGTAG  CAGAAAAACG  TGTAGCGGCA  AAAGATTATG  AAAATCCAGA    4087
AGATAAAACA  CCGTCTTTAA  CTTTAAAAGA  TGCCCTGAAG  CTTTCATATC  CAGATGAAAT    4147
AAAAGAAATA  GAGGGATTAT  TATATTATAA  AAACAAACCG  ATATACGAAT  CGAGCGTTAT    4207
GACTTACTTA  GATGAAAATA  CAGCAAAAGA  AGTGACCAAA  CAATTAAATG  ATACCACTGG    4267
GAAATTTAAA  GATGTAAGTC  ATTTATATGA  TGTAAAACTG  ACTCCAAAAA  TGAATGTTAC    4327
AATCAAATTG  TCTATACTTT  ATGATAATGC  TGAGTCTAAT  GATAACTCAA  TTGGTAAATG    4387
GACAAACACA  AATATTGTTT  CAGGTGGAAA  TAACGGAAAA  AACAATATT   CTTCTAATAA    4447
TCCGGATGCT  AATTTGACAT  TAAATACAGA  TGCTCAAGAA  AAATTAAATA  AAAATCGTGA    4507
CTATTATATA  AGTTTATATA  TGAAGTCAGA  AAAAAACACA  CAATGTGAGA  TTACTATAGA    4567
TGGGGAGATT  TATCCGATCA  CTACAAAAC   AGTGAATGTG  AATAAGACA   ATTACAAAAG    4627
ATTAGATATT  ATAGCTCATA  ATATAAAAG   TAATCCAATT  TCTTCACTTC  ATATTAAAAC    4687
GAATGATGAA  ATAACTTTAT  TTTGGGATGA  TATTTCTATA  ACAGATGTAG  CATCAATAAA    4747
ACCGGAAAAT  TTAACAGATT  CAGAAATTAA  ACAGATTTAT  AGTAGGTATG  GTATTAAGTT    4807
AGAAGATGGA  ATCCTTATTG  ATAAAAAGG   TGGGATTCAT  TATGGTGAAT  TTATTAATGA    4867
AGCTAGTTTT  AATATTGAAC  CATTGCAAAA  TTATGTGACC  AAATATGAAG  TTACTTATAG    4927
TAGTGAGTTA  GGACCAAACG  TGAGTGACAC  ACTTGAAAGT  GATAAAATTT  ACAAGGATGG    4987
GACAATTAAA  TTTGATTTTA  CCAAATATAG  TAAAAATGAA  CAAGGATTAT  TTTATGACAG    5047
TGGATTAAAT  TGGGACTTTA  AAATTAATGC  TATTACTTAT  GATGGTAAAG  AGATGAATGT    5107
TTTTCATAGA  TATAATAAAT  AGTTATTATA  TCTATGAAGC  TGGTGCTAAA  GATAGTGTAA    5167
AAGTTAATAT  ACTGTAGGAT  TGTAATAAAA  GTAATGGAAT  TGATATCGTA  CTTTGGAGTG    5227
GGGGATACTT  TGTAAATAGT  TCTATCAGAA  ACATTAGACT  AAGAAAAGTT  ACTACCCCA     5287
CTTGAAAATG  AAGATTCAAC  TGATTACAAA  CAACCTGTTA  AATATTATAA  GGTTTTAACA    5347
AAATATTAAA  CTCTTTATGT  TAATACTGTA  ATATAAAGAG  TTTAATTGTA  TTCAAATGAA    5407
GCTTTCCCAC  AAAATTAGAC  TGATTATCTA  ATGAAATAAT  CAGTCTAATT  TTGTAGAACA    5467
GGTCTGGTAT  TATTGTACGT  GGTCACTAAA  AGATATCTAA  TATTATTGGG  CAAGGCGTTC    5527
CATGATTGAA  TCCTCGAATG  TCTTGCCCTT  TTCATTTATT  TAAGAAGGAT  TGTGGAGAAA    5587
TTATGGTTTA  GATAATGAAG  AAAGACTTCA  CTTCTAATTT  TTGATGTTAA  ATAAATCAAA    5647
ATTTGGCGAT  TCACATTGTT  TAATCCACTG  ATAAACATA   CTGGAGTGTT  CTTAAAAAAT    5707
CAGCTTTTTT  CTTTATAAAA  TTTTGCTTAG  CGTACGAAAT  TCGTGTTTTG  TTGGTGGGAC    5767
CCCATGCCCA  TCAACTTAAG  AGTAAATTAG  TAATGAACTT  TCGTTCATCT  GGATTAAAAT    5827
AACCTCAAAT  TAGGACATGT  TTTTAAAAAT  AAGCAGACCA  AATAAGCCTA  GAATAGGTAT    5887
CATTTTAAA   AATTATGCTG  CTTTCTTTTG  TTTTCCAAAT  CCATTATACT  CATAAGCAAC    5947
ACCCATAATG  TCAAAGACTG  TTTTTGTCTC  ATATCGATAA  GCTTGATATC  GAATTCCTGC    6007
AGCCCGGGGG  ATCCACTAGT  TCTAGAGCGG  CCGCCACCGC  GG                        6049
```

( 2 ) INFORMATION FOR SEQ ID NO:2:

( i ) SEQUENCE CHARACTERISTICS:
        ( A ) LENGTH: 462 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Lys  Arg  Met  Glu  Gly  Lys  Leu  Phe  Met  Val  Ser  Lys  Lys  Leu  Gln
  1                  5                       10                       15

Val  Val  Thr  Lys  Thr  Val  Leu  Leu  Ser  Thr  Val  Phe  Ser  Ile  Ser  Leu
               20                       25                       30

Leu  Asn  Asn  Glu  Val  Ile  Lys  Ala  Glu  Gln  Leu  Asn  Ile  Asn  Ser  Gln
               35                       40                       45

Ser  Lys  Tyr  Thr  Asn  Leu  Gln  Asn  Leu  Lys  Ile  Thr  Asp  Lys  Val  Glu
          50                       55                       60

Asp  Phe  Lys  Glu  Asp  Lys  Glu  Lys  Ala  Lys  Glu  Trp  Gly  Lys  Glu  Lys
 65                       70                       75                       80

Glu  Lys  Glu  Trp  Lys  Leu  Thr  Ala  Thr  Glu  Lys  Gly  Lys  Met  Asn  Asn
               85                       90                       95

Phe  Leu  Asp  Asn  Lys  Asn  Asp  Ile  Lys  Thr  Asn  Tyr  Lys  Glu  Ile  Thr
              100                      105                      110

Phe  Ser  Met  Ala  Gly  Ser  Phe  Glu  Asp  Glu  Ile  Lys  Asp  Leu  Lys  Glu
              115                      120                      125

Ile  Asp  Lys  Met  Phe  Asp  Lys  Thr  Asn  Leu  Ser  Asn  Ser  Ile  Ile  Thr
         130                      135                      140

Tyr  Lys  Asn  Val  Glu  Pro  Thr  Thr  Ile  Gly  Phe  Asn  Lys  Ser  Leu  Thr
145                      150                      155                      160

Glu  Gly  Asn  Thr  Ile  Asn  Ser  Asp  Ala  Met  Ala  Gln  Phe  Lys  Glu  Gln
              165                      170                      175

Phe  Leu  Asp  Arg  Asp  Ile  Lys  Phe  Asp  Ser  Tyr  Leu  Asp  Thr  His  Leu
              180                      185                      190

Thr  Ala  Gln  Gln  Val  Ser  Ser  Lys  Glu  Arg  Val  Ile  Leu  Lys  Val  Thr
              195                      200                      205

Val  Pro  Ser  Gly  Lys  Gly  Ser  Thr  Thr  Pro  Thr  Lys  Ala  Gly  Val  Ile
     210                      215                      220

Leu  Asn  Asn  Ser  Glu  Tyr  Lys  Met  Leu  Ile  Asp  Asn  Gly  Tyr  Met  Val
225                      230                      235                      240

His  Val  Asp  Lys  Val  Ser  Lys  Val  Val  Lys  Lys  Gly  Val  Glu  Cys  Leu
               245                      250                      255

Gln  Ile  Glu  Gly  Thr  Leu  Lys  Lys  Ser  Leu  Asp  Phe  Lys  Asn  Asp  Ile
              260                      265                      270

Asn  Ala  Glu  Ala  His  Ser  Trp  Gly  Met  Lys  Asn  Tyr  Glu  Glu  Trp  Ala
              275                      280                      285

Lys  Asp  Leu  Thr  Asp  Ser  Gln  Arg  Glu  Ala  Leu  Asp  Gly  Tyr  Ala  Arg
     290                      295                      300

Gln  Asp  Tyr  Lys  Glu  Ile  Asn  Asn  Tyr  Leu  Arg  Asn  Gln  Gly  Gly  Ser
305                      310                      315                      320

Gly  Asn  Glu  Lys  Leu  Asp  Ala  Gln  Ile  Lys  Asn  Ile  Ser  Asp  Ala  Leu
                    325                      330                      335

Gly  Lys  Lys  Pro  Ile  Pro  Glu  Asn  Ile  Thr  Val  Tyr  Arg  Trp  Cys  Gly
               340                      345                      350

Met  Pro  Glu  Phe  Gly  Tyr  Gln  Ile  Ser  Asp  Pro  Leu  Pro  Ser  Leu  Lys
          355                      360                      365

Asp  Phe  Glu  Glu  Gln  Phe  Leu  Asn  Thr  Ile  Lys  Glu  Asp  Lys  Gly  Tyr
     370                      375                      380

Met  Ser  Thr  Ser  Leu  Ser  Ser  Glu  Arg  Leu  Ala  Ala  Phe  Gly  Ser  Arg
385                      390                      395                      400

Lys  Ile  Ile  Leu  Arg  Leu  Gln  Val  Pro  Lys  Gly  Ser  Thr  Gly  Ala  Tyr
                    405                      410                      415

Leu  Ser  Ala  Ile  Gly  Gly  Phe  Ala  Ser  Glu  Lys  Glu  Ile  Leu  Leu  Asp
```

|     |     |     |     |     |     | 4 2 0 |     |     |     | 4 2 5 |     |     |     | 4 3 0 |     |
| --- | --- | --- | --- | --- | --- | --- | --- | --- | --- | --- | --- | --- | --- | --- | --- |
| Lys | Asp | Ser | Lys | Tyr | His | Ile | Asp | Lys | Val | Thr | Glu | Val | Ile | Ile | Lys |
|     |     | 4 3 5 |     |     |     | 4 4 0 |     |     |     | 4 4 5 |     |     |     |     |     |
| Gly | Val | Lys | Arg | Tyr | Val | Val | Asp | Ala | Thr | Leu | Leu | Thr | Asn |     |     |
| 4 5 0 |     |     |     |     | 4 5 5 |     |     |     |     | 4 6 0 |     |     |     |     |     |

(2) INFORMATION FOR SEQ ID NO:3:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..20
        (D) OTHER INFORMATION: /note= "Signal peptide for vacuolar
            targetting"

(xi) SEQUENCE DESCRIPTION: SEQ ID NO:3:

| Ser | Ser | Ser | Ser | Phe | Ala | Asp | Ser | Asn | Pro | Ile | Arg | Val | Thr | Asp | Arg |
| --- | --- | --- | --- | --- | --- | --- | --- | --- | --- | --- | --- | --- | --- | --- | --- |
| 1 |     |     |     | 5 |     |     |     |     | 1 0 |     |     |     |     | 1 5 |     |
| Ala | Ala | Ser | Thr |     |     |     |     |     |     |     |     |     |     |     |     |
|     |     |     | 2 0 |     |     |     |     |     |     |     |     |     |     |     |     |

(2) INFORMATION FOR SEQ ID NO:4:

(i) SEQUENCE CHARACTERISTICS:
        (A) LENGTH: 2655 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bacillus cereus
        (B) STRAIN: AB78
        (C) INDIVIDUAL ISOLATE: NRRL B

```
                        530                           535                           540
GAT   CAA   CAA   ACA   GCA   AAT   AAA   CTA   TTA   GAT   AAA   AAA   CAA   CAA   GAA   TAT        288
Asp   Gln   Gln   Thr   Ala   Asn   Lys   Leu   Leu   Asp   Lys   Lys   Gln   Gln   Glu   Tyr
                  545                           550                           555

CAG   TCT   ATT   CGT   TGG   ATT   GGT   TTG   ATT   CAG   AGT   AAA   GAA   ACG   GGA   GAT        336
Gln   Ser   Ile   Arg   Trp   Ile   Gly   Leu   Ile   Gln   Ser   Lys   Glu   Thr   Gly   Asp
      560                           565                           570

TTC   ACA   TTT   AAC   TTA   TCT   GAG   GAT   GAA   CAG   GCA   ATT   ATA   GAA   ATC   AAT        384
Phe   Thr   Phe   Asn   Leu   Ser   Glu   Asp   Glu   Gln   Ala   Ile   Ile   Glu   Ile   Asn
575                           580                           585                           590

GGG   AAA   ATT   ATT   TCT   AAT   AAA   GGG   AAA   GAA   AAG   CAA   GTT   GTC   CAT   TTA        432
Gly   Lys   Ile   Ile   Ser   Asn   Lys   Gly   Lys   Glu   Lys   Gln   Val   Val   His   Leu
                        595                           600                           605

GAA   AAA   GGA   AAA   TTA   GTT   CCA   ATC   AAA   ATA   GAG   TAT   CAA   TCA   GAT   ACA        480
Glu   Lys   Gly   Lys   Leu   Val   Pro   Ile   Lys   Ile   Glu   Tyr   Gln   Ser   Asp   Thr
                  610                           615                           620

AAA   TTT   AAT   ATT   GAC   AGT   AAA   ACA   TTT   AAA   GAA   CTT   AAA   TTA   TTT   AAA        528
Lys   Phe   Asn   Ile   Asp   Ser   Lys   Thr   Phe   Lys   Glu   Leu   Lys   Leu   Phe   Lys
            625                           630                           635

ATA   GAT   AGT   CAA   AAC   CAA   CCC   CAG   CAA   GTC   CAG   CAA   GAT   GAA   CTG   AGA        576
Ile   Asp   Ser   Gln   Asn   Gln   Pro   Gln   Gln   Val   Gln   Gln   Asp   Glu   Leu   Arg
      640                           645                           650

AAT   CCT   GAA   TTT   AAC   AAG   AAA   GAA   TCA   CAG   GAA   TTC   TTA   GCG   AAA   CCA        624
Asn   Pro   Glu   Phe   Asn   Lys   Lys   Glu   Ser   Gln   Glu   Phe   Leu   Ala   Lys   Pro
655                           660                           665                           670

TCG   AAA   ATA   AAT   CTT   TTC   ACT   CAA   AAA   ATG   AAA   AGG   GAA   ATT   GAT   GAA        672
Ser   Lys   Ile   Asn   Leu   Phe   Thr   Gln   Lys   Met   Lys   Arg   Glu   Ile   Asp   Glu
                        675                           680                           685

GAC   ACG   GAT   ACG   GAT   GGG   GAC   TCT   ATT   CCT   GAC   CTT   TGG   GAA   GAA   AAT        720
Asp   Thr   Asp   Thr   Asp   Gly   Asp   Ser   Ile   Pro   Asp   Leu   Trp   Glu   Glu   Asn
                  690                           695                           700

GGG   TAT   ACG   ATT   CAA   AAT   AGA   ATC   GCT   GTA   AAG   TGG   GAC   GAT   TCT   CTA        768
Gly   Tyr   Thr   Ile   Gln   Asn   Arg   Ile   Ala   Val   Lys   Trp   Asp   Asp   Ser   Leu
            705                           710                           715

GCA   AGT   AAA   GGG   TAT   ACG   AAA   TTT   GTT   TCA   AAT   CCA   CTA   GAA   AGT   CAC        816
Ala   Ser   Lys   Gly   Tyr   Thr   Lys   Phe   Val   Ser   Asn   Pro   Leu   Glu   Ser   His
      720                           725                           730

ACA   GTT   GGT   GAT   CCT   TAT   ACA   GAT   TAT   GAA   AAG   GCA   GCA   AGA   GAT   CTA        864
Thr   Val   Gly   Asp   Pro   Tyr   Thr   Asp   Tyr   Glu   Lys   Ala   Ala   Arg   Asp   Leu
735                           740                           745                           750

GAT   TTG   TCA   AAT   GCA   AAG   GAA   ACG   TTT   AAC   CCA   TTG   GTA   GCT   GCT   TTT        912
Asp   Leu   Ser   Asn   Ala   Lys   Glu   Thr   Phe   Asn   Pro   Leu   Val   Ala   Ala   Phe
                        755                           760                           765

CCA   AGT   GTG   AAT   GTT   AGT   ATG   GAA   AAG   GTG   ATA   TTA   TCA   CCA   AAT   GAA        960
Pro   Ser   Val   Asn   Val   Ser   Met   Glu   Lys   Val   Ile   Leu   Ser   Pro   Asn   Glu
                  770                           775                           780

AAT   TTA   TCC   AAT   AGT   GTA   GAG   TCT   CAT   TCA   TCC   ACG   AAT   TGG   TCT   TAT       1008
Asn   Leu   Ser   Asn   Ser   Val   Glu   Ser   His   Ser   Ser   Thr   Asn   Trp   Ser   Tyr
            785                           790                           795

ACA   AAT   ACA   GAA   GGT   GCT   TCT   GTT   GAA   GCG   GGG   ATT   GGA   CCA   AAA   GGT       1056
Thr   Asn   Thr   Glu   Gly   Ala   Ser   Val   Glu   Ala   Gly   Ile   Gly   Pro   Lys   Gly
      800                           805                           810

ATT   TCG   TTC   GGA   GTT   AGC   GTA   AAC   TAT   CAA   CAC   TCT   GAA   ACA   GTT   GCA       1104
Ile   Ser   Phe   Gly   Val   Ser   Val   Asn   Tyr   Gln   His   Ser   Glu   Thr   Val   Ala
815                           820                           825                           830

CAA   GAA   TGG   GGA   ACA   TCT   ACA   GGA   AAT   ACT   TCG   CAA   TTC   AAT   ACG   GCT       1152
Gln   Glu   Trp   Gly   Thr   Ser   Thr   Gly   Asn   Thr   Ser   Gln   Phe   Asn   Thr   Ala
                        835                           840                           845

TCA   GCG   GGA   TAT   TTA   AAT   GCA   AAT   GTT   CGA   TAT   AAC   AAT   GTA   GGA   ACT       1200
Ser   Ala   Gly   Tyr   Leu   Asn   Ala   Asn   Val   Arg   Tyr   Asn   Asn   Val   Gly   Thr
```

|     |     |     |     |     |     |     |     |     |     |     |     |     |     |     |     |      |
|---|---|---|---|---|---|---|---|---|---|---|---|---|---|---|---|---|
|     |     |     |     | 850 |     |     |     |     | 855 |     |     |     |     | 860 |     |      |
| GGT | GCC | ATC | TAC | GAT | GTA | AAA | CCT | ACA | ACA | AGT | TTT | GTA | TTA | AAT | AAC | 1248 |
| Gly | Ala | Ile | Tyr | Asp | Val | Lys | Pro | Thr | Thr | Ser | Phe | Val | Leu | Asn | Asn |      |
|     |     | 865 |     |     |     | 870 |     |     |     | 875 |     |     |     |     |     |      |
| GAT | ACT | ATC | GCA | ACT | ATT | ACG | GCG | AAA | TCT | AAT | TCT | ACA | GCC | TTA | AAT | 1296 |
| Asp | Thr | Ile | Ala | Thr | Ile | Thr | Ala | Lys | Ser | Asn | Ser | Thr | Ala | Leu | Asn |      |
|     | 880 |     |     |     |     | 885 |     |     |     |     | 890 |     |     |     |     |      |
| ATA | TCT | CCT | GGA | GAA | AGT | TAC | CCG | AAA | AAA | GGA | CAA | AAT | GGA | ATC | GCA | 1344 |
| Ile | Ser | Pro | Gly | Glu | Ser | Tyr | Pro | Lys | Lys | Gly | Gln | Asn | Gly | Ile | Ala |      |
| 895 |     |     |     |     | 900 |     |     |     |     | 905 |     |     |     |     | 910 |      |
| ATA | ACA | TCA | ATG | GAT | GAT | TTT | AAT | TCC | CAT | CCG | ATT | ACA | TTA | AAT | AAA | 1392 |
| Ile | Thr | Ser | Met | Asp | Asp | Phe | Asn | Ser | His | Pro | Ile | Thr | Leu | Asn | Lys |      |
|     |     |     |     | 915 |     |     |     | 920 |     |     |     |     |     | 925 |     |      |
| AAA | CAA | GTA | GAT | AAT | CTG | CTA | AAT | AAT | AAA | CCT | ATG | ATG | TTG | GAA | ACA | 1440 |
| Lys | Gln | Val | Asp | Asn | Leu | Leu | Asn | Asn | Lys | Pro | Met | Met | Leu | Glu | Thr |      |
|     |     |     | 930 |     |     |     |     | 935 |     |     |     |     | 940 |     |     |      |
| AAC | CAA | ACA | GAT | GGT | GTT | TAT | AAG | ATA | AAA | GAT | ACA | CAT | GGA | AAT | ATA | 1488 |
| Asn | Gln | Thr | Asp | Gly | Val | Tyr | Lys | Ile | Lys | Asp | Thr | His | Gly | Asn | Ile |      |
|     |     | 945 |     |     |     |     | 950 |     |     |     |     | 955 |     |     |     |      |
| GTA | ACT | GGC | GGA | GAA | TGG | AAT | GGT | GTC | ATA | CAA | CAA | ATC | AAG | GCT | AAA | 1536 |
| Val | Thr | Gly | Gly | Glu | Trp | Asn | Gly | Val | Ile | Gln | Gln | Ile | Lys | Ala | Lys |      |
|     | 960 |     |     |     |     | 965 |     |     |     |     | 970 |     |     |     |     |      |
| ACA | GCG | TCT | ATT | ATT | GTG | GAT | GAT | GGG | GAA | CGT | GTA | GCA | GAA | AAA | CGT | 1584 |
| Thr | Ala | Ser | Ile | Ile | Val | Asp | Asp | Gly | Glu | Arg | Val | Ala | Glu | Lys | Arg |      |
| 975 |     |     |     |     | 980 |     |     |     |     | 985 |     |     |     |     | 990 |      |
| GTA | GCG | GCA | AAA | GAT | TAT | GAA | AAT | CCA | GAA | GAT | AAA | ACA | CCG | TCT | TTA | 1632 |
| Val | Ala | Ala | Lys | Asp | Tyr | Glu | Asn | Pro | Glu | Asp | Lys | Thr | Pro | Ser | Leu |      |
|     |     |     |     | 995 |     |     |     |     | 1000 |     |     |     |     | 1005 |     |      |
| ACT | TTA | AAA | GAT | GCC | CTG | AAG | CTT | TCA | TAT | CCA | GAT | GAA | ATA | AAA | GAA | 1680 |
| Thr | Leu | Lys | Asp | Ala | Leu | Lys | Leu | Ser | Tyr | Pro | Asp | Glu | Ile | Lys | Glu |      |
|     |     |     | 1010 |     |     |     |     | 1015 |     |     |     |     | 1020 |     |     |      |
| ATA | GAG | GGA | TTA | TTA | TAT | TAT | AAA | AAC | AAA | CCG | ATA | TAC | GAA | TCG | AGC | 1728 |
| Ile | Glu | Gly | Leu | Leu | Tyr | Tyr | Lys | Asn | Lys | Pro | Ile | Tyr | Glu | Ser | Ser |      |
|     |     | 1025 |     |     |     |     | 1030 |     |     |     |     | 1035 |     |     |     |      |
| GTT | ATG | ACT | TAC | TTA | GAT | GAA | AAT | ACA | GCA | AAA | GAA | GTG | ACC | AAA | CAA | 1776 |
| Val | Met | Thr | Tyr | Leu | Asp | Glu | Asn | Thr | Ala | Lys | Glu | Val | Thr | Lys | Gln |      |
|     | 1040 |     |     |     |     | 1045 |     |     |     |     | 1050 |     |     |     |     |      |
| TTA | AAT | GAT | ACC | ACT | GGG | AAA | TTT | AAA | GAT | GTA | AGT | CAT | TTA | TAT | GAT | 1824 |
| Leu | Asn | Asp | Thr | Thr | Gly | Lys | Phe | Lys | Asp | Val | Ser | His | Leu | Tyr | Asp |      |
| 1055 |     |     |     |     | 1060 |     |     |     |     | 1065 |     |     |     |     | 1070 |      |
| GTA | AAA | CTG | ACT | CCA | AAA | ATG | AAT | GTT | ACA | ATC | AAA | TTG | TCT | ATA | CTT | 1872 |
| Val | Lys | Leu | Thr | Pro | Lys | Met | Asn | Val | Thr | Ile | Lys | Leu | Ser | Ile | Leu |      |
|     |     |     |     | 1075 |     |     |     |     | 1080 |     |     |     |     | 1085 |     |      |
| TAT | GAT | AAT | GCT | GAG | TCT | AAT | GAT | AAC | TCA | ATT | GGT | AAA | TGG | ACA | AAC | 1920 |
| Tyr | Asp | Asn | Ala | Glu | Ser | Asn | Asp | Asn | Ser | Ile | Gly | Lys | Trp | Thr | Asn |      |
|     |     |     | 1090 |     |     |     |     | 1095 |     |     |     |     | 1100 |     |     |      |
| ACA | AAT | ATT | GTT | TCA | GGT | GGA | AAT | AAC | GGA | AAA | AAA | CAA | TAT | TCT | TCT | 1968 |
| Thr | Asn | Ile | Val | Ser | Gly | Gly | Asn | Asn | Gly | Lys | Lys | Gln | Tyr | Ser | Ser |      |
|     |     | 1105 |     |     |     |     | 1110 |     |     |     |     | 1115 |     |     |     |      |
| AAT | AAT | CCG | GAT | GCT | AAT | TTG | ACA | TTA | AAT | ACA | GAT | GCT | CAA | GAA | AAA | 2016 |
| Asn | Asn | Pro | Asp | Ala | Asn | Leu | Thr | Leu | Asn | Thr | Asp | Ala | Gln | Glu | Lys |      |
|     | 1120 |     |     |     |     | 1125 |     |     |     |     | 1130 |     |     |     |     |      |
| TTA | AAT | AAA | AAT | CGT | GAC | TAT | TAT | ATA | AGT | TTA | TAT | ATG | AAG | TCA | GAA | 2064 |
| Leu | Asn | Lys | Asn | Arg | Asp | Tyr | Tyr | Ile | Ser | Leu | Tyr | Met | Lys | Ser | Glu |      |
| 1135 |     |     |     |     | 1140 |     |     |     |     | 1145 |     |     |     |     | 1150 |      |
| AAA | AAC | ACA | CAA | TGT | GAG | ATT | ACT | ATA | GAT | GGG | GAG | ATT | TAT | CCG | ATC | 2112 |
| Lys | Asn | Thr | Gln | Cys | Glu | Ile | Thr | Ile | Asp | Gly | Glu | Ile | Tyr | Pro | Ile |      |
|     |     |     |     | 1155 |     |     |     |     | 1160 |     |     |     |     | 1165 |     |      |
| ACT | ACA | AAA | ACA | GTG | AAT | GTG | AAT | AAA | GAC | AAT | TAC | AAA | AGA | TTA | GAT | 2160 |
| Thr | Thr | Lys | Thr | Val | Asn | Val | Asn | Lys | Asp | Asn | Tyr | Lys | Arg | Leu | Asp |      |

-continued

```
                        1170                         1175                         1180
ATT  ATA  GCT  CAT  AAT  ATA  AAA  AGT  AAT  CCA  ATT  TCT  TCA  CTT  CAT  ATT         2208
Ile  Ile  Ala  His  Asn  Ile  Lys  Ser  Asn  Pro  Ile  Ser  Ser  Leu  His  Ile
               1185                    1190                         1195

AAA  ACG  AAT  GAT  GAA  ATA  ACT  TTA  TTT  TGG  GAT  GAT  ATT  TCT  ATA  ACA         2256
Lys  Thr  Asn  Asp  Glu  Ile  Thr  Leu  Phe  Trp  Asp  Asp  Ile  Ser  Ile  Thr
     1200                    1205                         1210

GAT  GTA  GCA  TCA  ATA  AAA  CCG  GAA  AAT  TTA  ACA  GAT  TCA  GAA  ATT  AAA         2304
Asp  Val  Ala  Ser  Ile  Lys  Pro  Glu  Asn  Leu  Thr  Asp  Ser  Glu  Ile  Lys
1215                    1220                         1225                         1230

CAG  ATT  TAT  AGT  AGG  TAT  GGT  ATT  AAG  TTA  GAA  GAT  GGA  ATC  CTT  ATT         2352
Gln  Ile  Tyr  Ser  Arg  Tyr  Gly  Ile  Lys  Leu  Glu  Asp  Gly  Ile  Leu  Ile
               1235                         1240                         1245

GAT  AAA  AAA  GGT  GGG  ATT  CAT  TAT  GGT  GAA  TTT  ATT  AAT  GAA  GCT  AGT         2400
Asp  Lys  Lys  Gly  Gly  Ile  His  Tyr  Gly  Glu  Phe  Ile  Asn  Glu  Ala  Ser
          1250                         1255                         1260

TTT  AAT  ATT  GAA  CCA  TTG  CAA  AAT  TAT  GTG  ACC  AAA  TAT  GAA  GTT  ACT         2448
Phe  Asn  Ile  Glu  Pro  Leu  Gln  Asn  Tyr  Val  Thr  Lys  Tyr  Glu  Val  Thr
               1265                         1270                    1275

TAT  AGT  AGT  GAG  TTA  GGA  CCA  AAC  GTG  AGT  GAC  ACA  CTT  GAA  AGT  GAT         2496
Tyr  Ser  Ser  Glu  Leu  Gly  Pro  Asn  Val  Ser  Asp  Thr  Leu  Glu  Ser  Asp
     1280                         1285                         1290

AAA  ATT  TAC  AAG  GAT  GGG  ACA  ATT  AAA  TTT  GAT  TTT  ACC  AAA  TAT  AGT         2544
Lys  Ile  Tyr  Lys  Asp  Gly  Thr  Ile  Lys  Phe  Asp  Phe  Thr  Lys  Tyr  Ser
1295                    1300                         1305                         1310

AAA  AAT  GAA  CAA  GGA  TTA  TTT  TAT  GAC  AGT  GGA  TTA  AAT  TGG  GAC  TTT         2592
Lys  Asn  Glu  Gln  Gly  Leu  Phe  Tyr  Asp  Ser  Gly  Leu  Asn  Trp  Asp  Phe
                    1315                         1320                    1325

AAA  ATT  AAT  GCT  ATT  ACT  TAT  GAT  GGT  AAA  GAG  ATG  AAT  GTT  TTT  CAT         2640
Lys  Ile  Asn  Ala  Ile  Thr  Tyr  Asp  Gly  Lys  Glu  Met  Asn  Val  Phe  His
               1330                         1335                    1340

AGA  TAT  AAT  AAA  TAG                                                                2655
Arg  Tyr  Asn  Lys
               1345
```

( 2 ) INFORMATION FOR SEQ ID NO:5:

( i ) SEQUENCE CHARACTERISTICS:
          ( A ) LENGTH: 884 amino acids
          ( B ) TYPE: amino acid
          ( D ) TOPOLOGY: linear ( i i ) MOLECULE TYPE: protein ( x i ) SEQUENCE DESCRIPTION: SEQ ID NO:5:

```
Met  Lys  Asn  Met  Lys  Lys  Lys  Leu  Ala  Ser  Val  Val  Thr  Cys  Thr  Leu
 1                    5                         10                        15

Leu  Ala  Pro  Met  Phe  Leu  Asn  Gly  Asn  Val  Asn  Ala  Val  Tyr  Ala  Asp
               20                        25                        30

Ser  Lys  Thr  Asn  Gln  Ile  Ser  Thr  Thr  Gln  Lys  Asn  Gln  Gln  Lys  Glu
          35                        40                        45

Met  Asp  Arg  Lys  Gly  Leu  Leu  Gly  Tyr  Tyr  Phe  Lys  Gly  Lys  Asp  Phe
     50                        55                        60

Ser  Asn  Leu  Thr  Met  Phe  Ala  Pro  Thr  Arg  Asp  Ser  Thr  Leu  Ile  Tyr
 65                        70                        75                        80

Asp  Gln  Gln  Thr  Ala  Asn  Lys  Leu  Leu  Asp  Lys  Lys  Gln  Gln  Glu  Tyr
                    85                        90                        95

Gln  Ser  Ile  Arg  Trp  Ile  Gly  Leu  Ile  Gln  Ser  Lys  Glu  Thr  Gly  Asp
                    100                       105                       110

Phe  Thr  Phe  Asn  Leu  Ser  Glu  Asp  Glu  Gln  Ala  Ile  Ile  Glu  Ile  Asn
```

|  |  |  | 115 |  |  |  | 120 |  |  |  | 125 |  |  |
|---|---|---|---|---|---|---|---|---|---|---|---|---|---|
| Gly | Lys 130 | Ile | Ile | Ser | Asn | Lys 135 | Gly | Lys | Glu | Lys 140 | Gln | Val | Val | His | Leu |
| Glu | Lys 145 | Gly | Lys | Leu | Val 150 | Pro | Ile | Lys | Ile 155 | Glu | Tyr | Gln | Ser | Asp 160 | Thr |
| Lys | Phe | Asn | Ile | Asp 165 | Ser | Lys | Thr | Phe | Lys 170 | Glu | Leu | Lys | Leu | Phe 175 | Lys |
| Ile | Asp | Ser | Gln 180 | Asn | Gln | Pro | Gln | Gln 185 | Val | Gln | Gln | Asp | Glu 190 | Leu | Arg |
| Asn | Pro | Glu 195 | Phe | Asn | Lys | Lys | Glu 200 | Ser | Gln | Glu | Phe | Leu 205 | Ala | Lys | Pro |
| Ser | Lys 210 | Ile | Asn | Leu | Phe | Thr 215 | Gln | Lys | Met | Lys | Arg 220 | Glu | Ile | Asp | Glu |
| Asp 225 | Thr | Asp | Thr | Asp | Gly 230 | Asp | Ser | Ile | Pro | Asp 235 | Leu | Trp | Glu | Glu | Asn 240 |
| Gly | Tyr | Thr | Ile | Gln 245 | Asn | Arg | Ile | Ala | Val 250 | Lys | Trp | Asp | Asp | Ser 255 | Leu |
| Ala | Ser | Lys | Gly 260 | Tyr | Thr | Lys | Phe | Val 265 | Ser | Asn | Pro | Leu | Glu 270 | Ser | His |
| Thr | Val | Gly 275 | Asp | Pro | Tyr | Thr | Asp 280 | Tyr | Glu | Lys | Ala | Ala 285 | Arg | Asp | Leu |
| Asp | Leu 290 | Ser | Asn | Ala | Lys | Glu 295 | Thr | Phe | Asn | Pro | Leu 300 | Val | Ala | Ala | Phe |
| Pro 305 | Ser | Val | Asn | Val | Ser 310 | Met | Glu | Lys | Val | Ile 315 | Leu | Ser | Pro | Asn | Glu 320 |
| Asn | Leu | Ser | Asn | Ser 325 | Val | Glu | Ser | His | Ser 330 | Ser | Thr | Asn | Trp | Ser 335 | Tyr |
| Thr | Asn | Thr | Glu 340 | Gly | Ala | Ser | Val | Glu 345 | Ala | Gly | Ile | Gly | Pro 350 | Lys | Gly |
| Ile | Ser | Phe 355 | Gly | Val | Ser | Val | Asn 360 | Tyr | Gln | His | Ser | Glu 365 | Thr | Val | Ala |
| Gln | Glu 370 | Trp | Gly | Thr | Ser | Thr 375 | Gly | Asn | Thr | Ser | Gln 380 | Phe | Asn | Thr | Ala |
| Ser 385 | Ala | Gly | Tyr | Leu | Asn 390 | Ala | Asn | Val | Arg | Tyr 395 | Asn | Asn | Val | Gly | Thr 400 |
| Gly | Ala | Ile | Tyr | Asp 405 | Val | Lys | Pro | Thr | Thr 410 | Ser | Phe | Val | Leu | Asn 415 | Asn |
| Asp | Thr | Ile | Ala 420 | Thr | Ile | Thr | Ala | Lys 425 | Ser | Asn | Ser | Thr | Ala 430 | Leu | Asn |
| Ile | Ser | Pro 435 | Gly | Glu | Ser | Tyr | Pro 440 | Lys | Lys | Gly | Gln | Asn 445 | Gly | Ile | Ala |
| Ile | Thr 450 | Ser | Met | Asp | Asp | Phe 455 | Asn | Ser | His | Pro | Ile 460 | Thr | Leu | Asn | Lys |
| Lys 465 | Gln | Val | Asp | Asn | Leu 470 | Leu | Asn | Asn | Lys | Pro 475 | Met | Met | Leu | Glu | Thr 480 |
| Asn | Gln | Thr | Asp | Gly 485 | Val | Tyr | Lys | Ile | Lys 490 | Asp | Thr | His | Gly | Asn 495 | Ile |
| Val | Thr | Gly | Gly 500 | Glu | Trp | Asn | Gly | Val 505 | Ile | Gln | Gln | Ile | Lys 510 | Ala | Lys |
| Thr | Ala | Ser | Ile 515 | Ile | Val | Asp | Asp | Gly 520 | Glu | Arg | Val | Ala 525 | Glu | Lys | Arg |
| Val | Ala | Ala | Lys 530 | Asp | Tyr | Glu | Asn | Pro 535 | Glu | Asp | Lys | Thr 540 | Pro | Ser | Leu |

| | | | | | | | | | | | | | | |
|---|---|---|---|---|---|---|---|---|---|---|---|---|---|---|
| Thr | Leu | Lys | Asp | Ala | Leu | Lys | Leu | Ser | Tyr | Pro | Asp | Glu | Ile | Lys | Glu |
| 545 | | | | 550 | | | | | 555 | | | | | 560 |
| Ile | Glu | Gly | Leu | Leu | Tyr | Tyr | Lys | Asn | Lys | Pro | Ile | Tyr | Glu | Ser | Ser |
| | | | | 565 | | | | | 570 | | | | | 575 |
| Val | Met | Thr | Tyr | Leu | Asp | Glu | Asn | Thr | Ala | Lys | Glu | Val | Thr | Lys | Gln |
| | | | 580 | | | | | 585 | | | | | 590 | | |
| Leu | Asn | Asp | Thr | Thr | Gly | Lys | Phe | Lys | Asp | Val | Ser | His | Leu | Tyr | Asp |
| | | 595 | | | | | 600 | | | | | 605 | | | |
| Val | Lys | Leu | Thr | Pro | Lys | Met | Asn | Val | Thr | Ile | Lys | Leu | Ser | Ile | Leu |
| | 610 | | | | | 615 | | | | | 620 | | | | |
| Tyr | Asp | Asn | Ala | Glu | Ser | Asn | Asp | Asn | Ser | Ile | Gly | Lys | Trp | Thr | Asn |
| 625 | | | | | 630 | | | | | 635 | | | | | 640 |
| Thr | Asn | Ile | Val | Ser | Gly | Gly | Asn | Asn | Gly | Lys | Lys | Gln | Tyr | Ser | Ser |
| | | | | 645 | | | | | 650 | | | | | 655 | |
| Asn | Asn | Pro | Asp | Ala | Asn | Leu | Thr | Leu | Asn | Thr | Asp | Ala | Gln | Glu | Lys |
| | | | 660 | | | | 665 | | | | | 670 | | | |
| Leu | Asn | Lys | Asn | Arg | Asp | Tyr | Tyr | Ile | Ser | Leu | Tyr | Met | Lys | Ser | Glu |
| | | 675 | | | | | 680 | | | | | 685 | | | |
| Lys | Asn | Thr | Gln | Cys | Glu | Ile | Thr | Ile | Asp | Gly | Glu | Ile | Tyr | Pro | Ile |
| | 690 | | | | | 695 | | | | | 700 | | | | |
| Thr | Thr | Lys | Thr | Val | Asn | Val | Asn | Lys | Asp | Asn | Tyr | Lys | Arg | Leu | Asp |
| 705 | | | | | 710 | | | | | 715 | | | | | 720 |
| Ile | Ile | Ala | His | Asn | Ile | Lys | Ser | Asn | Pro | Ile | Ser | Ser | Leu | His | Ile |
| | | | | 725 | | | | | 730 | | | | | 735 | |
| Lys | Thr | Asn | Asp | Glu | Ile | Thr | Leu | Phe | Trp | Asp | Asp | Ile | Ser | Ile | Thr |
| | | | 740 | | | | | 745 | | | | | 750 | | |
| Asp | Val | Ala | Ser | Ile | Lys | Pro | Glu | Asn | Leu | Thr | Asp | Ser | Glu | Ile | Lys |
| | | | 755 | | | | | 760 | | | | | 765 | | |
| Gln | Ile | Tyr | Ser | Arg | Tyr | Gly | Ile | Lys | Leu | Glu | Asp | Gly | Ile | Leu | Ile |
| | 770 | | | | | 775 | | | | | 780 | | | | |
| Asp | Lys | Lys | Gly | Gly | Ile | His | Tyr | Gly | Glu | Phe | Ile | Asn | Glu | Ala | Ser |
| 785 | | | | | 790 | | | | | 795 | | | | | 800 |
| Phe | Asn | Ile | Glu | Pro | Leu | Gln | Asn | Tyr | Val | Thr | Lys | Tyr | Glu | Val | Thr |
| | | | | 805 | | | | | 810 | | | | | 815 | |
| Tyr | Ser | Ser | Glu | Leu | Gly | Pro | Asn | Val | Ser | Asp | Thr | Leu | Glu | Ser | Asp |
| | | | 820 | | | | | 825 | | | | | 830 | | |
| Lys | Ile | Tyr | Lys | Asp | Gly | Thr | Ile | Lys | Phe | Asp | Phe | Thr | Lys | Tyr | Ser |
| | | | 835 | | | | | 840 | | | | | 845 | | |
| Lys | Asn | Glu | Gln | Gly | Leu | Phe | Tyr | Asp | Ser | Gly | Leu | Asn | Trp | Asp | Phe |
| | | | 850 | | | | | 855 | | | | | 860 | | |
| Lys | Ile | Asn | Ala | Ile | Thr | Tyr | Asp | Gly | Lys | Glu | Met | Asn | Val | Phe | His |
| 865 | | | | | 870 | | | | | 875 | | | | | 880 |
| Arg | Tyr | Asn | Lys | | | | | | | | | | | | |

( 2 ) INFORMATION FOR SEQ ID NO:6:

( i ) SEQUENCE CHARACTERISTICS:
    ( A ) LENGTH: 2004 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Bacillus cereus
  ( B ) STRAIN: AB78
  ( C ) INDIVIDUAL ISOLATE: NRRL B- 21058

( i x ) FEATURE:
( A ) NAME/KEY: CDS
( B ) LOCATION: 1..2001
( D ) OTHER INFORMATION: /product="80 kDa protein VIP1A(a)"
/ note= "This sequence is identical to that found in SEQ ID NO:1 between and including nucleotide positions 3126 and 5126"

( x i ) SEQUENCE DESCRIPTION: SEQ ID NO:6:

ATG AAA AGG GAA ATT GAT GAA GAC ACG GAT ACG GAT GGG GAC TCT ATT 48
Met Lys Arg Glu Ile Asp Glu Asp Thr Asp Thr Asp Gly Asp Ser Ile
885 890 895 900

CCT GAC CTT TGG GAA GAA AAT GGG TAT ACG ATT CAA AAT AGA ATC GCT 96
Pro Asp Leu Trp Glu Glu Asn Gly Tyr Thr Ile Gln Asn Arg Ile Ala
905 910 915

GTA AAG TGG GAC GAT TCT CTA GCA AGT AAA GGG TAT ACG AAA TTT GTT 144
Val Lys Trp Asp Asp Ser Leu Ala Ser Lys Gly Tyr Thr Lys Phe Val
920 925 930

TCA AAT CCA CTA GAA AGT CAC ACA GTT GGT GAT CCT TAT ACA GAT TAT 192
Ser Asn Pro Leu Glu Ser His Thr Val Gly Asp Pro Tyr Thr Asp Tyr
935 940 945

GAA AAG GCA GCA AGA GAT CTA GAT TTG TCA AAT GCA AAG GAA ACG TTT 240
Glu Lys Ala Ala Arg Asp Leu Asp Leu Ser Asn Ala Lys Glu Thr Phe
950 955 960

AAC CCA TTG GTA GCT GCT TTT CCA AGT GTG AAT GTT AGT ATG GAA AAG 288
Asn Pro Leu Val Ala Ala Phe Pro Ser Val Asn Val Ser Met Glu Lys
965 970 975 980

GTG ATA TTA TCA CCA AAT GAA AAT TTA TCC AAT AGT GTA GAG TCT CAT 336
Val Ile Leu Ser Pro Asn Glu Asn Leu Ser Asn Ser Val Glu Ser His
985 990 995

TCA TCC ACG AAT TGG TCT TAT ACA AAT ACA GAA GGT GCT TCT GTT GAA 384
Ser Ser Thr Asn Trp Ser Tyr Thr Asn Thr Glu Gly Ala Ser Val Glu
1000 1005 1010

GCG GGG ATT GGA CCA AAA GGT ATT TCG TTC GGA GTT AGC GTA AAC TAT 432
Ala Gly Ile Gly Pro Lys Gly Ile Ser Phe Gly Val Ser Val Asn Tyr
1015 1020 1025

CAA CAC TCT GAA ACA GTT GCA CAA GAA TGG GGA ACA TCT ACA GGA AAT 480
Gln His Ser Glu Thr Val Ala Gln Glu Trp Gly Thr Ser Thr Gly Asn
1030 1035 1040

ACT TCG CAA TTC AAT ACG GCT TCA GCG GGA TAT TTA AAT GCA AAT GTT 528
Thr Ser Gln Phe Asn Thr Ala Ser Ala Gly Tyr Leu Asn Ala Asn Val
1045 1050 1055 1060

CGA TAT AAC AAT GTA GGA ACT GGT GCC ATC TAC GAT GTA AAA CCT ACA 576
Arg Tyr Asn Asn Val Gly Thr Gly Ala Ile Tyr Asp Val Lys Pro Thr
1065 1070 1075

ACA AGT TTT GTA TTA AAT AAC GAT ACT ATC GCA ACT ATT ACG GCG AAA 624
Thr Ser Phe Val Leu Asn Asn Asp Thr Ile Ala Thr Ile Thr Ala Lys
1080 1085 1090

TCT AAT TCT ACA GCC TTA AAT ATA TCT CCT GGA GAA AGT TAC CCG AAA 672
Ser Asn Ser Thr Ala Leu Asn Ile Ser Pro Gly Glu Ser Tyr Pro Lys
1095 1100 1105

AAA GGA CAA AAT GGA ATC GCA ATA ACA TCA ATG GAT GAT TTT AAT TCC 720
Lys Gly Gln Asn Gly Ile Ala Ile Thr Ser Met Asp Asp Phe Asn Ser
1110 1115 1120

CAT CCG ATT ACA TTA AAT AAA AAA CAA GTA GAT AAT CTG CTA AAT AAT 768
His Pro Ile Thr Leu Asn Lys Lys Gln Val Asp Asn Leu Leu Asn Asn
1125 1130 1135 1140

AAA CCT ATG ATG TTG GAA ACA AAC CAA ACA GAT GGT GTT TAT AAG ATA 816

```
                                                            -continued

Lys Pro Met Met Leu Glu Thr Asn Gln Thr Asp Gly Val Tyr Lys Ile
            1145                1150                1155

AAA GAT ACA CAT GGA AAT ATA GTA ACT GGC GGA GAA TGG AAT GGT GTC         864
Lys Asp Thr His Gly Asn Ile Val Thr Gly Gly Glu Trp Asn Gly Val
            1160                1165                1170

ATA CAA CAA ATC AAG GCT AAA ACA GCG TCT ATT ATT GTG GAT GAT GGG         912
Ile Gln Gln Ile Lys Ala Lys Thr Ala Ser Ile Ile Val Asp Asp Gly
            1175                1180                1185

GAA CGT GTA GCA GAA AAA CGT GTA GCG GCA AAA GAT TAT GAA AAT CCA         960
Glu Arg Val Ala Glu Lys Arg Val Ala Ala Lys Asp Tyr Glu Asn Pro
            1190                1195                1200

GAA GAT AAA ACA CCG TCT TTA ACT TTA AAA GAT GCC CTG AAG CTT TCA        1008
Glu Asp Lys Thr Pro Ser Leu Thr Leu Lys Asp Ala Leu Lys Leu Ser
1205            1210                1215                1220

TAT CCA GAT GAA ATA AAA GAA ATA GAG GGA TTA TTA TAT TAT AAA AAC        1056
Tyr Pro Asp Glu Ile Lys Glu Ile Glu Gly Leu Leu Tyr Tyr Lys Asn
            1225                1230                1235

AAA CCG ATA TAC GAA TCG AGC GTT ATG ACT TAC TTA GAT GAA AAT ACA        1104
Lys Pro Ile Tyr Glu Ser Ser Val Met Thr Tyr Leu Asp Glu Asn Thr
            1240                1245                1250

GCA AAA GAA GTG ACC AAA CAA TTA AAT GAT ACC ACT GGG AAA TTT AAA        1152
Ala Lys Glu Val Thr Lys Gln Leu Asn Asp Thr Thr Gly Lys Phe Lys
            1255                1260                1265

GAT GTA AGT CAT TTA TAT GAT GTA AAA CTG ACT CCA AAA ATG AAT GTT        1200
Asp Val Ser His Leu Tyr Asp Val Lys Leu Thr Pro Lys Met Asn Val
            1270                1275                1280

ACA ATC AAA TTG TCT ATA CTT TAT GAT AAT GCT GAG TCT AAT GAT AAC        1248
Thr Ile Lys Leu Ser Ile Leu Tyr Asp Asn Ala Glu Ser Asn Asp Asn
1285            1290                1295                1300

TCA ATT GGT AAA TGG ACA AAC ACA AAT ATT GTT TCA GGT GGA AAT AAC        1296
Ser Ile Gly Lys Trp Thr Asn Thr Asn Ile Val Ser Gly Gly Asn Asn
            1305                1310                1315

GGA AAA AAA CAA TAT TCT TCT AAT AAT CCG GAT GCT AAT TTG ACA TTA        1344
Gly Lys Lys Gln Tyr Ser Ser Asn Asn Pro Asp Ala Asn Leu Thr Leu
            1320                1325                1330

AAT ACA GAT GCT CAA GAA AAA TTA AAT AAA AAT CGT GAC TAT TAT ATA        1392
Asn Thr Asp Ala Gln Glu Lys Leu Asn Lys Asn Arg Asp Tyr Tyr Ile
            1335                1340                1345

AGT TTA TAT ATG AAG TCA GAA AAA AAC ACA CAA TGT GAG ATT ACT ATA        1440
Ser Leu Tyr Met Lys Ser Glu Lys Asn Thr Gln Cys Glu Ile Thr Ile
1350            1355                1360

GAT GGG GAG ATT TAT CCG ATC ACT ACA AAA ACA GTG AAT GTG AAT AAA        1488
Asp Gly Glu Ile Tyr Pro Ile Thr Thr Lys Thr Val Asn Val Asn Lys
1365            1370                1375                1380

GAC AAT TAC AAA AGA TTA GAT ATT ATA GCT CAT AAT ATA AAA AGT AAT        1536
Asp Asn Tyr Lys Arg Leu Asp Ile Ile Ala His Asn Ile Lys Ser Asn
            1385                1390                1395

CCA ATT TCT TCA CTT CAT ATT AAA ACG AAT GAT GAA ATA ACT TTA TTT        1584
Pro Ile Ser Ser Leu His Ile Lys Thr Asn Asp Glu Ile Thr Leu Phe
            1400                1405                1410

TGG GAT GAT ATT TCT ATA ACA GAT GTA GCA TCA ATA AAA CCG GAA AAT        1632
Trp Asp Asp Ile Ser Ile Thr Asp Val Ala Ser Ile Lys Pro Glu Asn
            1415                1420                1425

TTA ACA GAT TCA GAA ATT AAA CAG ATT TAT AGT AGG TAT GGT ATT AAG        1680
Leu Thr Asp Ser Glu Ile Lys Gln Ile Tyr Ser Arg Tyr Gly Ile Lys
            1430                1435                1440

TTA GAA GAT GGA ATC CTT ATT GAT AAA AAA GGT GGG ATT CAT TAT GGT        1728
Leu Glu Asp Gly Ile Leu Ile Asp Lys Lys Gly Gly Ile His Tyr Gly
1445            1450                1455                1460

GAA TTT ATT AAT GAA GCT AGT TTT AAT ATT GAA CCA TTG CCA AAT TAT        1776
```

```
Glu  Phe  Ile  Asn  Glu  Ala  Ser  Phe  Asn  Ile  Glu  Pro  Leu  Pro  Asn  Tyr
               1465                    1470                    1475

GTG  ACC  AAA  TAT  GAA  GTT  ACT  TAT  AGT  AGT  GAG  TTA  GGA  CCA  AAC  GTG          1824
Val  Thr  Lys  Tyr  Glu  Val  Thr  Tyr  Ser  Ser  Glu  Leu  Gly  Pro  Asn  Val
               1480                    1485                    1490

AGT  GAC  ACA  CTT  GAA  AGT  GAT  AAA  ATT  TAC  AAG  GAT  GGG  ACA  ATT  AAA          1872
Ser  Asp  Thr  Leu  Glu  Ser  Asp  Lys  Ile  Tyr  Lys  Asp  Gly  Thr  Ile  Lys
               1495                    1500                    1505

TTT  GAT  TTT  ACC  AAA  TAT  AGT  AAA  AAT  GAA  CAA  GGA  TTA  TTT  TAT  GAC          1920
Phe  Asp  Phe  Thr  Lys  Tyr  Ser  Lys  Asn  Glu  Gln  Gly  Leu  Phe  Tyr  Asp
               1510                    1515                    1520

AGT  GGA  TTA  AAT  TGG  GAC  TTT  AAA  ATT  AAT  GCT  ATT  ACT  TAT  GAT  GGT          1968
Ser  Gly  Leu  Asn  Trp  Asp  Phe  Lys  Ile  Asn  Ala  Ile  Thr  Tyr  Asp  Gly
1525                     1530                    1535                    1540

AAA  GAG  ATG  AAT  GTT  TTT  CAT  AGA  TAT  AAT  AAA  TAG                              2004
Lys  Glu  Met  Asn  Val  Phe  His  Arg  Tyr  Asn  Lys
               1545                    1550
```

(2) INFORMATION FOR SEQ ID NO:7:

(i) SEQUENCE CHARACTERISTICS:
    (A) LENGTH: 667 amino acids
    (B) TYPE: amino acid
    (D) TOPOLOGY: linear (ii) MOLECULE TYPE: protein (xi) SEQUENCE DESCRIPTION: SEQ ID NO:7:

```
Met  Lys  Arg  Glu  Ile  Asp  Glu  Asp  Thr  Asp  Thr  Asp  Gly  Asp  Ser  Ile
 1                   5                   10                      15

Pro  Asp  Leu  Trp  Glu  Glu  Asn  Gly  Tyr  Thr  Ile  Gln  Asn  Arg  Ile  Ala
               20                   25                      30

Val  Lys  Trp  Asp  Asp  Ser  Leu  Ala  Ser  Lys  Gly  Tyr  Thr  Lys  Phe  Val
               35                   40                      45

Ser  Asn  Pro  Leu  Glu  Ser  His  Thr  Val  Gly  Asp  Pro  Tyr  Thr  Asp  Tyr
               50                   55                      60

Glu  Lys  Ala  Ala  Arg  Asp  Leu  Asp  Leu  Ser  Asn  Ala  Lys  Glu  Thr  Phe
 65                  70                   75                        80

Asn  Pro  Leu  Val  Ala  Ala  Phe  Pro  Ser  Val  Asn  Val  Ser  Met  Glu  Lys
               85                   90                      95

Val  Ile  Leu  Ser  Pro  Asn  Glu  Asn  Leu  Ser  Asn  Ser  Val  Glu  Ser  His
               100                  105                     110

Ser  Ser  Thr  Asn  Trp  Ser  Tyr  Thr  Asn  Thr  Glu  Gly  Ala  Ser  Val  Glu
               115                  120                     125

Ala  Gly  Ile  Gly  Pro  Lys  Gly  Ile  Ser  Phe  Gly  Val  Ser  Val  Asn  Tyr
               130                  135                     140

Gln  His  Ser  Glu  Thr  Val  Ala  Gln  Glu  Trp  Gly  Thr  Ser  Thr  Gly  Asn
145                  150                  155                     160

Thr  Ser  Gln  Phe  Asn  Thr  Ala  Ser  Ala  Gly  Tyr  Leu  Asn  Ala  Asn  Val
               165                  170                     175

Arg  Tyr  Asn  Asn  Val  Gly  Thr  Gly  Ala  Ile  Tyr  Asp  Val  Lys  Pro  Thr
               180                  185                     190

Thr  Ser  Phe  Val  Leu  Asn  Asn  Asp  Thr  Ile  Ala  Thr  Ile  Thr  Ala  Lys
               195                  200                     205

Ser  Asn  Ser  Thr  Ala  Leu  Asn  Ile  Ser  Pro  Gly  Glu  Ser  Tyr  Pro  Lys
               210                  215                     220

Lys  Gly  Gln  Asn  Gly  Ile  Ala  Ile  Thr  Ser  Met  Asp  Asp  Phe  Asn  Ser
225                  230                  235                     240
```

His Pro Ile Thr Leu Asn Lys Lys Gln Val Asp Asn Leu Leu Asn
            245                 250                 255
Lys Pro Met Met Leu Glu Thr Asn Thr Asp Gly Val Tyr Lys Ile
            260                 265                 270
Lys Asp Thr His Gly Asn Ile Val Thr Gly Gly Glu Trp Asn Gly Val
            275                 280                 285
Ile Gln Gln Ile Lys Ala Lys Thr Ala Ser Ile Ile Val Asp Asp Gly
            290                 295                 300
Glu Arg Val Ala Glu Lys Arg Val Ala Ala Lys Asp Tyr Glu Asn Pro
305                 310                 315                 320
Glu Asp Lys Thr Pro Ser Leu Thr Leu Lys Asp Ala Leu Lys Leu Ser
                325                 330                 335
Tyr Pro Asp Glu Ile Lys Glu Ile Glu Gly Leu Leu Tyr Tyr Lys Asn
            340                 345                 350
Lys Pro Ile Tyr Glu Ser Ser Val Met Thr Tyr Leu Asp Glu Asn Thr
            355                 360                 365
Ala Lys Glu Val Thr Lys Gln Leu Asn Asp Thr Thr Gly Lys Phe Lys
            370                 375                 380
Asp Val Ser His Leu Tyr Asp Val Lys Leu Thr Pro Lys Met Asn Val
385                 390                 395                 400
Thr Ile Lys Leu Ser Ile Leu Tyr Asp Asn Ala Glu Ser Asn Asp Asn
                405                 410                 415
Ser Ile Gly Lys Trp Thr Asn Thr Asn Ile Val Ser Gly Gly Asn Asn
            420                 425                 430
Gly Lys Lys Gln Tyr Ser Ser Asn Pro Asp Ala Asn Leu Thr Leu
            435                 440                 445
Asn Thr Asp Ala Gln Glu Lys Leu Asn Lys Asn Arg Asp Tyr Tyr Ile
    450                 455                 460
Ser Leu Tyr Met Lys Ser Glu Lys Asn Thr Gln Cys Glu Ile Thr Ile
465                 470                 475                 480
Asp Gly Glu Ile Tyr Pro Ile Thr Thr Lys Thr Val Asn Val Asn Lys
                485                 490                 495
Asp Asn Tyr Lys Arg Leu Asp Ile Ile Ala His Asn Ile Lys Ser Asn
            500                 505                 510
Pro Ile Ser Ser Leu His Ile Lys Thr Asn Asp Glu Ile Thr Leu Phe
            515                 520                 525
Trp Asp Asp Ile Ser Ile Thr Asp Val Ala Ser Ile Lys Pro Glu Asn
530                 535                 540
Leu Thr Asp Ser Glu Ile Lys Gln Ile Tyr Ser Arg Tyr Gly Ile Lys
545                 550                 555                 560
Leu Glu Asp Gly Ile Leu Ile Asp Lys Lys Gly Gly Ile His Tyr Gly
                565                 570                 575
Glu Phe Ile Asn Glu Ala Ser Phe Asn Ile Glu Pro Leu Pro Asn Tyr
            580                 585                 590
Val Thr Lys Tyr Glu Val Thr Tyr Ser Ser Glu Leu Gly Pro Asn Val
            595                 600                 605
Ser Asp Thr Leu Glu Ser Asp Lys Ile Tyr Lys Asp Gly Thr Ile Lys
    610                 615                 620
Phe Asp Phe Thr Lys Tyr Ser Lys Asn Glu Gln Gly Leu Phe Tyr Asp
625                 630                 635                 640
Ser Gly Leu Asn Trp Asp Phe Lys Ile Asn Ala Ile Thr Tyr Asp Gly
                645                 650                 655
Lys Glu Met Asn Val Phe His Arg Tyr Asn Lys
            660                 665

(2) INFORMATION FOR SEQ ID NO:8:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: N-terminal (vi) ORIGINAL SOURCE:
        (A) ORGANISM: Bacillus cereus
        (B) STRAIN: AB78
        (C) INDIVIDUAL ISOLATE: NRRL B- 21058

(ix) FEATURE:
        (A) NAME/KEY: Peptide
   &n ( D ) OTHER INFORMATION: /note= "N-terminal amino acid
sequence of protein known as anion exchange fraction 23
( s m a l l e r )"

( x i ) SEQUENCE DESCRIPTION: SEQ ID NO:10:

Xaa  Glu  Pro  Phe  Val  Ser  Ala  Xaa  Xaa  Xaa  Gln  Xaa  Xaa  Xaa
1                       5                          10

( 2 ) INFORMATION FOR SEQ ID NO:11:

( i ) SEQUENCE CHARACTERISTICS:
    ( A ) LENGTH: 13 amino acids
    ( B ) TYPE: amino acid
    ( C ) STRANDEDNESS: single
    ( D ) TOPOLOGY: linear ( v i ) ORIGINAL SOURCE:
    ( A ) ORGANISM: Bacillus thuringiensis ( x i ) SEQUENCE DESCRIPTION: SEQ ID NO:11:

Xaa  Glu  Tyr  Glu  Asn  Val  Glu  Pro  Phe  Val  Ser  Ala  Xaa
1                       5                          10

( 2 ) INFORMATION FOR SEQ ID NO:12:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: linear ( v i ) ORIGINAL SOURCE:
    ( A ) ORGANISM: Bacillus thurigiensis ( x i ) SEQUENCE DESCRIPTION: SEQ ID NO:12:

Met  Asn  Lys  Asn  Asn  Thr  Lys  Leu  Pro  Thr  Arg  Ala  Leu  Pro
1                       5                          10

( 2 ) INFORMATION FOR SEQ ID NO:13:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
    ( A ) ORGANISM: Bacillus thuringiensis
    ( B ) STRAIN: AB88

( i x ) FEATURE:
    ( A ) NAME/KEY: Peptide
    ( B ) LOCATION: 1..15
    ( D ) OTHER INFORMATION: /note= "N-terminal amino acid
sequence of 35 kDa VIP active against Agrotis ipsilon"

( x i ) SEQUENCE DESCRIPTION: SEQ ID NO:13:

Ala  Leu  Ser  Glu  Asn  Thr  Gly  Lys  Asp  Gly  Gly  Tyr  Ile  Val  Pro
1                       5                          10                         15

( 2 ) INFORMATION FOR SEQ ID NO:14:

( i ) SEQUENCE CHARACTERISTICS:
    ( A ) LENGTH: 9 amino acids
    ( B ) TYPE: amino acid
    ( C ) STRANDEDNESS: single (D) TOPOLOGY: linear (vi) ORIGINAL SOURCE:
    (A) ORGANISM: Bacillus thuringiensis (xi) SEQUENCE DESCRIPTION: SEQ ID NO:14:

Met Asp Asn Asn Pro Asn Ile Asn Glu
1 5

(2) INFORMATION FOR SEQ ID NO:15:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (iii) HYPOTHETICAL: NO (v) FRAGMENT TYPE: N-terminal (ix) FEATURE:
(A) NAME/KEY: Peptide
(B) LOCATION: 1..9
(D) OTHER INFORMATION: /note= "N-terminal sequence of 80 kDa delta- endotoxin"

(xi) SEQUENCE DESCRIPTION: SEQ ID NO:15:

Met Asp Asn Asn Pro Asn Ile Asn Glu
1 5

(2) INFORMATION FOR SEQ ID NO:16:

(i) SEQUENCE CHARACTERISTICS:
(A) LENGTH: 11 amino acids
(B) TYPE: amino acid
(C) STRANDEDNESS: single
(D) TOPOLOGY: linear (ii) MOLECULE TYPE: peptide (iii) HYPOTHETICAL: NO (v) FRAGMENT TYPE: N-terminal (vi) ORIGINAL SOURCE:
(A) ORGANISM: Bacillus thuringiensis (ix) FEATURE:
(A) NAME/KEY: Peptide
(B) LOCATION: 1..11
(D) OTHER INFORMATION: /note= "N-terminal sequence from 60 kDa delta- endotoxin"

(xi) SEQUENCE DESCRIPTION: SEQ ID NO:16:

Met Asn Val Leu Asn Ser Gly Arg Thr Thr Ile
1 5 10

(2) INFORMATION FOR SEQ ID NO:17:

(i) SEQUENCE CHARACTERISTICS:
(A) LENGTH: 2655 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO

– continued ( i x ) FEATURE:
    ( A ) NAME/KEY: misc_feature
    ( B ) LOCATION: 1..2652
    ( D ) OTHER INFORMATION: /note= "Maize optimized DNA sequence for 100 kd VIP1A(a) protein from AB78"

( x i ) SEQUENCE DESCRIPTION: SEQ ID NO:17:

| | | | | | | |
|---|---|---|---|---|---|---|
| ATGAA

-continued

| | | | | | | |
|---|---|---|---|---|---|---|
| ATCATCGCCC | ACAACATCAA | GAGCAACCCC | ATCAGCAGCC | TGCACATCAA | GACCAACGAC | 2220 |
| GAGATCACCC | TGTTCTGGGA | CGACATATCG | ATTACCGACG | TCGCCAGCAT | CAAGCCCGAG | 2280 |
| AACCTGACCG | ACAGCGAGAT | CAAGCAGATA | TACAGTCGCT | ACGGCATCAA | GCTGGAGGAC | 2340 |
| GGCATCCTGA | TCGACAAGAA | GGGCGGCATC | CACTACGGCG | AGTTCATCAA | CGAGGCCAGC | 2400 |
| TTCAACATCG | AGCCCCTGCA | GAACTACGTG | ACCAAGTACG | AGGTGACCTA | CAGCAGCGAG | 2460 |
| CTGGGCCCCA | ACGTGAGCGA | CACCCTGGAG | AGCGACAAGA | TTTACAAGGA | CGGCACCATC | 2520 |
| AAGTTCGACT | TCACCAAGTA | CAGCAAGAAC | GAGCAGGGCC | TGTTCTACGA | CAGCGGCCTG | 2580 |
| AACTGGGACT | TCAAGATCAA | CGCCATCACC | TACGACGGCA | AGGAGATGAA | CGTGTTCCAC | 2640 |
| CGCTACAACA | AGTAG | | | | | 2655 |

( 2 ) INFORMATION FOR SEQ ID NO:18:

( i ) SEQUENCE CHARACTERISTICS:
( A ) LENGTH: 2004 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
( A ) NAME/KEY: misc_feature
( B ) LOCATION: 1..2004
( D ) OTHER INFORMATION: /note= "Maize optimized DNA sequence for VIP1A(a) 80 kd protein from AB78"

( x i ) SEQUENCE DESCRIPTION: SEQ ID NO:18:

| | | | | | | |
|---|---|---|---|---|---|---|
| ATGAAGCGCG | AGATCGACGA | GGACACCGAC | ACCGACGGCG | ACAGCATCCC | CGACCTGTGG | 60 |
| GAGGAGAACG | GCTACACCAT | CCAGAACCGC | ATCGCCGTGA | AGTGGGACGA | CAGCCTGGCT | 120 |
| AGCAAGGGCT | ACACCAAGTT | CGTGAGCAAC | CCCCTGGAGA | GCCACACCGT | GGGCGACCCC | 180 |
| TACACCGACT | ACGAGAAGGC | CGCCCGCGAC | CTGGACCTGA | GCAACGCCAA | GGAGACCTTC | 240 |
| AACCCCCTGG | TGGCCGCCTT | CCCCAGCGTG | AACGTGAGCA | TGGAGAAGGT | GATCCTGAGC | 300 |
| CCCAACGAGA | ACCTGAGCAA | CAGCGTGGAG | AGCCACTCGA | GCACCAACTG | GAGCTACACC | 360 |
| AACACCGAGG | GCGCCAGCGT | GGAGGCCGGC | ATCGGTCCCA | AGGGCATCAG | CTTCGGCGTG | 420 |
| AGCGTGAACT | ACCAGCACAG | CGAGACCGTG | GCCCAGGAGT | GGGGCACCAG | CACCGGCAAC | 480 |
| ACCAGCCAGT | TCAACACCGC | CAGCGCCGGC | TACCTGAACG | CCAACGTGCG | CTACAACAAC | 540 |
| GTGGGCACCG | GCGCCATCTA | CGACGTGAAG | CCCACCACCA | GCTTCGTGCT | GAACAACGAC | 600 |
| ACCATCGCCA | CCATCACCGC | CAAGTCGAAT | TCCACCGCCC | TGAACATCAG | CCCCGGCGAG | 660 |
| AGCTACCCCA | AGAAGGGCCA | GAACGGCATC | GCCATCACCA | GCATGGACGA | CTTCAACAGC | 720 |
| CACCCCATCA | CCCTGAACAA | GAAGCAGGTG | GACAACCTGC | TGAACAACAA | GCCCATGATG | 780 |
| CTGGAGACCA | ACCAGACCGA | CGGCGTCTAC | AAGATCAAGG | ACACCCACGG | CAACATCGTG | 840 |
| ACCGGCGGCG | AGTGGAACGG | CGTGATCCAG | CAGATCAAGG | CCAAGACCGC | CAGCATCATC | 900 |
| GTCGACGACG | GCGAGCGCGT | GGCCGAGAAG | CGCGTGGCCG | CCAAGGACTA | CGAGAACCCC | 960 |
| GAGGACAAGA | CCCCCAGCCT | GACCCTGAAG | GACGCCCTGA | AGCTGAGCTA | CCCCGACGAG | 1020 |
| ATCAAGGAGA | TCGAGGGCCT | GCTGTACTAC | AAGAACAAGC | CCATCTACGA | GAGCAGCGTG | 1080 |
| ATGACCTATC | TAGACGAGAA | CACCGCCAAG | GAGGTGACCA | AGCAGCTGAA | CGACACCACC | 1140 |
| GGCAAGTTCA | AGGACGTGAG | CCACCTGTAC | GACGTGAAGC | TGACCCCCAA | GATGAACGTG | 1200 |

-continued

```
ACCATCAAGC TGAGCATCCT GTACGACAAC GCCGAGAGCA ACGACAACAG CATCGGCAAG 1260
TGGACCAACA CCAACATCGT GAGCGGCGGC AACAACGGCA AGAAGCAGTA CAGCAGCAAC 1320
AACCCCGACG CCAACCTGAC CCTGAACACC GACGCCCAGG AGAAGCTGAA CAAGAACCGC 1380
GACTACTACA TCAGCCTGTA CATGAAGAGC GAGAAGAACA CCCAGTGCGA GATCACCATC 1440
GACGGCGAGA TATACCCCAT CACCACCAAG ACCGTGAACG TGAACAAGGA CAACTACAAG 1500
CGCCTGGACA TCATCGCCCA CAACATCAAG AGCAACCCCA TCAGCAGCCT GCACATCAAG 1560
ACCAACGACG AGATCACCCT GTTCTGGGAC GACATATCGA TTACCGACGT CGCCAGCATC 1620
AAGCCCGAGA ACCTGACCGA CAGCGAGATC AAGCAGATAT ACAGTCGCTA CGGCATCAAG 1680
CTGGAGGACG GCATCCTGAT CGACAAGAAG GGCGGCATCC ACTACGGCGA GTTCATCAAC 1740
GAGGCCAGCT TCAACATCGA GCCCCTGCAG AACTACGTGA CCAAGTACGA GGTGACCTAC 1800
AGCAGCGAGC TGGGCCCCAA CGTGAGCGAC ACCCTGGAGA GCGACAAGAT TTACAAGGAC 1860
GGCACCATCA AGTTCGACTT CACCAAGTAC AGCAAGAACG AGCAGGGCCT GTTCTACGAC 1920
AGCGGCCTGA ACTGGGACTT CAAGATCAAC GCCATCACCT ACGACGGCAA GGAGATGAAC 1980
GTGTTCCACC GCTACAACAA GTAG 2004
```

( 2 ) INFORMATION FOR SEQ ID NO:19:

( i ) SEQUENCE CHARACTERISTICS:
( A ) LENGTH: 4074 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..1386
( D ) OTHER INFORMATION: /product="VIP2A(b) from Btt"

( i x ) FEATURE:
( A ) NAME/KEY: CDS
( B ) LOCATION: 1394..3895
( D ) OTHER INFORMATION: /product="VIP1A(b) from Btt"

( i x ) FEATURE:
( A ) NAME/KEY: misc_feature
( B ) LOCATION: 1..4074
( D ) OTHER INFORMATION: /note= "Cloned DNA sequence from Btt which contains the genes for both VIP1A(b) and VIP2A ( b )"

( x i ) SEQUENCE DESCRIPTION: SEQ ID NO:19:

```
ATG CAA AGA ATG GAG GGA AAG TTG TTT GTG GTG TCA AAA ACA TTA CAA    48
Met Gln Arg Met Glu Gly Lys Leu Phe Val Val Ser Lys Thr Leu Gln
        670                 675                 680

GTA GTT ACT AGA ACT GTA TTG CTT AGT ACA GTT TAC TCT ATA ACT TTA    96
Val Val Thr Arg Thr Val Leu Leu Ser Thr Val Tyr Ser Ile Thr Leu
    685                 690                 695

TTA AAT AAT GTA GTG ATA AAA GCT GAC CAA TTA AAT ATA AAT TCT CAA   144
Leu Asn Asn Val Val Ile Lys Ala Asp Gln Leu Asn Ile Asn Ser Gln
700                 705                 710                 715

AGT AAA TAT ACT AAC TTG CAA AAT CTA AAA ATC CCT GAT AAT GCA GAG   192
Ser Lys Tyr Thr Asn Leu Gln Asn Leu Lys Ile Pro Asp Asn Ala Glu
                720                 725                 730

GAT TTT AAA GAA GAT AAG GGG AAA GCG AAA GAA TGG GGG AAA GAG AAA   240
Asp Phe Lys Glu Asp Lys Gly Lys Ala Lys Glu Trp Gly Lys Glu Lys
            735                 740                 745

GGG GAA GAG TGG AGG CCT CCT GCT ACT GAG AAA GGA GAA ATG AAT AAT   288
```

```
Gly Glu Glu Trp Arg Pro Pro Ala Thr Glu Lys Gly Glu Met Asn Asn
        750                 755                 760

TTT TTA GAT AAT AAA AAT GAT ATA AAG ACC AAT TAT AAA GAA ATT ACT           336
Phe Leu Asp Asn Lys Asn Asp Ile Lys Thr Asn Tyr Lys Glu Ile Thr
765                 770                 775

TTT TCT ATG GCA GGT TCA TGT GAA GAT GAA ATA AAA GAT TTA GAA GAA           384
Phe Ser Met Ala Gly Ser Cys Glu Asp Glu Ile Lys Asp Leu Glu Glu
780                 785                 790                 795

ATT GAT AAG ATC TTT GAT AAA GCC AAT CTC TCG AGT TCT ATT ATC ACC           432
Ile Asp Lys Ile Phe Asp Lys Ala Asn Leu Ser Ser Ser Ile Ile Thr
                800                 805                 810

TAT AAA AAT GTG GAA CCA GCA ACA ATT GGA TTT AAT AAA TCT TTA ACA           480
Tyr Lys Asn Val Glu Pro Ala Thr Ile Gly Phe Asn Lys Ser Leu Thr
            815                 820                 825

GAA GGT AAT ACG ATT AAT TCT GAT GCA ATG GCA CAG TTT AAA GAA CAA           528
Glu Gly Asn Thr Ile Asn Ser Asp Ala Met Ala Gln Phe Lys Glu Gln
        830                 835                 840

TTT TTA GGT AAG GAT ATG AAG TTT GAT AGT TAT CTA GAT ACT CAT TTA           576
Phe Leu Gly Lys Asp Met Lys Phe Asp Ser Tyr Leu Asp Thr His Leu
    845                 850                 855

ACT GCT CAA CAA GTT TCC AGT AAA AAA AGA GTT ATT TTG AAG GTT ACG           624
Thr Ala Gln Gln Val Ser Ser Lys Lys Arg Val Ile Leu Lys Val Thr
860                 865                 870                 875

GTT CCG AGT GGG AAA GGT TCT ACT ACT CCA ACA AAA GCA GGT GTC ATT           672
Val Pro Ser Gly Lys Gly Ser Thr Thr Pro Thr Lys Ala Gly Val Ile
                880                 885                 890

TTA AAC AAT AAT GAA TAC AAA ATG CTC ATT GAT AAT GGG TAT GTG CTC           720
Leu Asn Asn Asn Glu Tyr Lys Met Leu Ile Asp Asn Gly Tyr Val Leu
            895                 900                 905

CAT GTA GAT AAG GTA TCA AAA GTA GTA AAA AAA GGG ATG GAG TGC TTA           768
His Val Asp Lys Val Ser Lys Val Val Lys Lys Gly Met Glu Cys Leu
        910                 915                 920

CAA GTT GAA GGG ACT TTA AAA AAG AGT CTC GAC TTT AAA AAT GAT ATA           816
Gln Val Glu Gly Thr Leu Lys Lys Ser Leu Asp Phe Lys Asn Asp Ile
    925                 930                 935

AAT GCT GAA GCG CAT AGC TGG GGG ATG AAA ATT TAT GAA GAC TGG GCT           864
Asn Ala Glu Ala His Ser Trp Gly Met Lys Ile Tyr Glu Asp Trp Ala
940                 945                 950                 955

AAA AAT TTA ACC GCT TCG CAA AGG GAA GCT TTA GAT GGG TAT GCT AGG           912
Lys Asn Leu Thr Ala Ser Gln Arg Glu Ala Leu Asp Gly Tyr Ala Arg
                960                 965                 970

CAA GAT TAT AAA GAA ATC AAT AAT TAT TTG CGC AAT CAA GGC GGG AGT           960
Gln Asp Tyr Lys Glu Ile Asn Asn Tyr Leu Arg Asn Gln Gly Gly Ser
            975                 980                 985

GGA AAT GAA AAG CTG GAT GCC CAA TTA AAA AAT ATT TCT GAT GCT TTA          1008
Gly Asn Glu Lys Leu Asp Ala Gln Leu Lys Asn Ile Ser Asp Ala Leu
        990                 995                 1000

GGG AAG AAA CCC ATA CCA GAA AAT ATT ACC GTG TAT AGA TGG TGT GGC          1056
Gly Lys Lys Pro Ile Pro Glu Asn Ile Thr Val Tyr Arg Trp Cys Gly
    1005                1010                1015

ATG CCG GAA TTT GGT TAT CAA ATT AGT GAT CCG TTA CCT TCT TTA AAA          1104
Met Pro Glu Phe Gly Tyr Gln Ile Ser Asp Pro Leu Pro Ser Leu Lys
1020                1025                1030                1035

GAT TTT GAA GAA CAA TTT TTA AAT ACA ATT AAA GAA GAC AAA GGG TAT          1152
Asp Phe Glu Glu Gln Phe Leu Asn Thr Ile Lys Glu Asp Lys Gly Tyr
                1040                1045                1050

ATG AGT ACA AGC TTA TCG AGT GAA CGT CTT GCA GCT TTT GGA TCT AGA          1200
Met Ser Thr Ser Leu Ser Ser Glu Arg Leu Ala Ala Phe Gly Ser Arg
            1055                1060                1065

AAA ATT ATA TTA CGC TTA CAA GTT CCG AAA GGA AGT ACG GGG GCG TAT          1248
```

|     |     |     |     |     |     |     |     |     |     |     |     |     |     |     |     |
|---|---|---|---|---|---|---|---|---|---|---|---|---|---|---|---|
| Lys | Ile | Ile | Leu | Arg | Leu | Gln | Val | Pro | Lys | Gly | Ser | Thr | Gly | Ala | Tyr |
|     |     | 1070 |     |     |     | 1075 |     |     |     | 1080 |     |     |     |     |     |

| TTA | AGT | GCC | ATT | GGT | GGA | TTT | GCA | AGT | GAA | AAA | GAG | ATC | CTA | CTT | GAT | 1296 |
|---|---|---|---|---|---|---|---|---|---|---|---|---|---|---|---|---|
| Leu | Ser | Ala | Ile | Gly | Gly | Phe | Ala | Ser | Glu | Lys | Glu | Ile | Leu | Leu | Asp | |
|     | 1085 |     |     |     | 1090 |     |     |     |     | 1095 |     |     |     |     |     | |

| AAA | GAT | AGT | AAA | TAT | CAT | ATT | GAT | AAA | GCA | ACA | GAG | GTA | ATC | ATT | AAA | 1344 |
|---|---|---|---|---|---|---|---|---|---|---|---|---|---|---|---|---|
| Lys | Asp | Ser | Lys | Tyr | His | Ile | Asp | Lys | Ala | Thr | Glu | Val | Ile | Ile | Lys | |
| 1100 |     |     |     | 1105 |     |     |     |     | 1110 |     |     |     |     |     | 1115 | |

| GGT | GTT | AAG | CGA | TAT | GTA | GTG | GAT | GCA | ACA | TTA | TTA | ACA | AAT |     |     | 1386 |
|---|---|---|---|---|---|---|---|---|---|---|---|---|---|---|---|---|
| Gly | Val | Lys | Arg | Tyr | Val | Val | Asp | Ala | Thr | Leu | Leu | Thr | Asn |     |     | |
|     |     |     |     | 1120 |     |     |     |     | 1125 |     |     |     |     |     |     | |

| TAAGGAG | ATG | AAA | AAT | ATG | AAG | AAA | AAG | TTA | GCA | AGT | GTT | GTA | ACC | TGT | 1435 |
|---|---|---|---|---|---|---|---|---|---|---|---|---|---|---|---|
|     | Met | Lys | Asn | Met | Lys | Lys | Lys | Leu | Ala | Ser | Val | Val | Thr | Cys | |
|     | 1 |     |     |     | 5 |     |     |     |     | 10 |     |     |     |     | |

| ATG | TTA | TTA | GCT | CCT | ATG | TTT | TTG | AAT | GGA | AAT | GTG | AAT | GCT | GTT | AAC | 1483 |
|---|---|---|---|---|---|---|---|---|---|---|---|---|---|---|---|---|
| Met | Leu | Leu | Ala | Pro | Met | Phe | Leu | Asn | Gly | Asn | Val | Asn | Ala | Val | Asn | |
| 15 |     |     |     |     | 20 |     |     |     | 25 |     |     |     |     |     | 30 | |

| GCG | GAT | AGT | AAA | ATA | AAT | CAG | ATT | TCT | ACA | ACG | CAG | GAA | AAC | CAA | CAG | 1531 |
|---|---|---|---|---|---|---|---|---|---|---|---|---|---|---|---|---|
| Ala | Asp | Ser | Lys | Ile | Asn | Gln | Ile | Ser | Thr | Thr | Gln | Glu | Asn | Gln | Gln | |
|     |     |     |     | 35 |     |     |     |     | 40 |     |     |     |     | 45 |     | |

| AAA | GAG | ATG | GAC | CGA | AAG | GGA | TTA | TTG | GGA | TAT | TAT | TTC | AAA | GGA | AAA | 1579 |
|---|---|---|---|---|---|---|---|---|---|---|---|---|---|---|---|---|
| Lys | Glu | Met | Asp | Arg | Lys | Gly | Leu | Leu | Gly | Tyr | Tyr | Phe | Lys | Gly | Lys | |
|     |     |     | 50 |     |     |     |     | 55 |     |     |     |     | 60 |     |     | |

| GAT | TTT | AAT | AAT | CTT | ACT | ATG | TTT | GCA | CCG | ACA | CGT | GAT | AAT | ACC | CTT | 1627 |
|---|---|---|---|---|---|---|---|---|---|---|---|---|---|---|---|---|
| Asp | Phe | Asn | Asn | Leu | Thr | Met | Phe | Ala | Pro | Thr | Arg | Asp | Asn | Thr | Leu | |
|     |     | 65 |     |     |     | 70 |     |     |     |     |     | 75 |     |     |     | |

| ATG | TAT | GAC | CAA | CAA | ACA | GCG | AAT | GCA | TTA | TTA | GAT | AAA | AAA | CAA | CAA | 1675 |
|---|---|---|---|---|---|---|---|---|---|---|---|---|---|---|---|---|
| Met | Tyr | Asp | Gln | Gln | Thr | Ala | Asn | Ala | Leu | Leu | Asp | Lys | Lys | Gln | Gln | |
|     | 80 |     |     |     |     | 85 |     |     |     |     | 90 |     |     |     |     | |

| GAA | TAT | CAG | TCC | ATT | CGT | TGG | ATT | GGT | TTG | ATT | CAG | CGT | AAA | GAA | ACG | 1723 |
|---|---|---|---|---|---|---|---|---|---|---|---|---|---|---|---|---|
| Glu | Tyr | Gln | Ser | Ile | Arg | Trp | Ile | Gly | Leu | Ile | Gln | Arg | Lys | Glu | Thr | |
| 95 |     |     |     |     | 100 |     |     |     |     | 105 |     |     |     |     | 110 | |

| GGC | GAT | TTC | ACA | TTT | AAC | TTA | TCA | AAG | GAT | GAA | CAG | GCA | ATT | ATA | GAA | 1771 |
|---|---|---|---|---|---|---|---|---|---|---|---|---|---|---|---|---|
| Gly | Asp | Phe | Thr | Phe | Asn | Leu | Ser | Lys | Asp | Glu | Gln | Ala | Ile | Ile | Glu | |
|     |     |     |     | 115 |     |     |     |     | 120 |     |     |     |     | 125 |     | |

| ATC | GAT | GGG | AAA | ATC | ATT | TCT | AAT | AAA | GGG | AAA | GAA | AAG | CAA | GTT | GTC | 1819 |
|---|---|---|---|---|---|---|---|---|---|---|---|---|---|---|---|---|
| Ile | Asp | Gly | Lys | Ile | Ile | Ser | Asn | Lys | Gly | Lys | Glu | Lys | Gln | Val | Val | |
|     |     | 130 |     |     |     |     | 135 |     |     |     |     | 140 |     |     |     | |

| CAT | TTA | GAA | AAA | GAA | AAA | TTA | GTT | CCA | ATC | AAA | ATA | GAG | TAT | CAA | TCA | 1867 |
|---|---|---|---|---|---|---|---|---|---|---|---|---|---|---|---|---|
| His | Leu | Glu | Lys | Glu | Lys | Leu | Val | Pro | Ile | Lys | Ile | Glu | Tyr | Gln | Ser | |
|     |     | 145 |     |     |     |     | 150 |     |     |     |     | 155 |     |     |     | |

| GAT | ACG | AAA | TTT | AAT | ATT | GAT | AGT | AAA | ACA | TTT | AAA | GAA | CTT | AAA | TTA | 1915 |
|---|---|---|---|---|---|---|---|---|---|---|---|---|---|---|---|---|
| Asp | Thr | Lys | Phe | Asn | Ile | Asp | Ser | Lys | Thr | Phe | Lys | Glu | Leu | Lys | Leu | |
|     | 160 |     |     |     |     | 165 |     |     |     |     | 170 |     |     |     |     | |

| TTT | AAA | ATA | GAT | AGT | CAA | AAC | CAA | TCT | CAA | CAA | GTT | CAA | CTG | AGA | AAC | 1963 |
|---|---|---|---|---|---|---|---|---|---|---|---|---|---|---|---|---|
| Phe | Lys | Ile | Asp | Ser | Gln | Asn | Gln | Ser | Gln | Gln | Val | Gln | Leu | Arg | Asn | |
| 175 |     |     |     |     | 180 |     |     |     |     | 185 |     |     |     |     | 190 | |

| CCT | GAA | TTT | AAC | AAA | AAA | GAA | TCA | CAG | GAA | TTT | TTA | GCA | AAA | GCA | TCA | 2011 |
|---|---|---|---|---|---|---|---|---|---|---|---|---|---|---|---|---|
| Pro | Glu | Phe | Asn | Lys | Lys | Glu | Ser | Gln | Glu | Phe | Leu | Ala | Lys | Ala | Ser | |
|     |     |     |     | 195 |     |     |     |     | 200 |     |     |     |     | 205 |     | |

| AAA | ACA | AAC | CTT | TTT | AAG | CAA | AAA | ATG | AAA | AGA | GAT | ATT | GAT | GAA | GAT | 2059 |
|---|---|---|---|---|---|---|---|---|---|---|---|---|---|---|---|---|
| Lys | Thr | Asn | Leu | Phe | Lys | Gln | Lys | Met | Lys | Arg | Asp | Ile | Asp | Glu | Asp | |
|     |     |     | 210 |     |     |     |     | 215 |     |     |     |     | 220 |     |     | |

| ACG | GAT | ACA | GAT | GGA | GAC | TCC | ATT | CCT | GAT | CTT | TGG | GAA | GAA | AAT | GGG | 2107 |
|---|---|---|---|---|---|---|---|---|---|---|---|---|---|---|---|---|
| Thr | Asp | Thr | Asp | Gly | Asp | Ser | Ile | Pro | Asp | Leu | Trp | Glu | Glu | Asn | Gly | |
|     |     | 225 |     |     |     |     | 230 |     |     |     |     | 235 |     |     |     | |

| TAC | ACG | ATT | CAA | AAT | AAA | GTT | GCT | GTC | AAA | TGG | GAT | GAT | TCG | CTA | GCA | 2155 |
|---|---|---|---|---|---|---|---|---|---|---|---|---|---|---|---|---|
| Tyr | Thr | Ile | Gln | Asn | Lys | Val | Ala | Val | Lys | Trp | Asp | Asp | Ser | Leu | Ala | |
|     | 240 |     |     |     |     | 245 |     |     |     |     | 250 |     |     |     |     | |

| AGT | AAG | GGA | TAT | ACA | AAA | TTT | GTT | TCG | AAT | CCA | TTA | GAC | AGC | CAC | ACA | 2203 |
|---|---|---|---|---|---|---|---|---|---|---|---|---|---|---|---|---|

| | | | | | | | | | | | | | | | |
|---|---|---|---|---|---|---|---|---|---|---|---|---|---|---|---|
| Ser | Lys | Gly | Tyr | Thr | Lys | Phe | Val | Ser | Asn | Pro | Leu | Asp | Ser | His | Thr |
| 255 | | | | 260 | | | | | 265 | | | | | | 270 |

| GTT | GGC | GAT | CCC | TAT | ACT | GAT | TAT | GAA | AAG | GCC | GCA | AGG | GAT | TTA | GAT | 2251 |
|---|---|---|---|---|---|---|---|---|---|---|---|---|---|---|---|---|
| Val | Gly | Asp | Pro | Tyr | Thr | Asp | Tyr | Glu | Lys | Ala | Ala | Arg | Asp | Leu | Asp | |
| | | | | 275 | | | | | 280 | | | | | 285 | | |

| TTA | TCA | AAT | GCA | AAG | GAA | ACG | TTC | AAC | CCA | TTG | GTA | GCT | GCT | TTT | CCA | 2299 |
|---|---|---|---|---|---|---|---|---|---|---|---|---|---|---|---|---|
| Leu | Ser | Asn | Ala | Lys | Glu | Thr | Phe | Asn | Pro | Leu | Val | Ala | Ala | Phe | Pro | |
| | | | 290 | | | | 295 | | | | | 300 | | | | |

| AGT | GTG | AAT | GTT | AGT | ATG | GAA | AAG | GTG | ATA | TTA | TCA | CCA | AAT | GAA | AAT | 2347 |
|---|---|---|---|---|---|---|---|---|---|---|---|---|---|---|---|---|
| Ser | Val | Asn | Val | Ser | Met | Glu | Lys | Val | Ile | Leu | Ser | Pro | Asn | Glu | Asn | |
| | | 305 | | | | | 310 | | | | 315 | | | | | |

| TTA | TCC | AAT | AGT | GTA | GAG | TCT | CAT | TCA | TCC | ACG | AAT | TGG | TCT | TAT | ACG | 2395 |
|---|---|---|---|---|---|---|---|---|---|---|---|---|---|---|---|---|
| Leu | Ser | Asn | Ser | Val | Glu | Ser | His | Ser | Ser | Thr | Asn | Trp | Ser | Tyr | Thr | |
| | 320 | | | | 325 | | | | | 330 | | | | | | |

| AAT | ACA | GAA | GGA | GCT | TCC | ATT | GAA | GCT | GGT | GGC | GGT | CCA | TTA | GGC | CTT | 2443 |
|---|---|---|---|---|---|---|---|---|---|---|---|---|---|---|---|---|
| Asn | Thr | Glu | Gly | Ala | Ser | Ile | Glu | Ala | Gly | Gly | Gly | Pro | Leu | Gly | Leu | |
| 335 | | | | | 340 | | | | | 345 | | | | | 350 | |

| TCT | TTT | GGC | GTG | AGT | GTT | ACT | TAT | CAA | CAC | TCT | GAA | ACA | GTT | GCA | CAA | 2491 |
|---|---|---|---|---|---|---|---|---|---|---|---|---|---|---|---|---|
| Ser | Phe | Gly | Val | Ser | Val | Thr | Tyr | Gln | His | Ser | Glu | Thr | Val | Ala | Gln | |
| | | | | 355 | | | | | 360 | | | | | 365 | | |

| GAA | TGG | GGA | ACA | TCT | ACA | GGA | AAT | ACT | TCA | CAA | TTC | AAT | ACG | GCT | TCA | 2539 |
|---|---|---|---|---|---|---|---|---|---|---|---|---|---|---|---|---|
| Glu | Trp | Gly | Thr | Ser | Thr | Gly | Asn | Thr | Ser | Gln | Phe | Asn | Thr | Ala | Ser | |
| | | | 370 | | | | 375 | | | | | 380 | | | | |

| GCG | GGA | TAT | TTA | AAT | GCA | AAT | GTT | CGG | TAT | AAC | AAT | GTA | GGG | ACT | GGT | 2587 |
|---|---|---|---|---|---|---|---|---|---|---|---|---|---|---|---|---|
| Ala | Gly | Tyr | Leu | Asn | Ala | Asn | Val | Arg | Tyr | Asn | Asn | Val | Gly | Thr | Gly | |
| | | 385 | | | | | 390 | | | | | 395 | | | | |

| GCC | ATC | TAT | GAT | GTA | AAA | CCT | ACA | ACA | AGT | TTT | GTA | TTA | AAT | AAC | AAT | 2635 |
|---|---|---|---|---|---|---|---|---|---|---|---|---|---|---|---|---|
| Ala | Ile | Tyr | Asp | Val | Lys | Pro | Thr | Thr | Ser | Phe | Val | Leu | Asn | Asn | Asn | |
| | | 400 | | | | 405 | | | | | 410 | | | | | |

| ACC | ATC | GCA | ACG | ATT | ACA | GCA | AAA | TCA | AAT | TCA | ACA | GCT | TTA | CGT | ATA | 2683 |
|---|---|---|---|---|---|---|---|---|---|---|---|---|---|---|---|---|
| Thr | Ile | Ala | Thr | Ile | Thr | Ala | Lys | Ser | Asn | Ser | Thr | Ala | Leu | Arg | Ile | |
| 415 | | | | | 420 | | | | | 425 | | | | | 430 | |

| TCT | CCG | GGG | GAT | AGT | TAT | CCA | GAA | ATA | GGA | GAA | AAC | GCT | ATT | GCG | ATT | 2731 |
|---|---|---|---|---|---|---|---|---|---|---|---|---|---|---|---|---|
| Ser | Pro | Gly | Asp | Ser | Tyr | Pro | Glu | Ile | Gly | Glu | Asn | Ala | Ile | Ala | Ile | |
| | | | | 435 | | | | | 440 | | | | | 445 | | |

| ACA | TCT | ATG | GAT | GAT | TTT | AAT | TCT | CAT | CCA | ATT | ACA | TTA | AAT | AAA | CAA | 2779 |
|---|---|---|---|---|---|---|---|---|---|---|---|---|---|---|---|---|
| Thr | Ser | Met | Asp | Asp | Phe | Asn | Ser | His | Pro | Ile | Thr | Leu | Asn | Lys | Gln | |
| | | | 450 | | | | 455 | | | | | 460 | | | | |

| CAG | GTA | AAT | CAA | TTG | ATA | AAT | AAT | AAG | CCA | ATT | ATG | CTA | GAG | ACA | GAC | 2827 |
|---|---|---|---|---|---|---|---|---|---|---|---|---|---|---|---|---|
| Gln | Val | Asn | Gln | Leu | Ile | Asn | Asn | Lys | Pro | Ile | Met | Leu | Glu | Thr | Asp | |
| | | 465 | | | | | 470 | | | | | 475 | | | | |

| CAA | ACA | GAT | GGT | GTT | TAT | AAA | ATA | AGA | GAT | ACA | CAT | GGA | AAT | ATT | GTA | 2875 |
|---|---|---|---|---|---|---|---|---|---|---|---|---|---|---|---|---|
| Gln | Thr | Asp | Gly | Val | Tyr | Lys | Ile | Arg | Asp | Thr | His | Gly | Asn | Ile | Val | |
| | 480 | | | | | 485 | | | | | 490 | | | | | |

| ACT | GGT | GGA | GAA | TGG | AAT | GGT | GTA | ACA | CAA | CAA | ATT | AAA | GCA | AAA | ACA | 2923 |
|---|---|---|---|---|---|---|---|---|---|---|---|---|---|---|---|---|
| Thr | Gly | Gly | Glu | Trp | Asn | Gly | Val | Thr | Gln | Gln | Ile | Lys | Ala | Lys | Thr | |
| 495 | | | | | 500 | | | | | 505 | | | | | 510 | |

| GCG | TCT | ATT | ATT | GTG | GAT | GAC | GGG | AAA | CAG | GTA | GCA | GAA | AAA | CGT | GTG | 2971 |
|---|---|---|---|---|---|---|---|---|---|---|---|---|---|---|---|---|
| Ala | Ser | Ile | Ile | Val | Asp | Asp | Gly | Lys | Gln | Val | Ala | Glu | Lys | Arg | Val | |
| | | | | 515 | | | | | 520 | | | | | 525 | | |

| GCG | GCA | AAA | GAT | TAT | GGT | CAT | CCA | GAA | GAT | AAA | ACA | CCA | CCT | TTA | ACT | 3019 |
|---|---|---|---|---|---|---|---|---|---|---|---|---|---|---|---|---|
| Ala | Ala | Lys | Asp | Tyr | Gly | His | Pro | Glu | Asp | Lys | Thr | Pro | Pro | Leu | Thr | |
| | | | 530 | | | | 535 | | | | | 540 | | | | |

| TTA | AAA | GAT | ACC | CTG | AAG | CTT | TCA | TAC | CCA | GAT | GAA | ATA | AAA | GAA | ACT | 3067 |
|---|---|---|---|---|---|---|---|---|---|---|---|---|---|---|---|---|
| Leu | Lys | Asp | Thr | Leu | Lys | Leu | Ser | Tyr | Pro | Asp | Glu | Ile | Lys | Glu | Thr | |
| | | 545 | | | | | 550 | | | | | 555 | | | | |

| AAT | GGA | TTG | TTG | TAC | TAT | GAT | GAC | AAA | CCA | ATC | TAT | GAA | TCG | AGT | GTC | 3115 |
|---|---|---|---|---|---|---|---|---|---|---|---|---|---|---|---|---|
| Asn | Gly | Leu | Leu | Tyr | Tyr | Asp | Asp | Lys | Pro | Ile | Tyr | Glu | Ser | Ser | Val | |
| | 560 | | | | | 565 | | | | | 570 | | | | | |

| ATG | ACT | TAT | CTG | GAT | GAA | AAT | ACG | GCA | AAA | GAA | GTC | AAA | AAA | CAA | ATA | 3163 |

| | | | | | | | | | | | | | | | |
|---|---|---|---|---|---|---|---|---|---|---|---|---|---|---|---|
| Met | Thr | Tyr | Leu | Asp | Glu | Asn | Thr | Ala | Lys | Glu | Val | Lys | Lys | Gln | Ile |
| 575 | | | | | 580 | | | | 585 | | | | | | 590 |

| AAT | GAT | ACA | ACC | GGA | AAA | TTT | AAG | GAT | GTA | AAT | CAC | TTA | TAT | GAT | GTA | 3211 |
|---|---|---|---|---|---|---|---|---|---|---|---|---|---|---|---|---|
| Asn | Asp | Thr | Thr | Gly | Lys | Phe | Lys | Asp | Val | Asn | His | Leu | Tyr | Asp | Val | |
| | | | | 595 | | | | | 600 | | | | | 605 | | |

| AAA | CTG | ACT | CCA | AAA | ATG | AAT | TTT | ACG | ATT | AAA | ATG | GCT | TCC | TTG | TAT | 3259 |
|---|---|---|---|---|---|---|---|---|---|---|---|---|---|---|---|---|
| Lys | Leu | Thr | Pro | Lys | Met | Asn | Phe | Thr | Ile | Lys | Met | Ala | Ser | Leu | Tyr | |
| | | | 610 | | | | | 615 | | | | | 620 | | | |

| GAT | GGG | GCT | GAA | AAT | AAT | CAT | AAC | TCT | TTA | GGA | ACC | TGG | TAT | TTA | ACA | 3307 |
|---|---|---|---|---|---|---|---|---|---|---|---|---|---|---|---|---|
| Asp | Gly | Ala | Glu | Asn | Asn | His | Asn | Ser | Leu | Gly | Thr | Trp | Tyr | Leu | Thr | |
| | | | 625 | | | | 630 | | | | | 635 | | | | |

| TAT | AAT | GTT | GCT | GGT | GGA | AAT | ACT | GGG | AAG | AGA | CAA | TAT | CGT | TCA | GCT | 3355 |
|---|---|---|---|---|---|---|---|---|---|---|---|---|---|---|---|---|
| Tyr | Asn | Val | Ala | Gly | Gly | Asn | Thr | Gly | Lys | Arg | Gln | Tyr | Arg | Ser | Ala | |
| | 640 | | | | | 645 | | | | | 650 | | | | | |

| CAT | TCT | TGT | GCA | CAT | GTA | GCT | CTA | TCT | TCA | GAA | GCG | AAA | AAG | AAA | CTA | 3403 |
|---|---|---|---|---|---|---|---|---|---|---|---|---|---|---|---|---|
| His | Ser | Cys | Ala | His | Val | Ala | Leu | Ser | Ser | Glu | Ala | Lys | Lys | Lys | Leu | |
| 655 | | | | | 660 | | | | | 665 | | | | | 670 | |

| AAT | CAA | AAT | GCG | AAT | TAC | TAT | CTT | AGC | ATG | TAT | ATG | AAG | GCT | GAT | TCT | 3451 |
|---|---|---|---|---|---|---|---|---|---|---|---|---|---|---|---|---|
| Asn | Gln | Asn | Ala | Asn | Tyr | Tyr | Leu | Ser | Met | Tyr | Met | Lys | Ala | Asp | Ser | |
| | | | | 675 | | | | | 680 | | | | | 685 | | |

| ACT | ACG | GAA | CCT | ACA | ATA | GAA | GTA | GCT | GGG | GAA | AAA | TCT | GCA | ATA | ACA | 3499 |
|---|---|---|---|---|---|---|---|---|---|---|---|---|---|---|---|---|
| Thr | Thr | Glu | Pro | Thr | Ile | Glu | Val | Ala | Gly | Glu | Lys | Ser | Ala | Ile | Thr | |
| | | | 690 | | | | | 695 | | | | | 700 | | | |

| AGT | AAA | AAA | GTA | AAA | TTA | AAT | AAT | CAA | AAT | TAT | CAA | AGA | GTT | GAT | ATT | 3547 |
|---|---|---|---|---|---|---|---|---|---|---|---|---|---|---|---|---|
| Ser | Lys | Lys | Val | Lys | Leu | Asn | Asn | Gln | Asn | Tyr | Gln | Arg | Val | Asp | Ile | |
| | | 705 | | | | | 710 | | | | | 715 | | | | |

| TTA | GTG | AAA | AAT | TCT | GAA | AGA | AAT | CCA | ATG | GAT | AAA | ATA | TAT | ATA | AGA | 3595 |
|---|---|---|---|---|---|---|---|---|---|---|---|---|---|---|---|---|
| Leu | Val | Lys | Asn | Ser | Glu | Arg | Asn | Pro | Met | Asp | Lys | Ile | Tyr | Ile | Arg | |
| | 720 | | | | | 725 | | | | | 730 | | | | | |

| GGA | AAT | GGC | ACG | ACA | AAT | GTT | TAT | GGG | GAT | GAT | GTT | ACT | ATC | CCA | GAG | 3643 |
|---|---|---|---|---|---|---|---|---|---|---|---|---|---|---|---|---|
| Gly | Asn | Gly | Thr | Thr | Asn | Val | Tyr | Gly | Asp | Asp | Val | Thr | Ile | Pro | Glu | |
| 735 | | | | | 740 | | | | | 745 | | | | | 750 | |

| GTA | TCA | GCT | ATA | AAT | CCG | GCT | AGT | CTA | TCA | GAT | GAA | GAA | ATT | CAA | GAA | 3691 |
|---|---|---|---|---|---|---|---|---|---|---|---|---|---|---|---|---|
| Val | Ser | Ala | Ile | Asn | Pro | Ala | Ser | Leu | Ser | Asp | Glu | Glu | Ile | Gln | Glu | |
| | | | | 755 | | | | | 760 | | | | | 765 | | |

| ATA | TTT | AAA | GAC | TCA | ACT | ATT | GAA | TAT | GGA | AAT | CCT | AGT | TTC | GTT | GCT | 3739 |
|---|---|---|---|---|---|---|---|---|---|---|---|---|---|---|---|---|
| Ile | Phe | Lys | Asp | Ser | Thr | Ile | Glu | Tyr | Gly | Asn | Pro | Ser | Phe | Val | Ala | |
| | | | 770 | | | | | 775 | | | | | 780 | | | |

| GAT | GCC | GTA | ACA | TTT | AAA | AAT | ATA | AAA | CCT | TTA | CAA | AAT | TAT | GTA | AAG | 3787 |
|---|---|---|---|---|---|---|---|---|---|---|---|---|---|---|---|---|
| Asp | Ala | Val | Thr | Phe | Lys | Asn | Ile | Lys | Pro | Leu | Gln | Asn | Tyr | Val | Lys | |
| | | 785 | | | | | 790 | | | | | 795 | | | | |

| GAA | TAT | GAA | ATA | TAT | CAT | AAA | TCT | CAT | CGA | TAT | GAA | AAG | AAA | ACG | GTC | 3835 |
|---|---|---|---|---|---|---|---|---|---|---|---|---|---|---|---|---|
| Glu | Tyr | Glu | Ile | Tyr | His | Lys | Ser | His | Arg | Tyr | Glu | Lys | Lys | Thr | Val | |
| | | 800 | | | | | 805 | | | | | 810 | | | | |

| TTT | GAT | ATC | ATG | GGT | GTT | CAT | TAT | GAG | TAT | AGT | ATA | GCT | AGG | GAA | CAA | 3883 |
|---|---|---|---|---|---|---|---|---|---|---|---|---|---|---|---|---|
| Phe | Asp | Ile | Met | Gly | Val | His | Tyr | Glu | Tyr | Ser | Ile | Ala | Arg | Glu | Gln | |
| 815 | | | | | 820 | | | | | 825 | | | | | 830 | |

| AAG | AAA | GCC | GCA | TAATTTAAA | AATAAACTC | GTTAGAGTTT | ATTTAGCATG | 3935 |
|---|---|---|---|---|---|---|---|---|
| Lys | Lys | Ala | Ala | | | | | |

GTATTTTTAA GAATAATCAA TATGTTGAAC CGTTTGTAGC TGTTTTGGAA GGGAATTTCA    3995

TTTTATTTGG TCTCTTAAGT TGATGGGCAT GGGATATGTT CAGCATCCAA GCGTTTNGGG    4055

GGTTANAAAA TCCAATTTT                                                 4074

( 2 ) INFORMATION FOR SEQ ID NO:20:

( i ) SEQUENCE CHARACTERISTICS:
        ( A ) LENGTH: 462 amino acids
        ( B ) TYPE: amino acid
        ( D ) TOPOLOGY: linear (i i) MOLECULE TYPE: protein (x i) SEQUENCE DESCRIPTION: SEQ ID NO:20:

| Met | Gln | Arg | Met | Glu | Gly | Lys | Leu | Phe | Val | Val | Ser | Lys | Thr | Leu | Gln |
|---|---|---|---|---|---|---|---|---|---|---|---|---|---|---|---|
| 1 | | | | 5 | | | | | 10 | | | | | 15 | |
| Val | Val | Thr | Arg | Thr | Val | Leu | Leu | Ser | Thr | Val | Tyr | Ser | Ile | Thr | Leu |
| | | | 20 | | | | | 25 | | | | | 30 | | |
| Leu | Asn | Asn | Val | Val | Ile | Lys | Ala | Asp | Gln | Leu | Asn | Ile | Asn | Ser | Gln |
| | | 35 | | | | | 40 | | | | | 45 | | | |
| Ser | Lys | Tyr | Thr | Asn | Leu | Gln | Asn | Leu | Lys | Ile | Pro | Asp | Asn | Ala | Glu |
| | 50 | | | | | 55 | | | | | 60 | | | | |
| Asp | Phe | Lys | Glu | Asp | Lys | Gly | Lys | Ala | Lys | Glu | Trp | Gly | Lys | Glu | Lys |
| 65 | | | | | 70 | | | | | 75 | | | | | 80 |
| Gly | Glu | Glu | Trp | Arg | Pro | Pro | Ala | Thr | Glu | Lys | Gly | Glu | Met | Asn | Asn |
| | | | | 85 | | | | | 90 | | | | | 95 | |
| Phe | Leu | Asp | Asn | Lys | Asn | Asp | Ile | Lys | Thr | Asn | Tyr | Lys | Glu | Ile | Thr |
| | | | 100 | | | | | 105 | | | | | 110 | | |
| Phe | Ser | Met | Ala | Gly | Ser | Cys | Glu | Asp | Glu | Ile | Lys | Asp | Leu | Glu | Glu |
| | | 115 | | | | | 120 | | | | | 125 | | | |
| Ile | Asp | Lys | Ile | Phe | Asp | Lys | Ala | Asn | Leu | Ser | Ser | Ser | Ile | Ile | Thr |
| | 130 | | | | | 135 | | | | | 140 | | | | |
| Tyr | Lys | Asn | Val | Glu | Pro | Ala | Thr | Ile | Gly | Phe | Asn | Lys | Ser | Leu | Thr |
| 145 | | | | | 150 | | | | | 155 | | | | | 160 |
| Glu | Gly | Asn | Thr | Ile | Asn | Ser | Asp | Ala | Met | Ala | Gln | Phe | Lys | Glu | Gln |
| | | | | 165 | | | | | 170 | | | | | 175 | |
| Phe | Leu | Gly | Lys | Asp | Met | Lys | Phe | Asp | Ser | Tyr | Leu | Asp | Thr | His | Leu |
| | | | 180 | | | | | 185 | | | | | 190 | | |
| Thr | Ala | Gln | Gln | Val | Ser | Ser | Lys | Lys | Arg | Val | Ile | Leu | Lys | Val | Thr |
| | | 195 | | | | | 200 | | | | | 205 | | | |
| Val | Pro | Ser | Gly | Lys | Gly | Ser | Thr | Thr | Pro | Thr | Lys | Ala | Gly | Val | Ile |
| | 210 | | | | | 215 | | | | | 220 | | | | |
| Leu | Asn | Asn | Asn | Glu | Tyr | Lys | Met | Leu | Ile | Asp | Asn | Gly | Tyr | Val | Leu |
| 225 | | | | | 230 | | | | | 235 | | | | | 240 |
| His | Val | Asp | Lys | Val | Ser | Lys | Val | Val | Lys | Lys | Gly | Met | Glu | Cys | Leu |
| | | | | 245 | | | | | 250 | | | | | 255 | |
| Gln | Val | Glu | Gly | Thr | Leu | Lys | Lys | Ser | Leu | Asp | Phe | Lys | Asn | Asp | Ile |
| | | | 260 | | | | | 265 | | | | | 270 | | |
| Asn | Ala | Glu | Ala | His | Ser | Trp | Gly | Met | Lys | Ile | Tyr | Glu | Asp | Trp | Ala |
| | | 275 | | | | | 280 | | | | | 285 | | | |
| Lys | Asn | Leu | Thr | Ala | Ser | Gln | Arg | Glu | Ala | Leu | Asp | Gly | Tyr | Ala | Arg |
| | 290 | | | | | 295 | | | | | 300 | | | | |
| Gln | Asp | Tyr | Lys | Glu | Ile | Asn | Asn | Tyr | Leu | Arg | Asn | Gln | Gly | Gly | Ser |
| 305 | | | | | 310 | | | | | 315 | | | | | 320 |
| Gly | Asn | Glu | Lys | Leu | Asp | Ala | Gln | Leu | Lys | Asn | Ile | Ser | Asp | Ala | Leu |
| | | | | 325 | | | | | 330 | | | | | 335 | |
| Gly | Lys | Lys | Pro | Ile | Pro | Glu | Asn | Ile | Thr | Val | Tyr | Arg | Trp | Cys | Gly |
| | | | 340 | | | | | 345 | | | | | 350 | | |
| Met | Pro | Glu | Phe | Gly | Tyr | Gln | Ile | Ser | Asp | Pro | Leu | Pro | Ser | Leu | Lys |
| | | 355 | | | | | 360 | | | | | 365 | | | |
| Asp | Phe | Glu | Glu | Gln | Phe | Leu | Asn | Thr | Ile | Lys | Glu | Asp | Lys | Gly | Tyr |
| | 370 | | | | | 375 | | | | | 380 | | | | |
| Met | Ser | Thr | Ser | Leu | Ser | Ser | Glu | Arg | Leu | Ala | Ala | Phe | Gly | Ser | Arg |
| 385 | | | | | 390 | | | | | 395 | | | | | 400 |
| Lys | Ile | Ile | Leu | Arg | Leu | Gln | Val | Pro | Lys | Gly | Ser | Thr | Gly | Ala | Tyr |

-continued

```
                        405                              410                              415
Leu  Ser  Ala  Ile  Gly  Gly  Phe  Ala  Ser  Glu  Lys  Glu  Ile  Leu  Leu  Asp
               420                      425                      430

Lys  Asp  Ser  Lys  Tyr  His  Ile  Asp  Lys  Ala  Thr  Glu  Val  Ile  Ile  Lys
               435                      440                      445

Gly  Val  Lys  Arg  Tyr  Val  Val  Asp  Ala  Thr  Leu  Leu  Thr  Asn
     450                      455                      460
```

( 2 ) INFORMATION FOR SEQ ID NO:21:

( i ) SEQUENCE CHARACTERISTICS:
     ( A ) LENGTH: 834 amino acids
     ( B ) TYPE: amino acid
     ( D ) TOPOLOGY: linear ( i i ) MOLECULE TYPE: protein ( x i ) SEQUENCE DESCRIPTION: SEQ ID NO:21:

```
Met  Lys  Asn  Met  Lys  Lys  Lys  Leu  Ala  Ser  Val  Val  Thr  Cys  Met  Leu
 1                    5                    10                        15

Leu  Ala  Pro  Met  Phe  Leu  Asn  Gly  Asn  Val  Asn  Ala  Val  Asn  Ala  Asp
               20                        25                        30

Ser  Lys  Ile  Asn  Gln  Ile  Ser  Thr  Thr  Gln  Glu  Asn  Gln  Gln  Lys  Glu
               35                        40                        45

Met  Asp  Arg  Lys  Gly  Leu  Leu  Gly  Tyr  Tyr  Phe  Lys  Gly  Lys  Asp  Phe
     50                    55                        60

Asn  Asn  Leu  Thr  Met  Phe  Ala  Pro  Thr  Arg  Asp  Asn  Thr  Leu  Met  Tyr
 65                        70                        75                    80

Asp  Gln  Gln  Thr  Ala  Asn  Ala  Leu  Leu  Asp  Lys  Lys  Gln  Gln  Glu  Tyr
                    85                        90                        95

Gln  Ser  Ile  Arg  Trp  Ile  Gly  Leu  Ile  Gln  Arg  Lys  Glu  Thr  Gly  Asp
               100                       105                       110

Phe  Thr  Phe  Asn  Leu  Ser  Lys  Asp  Glu  Gln  Ala  Ile  Ile  Glu  Ile  Asp
               115                       120                       125

Gly  Lys  Ile  Ile  Ser  Asn  Lys  Gly  Lys  Glu  Lys  Gln  Val  Val  His  Leu
     130                       135                       140

Glu  Lys  Glu  Lys  Leu  Val  Pro  Ile  Lys  Ile  Glu  Tyr  Gln  Ser  Asp  Thr
145                       150                       155                       160

Lys  Phe  Asn  Ile  Asp  Ser  Lys  Thr  Phe  Lys  Glu  Leu  Lys  Leu  Phe  Lys
               165                       170                       175

Ile  Asp  Ser  Gln  Asn  Gln  Ser  Gln  Gln  Val  Gln  Leu  Arg  Asn  Pro  Glu
               180                       185                       190

Phe  Asn  Lys  Lys  Glu  Ser  Gln  Glu  Phe  Leu  Ala  Lys  Ala  Ser  Lys  Thr
          195                       200                       205

Asn  Leu  Phe  Lys  Gln  Lys  Met  Lys  Arg  Asp  Ile  Asp  Glu  Asp  Thr  Asp
     210                       215                       220

Thr  Asp  Gly  Asp  Ser  Ile  Pro  Asp  Leu  Trp  Glu  Glu  Asn  Gly  Tyr  Thr
225                       230                       235                       240

Ile  Gln  Asn  Lys  Val  Ala  Val  Lys  Trp  Asp  Asp  Ser  Leu  Ala  Ser  Lys
                    245                       250                       255

Gly  Tyr  Thr  Lys  Phe  Val  Ser  Asn  Pro  Leu  Asp  Ser  His  Thr  Val  Gly
               260                       265                       270

Asp  Pro  Tyr  Thr  Asp  Tyr  Glu  Lys  Ala  Ala  Arg  Asp  Leu  Asp  Leu  Ser
               275                       280                       285

Asn  Ala  Lys  Glu  Thr  Phe  Asn  Pro  Leu  Val  Ala  Ala  Phe  Pro  Ser  Val
     290                       295                       300
```

```
Asn  Val  Ser  Met  Glu  Lys  Val  Ile  Leu  Ser  Pro  Asn  Glu  Asn  Leu  Ser
305            310                      315                      320

Asn  Ser  Val  Glu  Ser  His  Ser  Ser  Thr  Asn  Trp  Ser  Tyr  Thr  Asn  Thr
                    325                      330                      335

Glu  Gly  Ala  Ser  Ile  Glu  Ala  Gly  Gly  Pro  Leu  Gly  Leu  Ser  Phe
               340                      345                      350

Gly  Val  Ser  Val  Thr  Tyr  Gln  His  Ser  Glu  Thr  Val  Ala  Gln  Glu  Trp
               355                      360                      365

Gly  Thr  Ser  Thr  Gly  Asn  Thr  Ser  Gln  Phe  Asn  Thr  Ala  Ser  Ala  Gly
               370                      375                      380

Tyr  Leu  Asn  Ala  Asn  Val  Arg  Tyr  Asn  Asn  Val  Gly  Thr  Gly  Ala  Ile
385                      390                      395                      400

Tyr  Asp  Val  Lys  Pro  Thr  Thr  Ser  Phe  Val  Leu  Asn  Asn  Asn  Thr  Ile
                    405                      410                      415

Ala  Thr  Ile  Thr  Ala  Lys  Ser  Asn  Ser  Thr  Ala  Leu  Arg  Ile  Ser  Pro
               420                      425                      430

Gly  Asp  Ser  Tyr  Pro  Glu  Ile  Gly  Glu  Asn  Ala  Ile  Ala  Ile  Thr  Ser
               435                      440                      445

Met  Asp  Asp  Phe  Asn  Ser  His  Pro  Ile  Thr  Leu  Asn  Lys  Gln  Gln  Val
     450                      455                      460

Asn  Gln  Leu  Ile  Asn  Asn  Lys  Pro  Ile  Met  Leu  Glu  Thr  Asp  Gln  Thr
465                      470                      475                      480

Asp  Gly  Val  Tyr  Lys  Ile  Arg  Asp  Thr  His  Gly  Asn  Ile  Val  Thr  Gly
                    485                      490                      495

Gly  Glu  Trp  Asn  Gly  Val  Thr  Gln  Gln  Ile  Lys  Ala  Lys  Thr  Ala  Ser
               500                      505                      510

Ile  Ile  Val  Asp  Asp  Gly  Lys  Gln  Val  Ala  Glu  Lys  Arg  Val  Ala  Ala
          515                      520                      525

Lys  Asp  Tyr  Gly  His  Pro  Glu  Asp  Lys  Thr  Pro  Pro  Leu  Thr  Leu  Lys
     530                      535                      540

Asp  Thr  Leu  Lys  Leu  Ser  Tyr  Pro  Asp  Glu  Ile  Lys  Glu  Thr  Asn  Gly
545                      550                      555                      560

Leu  Leu  Tyr  Tyr  Asp  Asp  Lys  Pro  Ile  Tyr  Glu  Ser  Ser  Val  Met  Thr
                    565                      570                      575

Tyr  Leu  Asp  Glu  Asn  Thr  Ala  Lys  Glu  Val  Lys  Lys  Gln  Ile  Asn  Asp
               580                      585                      590

Thr  Thr  Gly  Lys  Phe  Lys  Asp  Val  Asn  His  Leu  Tyr  Asp  Val  Lys  Leu
          595                      600                      605

Thr  Pro  Lys  Met  Asn  Phe  Thr  Ile  Lys  Met  Ala  Ser  Leu  Tyr  Asp  Gly
     610                      615                      620

Ala  Glu  Asn  Asn  His  Asn  Ser  Leu  Gly  Thr  Trp  Tyr  Leu  Thr  Tyr  Asn
625                      630                      635                      640

Val  Ala  Gly  Gly  Asn  Thr  Gly  Lys  Arg  Gln  Tyr  Arg  Ser  Ala  His  Ser
                    645                      650                      655

Cys  Ala  His  Val  Ala  Leu  Ser  Ser  Glu  Ala  Lys  Lys  Lys  Leu  Asn  Gln
               660                      665                      670

Asn  Ala  Asn  Tyr  Tyr  Leu  Ser  Met  Tyr  Met  Lys  Ala  Asp  Ser  Thr  Thr
          675                      680                      685

Glu  Pro  Thr  Ile  Glu  Val  Ala  Gly  Glu  Lys  Ser  Ala  Ile  Thr  Ser  Lys
     690                      695                      700

Lys  Val  Lys  Leu  Asn  Asn  Gln  Asn  Tyr  Gln  Arg  Val  Asp  Ile  Leu  Val
705                      710                      715                      720

Lys  Asn  Ser  Glu  Arg  Asn  Pro  Met  Asp  Lys  Ile  Tyr  Ile  Arg  Gly  Asn
                    725                      730                      735
```

| | | | | | | | | | | | | | | |
|---|---|---|---|---|---|---|---|---|---|---|---|---|---|---|
| Gly | Thr | Thr | Asn<br>740 | Val | Tyr | Gly | Asp<br>745 | Val | Thr | Ile | Pro | Glu<br>750 | Val | Ser |
| Ala | Ile | Asn<br>755 | Pro | Ala | Ser | Leu | Ser<br>760 | Asp | Glu | Glu | Ile | Gln<br>765 | Glu | Ile | Phe |
| Lys | Asp<br>770 | Ser | Thr | Ile | Glu | Tyr<br>775 | Gly | Asn | Pro | Ser | Phe<br>780 | Val | Ala | Asp | Ala |
| Val<br>785 | Thr | Phe | Lys | Asn | Ile<br>790 | Lys | Pro | Leu | Gln | Asn<br>795 | Tyr | Val | Lys | Glu | Tyr<br>800 |
| Glu | Ile | Tyr | His | Lys<br>805 | Ser | His | Arg | Tyr | Glu<br>810 | Lys | Lys | Thr | Val | Phe<br>815 | Asp |
| Ile | Met | Gly | Val<br>820 | His | Tyr | Glu | Tyr | Ser<br>825 | Ile | Ala | Arg | Glu | Gln<br>830 | Lys | Lys |
| Ala | Ala |

(2) INFORMATION FOR SEQ ID NO:22:

(i) SEQUENCE CHARACTERISTICS:
        (A) LENGTH: 4041 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..4038
        (D) OTHER INFORMATION: /product="VIP1A(a)/VIP2A(a) fusion

```
GAA GGT AAT ACG ATT AAT TCT GAT GCA ATG GCA CAG TTT AAA GAA CAA      528
Glu Gly Asn Thr Ile Asn Ser Asp Ala Met Ala Gln Phe Lys Glu Gln
995             1000            1005            1010

TTT TTA GAT AGG GAT ATT AAG TTT GAT AGT TAT CTA GAT ACG CAT TTA      576
Phe Leu Asp Arg Asp Ile Lys Phe Asp Ser Tyr Leu Asp Thr His Leu
        1015            1020            1025

ACT GCT CAA CAA GTT TCC AGT AAA GAA AGA GTT ATT TTG AAG GTT ACG      624
Thr Ala Gln Gln Val Ser Ser Lys Glu Arg Val Ile Leu Lys Val Thr
            1030            1035            1040

GTT CCG AGT GGG AAA GGT TCT ACT ACT CCA ACA AAA GCA GGT GTC ATT      672
Val Pro Ser Gly Lys Gly Ser Thr Thr Pro Thr Lys Ala Gly Val Ile
        1045            1050            1055

TTA AAT AAT AGT GAA TAC AAA ATG CTC ATT GAT AAT GGG TAT ATG GTC      720
Leu Asn Asn Ser Glu Tyr Lys Met Leu Ile Asp Asn Gly Tyr Met Val
            1060            1065            1070

CAT GTA GAT AAG GTA TCA AAA GTG GTG AAA AAA GGG GTG GAG TGC TTA      768
His Val Asp Lys Val Ser Lys Val Val Lys Lys Gly Val Glu Cys Leu
1075            1080            1085            1090

CAA ATT GAA GGG ACT TTA AAA AAG AGT CTT GAC TTT AAA AAT GAT ATA      816
Gln Ile Glu Gly Thr Leu Lys Lys Ser Leu Asp Phe Lys Asn Asp Ile
            1095            1100            1105

AAT GCT GAA GCG CAT AGC TGG GGT ATG AAG AAT TAT GAA GAG TGG GCT      864
Asn Ala Glu Ala His Ser Trp Gly Met Lys Asn Tyr Glu Glu Trp Ala
        1110            1115            1120

AAA GAT TTA ACC GAT TCG CAA AGG GAA GCT TTA GAT GGG TAT GCT AGG      912
Lys Asp Leu Thr Asp Ser Gln Arg Glu Ala Leu Asp Gly Tyr Ala Arg
            1125            1130            1135

CAA GAT TAT AAA GAA ATC AAT AAT TAT TTA AGA AAT CAA GGC GGA AGT      960
Gln Asp Tyr Lys Glu Ile Asn Asn Tyr Leu Arg Asn Gln Gly Gly Ser
        1140            1145            1150

GGA AAT GAA AAA CTA GAT GCT CAA ATA AAA AAT ATT TCT GAT GCT TTA     1008
Gly Asn Glu Lys Leu Asp Ala Gln Ile Lys Asn Ile Ser Asp Ala Leu
1155            1160            1165            1170

GGG AAG AAA CCA ATA CCG GAA AAT ATT ACT GTG TAT AGA TGG TGT GGC     1056
Gly Lys Lys Pro Ile Pro Glu Asn Ile Thr Val Tyr Arg Trp Cys Gly
            1175            1180            1185

ATG CCG GAA TTT GGT TAT CAA ATT AGT GAT CCG TTA CCT TCT TTA AAA     1104
Met Pro Glu Phe Gly Tyr Gln Ile Ser Asp Pro Leu Pro Ser Leu Lys
        1190            1195            1200

GAT TTT GAA GAA CAA TTT TTA AAT ACA ATC AAA GAA GAC AAA GGA TAT     1152
Asp Phe Glu Glu Gln Phe Leu Asn Thr Ile Lys Glu Asp Lys Gly Tyr
        1205            1210            1215

ATG AGT ACA AGC TTA TCG AGT GAA CGT CTT GCA GCT TTT GGA TCT AGA     1200
Met Ser Thr Ser Leu Ser Ser Glu Arg Leu Ala Ala Phe Gly Ser Arg
        1220            1225            1230

AAA ATT ATA TTA CGA TTA CAA GTT CCG AAA GGA AGT ACG GGT GCG TAT     1248
Lys Ile Ile Leu Arg Leu Gln Val Pro Lys Gly Ser Thr Gly Ala Tyr
1235            1240            1245            1250

TTA AGT GCC ATT GGT GGA TTT GCA AGT GAA AAA GAG ATC CTA CTT GAT     1296
Leu Ser Ala Ile Gly Gly Phe Ala Ser Glu Lys Glu Ile Leu Leu Asp
            1255            1260            1265

AAA GAT AGT AAA TAT CAT ATT GAT AAA GTA ACA GAG GTA ATT ATT AAA     1344
Lys Asp Ser Lys Tyr His Ile Asp Lys Val Thr Glu Val Ile Ile Lys
        1270            1275            1280

GGT GTT AAG CGA TAT GTA GTG GAT GCA ACA TTA TTA ACA AAT ATG AAA     1392
Gly Val Lys Arg Tyr Val Val Asp Ala Thr Leu Leu Thr Asn Met Lys
        1285            1290            1295

AAT ATG AAG AAA AAG TTA GCA AGT GTT GTA ACG TGT ACG TTA TTA GCT     1440
Asn Met Lys Lys Lys Leu Ala Ser Val Val Thr Cys Thr Leu Leu Ala
        1300            1305            1310
```

```
CCT  ATG  TTT  TTG  AAT  GGA  AAT  GTG  AAT  GCT  GTT  TAC  GCA  GAC  AGC  AAA         1488
Pro  Met  Phe  Leu  Asn  Gly  Asn  Val  Asn  Ala  Val  Tyr  Ala  Asp  Ser  Lys
1315                      1320                     1325                    1330

ACA  AAT  CAA  ATT  TCT  ACA  ACA  CAG  AAA  AAT  CAA  CAG  AAA  GAG  ATG  GAC         1536
Thr  Asn  Gln  Ile  Ser  Thr  Thr  Gln  Lys  Asn  Gln  Gln  Lys  Glu  Met  Asp
                    1335                     1340                     1345

CGA  AAA  GGA  TTA  CTT  GGG  TAT  TAT  TTC  AAA  GGA  AAA  GAT  TTT  AGT  AAT         1584
Arg  Lys  Gly  Leu  Leu  Gly  Tyr  Tyr  Phe  Lys  Gly  Lys  Asp  Phe  Ser  Asn
               1350                     1355                     1360

CTT  ACT  ATG  TTT  GCA  CCG  ACA  CGT  GAT  AGT  ACT  CTT  ATT  TAT  GAT  CAA         1632
Leu  Thr  Met  Phe  Ala  Pro  Thr  Arg  Asp  Ser  Thr  Leu  Ile  Tyr  Asp  Gln
          1365                     1370                     1375

CAA  ACA  GCA  AAT  AAA  CTA  TTA  GAT  AAA  AAA  CAA  CAA  GAA  TAT  CAG  TCT         1680
Gln  Thr  Ala  Asn  Lys  Leu  Leu  Asp  Lys  Lys  Gln  Gln  Glu  Tyr  Gln  Ser
     1380                     1385                     1390

ATT  CGT  TGG  ATT  GGT  TTG  ATT  CAG  AGT  AAA  GAA  ACG  GGA  GAT  TTC  ACA         1728
Ile  Arg  Trp  Ile  Gly  Leu  Ile  Gln  Ser  Lys  Glu  Thr  Gly  Asp  Phe  Thr
1395                     1400                     1405                     1410

TTT  AAC  TTA  TCT  GAG  GAT  GAA  CAG  GCA  ATT  ATA  GAA  ATC  AAT  GGG  AAA         1776
Phe  Asn  Leu  Ser  Glu  Asp  Glu  Gln  Ala  Ile  Ile  Glu  Ile  Asn  Gly  Lys
                    1415                     1420                     1425

ATT  ATT  TCT  AAT  AAA  GGG  AAA  GAA  AAG  CAA  GTT  GTC  CAT  TTA  GAA  AAA         1824
Ile  Ile  Ser  Asn  Lys  Gly  Lys  Glu  Lys  Gln  Val  Val  His  Leu  Glu  Lys
               1430                     1435                     1440

GGA  AAA  TTA  GTT  CCA  ATC  AAA  ATA  GAG  TAT  CAA  TCA  GAT  ACA  AAA  TTT         1872
Gly  Lys  Leu  Val  Pro  Ile  Lys  Ile  Glu  Tyr  Gln  Ser  Asp  Thr  Lys  Phe
          1445                     1450                     1455

AAT  ATT  GAC  AGT  AAA  ACA  TTT  AAA  GAA  CTT  AAA  TTA  TTT  AAA  ATA  GAT         1920
Asn  Ile  Asp  Ser  Lys  Thr  Phe  Lys  Glu  Leu  Lys  Leu  Phe  Lys  Ile  Asp
     1460                     1465                     1470

AGT  CAA  AAC  CAA  CCC  CAG  CAA  GTC  CAG  CAA  GAT  GAA  CTG  AGA  AAT  CCT         1968
Ser  Gln  Asn  Gln  Pro  Gln  Gln  Val  Gln  Gln  Asp  Glu  Leu  Arg  Asn  Pro
1475                     1480                     1485                     1490

GAA  TTT  AAC  AAG  AAA  GAA  TCA  CAG  GAA  TTC  TTA  GCG  AAA  CCA  TCG  AAA         2016
Glu  Phe  Asn  Lys  Lys  Glu  Ser  Gln  Glu  Phe  Leu  Ala  Lys  Pro  Ser  Lys
                    1495                     1500                     1505

ATA  AAT  CTT  TTC  ACT  CAA  AAA  ATG  AAA  AGG  GAA  ATT  GAT  GAA  GAC  ACG         2064
Ile  Asn  Leu  Phe  Thr  Gln  Lys  Met  Lys  Arg  Glu  Ile  Asp  Glu  Asp  Thr
               1510                     1515                     1520

GAT  ACG  GAT  GGG  GAC  TCT  ATT  CCT  GAC  CTT  TGG  GAA  GAA  AAT  GGG  TAT         2112
Asp  Thr  Asp  Gly  Asp  Ser  Ile  Pro  Asp  Leu  Trp  Glu  Glu  Asn  Gly  Tyr
          1525                     1530                     1535

ACG  ATT  CAA  AAT  AGA  ATC  GCT  GTA  AAG  TGG  GAC  GAT  TCT  CTA  GCA  AGT         2160
Thr  Ile  Gln  Asn  Arg  Ile  Ala  Val  Lys  Trp  Asp  Asp  Ser  Leu  Ala  Ser
     1540                     1545                     1550

AAA  GGG  TAT  ACG  AAA  TTT  GTT  TCA  AAT  CCA  CTA  GAA  AGT  CAC  ACA  GTT         2208
Lys  Gly  Tyr  Thr  Lys  Phe  Val  Ser  Asn  Pro  Leu  Glu  Ser  His  Thr  Val
1555                     1560                     1565                     1570

GGT  GAT  CCT  TAT  ACA  GAT  TAT  GAA  AAG  GCA  GCA  AGA  GAT  CTA  GAT  TTG         2256
Gly  Asp  Pro  Tyr  Thr  Asp  Tyr  Glu  Lys  Ala  Ala  Arg  Asp  Leu  Asp  Leu
                    1575                     1580                     1585

TCA  AAT  GCA  AAG  GAA  ACG  TTT  AAC  CCA  TTG  GTA  GCT  GCT  TTT  CCA  AGT         2304
Ser  Asn  Ala  Lys  Glu  Thr  Phe  Asn  Pro  Leu  Val  Ala  Ala  Phe  Pro  Ser
               1590                     1595                     1600

GTG  AAT  GTT  AGT  ATG  GAA  AAG  GTG  ATA  TTA  TCA  CCA  AAT  GAA  AAT  TTA         2352
Val  Asn  Val  Ser  Met  Glu  Lys  Val  Ile  Leu  Ser  Pro  Asn  Glu  Asn  Leu
          1605                     1610                     1615

TCC  AAT  AGT  GTA  GAG  TCT  CAT  TCA  TCC  ACG  AAT  TGG  TCT  TAT  ACA  AAT         2400
Ser  Asn  Ser  Val  Glu  Ser  His  Ser  Ser  Thr  Asn  Trp  Ser  Tyr  Thr  Asn
     1620                     1625                     1630
```

| | | | | | | | | | | | | | | | | |
|---|---|---|---|---|---|---|---|---|---|---|---|---|---|---|---|---|
| ACA | GAA | GGT | GCT | TCT | GTT | GAA | GCG | GGG | ATT | GGA | CCA | AAA | GGT | ATT | TCG | 2448 |
| Thr | Glu | Gly | Ala | Ser | Val | Glu | Ala | Gly | Ile | Gly | Pro | Lys | Gly | Ile | Ser | |
| 1635 | | | | 1640 | | | | 1645 | | | | | 1650 | | | |
| TTC | GGA | GTT | AGC | GTA | AAC | TAT | CAA | CAC | TCT | GAA | ACA | GTT | GCA | CAA | GAA | 2496 |
| Phe | Gly | Val | Ser | Val | Asn | Tyr | Gln | His | Ser | Glu | Thr | Val | Ala | Gln | Glu | |
| | | | 1655 | | | | 1660 | | | | | 1665 | | | | |
| TGG | GGA | ACA | TCT | ACA | GGA | AAT | ACT | TCG | CAA | TTC | AAT | ACG | GCT | TCA | GCG | 2544 |
| Trp | Gly | Thr | Ser | Thr | Gly | Asn | Thr | Ser | Gln | Phe | Asn | Thr | Ala | Ser | Ala | |
| | | | 1670 | | | | 1675 | | | | | 1680 | | | | |
| GGA | TAT | TTA | AAT | GCA | AAT | GTT | CGA | TAT | AAC | AAT | GTA | GGA | ACT | GGT | GCC | 2592 |
| Gly | Tyr | Leu | Asn | Ala | Asn | Val | Arg | Tyr | Asn | Asn | Val | Gly | Thr | Gly | Ala | |
| | | | 1685 | | | | 1690 | | | | | 1695 | | | | |
| ATC | TAC | GAT | GTA | AAA | CCT | ACA | ACA | AGT | TTT | GTA | TTA | AAT | AAC | GAT | ACT | 2640 |
| Ile | Tyr | Asp | Val | Lys | Pro | Thr | Thr | Ser | Phe | Val | Leu | Asn | Asn | Asp | Thr | |
| 1700 | | | | | 1705 | | | | 1710 | | | | | | | |
| ATC | GCA | ACT | ATT | ACG | GCG | AAA | TCT | AAT | TCT | ACA | GCC | TTA | AAT | ATA | TCT | 2688 |
| Ile | Ala | Thr | Ile | Thr | Ala | Lys | Ser | Asn | Ser | Thr | Ala | Leu | Asn | Ile | Ser | |
| 1715 | | | | 1720 | | | | | 1725 | | | | | 1730 | | |
| CCT | GGA | GAA | AGT | TAC | CCG | AAA | AAA | GGA | CAA | AAT | GGA | ATC | GCA | ATA | ACA | 2736 |
| Pro | Gly | Glu | Ser | Tyr | Pro | Lys | Lys | Gly | Gln | Asn | Gly | Ile | Ala | Ile | Thr | |
| | | | | 1735 | | | | 1740 | | | | | 1745 | | | |
| TCA | ATG | GAT | GAT | TTT | AAT | TCC | CAT | CCG | ATT | ACA | TTA | AAT | AAA | AAA | CAA | 2784 |
| Ser | Met | Asp | Asp | Phe | Asn | Ser | His | Pro | Ile | Thr | Leu | Asn | Lys | Lys | Gln | |
| | | | 1750 | | | | 1755 | | | | | 1760 | | | | |
| GTA | GAT | AAT | CTG | CTA | AAT | AAT | AAA | CCT | ATG | ATG | TTG | GAA | ACA | AAC | CAA | 2832 |
| Val | Asp | Asn | Leu | Leu | Asn | Asn | Lys | Pro | Met | Met | Leu | Glu | Thr | Asn | Gln | |
| | | | 1765 | | | | 1770 | | | | | 1775 | | | | |
| ACA | GAT | GGT | GTT | TAT | AAG | ATA | AAA | GAT | ACA | CAT | GGA | AAT | ATA | GTA | ACT | 2880 |
| Thr | Asp | Gly | Val | Tyr | Lys | Ile | Lys | Asp | Thr | His | Gly | Asn | Ile | Val | Thr | |
| | | | 1780 | | | | 1785 | | | | | 1790 | | | | |
| GGC | GGA | GAA | TGG | AAT | GGT | GTC | ATA | CAA | CAA | ATC | AAG | GCT | AAA | ACA | GCG | 2928 |
| Gly | Gly | Glu | Trp | Asn | Gly | Val | Ile | Gln | Gln | Ile | Lys | Ala | Lys | Thr | Ala | |
| 1795 | | | | | 1800 | | | | 1805 | | | | | 1810 | | |
| TCT | ATT | ATT | GTG | GAT | GAT | GGG | GAA | CGT | GTA | GCA | GAA | AAA | CGT | GTA | GCG | 2976 |
| Ser | Ile | Ile | Val | Asp | Asp | Gly | Glu | Arg | Val | Ala | Glu | Lys | Arg | Val | Ala | |
| | | | | 1815 | | | | 1820 | | | | | 1825 | | | |
| GCA | AAA | GAT | TAT | GAA | AAT | CCA | GAA | GAT | AAA | ACA | CCG | TCT | TTA | ACT | TTA | 3024 |
| Ala | Lys | Asp | Tyr | Glu | Asn | Pro | Glu | Asp | Lys | Thr | Pro | Ser | Leu | Thr | Leu | |
| | | | | 1830 | | | | 1835 | | | | | 1840 | | | |
| AAA | GAT | GCC | CTG | AAG | CTT | TCA | TAT | CCA | GAT | GAA | ATA | AAA | GAA | ATA | GAG | 3072 |
| Lys | Asp | Ala | Leu | Lys | Leu | Ser | Tyr | Pro | Asp | Glu | Ile | Lys | Glu | Ile | Glu | |
| | | | 1845 | | | | 1850 | | | | | 1855 | | | | |
| GGA | TTA | TTA | TAT | TAT | AAA | AAC | AAA | CCG | ATA | TAC | GAA | TCG | AGC | GTT | ATG | 3120 |
| Gly | Leu | Leu | Tyr | Tyr | Lys | Asn | Lys | Pro | Ile | Tyr | Glu | Ser | Ser | Val | Met | |
| | | | 1860 | | | | 1865 | | | | | 1870 | | | | |
| ACT | TAC | TTA | GAT | GAA | AAT | ACA | GCA | AAA | GAA | GTG | ACC | AAA | CAA | TTA | AAT | 3168 |
| Thr | Tyr | Leu | Asp | Glu | Asn | Thr | Ala | Lys | Glu | Val | Thr | Lys | Gln | Leu | Asn | |
| 1875 | | | | | 1880 | | | | 1885 | | | | | 1890 | | |
| GAT | ACC | ACT | GGG | AAA | TTT | AAA | GAT | GTA | AGT | CAT | TTA | TAT | GAT | GTA | AAA | 3216 |
| Asp | Thr | Thr | Gly | Lys | Phe | Lys | Asp | Val | Ser | His | Leu | Tyr | Asp | Val | Lys | |
| | | | | 1895 | | | | 1900 | | | | | 1905 | | | |
| CTG | ACT | CCA | AAA | ATG | AAT | GTT | ACA | ATC | AAA | TTG | TCT | ATA | CTT | TAT | GAT | 3264 |
| Leu | Thr | Pro | Lys | Met | Asn | Val | Thr | Ile | Lys | Leu | Ser | Ile | Leu | Tyr | Asp | |
| | | | 1910 | | | | 1915 | | | | | 1920 | | | | |
| AAT | GCT | GAG | TCT | AAT | GAT | AAC | TCA | ATT | GGT | AAA | TGG | ACA | AAC | ACA | AAT | 3312 |
| Asn | Ala | Glu | Ser | Asn | Asp | Asn | Ser | Ile | Gly | Lys | Trp | Thr | Asn | Thr | Asn | |
| | | | | 1925 | | | | 1930 | | | | | 1935 | | | |
| ATT | GTT | TCA | GGT | GGA | AAT | AAC | GGA | AAA | AAA | CAA | TAT | TCT | TCT | AAT | AAT | 3360 |
| Ile | Val | Ser | Gly | Gly | Asn | Asn | Gly | Lys | Lys | Gln | Tyr | Ser | Ser | Asn | Asn | |
| | | | 1940 | | | | 1945 | | | | | 1950 | | | | |

| | | | | | | | | | | | | | | | | |
|---|---|---|---|---|---|---|---|---|---|---|---|---|---|---|---|---|
| CCG | GAT | GCT | AAT | TTG | ACA | TTA | AAT | ACA | GAT | GCT | CAA | GAA | AAA | TTA | AAT | 3408 |
| Pro | Asp | Ala | Asn | Leu | Thr | Leu | Asn | Thr | Asp | Ala | Gln | Glu | Lys | Leu | Asn | |
| 1955 | | | | 1960 | | | | | 1965 | | | | | | 1970 | |
| AAA | AAT | CGT | GAC | TAT | TAT | ATA | AGT | TTA | TAT | ATG | AAG | TCA | GAA | AAA | AAC | 3456 |
| Lys | Asn | Arg | Asp | Tyr | Tyr | Ile | Ser | Leu | Tyr | Met | Lys | Ser | Glu | Lys | Asn | |
| | | | 1975 | | | | | 1980 | | | | | 1985 | | | |
| ACA | CAA | TGT | GAG | ATT | ACT | ATA | GAT | GGG | GAG | ATT | TAT | CCG | ATC | ACT | ACA | 3504 |
| Thr | Gln | Cys | Glu | Ile | Thr | Ile | Asp | Gly | Glu | Ile | Tyr | Pro | Ile | Thr | Thr | |
| | | | 1990 | | | | | 1995 | | | | | 2000 | | | |
| AAA | ACA | GTG | AAT | GTG | AAT | AAA | GAC | AAT | TAC | AAA | AGA | TTA | GAT | ATT | ATA | 3552 |
| Lys | Thr | Val | Asn | Val | Asn | Lys | Asp | Asn | Tyr | Lys | Arg | Leu | Asp | Ile | Ile | |
| | | 2005 | | | | | 2010 | | | | | 2015 | | | | |
| GCT | CAT | AAT | ATA | AAA | AGT | AAT | CCA | ATT | TCT | TCA | CTT | CAT | ATT | AAA | ACG | 3600 |
| Ala | His | Asn | Ile | Lys | Ser | Asn | Pro | Ile | Ser | Ser | Leu | His | Ile | Lys | Thr | |
| | | 2020 | | | | | 2025 | | | | | 2030 | | | | |
| AAT | GAT | GAA | ATA | ACT | TTA | TTT | TGG | GAT | GAT | ATT | TCT | ATA | ACA | GAT | GTA | 3648 |
| Asn | Asp | Glu | Ile | Thr | Leu | Phe | Trp | Asp | Asp | Ile | Ser | Ile | Thr | Asp | Val | |
| 2035 | | | | | 2040 | | | | | 2045 | | | | | 2050 | |
| GCA | TCA | ATA | AAA | CCG | GAA | AAT | TTA | ACA | GAT | TCA | GAA | ATT | AAA | CAG | ATT | 3696 |
| Ala | Ser | Ile | Lys | Pro | Glu | Asn | Leu | Thr | Asp | Ser | Glu | Ile | Lys | Gln | Ile | |
| | | | | 2055 | | | | | 2060 | | | | | 2065 | | |
| TAT | AGT | AGG | TAT | GGT | ATT | AAG | TTA | GAA | GAT | GGA | ATC | CTT | ATT | GAT | AAA | 3744 |
| Tyr | Ser | Arg | Tyr | Gly | Ile | Lys | Leu | Glu | Asp | Gly | Ile | Leu | Ile | Asp | Lys | |
| | | | 2070 | | | | | 2075 | | | | | 2080 | | | |
| AAA | GGT | GGG | ATT | CAT | TAT | GGT | GAA | TTT | ATT | AAT | GAA | GCT | AGT | TTT | AAT | 3792 |
| Lys | Gly | Gly | Ile | His | Tyr | Gly | Glu | Phe | Ile | Asn | Glu | Ala | Ser | Phe | Asn | |
| | | | 2085 | | | | | 2090 | | | | | 2095 | | | |
| ATT | GAA | CCA | TTG | CAA | AAT | TAT | GTG | ACC | AAA | TAT | GAA | GTT | ACT | TAT | AGT | 3840 |
| Ile | Glu | Pro | Leu | Gln | Asn | Tyr | Val | Thr | Lys | Tyr | Glu | Val | Thr | Tyr | Ser | |
| | | | 2100 | | | | | 2105 | | | | | 2110 | | | |
| AGT | GAG | TTA | GGA | CCA | AAC | GTG | AGT | GAC | ACA | CTT | GAA | AGT | GAT | AAA | ATT | 3888 |
| Ser | Glu | Leu | Gly | Pro | Asn | Val | Ser | Asp | Thr | Leu | Glu | Ser | Asp | Lys | Ile | |
| 2115 | | | | | 2120 | | | | | 2125 | | | | | 2130 | |
| TAC | AAG | GAT | GGG | ACA | ATT | AAA | TTT | GAT | TTT | ACC | AAA | TAT | AGT | AAA | AAT | 3936 |
| Tyr | Lys | Asp | Gly | Thr | Ile | Lys | Phe | Asp | Phe | Thr | Lys | Tyr | Ser | Lys | Asn | |
| | | | | 2135 | | | | | 2140 | | | | | 2145 | | |
| GAA | CAA | GGA | TTA | TTT | TAT | GAC | AGT | GGA | TTA | AAT | TGG | GAC | TTT | AAA | ATT | 3984 |
| Glu | Gln | Gly | Leu | Phe | Tyr | Asp | Ser | Gly | Leu | Asn | Trp | Asp | Phe | Lys | Ile | |
| | | | | 2150 | | | | | 2155 | | | | | 2160 | | |
| AAT | GCT | ATT | ACT | TAT | GAT | GGT | AAA | GAG | ATG | AAT | GTT | TTT | CAT | AGA | TAT | 4032 |
| Asn | Ala | Ile | Thr | Tyr | Asp | Gly | Lys | Glu | Met | Asn | Val | Phe | His | Arg | Tyr | |
| | | | | 2165 | | | | | 2170 | | | | | 2175 | | |
| AAT | AAA | TAG | | | | | | | | | | | | | | 4041 |
| Asn | Lys | | | | | | | | | | | | | | | |
| | 2180 | | | | | | | | | | | | | | | |

( 2 ) INFORMATION FOR SEQ ID NO:23:

( i ) SEQUENCE CHARACTERISTICS:
        ( A ) LENGTH: 1346 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

| | | | | | | | | | | | | | | |
|---|---|---|---|---|---|---|---|---|---|---|---|---|---|---|
| Met | Lys | Arg | Met | Glu | Gly | Lys | Leu | Phe | Met | Val | Ser | Lys | Lys | Leu | Gln |
| 1 | | | | 5 | | | | | 10 | | | | | 15 | |
| Val | Val | Thr | Lys | Thr | Val | Leu | Leu | Ser | Thr | Val | Phe | Ser | Ile | Ser | Leu |
| | | | 20 | | | | | 25 | | | | | 30 | | |
| Leu | Asn | Asn | Glu | Val | Ile | Lys | Ala | Glu | Gln | Leu | Asn | Ile | Asn | Ser | Gln |
| | | 35 | | | | | 40 | | | | | 45 | | | |

Ser Lys Tyr Thr Asn Leu Gln Asn Leu Lys Ile Thr Asp Lys Val Glu
    50                      55                  60

Asp Phe Lys Glu Asp Lys Glu Lys Ala Lys Glu Trp Gly Lys Glu Lys
65                  70                  75                  80

Glu Lys Glu Trp Lys Leu Thr Ala Thr Glu Lys Gly Lys Met Asn Asn
            85                  90                      95

Phe Leu Asp Asn Lys Asn Asp Ile Lys Thr Asn Tyr Lys Glu Ile Thr
            100                 105                 110

Phe Ser Met Ala Gly Ser Phe Glu Asp Glu Ile Lys Asp Leu Lys Glu
        115                 120                 125

Ile Asp Lys Met Phe Asp Lys Thr Asn Leu Ser Asn Ser Ile Ile Thr
    130                 135                 140

Tyr Lys Asn Val Glu Pro Thr Thr Ile Gly Phe Asn Lys Ser Leu Thr
145                 150                 155                 160

Glu Gly Asn Thr Ile Asn Ser Asp Ala Met Ala Gln Phe Lys Glu Gln
                165                 170                 175

Phe Leu Asp Arg Asp Ile Lys Phe Asp Ser Tyr Leu Asp Thr His Leu
            180                 185                 190

Thr Ala Gln Gln Val Ser Ser Lys Glu Arg Val Ile Leu Lys Val Thr
        195                 200                 205

Val Pro Ser Gly Lys Gly Ser Thr Thr Pro Thr Lys Ala Gly Val Ile
    210                 215                 220

Leu Asn Asn Ser Glu Tyr Lys Met Leu Ile Asp Asn Gly Tyr Met Val
225                 230                 235                 240

His Val Asp Lys Val Ser Lys Val Val Lys Lys Gly Val Glu Cys Leu
                245                 250                 255

Gln Ile Glu Gly Thr Leu Lys Lys Ser Leu Asp Phe Lys Asn Asp Ile
            260                 265                 270

Asn Ala Glu Ala His Ser Trp Gly Met Lys Asn Tyr Glu Glu Trp Ala
        275                 280                 285

Lys Asp Leu Thr Asp Ser Gln Arg Glu Ala Leu Asp Gly Tyr Ala Arg
    290                 295                 300

Gln Asp Tyr Lys Glu Ile Asn Asn Tyr Leu Arg Asn Gln Gly Gly Ser
305                 310                 315                 320

Gly Asn Glu Lys Leu Asp Ala Gln Ile Lys Asn Ile Ser Asp Ala Leu
                325                 330                 335

Gly Lys Lys Pro Ile Pro Glu Asn Ile Thr Val Tyr Arg Trp Cys Gly
            340                 345                 350

Met Pro Glu Phe Gly Tyr Gln Ile Ser Asp Pro Leu Pro Ser Leu Lys
        355                 360                 365

Asp Phe Glu Glu Gln Phe Leu Asn Thr Ile Lys Glu Asp Lys Gly Tyr
    370                 375                 380

Met Ser Thr Ser Leu Ser Ser Glu Arg Leu Ala Ala Phe Gly Ser Arg
385                 390                 395                 400

Lys Ile Ile Leu Arg Leu Gln Val Pro Lys Gly Ser Thr Gly Ala Tyr
                405                 410                 415

Leu Ser Ala Ile Gly Gly Phe Ala Ser Glu Lys Glu Ile Leu Leu Asp
            420                 425                 430

Lys Asp Ser Lys Tyr His Ile Asp Lys Val Thr Glu Val Ile Ile Lys
        435                 440                 445

Gly Val Lys Arg Tyr Val Val Asp Ala Thr Leu Leu Thr Asn Met Lys
450                 455                 460

Asn Met Lys Lys Lys Leu Ala Ser Val Val Thr Cys Thr Leu Leu Ala

```
465                    470                    475                    480
Pro  Met  Phe  Leu  Asn  Gly  Asn  Val  Asn  Ala  Val  Tyr  Ala  Asp  Ser  Lys
                         485                    490                    495
Thr  Asn  Gln  Ile  Ser  Thr  Thr  Gln  Lys  Asn  Gln  Lys  Glu  Met  Asp
               500                    505                    510
Arg  Lys  Gly  Leu  Leu  Gly  Tyr  Tyr  Phe  Lys  Gly  Lys  Asp  Phe  Ser  Asn
               515                    520                    525
Leu  Thr  Met  Phe  Ala  Pro  Thr  Arg  Asp  Ser  Thr  Leu  Ile  Tyr  Asp  Gln
     530                    535                    540
Gln  Thr  Ala  Asn  Lys  Leu  Leu  Asp  Lys  Lys  Gln  Gln  Glu  Tyr  Gln  Ser
545                      550                    555                    560
Ile  Arg  Trp  Ile  Gly  Leu  Ile  Gln  Ser  Lys  Glu  Thr  Gly  Asp  Phe  Thr
                         565                    570                    575
Phe  Asn  Leu  Ser  Glu  Asp  Glu  Gln  Ala  Ile  Ile  Glu  Ile  Asn  Gly  Lys
               580                    585                    590
Ile  Ile  Ser  Asn  Lys  Gly  Lys  Glu  Lys  Gln  Val  Val  His  Leu  Glu  Lys
               595                    600                    605
Gly  Lys  Leu  Val  Pro  Ile  Lys  Ile  Glu  Tyr  Gln  Ser  Asp  Thr  Lys  Phe
     610                    615                    620
Asn  Ile  Asp  Ser  Lys  Thr  Phe  Lys  Glu  Leu  Lys  Leu  Phe  Lys  Ile  Asp
625                      630                    635                    640
Ser  Gln  Asn  Gln  Pro  Gln  Gln  Val  Gln  Gln  Asp  Glu  Leu  Arg  Asn  Pro
                         645                    650                    655
Glu  Phe  Asn  Lys  Lys  Glu  Ser  Gln  Glu  Phe  Leu  Ala  Lys  Pro  Ser  Lys
               660                    665                    670
Ile  Asn  Leu  Phe  Thr  Gln  Lys  Met  Lys  Arg  Glu  Ile  Asp  Glu  Asp  Thr
               675                    680                    685
Asp  Thr  Asp  Gly  Asp  Ser  Ile  Pro  Asp  Leu  Trp  Glu  Glu  Asn  Gly  Tyr
     690                    695                    700
Thr  Ile  Gln  Asn  Arg  Ile  Ala  Val  Lys  Trp  Asp  Asp  Ser  Leu  Ala  Ser
705                      710                    715                    720
Lys  Gly  Tyr  Thr  Lys  Phe  Val  Ser  Asn  Pro  Leu  Glu  Ser  His  Thr  Val
                         725                    730                    735
Gly  Asp  Pro  Tyr  Thr  Asp  Tyr  Glu  Lys  Ala  Ala  Arg  Asp  Leu  Asp  Leu
               740                    745                    750
Ser  Asn  Ala  Lys  Glu  Thr  Phe  Asn  Pro  Leu  Val  Ala  Ala  Phe  Pro  Ser
               755                    760                    765
Val  Asn  Val  Ser  Met  Glu  Lys  Val  Ile  Leu  Ser  Pro  Asn  Glu  Asn  Leu
     770                    775                    780
Ser  Asn  Ser  Val  Glu  Ser  His  Ser  Ser  Thr  Asn  Trp  Ser  Tyr  Thr  Asn
785                      790                    795                    800
Thr  Glu  Gly  Ala  Ser  Val  Glu  Ala  Gly  Ile  Gly  Pro  Lys  Gly  Ile  Ser
                         805                    810                    815
Phe  Gly  Val  Ser  Val  Asn  Tyr  Gln  His  Ser  Glu  Thr  Val  Ala  Gln  Glu
               820                    825                    830
Trp  Gly  Thr  Ser  Thr  Gly  Asn  Thr  Ser  Gln  Phe  Asn  Thr  Ala  Ser  Ala
               835                    840                    845
Gly  Tyr  Leu  Asn  Ala  Asn  Val  Arg  Tyr  Asn  Asn  Val  Gly  Thr  Gly  Ala
     850                    855                    860
Ile  Tyr  Asp  Val  Lys  Pro  Thr  Thr  Ser  Phe  Val  Leu  Asn  Asn  Asp  Thr
865                      870                    875                    880
Ile  Ala  Thr  Ile  Thr  Ala  Lys  Ser  Asn  Ser  Thr  Ala  Leu  Asn  Ile  Ser
                         885                    890                    895
```

```
Pro  Gly  Glu  Ser  Tyr  Pro  Lys  Lys  Gly  Gln  Asn  Gly  Ile  Ala  Ile  Thr
               900                 905                           910

Ser  Met  Asp  Asp  Phe  Asn  Ser  His  Pro  Ile  Thr  Leu  Asn  Lys  Lys  Gln
          915                      920                 925

Val  Asp  Asn  Leu  Leu  Asn  Asn  Lys  Pro  Met  Met  Leu  Glu  Thr  Asn  Gln
930                           935                 940

Thr  Asp  Gly  Val  Tyr  Lys  Ile  Lys  Asp  Thr  His  Gly  Asn  Ile  Val  Thr
945                      950                      955                           960

Gly  Gly  Glu  Trp  Asn  Gly  Val  Ile  Gln  Gln  Ile  Lys  Ala  Lys  Thr  Ala
               965                      970                           975

Ser  Ile  Ile  Val  Asp  Asp  Gly  Glu  Arg  Val  Ala  Glu  Lys  Arg  Val  Ala
               980                 985                           990

Ala  Lys  Asp  Tyr  Glu  Asn  Pro  Glu  Asp  Lys  Thr  Pro  Ser  Leu  Thr  Leu
          995                      1000                     1005

Lys  Asp  Ala  Leu  Lys  Leu  Ser  Tyr  Pro  Asp  Glu  Ile  Lys  Glu  Ile  Glu
     1010                     1015                     1020

Gly  Leu  Leu  Tyr  Tyr  Lys  Asn  Lys  Pro  Ile  Tyr  Glu  Ser  Ser  Val  Met
1025                     1030                     1035                          1040

Thr  Tyr  Leu  Asp  Glu  Asn  Thr  Ala  Lys  Glu  Val  Thr  Lys  Gln  Leu  Asn
               1045                     1050                     1055

Asp  Thr  Thr  Gly  Lys  Phe  Lys  Asp  Val  Ser  His  Leu  Tyr  Asp  Val  Lys
               1060                     1065                     1070

Leu  Thr  Pro  Lys  Met  Asn  Val  Thr  Ile  Lys  Leu  Ser  Ile  Leu  Tyr  Asp
          1075                     1080                     1085

Asn  Ala  Glu  Ser  Asn  Asp  Asn  Ser  Ile  Gly  Lys  Trp  Thr  Asn  Thr  Asn
     1090                     1095                     1100

Ile  Val  Ser  Gly  Gly  Asn  Asn  Gly  Lys  Lys  Gln  Tyr  Ser  Ser  Asn  Asn
1105                     1110                     1115                          1120

Pro  Asp  Ala  Asn  Leu  Thr  Leu  Asn  Thr  Asp  Ala  Gln  Glu  Lys  Leu  Asn
               1125                     1130                     1135

Lys  Asn  Arg  Asp  Tyr  Tyr  Ile  Ser  Leu  Tyr  Met  Lys  Ser  Glu  Lys  Asn
               1140                     1145                     1150

Thr  Gln  Cys  Glu  Ile  Thr  Ile  Asp  Gly  Glu  Ile  Tyr  Pro  Ile  Thr  Thr
               1155                     1160                     1165

Lys  Thr  Val  Asn  Val  Asn  Lys  Asp  Asn  Tyr  Lys  Arg  Leu  Asp  Ile  Ile
     1170                     1175                     1180

Ala  His  Asn  Ile  Lys  Ser  Asn  Pro  Ile  Ser  Ser  Leu  His  Ile  Lys  Thr
1185                     1190                     1195                          1200

Asn  Asp  Glu  Ile  Thr  Leu  Phe  Trp  Asp  Asp  Ile  Ser  Ile  Thr  Asp  Val
               1205                     1210                     1215

Ala  Ser  Ile  Lys  Pro  Glu  Asn  Leu  Thr  Asp  Ser  Glu  Ile  Lys  Gln  Ile
               1220                     1225                     1230

Tyr  Ser  Arg  Tyr  Gly  Ile  Lys  Leu  Glu  Asp  Gly  Ile  Leu  Ile  Asp  Lys
               1235                     1240                     1245

Lys  Gly  Gly  Ile  His  Tyr  Gly  Glu  Phe  Ile  Asn  Glu  Ala  Ser  Phe  Asn
     1250                     1255                     1260

Ile  Glu  Pro  Leu  Gln  Asn  Tyr  Val  Thr  Lys  Tyr  Glu  Val  Thr  Tyr  Ser
1265                     1270                     1275                          1280

Ser  Glu  Leu  Gly  Pro  Asn  Val  Ser  Asp  Thr  Leu  Glu  Ser  Asp  Lys  Ile
               1285                     1290                     1295

Tyr  Lys  Asp  Gly  Thr  Ile  Lys  Phe  Asp  Phe  Thr  Lys  Tyr  Ser  Lys  Asn
               1300                     1305                     1310

Glu  Gln  Gly  Leu  Phe  Tyr  Asp  Ser  Gly  Leu  Asn  Trp  Asp  Phe  Lys  Ile
               1315                     1320                     1325
```

Asn Ala Ile Thr Tyr Asp Gly Lys Glu Met Asn Val Phe His Arg Tyr
    1330                1335                1340

Asn Lys
1345

( 2 ) INFORMATION FOR SEQ ID NO:24:

( i ) SEQUENCE CHARACTERISTICS:
        ( A ) LENGTH: 1399 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..1386
        ( D ) OTHER INFORMATION: /note= "Maize optimized DNA
            sequence for VIP2A(a) protein from AB78"

( x i ) SEQUENCE DESCRIPTION: SEQ ID NO:24:

```
ATGAAGCGCA  TGGAGGGCAA  GCTGTTCATG  GTGAGCAAGA  AGCTCCAGGT  GGTGACCAAG      60
ACCGTGCTGC  TGAGCACCGT  GTTCAGCATC  AGCCTGCTGA  ACAACGAGGT  GATCAAGGCC     120
GAGCAGCTGA  ACATCAACAG  CCAGAGCAAG  TACACCAACC  TCCAGAACCT  GAAGATCACC     180
GACAAGGTGG  AGGACTTCAA  GGAGGACAAG  GAGAAGGCCA  GGAGTGGGG   CAAGGAGAAG     240
GAGAAGGAGT  GGAAGCTTAC  CGCCACCGAG  AAGGGCAAGA  TGAACAACTT  CCTGGACAAC     300
AAGAACGACA  TCAAGACCAA  CTACAAGGAG  ATCACCTTCA  GCATGGCCGG  CAGCTTCGAG     360
GACGAGATCA  AGGACCTGAA  GGAGATCGAC  AAGATGTTCG  ACAAGACCAA  CCTGAGCAAC     420
AGCATCATCA  CCTACAAGAA  CGTGGAGCCC  ACCACCATCG  GCTTCAACAA  GAGCCTGACC     480
GAGGGCAACA  CCATCAACAG  CGACGCCATG  GCCCAGTTCA  AGGAGCAGTT  CCTGGACCGC     540
GACATCAAGT  TCGACAGCTA  CCTGGACACC  CACCTGACCG  CCCAGCAGGT  GAGCAGCAAG     600
GAGCGCGTGA  TCCTGAAGGT  GACCGTCCCC  AGCGGCAAGG  GCAGCACCAC  CCCCACCAAG     660
GCCGGCGTGA  TCCTGAACAA  CAGCGAGTAC  AAGATGCTGA  TCGACAACGG  CTACATGGTG     720
CACGTGGACA  AGGTGAGCAA  GGTGGTGAAG  AAGGGCGTGG  AGTGCCTCCA  GATCGAGGGC     780
ACCCTGAAGA  AGAGTCTAGA  CTTCAAGAAC  GACATCAACG  CCGAGGCCCA  CAGCTGGGGC     840
ATGAAGAACT  ACGAGGAGTG  GGCCAAGGAC  CTGACCGACA  GCCAGCGCGA  GGCCCTGGAC     900
GGCTACGCCC  GCCAGGACTA  CAAGGAGATC  AACAACTACC  TGCGCAACCA  GGGCGGCAGC     960
GGCAACGAGA  AGCTGGACGC  CCAGATCAAG  AACATCAGCG  ACGCCCTGGG  CAAGAAGCCC    1020
ATCCCCGAGA  ACATCACCGT  GTACCGCTGG  TGCGGCATGC  CCGAGTTCGG  CTACCAGATC    1080
AGCGACCCCC  TGCCCAGCCT  GAAGGACTTC  GAGGAGCAGT  TCCTGAACAC  CATCAAGGAG    1140
GACAAGGGCT  ACATGAGCAC  CAGCCTGAGC  AGCGAGCGCC  TGGCCGCCTT  CGGCAGCCGC    1200
AAGATCATCC  TGCGCCTGCA  GGTGCCCAAG  GGCAGCACCG  GCGCCTACCT  GAGCGCCATC    1260
GGCGGCTTCG  CCAGCGAGAA  GGAGATCCTG  CTGGACAAGG  ACAGCAAGTA  CCACATCGAC    1320
AAGGTGACCG  AGGTGATCAT  CAAGGGCGTG  AAGCGCTACG  TGGTGGACGC  CACCCTGCTG    1380
ACCAACTAGA  TCTGAGCTC                                                    1399
```

( 2 ) INFORMATION FOR SEQ ID NO:25:

( i ) SEQUENCE CHARACTERISTICS:
        ( A ) LENGTH: 19 amino acids
        ( B ) TYPE: amino acid ( C ) STRANDEDNESS: single
              ( D ) TOPOLOGY: linear ( i i ) MOLECULE TYPE: peptide ( i x ) FEATURE:
              ( A ) NAME/KEY: Peptide
              ( B ) LOCATION: 1..19
              ( D ) OTHER INFORMATION: /note= "Secretion signal peptide to
                    secrete VIP2 out of a cell"

( x i ) SEQUENCE DESCRIPTION: SEQ ID NO:25:

Gly  Trp  Ser  Trp  Ile  Phe  Leu  Phe  Leu  Leu Ser Gly Ala Ala Gly Val
1 5 10 15

His Cys Leu ( 2 ) INFORMATION FOR SEQ ID NO:26:

( i ) SEQUENCE CHARACTERISTICS:
( A ) LENGTH: 2655 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Synthetic DNA"

( i i i ) HYPOTHETICAL: NO ( i x ) FEATURE:
( A ) NAME/KEY: misc_feature
( B ) LOCATION: 1..2655
( D ) OTHER INFORMATION: /note= "maize optimized DNA sequence encoding VIP1A(a)"

( x i ) SEQUENCE DESCRIPTION: SEQ ID NO:26:

ATGAAGAACA TGAAGAAGAA GCTGGCCAGC GTGGTGACCT GCACCCTGCT GGCCCCCATG 60

TTCCTGAACG GCAACGTGAA CGCCGTGTAC GCCGACAGCA AGACCAACCA GATCAGCACC 120

ACCCAGAAGA ACCAGCAGAA GGAGATGGAC CGCAAGGGCC TGCTGGGCTA CTACTTCAAG 180

GGCAAGGACT TCAGCAACCT GACCATGTTC GCCCCCACGC GTGACAGCAC CCTGATCTAC 240

GACCAGCAGA CCGCCAACAA GCTGCTGGAC AAGAAGCAGC AGGAGTACCA GAGCATCCGC 300

TGGATCGGCC TGATCCAGAG CAAGGAGACC GGCGACTTCA CCTTCAACCT GAGCGAGGAC 360

GAGCAGGCCA TCATCGAGAT CAACGGCAAG ATCATCAGCA ACAAGGGCAA GGAGAAGCAG 420

GTGGTGCACC TGGAGAAGGG CAAGCTGGTG CCCATCAAGA TCGAGTACCA GAGCGACACC 480

AAGTTCAACA TCGACAGCAA GACCTTCAAG GAGCTGAAGC TTTTCAAGAT CGACAGCCAG 540

AACCAGCCCC AGCAGGTGCA GCAGGACGAG CTGCGCAACC CCGAGTTCAA CAAGAAGGAG 600

AGCCAGGAGT TCCTGGCCAA GCCCAGCAAG ATCAACCTGT TCACCCAGCA GATGAAGCGC 660

GAGATCGACG AGGACACCGA CACCGACGGC GACAGCATCC CCGACCTGTG GGAGGAGAAC 720

GGCTACACCA TCCAGAACCG CATCGCCGTG AAGTGGGACG ACAGCCTGGC TAGCAAGGGC 780

TACACCAAGT TCGTGAGCAA CCCCCTGGAG AGCCACACCG TGGGCGACCC CTACACCGAC 840

TACGAGAAGG CCGCCCGCGA CCTGGACCTG AGCAACGCCA AGGAGACCTT CAACCCCCTG 900

GTGGCCGCCT TCCCCAGCGT GAACGTGAGC ATGGAGAAGG TGATCCTGAG CCCCAACGAG 960

AACCTGAGCA ACAGCGTGGA GAGCCACTCG AGCACCAACT GGAGCTACAC CAACACCGAG 1020

GGCGCCAGCG TGGAGGCCGG CATCGGTCCC AAGGGCATCA GCTTCGGCGT GAGCGTGAAC 1080

TACCAGCACA GCGAGACCGT GGCCCAGGAG TGGGGCACCA GCACCGGCAA CACCAGCCAG 1140

TTCAACACCG CCAGCGCCGG CTACCTGAAC GCCAACGTGC GCTACAACAA CGTGGGCACC 1200

| | | | | | |
|---|---|---|---|---|---|
|GGCGCCATCT|ACGACGTGAA|GCCCACCACC|AGCTTCGTGC|TGAACAACGA|CACCATCGCC|1260|
|ACCATCACCG|CCAAGTCGAA|TTCCACCGCC|CTGAACATCA|GCCCGGCGA|GAGCTACCCC|1320|
|AAGAAGGGCC|AGAACGGCAT|CGCCATCACC|AGCATGGACG|ACTTCAACAG|CCACCCCATC|1380|
|ACCCTGAACA|AGAAGCAGGT|GGACAACCTG|CTGAACAACA|AGCCCATGAT|GCTGGAGACC|1440|
|AACCAGACCG|ACGGCGTCTA|CAAGATCAAG|GACACCCACG|GCAACATCGT|GACGGGCGGC|1500|
|GAGTGGAACG|GCGTGATCCA|GCAGATCAAG|GCCAAGACCG|CCAGCATCAT|CGTCGACGAC|1560|
|GGCGAGCGCG|TGGCCGAGAA|GCGCGTGGCC|GCCAAGGACT|ACGAGAACCC|CGAGGACAAG|1620|
|ACCCCCAGCC|TGACCCTGAA|GGACGCCCTG|AAGCTGAGCT|ACCCCGACGA|GATCAAGGAG|1680|
|ATCGAGGGCT|TGCTGTACTA|CAAGAACAAG|CCCATCTACG|AGAGCAGCGT|GATGACCTAT|1740|
|CTAGACGAGA|ACACCGCCAA|GGAGGTGACC|AAGCAGCTGA|ACGACACCAC|CGGCAAGTTC|1800|
|AAGGACGTGA|GCCACCTGTA|CGACGTGAAG|CTGACCCCCA|AGATGAACGT|GACCATCAAG|1860|
|CTGAGCATCC|TGTACGACAA|CGCCGAGAGC|AACGACAACA|GCATCGGCAA|GTGGACCAAC|1920|
|ACCAACATCG|TGAGCGGCGG|CAACAACGGC|AAGAAGCAGT|ACAGCAGCAA|CAACCCCGAC|1980|
|GCCAACCTGA|CCCTGAACAC|CGACGCCCAG|GAGAAGCTGA|ACAAGAACCG|CGACTACTAC|2040|
|ATCAGCCTGT|ACATGAAGAG|CGAGAAGAAC|ACCCAGTGCG|AGATCACCAT|CGACGGCGAG|2100|
|ATATACCCCA|TCACCACCAA|GACCGTGAAC|GTGAACAAGG|ACAACTACAA|GCGCCTGGAC|2160|
|ATCATCGCCC|ACAACATCAA|GAGCAACCCC|ATCAGCAGCC|TGCACATCAA|GACCAACGAC|2220|
|GAGATCACCC|TGTTCTGGGA|CGACATATCG|ATTACCGACG|TCGCCAGCAT|CAAGCCCGAG|2280|
|AACCTGACCG|ACAGCGAGAT|CAAGCAGATA|TACAGTCGCT|ACGGCATCAA|GCTGGAGGAC|2340|
|GGCATCCTGA|TCGACAAGAA|AGGCGGCATC|CACTACGGCG|AGTTCATCAA|CGAGGCCAGC|2400|
|TTCAACATCG|AGCCCCTGCA|GAACTACGTG|ACCAAGTACG|AGGTGACCTA|CAGCAGCGAG|2460|
|CTGGGCCCCA|ACGTGAGCGA|CACCCTGGAG|AGCGACAAGA|TTTACAAGGA|CGGCACCATC|2520|
|AAGTTCGACT|TCACCAAGTA|CAGCAAGAAC|GAGCAGGGCC|TGTTCTACGA|CAGCGGCCTG|2580|
|AACTGGGACT|TCAAGATCAA|CGCCATCACC|TACGACGGCA|AGGAGATGAA|CGTGTTCCAC|2640|
|CGCTACAACA|AGTAG|||||2655|

( 2 ) INFORMATION FOR SEQ ID NO:27:

( i ) SEQUENCE CHARACTERISTICS:
        ( A ) LENGTH: 1389 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i x ) FEATURE:
        ( A ) NAME/KEY: misc_feature
        ( B ) LOCATION: 1..1389
        ( D ) OTHER INFORMATION: /note= "maize optimized DNA
            sequence encoding VIP2A(a)"

( x i ) SEQUENCE DESCRIPTION: SEQ ID NO:27:

```
ATGAAGCGCA TGGAGGGCAA GCTGTTCATG GTGAGCAAGA AGCTCCAGGT GGTGACCAAG      60
ACCGTGCTGC TGAGCACCGT GTTCAGCATC AGCCTGCTGA ACAACGAGGT GATCAAGGCC     120
GAGCAGCTGA ACATCAACAG CCAGAGCAAG TACACCAACC TCCAGAACCT GAAGATCACC     180
GACAAGGTGG AGGACTTCAA GGAGGACAAG GAGAAGGCCA AGGAGTGGGG CAAGGAGAAG     240
```

```
GAGAAGGAGT  GGAAGCTTAC  CGCCACCGAG  AAGGGCAAGA  TGAACAACTT  CCTGGACAAC      300

AAGAACGACA  TCAAGACCAA  CTACAAGGAG  ATCACCTTCA  GCATAGCCGG  CAGCTTCGAG      360

GACGAGATCA  AGGACCTGAA  GGAGATCGAC  AAGATGTTCG  ACAAGACCAA  CCTGAGCAAC      420

AGCATCATCA  CCTACAAGAA  CGTGGAGCCC  ACCACCATCG  GCTTCAACAA  GAGCCTGACC      480

GAGGGCAACA  CCATCAACAG  CGACGCCATG  GCCCAGTTCA  AGGAGCAGTT  CCTGGACCGC      540

GACATCAAGT  TCGACAGCTA  CCTGGACACC  CACCTGACCG  CCCAGCAGGT  GAGCAGCAAG      600

GAGCGCGTGA  TCCTGAAGGT  GACCGTCCCC  AGCGGCAAGG  GCAGCACCAC  CCCCACCAAG      660

GCCGGCGTGA  TCCTGAACAA  CAGCGAGTAC  AAGATGCTGA  TCGACAACGG  CTACATGGTG      720

CACGTGGACA  AGGTGAGCAA  GGTGGTGAAG  AAGGGCGTGG  AGTGCCTCCA  GATCGAGGGC      780

ACCCTGAAGA  AGAGTCTAGA  CTTCAAGAAC  GACATCAACG  CCGAGGCCCA  CAGCTGGGGC      840

ATGAAGAACT  ACGAGGAGTG  GGCCAAGGAC  CTGACCGACA  GCCAGCGCGA  GGCCCTGGAC      900

GGCTACGCCC  GCCAGGACTA  CAAGGAGATC  AACAACTACC  TGCGCAACCA  GGGCGGCAGC      960

GGCAACGAGA  AGCTGGACGC  CCAGATCAAG  AACATCAGCG  ACGCCCTGGG  CAAGAAGCCC     1020

ATCCCCGAGA  ACATCACCGT  GTACCGCTGG  TGCGGCATGC  CCGAGTTCGG  CTACCAGATC     1080

AGCGACCCCC  TGCCCAGCCT  GAAGGACTTC  GAGGAGCAGT  TCCTGAACAC  CATCAAGGAG     1140

GACAAGGGCT  ACATGAGCAC  CAGCCTGAGC  AGCGAGCGCC  TGGCCGCCTT  CGGCAGCCGC     1200

AAGATCATCC  TGCGCCTGCA  GGTGCCCAAG  GGCAGCACTG  GTGCCTACCT  GAGCGCCATC     1260

GGCGGCTTCG  CCAGCGAGAA  GGAGATCCTG  CTGGATAAGG  ACAGCAAGTA  CCACATCGAC     1320

AAGGTGACCG  AGGTGATCAT  CAAGGGCGTG  AAGCGCTACG  TGGTGGACGC  CACCCTGCTG     1380

ACCAACTAG                                                                 1389
```

( 2 ) INFORMATION FOR SEQ ID NO:28:

( i ) SEQUENCE CHARACTERISTICS:
        ( A ) LENGTH: 2378 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i x ) FEATURE:
        ( A ) NAME/KEY: CDS
        ( B ) LOCATION: 9..2375
        ( D ) OTHER INFORMATION: /note= "Native DNA sequence
            encoding VIP3A(a) protein from AB88 as contained in
            pCIB7104"

( x i ) SEQUENCE DESCRIPTION: SEQ ID NO:28:

```
AGATGAAC  ATG  AAC  AAG  AAT  AAT  ACT  AAA  TTA  AGC  ACA  AGA  GCC  TTA  CCA        50
          Met  Asn  Lys  Asn  Asn  Thr  Lys  Leu  Ser  Thr  Arg  Ala  Leu  Pro
            1              5                        10

AGT  TTT  ATT  GAT  TAT  TTT  AAT  GGC  ATT  TAT  GGA  TTT  GCC  ACT  GGT  ATC        98
Ser  Phe  Ile  Asp  Tyr  Phe  Asn  Gly  Ile  Tyr  Gly  Phe  Ala  Thr  Gly  Ile
 15             20                       25                        30

AAA  GAC  ATT  ATG  AAC  ATG  ATT  TTT  AAA  ACG  GAT  ACA  GGT  GGT  GAT  CTA       146
Lys  Asp  Ile  Met  Asn  Met  Ile  Phe  Lys  Thr  Asp  Thr  Gly  Gly  Asp  Leu
                      35                       40                       45

ACC  CTA  GAC  GAA  ATT  TTA  AAG  AAT  CAG  CAG  TTA  CTA  AAT  GAT  ATT  TCT       194
Thr  Leu  Asp  Glu  Ile  Leu  Lys  Asn  Gln  Gln  Leu  Leu  Asn  Asp  Ile  Ser
                 50                       55                       60

GGT  AAA  TTG  GAT  GGG  GTG  AAT  GGA  AGC  TTA  AAT  GAT  CTT  ATC  GCA  CAG       242
Gly  Lys  Leu  Asp  Gly  Val  Asn  Gly  Ser  Leu  Asn  Asp  Leu  Ile  Ala  Gln
```

-continued

```
                      65                              70                              75

GGA  AAC  TTA  AAT  ACA  GAA  TTA  TCT  AAG  GAA  ATA  TTA  AAA  ATT  GCA  AAT      290
Gly  Asn  Leu  Asn  Thr  Glu  Leu  Ser  Lys  Glu  Ile  Leu  Lys  Ile  Ala  Asn
          80                       85                       90

GAA  CAA  AAT  CAA  GTT  TTA  AAT  GAT  GTT  AAT  AAC  AAA  CTC  GAT  GCG  ATA      338
Glu  Gln  Asn  Gln  Val  Leu  Asn  Asp  Val  Asn  Asn  Lys  Leu  Asp  Ala  Ile
95                       100                      105                      110

AAT  ACG  ATG  CTT  CGG  GTA  TAT  CTA  CCT  AAA  ATT  ACC  TCT  ATG  TTG  AGT      386
Asn  Thr  Met  Leu  Arg  Val  Tyr  Leu  Pro  Lys  Ile  Thr  Ser  Met  Leu  Ser
                    115                      120                      125

GAT  GTA  ATG  AAA  CAA  AAT  TAT  GCG  CTA  AGT  CTG  CAA  ATA  GAA  TAC  TTA      434
Asp  Val  Met  Lys  Gln  Asn  Tyr  Ala  Leu  Ser  Leu  Gln  Ile  Glu  Tyr  Leu
               130                      135                      140

AGT  AAA  CAA  TTG  CAA  GAG  ATT  TCT  GAT  AAG  TTG  GAT  ATT  ATT  AAT  GTA      482
Ser  Lys  Gln  Leu  Gln  Glu  Ile  Ser  Asp  Lys  Leu  Asp  Ile  Ile  Asn  Val
          145                      150                      155

AAT  GTA  CTT  ATT  AAC  TCT  ACA  CTT  ACT  GAA  ATT  ACA  CCT  GCG  TAT  CAA      530
Asn  Val  Leu  Ile  Asn  Ser  Thr  Leu  Thr  Glu  Ile  Thr  Pro  Ala  Tyr  Gln
160                      165                      170

AGG  ATT  AAA  TAT  GTG  AAC  GAA  AAA  TTT  GAG  GAA  TTA  ACT  TTT  GCT  ACA      578
Arg  Ile  Lys  Tyr  Val  Asn  Glu  Lys  Phe  Glu  Glu  Leu  Thr  Phe  Ala  Thr
175                      180                      185                      190

GAA  ACT  AGT  TCA  AAA  GTA  AAA  AAG  GAT  GGC  TCT  CCT  GCA  GAT  ATT  CTT      626
Glu  Thr  Ser  Ser  Lys  Val  Lys  Lys  Asp  Gly  Ser  Pro  Ala  Asp  Ile  Leu
                    195                      200                      205

GAT  GAG  TTA  ACT  GAG  TTA  ACT  GAA  CTA  GCG  AAA  AGT  GTA  ACA  AAA  AAT      674
Asp  Glu  Leu  Thr  Glu  Leu  Thr  Glu  Leu  Ala  Lys  Ser  Val  Thr  Lys  Asn
               210                      215                      220

GAT  GTG  GAT  GGT  TTT  GAA  TTT  TAC  CTT  AAT  ACA  TTC  CAC  GAT  GTA  ATG      722
Asp  Val  Asp  Gly  Phe  Glu  Phe  Tyr  Leu  Asn  Thr  Phe  His  Asp  Val  Met
          225                      230                      235

GTA  GGA  AAT  AAT  TTA  TTC  GGG  CGT  TCA  GCT  TTA  AAA  ACT  GCA  TCG  GAA      770
Val  Gly  Asn  Asn  Leu  Phe  Gly  Arg  Ser  Ala  Leu  Lys  Thr  Ala  Ser  Glu
     240                      245                      250

TTA  ATT  ACT  AAA  GAA  AAT  GTG  AAA  ACA  AGT  GGC  AGT  GAG  GTC  GGA  AAT      818
Leu  Ile  Thr  Lys  Glu  Asn  Val  Lys  Thr  Ser  Gly  Ser  Glu  Val  Gly  Asn
255                      260                      265                      270

GTT  TAT  AAC  TTC  TTA  ATT  GTA  TTA  ACA  GCT  CTG  CAA  GCC  CAA  GCT  TTT      866
Val  Tyr  Asn  Phe  Leu  Ile  Val  Leu  Thr  Ala  Leu  Gln  Ala  Gln  Ala  Phe
                    275                      280                      285

CTT  ACT  TTA  ACA  ACA  TGC  CGA  AAA  TTA  TTA  GGC  TTA  GCA  GAT  ATT  GAT      914
Leu  Thr  Leu  Thr  Thr  Cys  Arg  Lys  Leu  Leu  Gly  Leu  Ala  Asp  Ile  Asp
               290                      295                      300

TAT  ACT  TCT  ATT  ATG  AAT  GAA  CAT  TTA  AAT  AAG  GAA  AAA  GAG  GAA  TTT      962
Tyr  Thr  Ser  Ile  Met  Asn  Glu  His  Leu  Asn  Lys  Glu  Lys  Glu  Glu  Phe
          305                      310                      315

AGA  GTA  AAC  ATC  CTC  CCT  ACA  CTT  TCT  AAT  ACT  TTT  TCT  AAT  CCT  AAT     1010
Arg  Val  Asn  Ile  Leu  Pro  Thr  Leu  Ser  Asn  Thr  Phe  Ser  Asn  Pro  Asn
     320                      325                      330

TAT  GCA  AAA  GTT  AAA  GGA  AGT  GAT  GAA  GAT  GCA  AAG  ATG  ATT  GTG  GAA     1058
Tyr  Ala  Lys  Val  Lys  Gly  Ser  Asp  Glu  Asp  Ala  Lys  Met  Ile  Val  Glu
335                      340                      345                      350

GCT  AAA  CCA  GGA  CAT  GCA  TTG  ATT  GGG  TTT  GAA  ATT  AGT  AAT  GAT  TCA     1106
Ala  Lys  Pro  Gly  His  Ala  Leu  Ile  Gly  Phe  Glu  Ile  Ser  Asn  Asp  Ser
                    355                      360                      365

ATT  ACA  GTA  TTA  AAA  GTA  TAT  GAG  GCT  AAG  CTA  AAA  CAA  AAT  TAT  CAA     1154
Ile  Thr  Val  Leu  Lys  Val  Tyr  Glu  Ala  Lys  Leu  Lys  Gln  Asn  Tyr  Gln
               370                      375                      380

GTC  GAT  AAG  GAT  TCC  TTA  TCG  GAA  GTT  ATT  TAT  GGT  GAT  ATG  GAT  AAA     1202
Val  Asp  Lys  Asp  Ser  Leu  Ser  Glu  Val  Ile  Tyr  Gly  Asp  Met  Asp  Lys
```

|     |     |     |     | 385 |     |     |     |     | 390 |     |     |     |     | 395 |     |     |     |      |
|-----|-----|-----|-----|-----|-----|-----|-----|-----|-----|-----|-----|-----|-----|-----|-----|-----|-----|------|
| TTA | TTG | TGC | CCA | GAT | CAA | TCT | GAA | CAA | ATC | TAT | TAT | ACA | AAT | AAC | ATA |     |     | 1250 |
| Leu | Leu | Cys | Pro | Asp | Gln | Ser | Glu | Gln | Ile | Tyr | Tyr | Thr | Asn | Asn | Ile |     |     |      |
|     | 400 |     |     |     |     | 405 |     |     |     |     | 410 |     |     |     |     |     |     |      |

GTA TTT CCA AAT GAA TAT GTA ATT ACT AAA ATT GAT TTC ACT AAA AAA    1298
Val Phe Pro Asn Glu Tyr Val Ile Thr Lys Ile Asp Phe Thr Lys Lys
415             420             425                 430

ATG AAA ACT TTA AGA TAT GAG GTA ACA GCG AAT TTT TAT GAT TCT TCT    1346
Met Lys Thr Leu Arg Tyr Glu Val Thr Ala Asn Phe Tyr Asp Ser Ser
                435             440             445

ACA GGA GAA ATT GAC TTA AAT AAG AAA AAA GTA GAA TCA AGT GAA GCG    1394
Thr Gly Glu Ile Asp Leu Asn Lys Lys Lys Val Glu Ser Ser Glu Ala
            450             455             460

GAG TAT AGA ACG TTA AGT GCT AAT GAT GAT GGG GTG TAT ATG CCG TTA    1442
Glu Tyr Arg Thr Leu Ser Ala Asn Asp Asp Gly Val Tyr Met Pro Leu
        465             470             475

GGT GTC ATC AGT GAA ACA TTT TTG ACT CCG ATT AAT GGG TTT GGC CTC    1490
Gly Val Ile Ser Glu Thr Phe Leu Thr Pro Ile Asn Gly Phe Gly Leu
    480             485             490

CAA GCT GAT GAA AAT TCA AGA TTA ATT ACT TTA ACA TGT AAA TCA TAT    1538
Gln Ala Asp Glu Asn Ser Arg Leu Ile Thr Leu Thr Cys Lys Ser Tyr
495             500             505                 510

TTA AGA GAA CTA CTG CTA GCA ACA GAC TTA AGC AAT AAA GAA ACT AAA    1586
Leu Arg Glu Leu Leu Leu Ala Thr Asp Leu Ser Asn Lys Glu Thr Lys
                515             520             525

TTG ATC GTC CCG CCA AGT GGT TTT ATT AGC AAT ATT GTA GAG AAC GGG    1634
Leu Ile Val Pro Pro Ser Gly Phe Ile Ser Asn Ile Val Glu Asn Gly
            530             535             540

TCC ATA GAA GAG GAC AAT TTA GAG CCG TGG AAA GCA AAT AAT AAG AAT    1682
Ser Ile Glu Glu Asp Asn Leu Glu Pro Trp Lys Ala Asn Asn Lys Asn
        545             550             555

GCG TAT GTA GAT CAT ACA GGC GGA GTG AAT GGA ACT AAA GCT TTA TAT    1730
Ala Tyr Val Asp His Thr Gly Gly Val Asn Gly Thr Lys Ala Leu Tyr
    560             565             570

GTT CAT AAG GAC GGA GGA ATT TCA CAA TTT ATT GGA GAT AAG TTA AAA    1778
Val His Lys Asp Gly Gly Ile Ser Gln Phe Ile Gly Asp Lys Leu Lys
575             580             585                 590

CCG AAA ACT GAG TAT GTA ATC CAA TAT ACT GTT AAA GGA AAA CCT TCT    1826
Pro Lys Thr Glu Tyr Val Ile Gln Tyr Thr Val Lys Gly Lys Pro Ser
                595             600             605

ATT CAT TTA AAA GAT GAA AAT ACT GGA TAT ATT CAT TAT GAA GAT ACA    1874
Ile His Leu Lys Asp Glu Asn Thr Gly Tyr Ile His Tyr Glu Asp Thr
            610             615             620

AAT AAT AAT TTA GAA GAT TAT CAA ACT ATT AAT AAA CGT TTT ACT ACA    1922
Asn Asn Asn Leu Glu Asp Tyr Gln Thr Ile Asn Lys Arg Phe Thr Thr
        625             630             635

GGA ACT GAT TTA AAG GGA GTG TAT TTA ATT TTA AAA AGT CAA AAT GGA    1970
Gly Thr Asp Leu Lys Gly Val Tyr Leu Ile Leu Lys Ser Gln Asn Gly
    640             645             650

GAT GAA GCT TGG GGA GAT AAC TTT ATT ATT TTG GAA ATT AGT CCT TCT    2018
Asp Glu Ala Trp Gly Asp Asn Phe Ile Ile Leu Glu Ile Ser Pro Ser
655             660             665                 670

GAA AAG TTA TTA AGT CCA GAA TTA ATT AAT ACA AAT AAT TGG ACG AGT    2066
Glu Lys Leu Leu Ser Pro Glu Leu Ile Asn Thr Asn Asn Trp Thr Ser
                675             680             685

ACG GGA TCA ACT AAT ATT AGC GGT AAT ACA CTC ACT CTT TAT CAG GGA    2114
Thr Gly Ser Thr Asn Ile Ser Gly Asn Thr Leu Thr Leu Tyr Gln Gly
            690             695             700

GGA CGA GGG ATT CTA AAA CAA AAC CTT CAA TTA GAT AGT TTT TCA ACT    2162
Gly Arg Gly Ile Leu Lys Gln Asn Leu Gln Leu Asp Ser Phe Ser Thr

|  |  |  | 705 |  |  |  |  | 710 |  |  |  |  | 715 |  |  |  |
|---|---|---|---|---|---|---|---|---|---|---|---|---|---|---|---|---|
| TAT | AGA | GTG | TAT | TTT | TCT | GTG | TCC | GGA | GAT | GCT | AAT | GTA | AGG | ATT | AGA | 2210 |
| Tyr | Arg | Val | Tyr | Phe | Ser | Val | Ser | Gly | Asp | Ala | Asn | Val | Arg | Ile | Arg |  |
|  | 720 |  |  |  |  | 725 |  |  |  |  | 730 |  |  |  |  |  |
| AAT | TCT | AGG | GAA | GTG | TTA | TTT | GAA | AAA | AGA | TAT | ATG | AGC | GGT | GCT | AAA | 2258 |
| Asn | Ser | Arg | Glu | Val | Leu | Phe | Glu | Lys | Arg | Tyr | Met | Ser | Gly | Ala | Lys |  |
| 735 |  |  |  |  | 740 |  |  |  |  | 745 |  |  |  |  | 750 |  |
| GAT | GTT | TCT | GAA | ATG | TTC | ACT | ACA | AAA | TTT | GAG | AAA | GAT | AAC | TTT | TAT | 2306 |
| Asp | Val | Ser | Glu | Met | Phe | Thr | Thr | Lys | Phe | Glu | Lys | Asp | Asn | Phe | Tyr |  |
|  |  |  |  | 755 |  |  |  |  | 760 |  |  |  |  | 765 |  |  |
| ATA | GAG | CTT | TCT | CAA | GGG | AAT | AAT | TTA | TAT | GGT | GGT | CCT | ATT | GTA | CAT | 2354 |
| Ile | Glu | Leu | Ser | Gln | Gly | Asn | Asn | Leu | Tyr | Gly | Gly | Pro | Ile | Val | His |  |
|  |  |  | 770 |  |  |  |  | 775 |  |  |  |  | 780 |  |  |  |
| TTT | TAC | GAT | GTC | TCT | ATT | AAG | TAA |  |  |  |  |  |  |  |  | 2378 |
| Phe | Tyr | Asp | Val | Ser | Ile | Lys |  |  |  |  |  |  |  |  |  |  |
|  |  | 785 |  |  |  |  |  |  |  |  |  |  |  |  |  |  |

( 2 ) INFORMATION FOR SEQ ID NO:29:

( i ) SEQUENCE CHARACTERISTICS:
        ( A ) LENGTH: 789 amino acids
        ( B ) TYPE: amino acid
        ( D ) TOPOLOGY: linear ( i i ) MOLECULE TYPE: protein ( x i ) SEQUENCE DESCRIPTION: SEQ ID NO:29:

| Met | Asn | Lys | Asn | Asn | Thr | Lys | Leu | Ser | Thr | Arg | Ala | Leu | Pro | Ser | Phe |
|---|---|---|---|---|---|---|---|---|---|---|---|---|---|---|---|
| 1 |  |  |  | 5 |  |  |  |  | 10 |  |  |  |  | 15 |  |
| Ile | Asp | Tyr | Phe | Asn | Gly | Ile | Tyr | Gly | Phe | Ala | Thr | Gly | Ile | Lys | Asp |
|  |  |  | 20 |  |  |  | 25 |  |  |  |  | 30 |  |  |  |
| Ile | Met | Asn | Met | Ile | Phe | Lys | Thr | Asp | Thr | Gly | Gly | Asp | Leu | Thr | Leu |
|  |  | 35 |  |  |  |  | 40 |  |  |  |  | 45 |  |  |  |
| Asp | Glu | Ile | Leu | Lys | Asn | Gln | Gln | Leu | Leu | Asn | Asp | Ile | Ser | Gly | Lys |
|  | 50 |  |  |  |  | 55 |  |  |  |  | 60 |  |  |  |  |
| Leu | Asp | Gly | Val | Asn | Gly | Ser | Leu | Asn | Asp | Leu | Ile | Ala | Gln | Gly | Asn |
| 65 |  |  |  |  | 70 |  |  |  |  | 75 |  |  |  |  | 80 |
| Leu | Asn | Thr | Glu | Leu | Ser | Lys | Glu | Ile | Leu | Lys | Ile | Ala | Asn | Glu | Gln |
|  |  |  |  | 85 |  |  |  |  | 90 |  |  |  |  | 95 |  |
| Asn | Gln | Val | Leu | Asn | Asp | Val | Asn | Asn | Lys | Leu | Asp | Ala | Ile | Asn | Thr |
|  |  |  | 100 |  |  |  |  | 105 |  |  |  |  | 110 |  |  |
| Met | Leu | Arg | Val | Tyr | Leu | Pro | Lys | Ile | Thr | Ser | Met | Leu | Ser | Asp | Val |
|  |  | 115 |  |  |  |  | 120 |  |  |  |  | 125 |  |  |  |
| Met | Lys | Gln | Asn | Tyr | Ala | Leu | Ser | Leu | Gln | Ile | Glu | Tyr | Leu | Ser | Lys |
|  | 130 |  |  |  |  | 135 |  |  |  |  | 140 |  |  |  |  |
| Gln | Leu | Gln | Glu | Ile | Ser | Asp | Lys | Leu | Asp | Ile | Ile | Asn | Val | Asn | Val |
| 145 |  |  |  |  | 150 |  |  |  |  | 155 |  |  |  |  | 160 |
| Leu | Ile | Asn | Ser | Thr | Leu | Thr | Glu | Ile | Thr | Pro | Ala | Tyr | Gln | Arg | Ile |
|  |  |  |  | 165 |  |  |  |  | 170 |  |  |  |  | 175 |  |
| Lys | Tyr | Val | Asn | Glu | Lys | Phe | Glu | Glu | Leu | Thr | Phe | Ala | Thr | Glu | Thr |
|  |  |  | 180 |  |  |  |  | 185 |  |  |  |  | 190 |  |  |
| Ser | Ser | Lys | Val | Lys | Lys | Asp | Gly | Ser | Pro | Ala | Asp | Ile | Leu | Asp | Glu |
|  |  | 195 |  |  |  |  | 200 |  |  |  |  | 205 |  |  |  |
| Leu | Thr | Glu | Leu | Thr | Glu | Leu | Ala | Lys | Ser | Val | Thr | Lys | Asn | Asp | Val |
|  | 210 |  |  |  |  | 215 |  |  |  |  | 220 |  |  |  |  |
| Asp | Gly | Phe | Glu | Phe | Tyr | Leu | Asn | Thr | Phe | His | Asp | Val | Met | Val | Gly |
| 225 |  |  |  |  | 230 |  |  |  |  | 235 |  |  |  |  | 240 |
| Asn | Asn | Leu | Phe | Gly | Arg | Ser | Ala | Leu | Lys | Thr | Ala | Ser | Glu | Leu | Ile |

-continued

|     |     |     |     | 245 |     |     |     | 250 |     |     |     | 255 |     |     |
|-----|-----|-----|-----|-----|-----|-----|-----|-----|-----|-----|-----|-----|-----|-----|
| Thr | Lys | Glu | Asn | Val | Lys | Thr | Ser | Gly | Ser | Glu | Val | Gly | Asn | Val | Tyr |
|     |     |     | 260 |     |     |     | 265 |     |     |     | 270 |     |     |     |

Thr Lys Glu Asn Val Lys Thr Ser Gly Ser Glu Val Gly Asn Val Tyr
                260                 265                 270

Asn Phe Leu Ile Val Leu Thr Ala Leu Gln Ala Gln Ala Phe Leu Thr
        275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Ile Gly Phe Glu Ile Ser Asn Asp Ser Ile Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Phe Tyr Asp Ser Ser Thr Gly
        435                 440                 445

Glu Ile Asp Leu Asn Lys Lys Val Glu Ser Ser Glu Ala Glu Tyr
    450                 455                 460

Arg Thr Leu Ser Ala Asn Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
        515                 520                 525

Val Pro Pro Ser Gly Phe Ile Ser Asn Ile Val Glu Asn Gly Ser Ile
    530                 535                 540

Glu Glu Asp Asn Leu Glu Pro Trp Lys Ala Asn Asn Lys Asn Ala Tyr
545                 550                 555                 560

Val Asp His Thr Gly Gly Val Asn Gly Thr Lys Ala Leu Tyr Val His
                565                 570                 575

Lys Asp Gly Gly Ile Ser Gln Phe Ile Gly Asp Lys Leu Lys Pro Lys
            580                 585                 590

Thr Glu Tyr Val Ile Gln Tyr Thr Val Lys Gly Lys Pro Ser Ile His
        595                 600                 605

Leu Lys Asp Glu Asn Thr Gly Tyr Ile His Tyr Glu Asp Thr Asn Asn
    610                 615                 620

Asn Leu Glu Asp Tyr Gln Thr Ile Asn Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Asn Phe Ile Ile Leu Glu Ile Ser Pro Ser Glu Lys
            660                 665                 670

| | | | | | | | | | | | | | | |
|---|---|---|---|---|---|---|---|---|---|---|---|---|---|---|
| Leu | Leu | Ser 675 | Pro | Glu | Leu | Ile | Asn 680 | Thr | Asn | Asn | Trp | Thr | Ser 685 | Thr | Gly |
| Ser | Thr 690 | Asn | Ile | Ser | Gly | Asn 695 | Thr | Leu | Thr | Leu | Tyr 700 | Gln | Gly | Gly | Arg |
| Gly 705 | Ile | Leu | Lys | Gln | Asn 710 | Leu | Gln | Leu | Asp | Ser 715 | Phe | Ser | Thr | Tyr | Arg 720 |
| Val | Tyr | Phe | Ser | Val 725 | Ser | Gly | Asp | Ala | Asn 730 | Val | Arg | Ile | Arg | Asn 735 | Ser |
| Arg | Glu | Val | Leu 740 | Phe | Glu | Lys | Arg | Tyr 745 | Met | Ser | Gly | Ala | Lys 750 | Asp | Val |
| Ser | Glu | Met 755 | Phe | Thr | Thr | Lys | Phe 760 | Glu | Lys | Asp | Asn | Phe 765 | Tyr | Ile | Glu |
| Leu | Ser | Gln 770 | Gly | Asn | Asn | Leu | Tyr 775 | Gly | Gly | Pro | Ile 780 | Val | His | Phe | Tyr |
| Asp 785 | Val | Ser | Ile | Lys | | | | | | | | | | | |

(2) INFORMATION FOR SEQ ID NO:30:

(i) SEQUENCE CHARACTERISTICS:
        (A) LENGTH: 2403 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(iii) HYPOTHETICAL: NO (ix) FEATURE:
        (A) NAME/KEY: misc_feature
        (B) LOCATION: 11..2389
        (D) OTHER INFORMATION: /note= "maize optimized DNA
            sequence encoding VIP3A(a)"

(xi) SEQUENCE DESCRIPTION: SEQ ID NO:30:

```
GGATCCACCA ATGAACATGA ACAAGAACAA CACCAAGCTG AGCACCCGCG CCCTGCCGAG    60
CTTCATCGAC TACTTCAACG GCATCTACGG CTTCGCCACC GGCATCAAGG ACATCATGAA   120
CATGATCTTC AAGACCGACA CCGGCGGCGA CCTGACCCTG GACGAGATCC TGAAGAACCA   180
GCAGCTGCTG AACGACATCA GCGGCAAGCT GGACGGCGTG AACGGCAGCC TGAACGACCT   240
GATCGCCCAG GGCAACCTGA ACACCGAGCT GAGCAAGGAG ATCCTTAAGA TCGCCAACGA   300
GCAGAACCAG GTGCTGAACG ACGTGAACAA CAAGCTGGAC GCCATCAACA CCATGCTGCG   360
CGTGTACCTG CCGAAGATCA CCAGCATGCT GAGCGACGTG ATGAAGCAGA ACTACGCCCT   420
GAGCCTGCAG ATCGAGTACC TGAGCAAGCA GCTGCAGGAG ATCAGCGACA AGCTGGACAT   480
CATCAACGTG AACGTCCTGA TCAACAGCAC CCTGACCGAG ATCACCCCGG CCTACCAGCG   540
CATCAAGTAC GTGAACGAGA AGTTCGAAGA GCTGACCTTC GCCACCGAGA CCAGCAGCAA   600
GGTGAAGAAG GACGGCAGCC CGGCCGACAT CCTGGACGAG CTGACCGAGC TGACCGAGCT   660
GGCCAAGAGC GTGACCAAGA ACGACGTGGA CGGCTTCGAG TTCTACCTGA ACACCTTCCA   720
CGACGTGATG GTGGGCAACA ACCTGTTCGG CCGCAGCGCC CTGAAGACCG CCAGCGAGCT   780
GATCACCAAG GAGAACGTGA AGACCAGCGG CAGCGAGGTG GGCAACGTGT ACAACTTCCT   840
GATCGTGCTG ACCGCCCTGC AGGCCCAGGC CTTCCTGACC CTGACCACCT GTCGCAAGCT   900
GCTGGGCCTG GCCGACATCG ACTACACCAG CATCATGAAC GAGCACTTGA ACAAGGAGAA   960
GGAGGAGTTC CGCGTGAACA TCCTGCCGAC CCTGAGCAAC ACCTTCAGCA ACCCGAACTA  1020
```

-continued

| | | | | | |
|---|---|---|---|---|---|
| CGCCAAGGTG | AAGGGCAGCG | ACGAGGACGC | CAAGATGATC | GTGGAGGCTA | AGCCGGGCCA | 1080 |
| CGCGTTGATC | GGCTTCGAGA | TCAGCAACGA | CAGCATCACC | GTGCTGAAGG | TGTACGAGGC | 1140 |
| CAAGCTGAAG | CAGAACTACC | AGGTGGACAA | GGACAGCTTG | AGCGAGGTGA | TCTACGGCGA | 1200 |
| CATGGACAAG | CTGCTGTGTC | CGGACCAGAG | CGAGCAAATC | TACTACACCA | ACAACATCGT | 1260 |
| GTTCCCGAAC | GAGTACGTGA | TCACCAAGAT | CGACTTCACC | AAGAAGATGA | AGACCCTGCG | 1320 |
| CTACGAGGTG | ACCGCCAACT | TCTACGACAG | CAGCACCGGC | GAGATCGACC | TGAACAAGAA | 1380 |
| GAAGGTGGAG | AGCAGCGAGG | CCGAGTACCG | CACCCTGAGC | GCGAACGACG | ACGGCGTCTA | 1440 |
| CATGCCACTG | GGCGTGATCA | GCGAGACCTT | CCTGACCCCG | ATCAACGGCT | TTGGCCTGCA | 1500 |
| GGCCGACGAG | AACAGCCGCC | TGATCACCCT | GACCTGTAAG | AGCTACCTGC | GCGAGCTGCT | 1560 |
| GCTAGCCACC | GACCTGAGCA | ACAAGGAGAC | CAAGCTGATC | GTGCCACCGA | GCGGCTTCAT | 1620 |
| CAGCAACATC | GTGGAGAACG | GCAGCATCGA | GGAGGACAAC | CTGGAGCCGT | GGAAGGCCAA | 1680 |
| CAACAAGAAC | GCCTACGTGG | ACCACACCGG | CGGCGTGAAC | GGCACCAAGG | CCCTGTACGT | 1740 |
| GCACAAGGAC | GGCGGCATCA | GCCAGTTCAT | CGGCGACAAG | CTGAAGCCGA | AGACCGAGTA | 1800 |
| CGTGATCCAG | TACACCGTGA | AGGGCAAGCC | ATCGATTCAC | CTGAAGGACG | AGAACACCGG | 1860 |
| CTACATCCAC | TACGAGGACA | CCAACAACAA | CCTGGAGGAC | TACCAGACCA | TCAACAAGCG | 1920 |
| CTTCACCACC | GGCACCGACC | TGAAGGGCGT | GTACCTGATC | CTGAAGAGCC | AGAACGGCGA | 1980 |
| CGAGGCCTGG | GGCGACAACT | TCATCATCCT | GGAGATCAGC | CCGAGCGAGA | AGCTGCTGAG | 2040 |
| CCCGGAGCTG | ATCAACACCA | ACAACTGGAC | CAGCACCGGC | AGCACCAACA | TCAGCGGCAA | 2100 |
| CACCCTGACC | CTGTACCAGG | GCGGCCGCGG | CATCCTGAAG | CAGAACCTGC | AGCTGGACAG | 2160 |
| CTTCAGCACC | TACCGCGTGT | ACTTCAGCGT | GAGCGGCGAC | GCCAACGTGC | GCATCCGCAA | 2220 |
| CAGCCGCGAG | GTGCTGTTCG | AGAAGAGGTA | CATGAGCGGC | GCCAAGGACG | TGAGCGAGAT | 2280 |
| GTTCACCACC | AAGTTCGAGA | AGGACAACTT | CTACATCGAG | CTGAGCCAGG | GCAACAACCT | 2340 |
| GTACGGCGGC | CCGATCGTGC | ACTTCTACGA | CGTGAGCATC | AAGTTAACGT | AGAGCTCAGA | 2400 |
| TCT | | | | | | 2403 |

( 2 ) INFORMATION FOR SEQ ID NO:31:

( i ) SEQUENCE CHARACTERISTICS:
        ( A ) LENGTH: 2612 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i x ) FEATURE:
        ( A ) NAME/KEY: CDS
        ( B ) LOCATION: 118..2484
        ( D ) OTHER INFORMATION: /note= "Native DNA sequence
            encoding VIP3A(b) from AB424"

( x i ) SEQUENCE DESCRIPTION: SEQ ID NO:31:

| | | | | | | |
|---|---|---|---|---|---|---|
| ATTGAAATTG | ATAAAAGTT | ATGAGTGTTT | AATAATCAGT | AATTACCAAT | AAAGAATTAA | 60 |
| GAATACAAGT | TTACAAGAAA | TAAGTGTTAC | AAAAAATAGC | TGAAAAGGAA | GATGAAC | 117 |

```
ATG AAC AAG AAT AAT ACT AAA TTA AGC ACA AGA GCC TTA CCA AGT TTT       165
Met Asn Lys Asn Asn Thr Lys Leu Ser Thr Arg Ala Leu Pro Ser Phe
790             795                 800                 805

ATT GAT TAT TTC AAT GGC ATT TAT GGA TTT GCC ACT GGT ATC AAA GAC       213
Ile Asp Tyr Phe Asn Gly Ile Tyr Gly Phe Ala Thr Gly Ile Lys Asp
            810                 815                 820
```

```
ATT ATG AAC ATG ATT TTT AAA ACG GAT ACA GGT GGT GAT CTA ACC CTA      261
Ile Met Asn Met Ile Phe Lys Thr Asp Thr Gly Gly Asp Leu Thr Leu
        825                     830                 835

GAC GAA ATT TTA AAG AAT CAG CAG CTA CTA AAT GAT ATT TCT GGT AAA      309
Asp Glu Ile Leu Lys Asn Gln Gln Leu Leu Asn Asp Ile Ser Gly Lys
        840                 845                     850

TTG GAT GGG GTG AAT GGA AGC TTA AAT GAT CTT ATC GCA CAG GGA AAC      357
Leu Asp Gly Val Asn Gly Ser Leu Asn Asp Leu Ile Ala Gln Gly Asn
855                         860                  865

TTA AAT ACA GAA TTA TCT AAG GAA ATA TTA AAA ATT GCA AAT GAA CAA      405
Leu Asn Thr Glu Leu Ser Lys Glu Ile Leu Lys Ile Ala Asn Glu Gln
870                     875                 880                 885

AAT CAA GTT TTA AAT GAT GTT AAT AAC AAA CTC GAT GCG ATA AAT ACG      453
Asn Gln Val Leu Asn Asp Val Asn Asn Lys Leu Asp Ala Ile Asn Thr
                890                  895                 900

ATG CTT CGG GTA TAT CTA CCT AAA ATT ACC TCT ATG TTG AGT GAT GTA      501
Met Leu Arg Val Tyr Leu Pro Lys Ile Thr Ser Met Leu Ser Asp Val
            905                 910                 915

ATG AAA CAA AAT TAT GCG CTA AGT CTG CAA ATA GAA TAC TTA AGT AAA      549
Met Lys Gln Asn Tyr Ala Leu Ser Leu Gln Ile Glu Tyr Leu Ser Lys
        920                 925                 930

CAA TTG CAA GAG ATT TCT GAT AAG TTG GAT ATT ATT AAT GTA AAT GTA      597
Gln Leu Gln Glu Ile Ser Asp Lys Leu Asp Ile Ile Asn Val Asn Val
935                         940                 945

CTT ATT AAC TCT ACA CTT ACT GAA ATT ACA CCT GCG TAT CAA AGG ATT      645
Leu Ile Asn Ser Thr Leu Thr Glu Ile Thr Pro Ala Tyr Gln Arg Ile
950                     955                 960                 965

AAA TAT GTG AAC GAA AAA TTT GAG GAA TTA ACT TTT GCT ACA GAA ACT      693
Lys Tyr Val Asn Glu Lys Phe Glu Glu Leu Thr Phe Ala Thr Glu Thr
                970                 975                 980

AGT TCA AAA GTA AAA AAG GAT GGC TCT CCT GCA GAT ATT CGT GAT GAG      741
Ser Ser Lys Val Lys Lys Asp Gly Ser Pro Ala Asp Ile Arg Asp Glu
            985                 990                 995

TTA ACT GAG TTA ACT GAA CTA GCG AAA AGT GTA ACA AAA AAT GAT GTG      789
Leu Thr Glu Leu Thr Glu Leu Ala Lys Ser Val Thr Lys Asn Asp Val
        1000                1005                1010

GAT GGT TTT GAA TTT TAC CTT AAT ACA TTC CAC GAT GTA ATG GTA GGA      837
Asp Gly Phe Glu Phe Tyr Leu Asn Thr Phe His Asp Val Met Val Gly
1015                        1020                1025

AAT AAT TTA TTC GGG CGT TCA GCT TTA AAA ACT GCA TCG GAA TTA ATT      885
Asn Asn Leu Phe Gly Arg Ser Ala Leu Lys Thr Ala Ser Glu Leu Ile
1030                1035                1040                1045

ACT AAA GAA AAT GTG AAA ACA AGT GGC AGT GAG GTC GGA AAT GTT TAT      933
Thr Lys Glu Asn Val Lys Thr Ser Gly Ser Glu Val Gly Asn Val Tyr
                1050                1055                1060

AAC TTC CTA ATT GTA TTA ACA GCT CTG CAA GCA AAA GCT TTT CTT ACT      981
Asn Phe Leu Ile Val Leu Thr Ala Leu Gln Ala Lys Ala Phe Leu Thr
            1065                1070                1075

TTA ACA CCA TGC CGA AAA TTA TTA GGC TTA GCA GAT ATT GAT TAT ACT     1029
Leu Thr Pro Cys Arg Lys Leu Leu Gly Leu Ala Asp Ile Asp Tyr Thr
        1080                1085                1090

TCT ATT ATG AAT GAA CAT TTA AAT AAG GAA AAA GAG GAA TTT AGA GTA     1077
Ser Ile Met Asn Glu His Leu Asn Lys Glu Lys Glu Glu Phe Arg Val
1095                    1100                1105

AAC ATC CTC CCT ACA CTT TCT AAT ACT TTT TCT AAT CCT AAT TAT GCA     1125
Asn Ile Leu Pro Thr Leu Ser Asn Thr Phe Ser Asn Pro Asn Tyr Ala
1110                1115                1120                1125

AAA GTT AAA GGA AGT GAT GAA GAT GCA AAG ATG ATT GTG GAA GCT AAA     1173
Lys Val Lys Gly Ser Asp Glu Asp Ala Lys Met Ile Val Glu Ala Lys
                1130                1135                1140
```

```
CCA GGA CAT GCA TTG ATT GGG TTT GAA ATT AGT AAT GAT TCA ATT ACA     1221
Pro Gly His Ala Leu Ile Gly Phe Glu Ile Ser Asn Asp Ser Ile Thr
            1145                1150                1155

GTA TTA AAA GTA TAT GAG GCT AAG CTA AAA CAA AAT TAT CAA GTC GAT     1269
Val Leu Lys Val Tyr Glu Ala Lys Leu Lys Gln Asn Tyr Gln Val Asp
    1160                1165                1170

AAG GAT TCC TTA TCG GAA GTT ATT TAT GGC GAT ATG GAT AAA TTA TTG     1317
Lys Asp Ser Leu Ser Glu Val Ile Tyr Gly Asp Met Asp Lys Leu Leu
        1175                1180                1185

TGC CCA GAT CAA TCT GGA CAA ATC TAT TAT ACA AAT AAC ATA GTA TTT     1365
Cys Pro Asp Gln Ser Gly Gln Ile Tyr Tyr Thr Asn Asn Ile Val Phe
1190                1195                1200                1205

CCA AAT GAA TAT GTA ATT ACT AAA ATT GAT TTC ACT AAA AAA ATG AAA     1413
Pro Asn Glu Tyr Val Ile Thr Lys Ile Asp Phe Thr Lys Lys Met Lys
            1210                1215                1220

ACT TTA AGA TAT GAG GTA ACA GCG AAT TTT TAT GAT TCT TCT ACA GGA     1461
Thr Leu Arg Tyr Glu Val Thr Ala Asn Phe Tyr Asp Ser Ser Thr Gly
                1225                1230                1235

GAA ATT GAC TTA AAT AAG AAA AAA GTA GAA TCA AGT GAA GCG GAG TAT     1509
Glu Ile Asp Leu Asn Lys Lys Lys Val Glu Ser Ser Glu Ala Glu Tyr
    1240                1245                1250

AGA ACG TTA AGT GCT AAT GAT GAT GGG GTG TAT ATG CCG TTA GGT GTC     1557
Arg Thr Leu Ser Ala Asn Asp Asp Gly Val Tyr Met Pro Leu Gly Val
        1255                1260                1265

ATC AGT GAA ACA TTT TTG ACT CCG ATT AAT GGG TTT GGC CTC CAA GCT     1605
Ile Ser Glu Thr Phe Leu Thr Pro Ile Asn Gly Phe Gly Leu Gln Ala
1270                1275                1280                1285

GAT GAA AAT TCA AGA TTA ATT ACT TTA ACA TGT AAA TCA TAT TTA AGA     1653
Asp Glu Asn Ser Arg Leu Ile Thr Leu Thr Cys Lys Ser Tyr Leu Arg
            1290                1295                1300

GAA CTA CTG CTA GCA ACA GAC TTA AGC AAT AAA GAA ACT AAA TTG ATC     1701
Glu Leu Leu Leu Ala Thr Asp Leu Ser Asn Lys Glu Thr Lys Leu Ile
                1305                1310                1315

GTC CCG CCA AGT GGT TTT ATT AGC AAT ATT GTA GAG AAC GGG TCC ATA     1749
Val Pro Pro Ser Gly Phe Ile Ser Asn Ile Val Glu Asn Gly Ser Ile
    1320                1325                1330

GAA GAG GAC AAT TTA GAG CCG TGG AAA GCA AAT AAT AAG AAT GCG TAT     1797
Glu Glu Asp Asn Leu Glu Pro Trp Lys Ala Asn Asn Lys Asn Ala Tyr
        1335                1340                1345

GTA GAT CAT ACA GGC GGA GTG AAT GGA ACT AAA GCT TTA TAT GTT CAT     1845
Val Asp His Thr Gly Gly Val Asn Gly Thr Lys Ala Leu Tyr Val His
1350                1355                1360                1365

AAG GAC GGA GGA ATT TCA CAA TTT ATT GGA GAT AAG TTA AAA CCG AAA     1893
Lys Asp Gly Gly Ile Ser Gln Phe Ile Gly Asp Lys Leu Lys Pro Lys
            1370                1375                1380

ACT GAG TAT GTA ATC CAA TAT ACT GTT AAA GGA AAA CCT TCT ATT CAT     1941
Thr Glu Tyr Val Ile Gln Tyr Thr Val Lys Gly Lys Pro Ser Ile His
                1385                1390                1395

TTA AAA GAT GAA AAT ACT GGA TAT ATT CAT TAT GAA GAT ACA AAT AAT     1989
Leu Lys Asp Glu Asn Thr Gly Tyr Ile His Tyr Glu Asp Thr Asn Asn
    1400                1405                1410

AAT TTA GAA GAT TAT CAA ACT ATT AAT AAA CGT TTT ACT ACA GGA ACT     2037
Asn Leu Glu Asp Tyr Gln Thr Ile Asn Lys Arg Phe Thr Thr Gly Thr
        1415                1420                1425

GAT TTA AAG GGA GTG TAT TTA ATT TTA AAA AGT CAA AAT GGA GAT GAA     2085
Asp Leu Lys Gly Val Tyr Leu Ile Leu Lys Ser Gln Asn Gly Asp Glu
1430                1435                1440                1445

GCT TGG GGA GAT AAC TTT ATT ATT TTG GAA ATT AGT CCT TCT GAA AAG     2133
Ala Trp Gly Asp Asn Phe Ile Ile Leu Glu Ile Ser Pro Ser Glu Lys
            1450                1455                1460
```

```
TTA  TTA  AGT  CCA  GAA  TTA  ATT  AAT  ACA  AAT  AAT  TGG  ACG  AGT  ACG  GGA      2181
Leu  Leu  Ser  Pro  Glu  Leu  Ile  Asn  Thr  Asn  Asn  Trp  Thr  Ser  Thr  Gly
               1465                1470                     1475

TCA  ACT  AAT  ATT  AGC  GGT  AAT  ACA  CTC  ACT  CTT  TAT  CAG  GGA  GGA  CGA      2229
Ser  Thr  Asn  Ile  Ser  Gly  Asn  Thr  Leu  Thr  Leu  Tyr  Gln  Gly  Gly  Arg
          1480                     1485                     1490

GGG  ATT  CTA  AAA  CAA  AAC  CTT  CAA  TTA  GAT  AGT  TTT  TCA  ACT  TAT  AGA      2277
Gly  Ile  Leu  Lys  Gln  Asn  Leu  Gln  Leu  Asp  Ser  Phe  Ser  Thr  Tyr  Arg
     1495                     1500                     1505

GTG  TAT  TTC  TCT  GTG  TCC  GGA  GAT  GCT  AAT  GTA  AGG  ATT  AGA  AAT  TCT      2325
Val  Tyr  Phe  Ser  Val  Ser  Gly  Asp  Ala  Asn  Val  Arg  Ile  Arg  Asn  Ser
1510                     1515                     1520                     1525

AGG  GAA  GTG  TTA  TTT  GAA  AAA  AGA  TAT  ATG  AGC  GGT  GCT  AAA  GAT  GTT      2373
Arg  Glu  Val  Leu  Phe  Glu  Lys  Arg  Tyr  Met  Ser  Gly  Ala  Lys  Asp  Val
                    1530                     1535                     1540

TCT  GAA  ATG  TTC  ACT  ACA  AAA  TTT  GAG  AAA  GAT  AAC  TTC  TAT  ATA  GAG      2421
Ser  Glu  Met  Phe  Thr  Thr  Lys  Phe  Glu  Lys  Asp  Asn  Phe  Tyr  Ile  Glu
               1545                     1550                     1555

CTT  TCT  CAA  GGG  AAT  AAT  TTA  TAT  GGT  GGT  CCT  ATT  GTA  CAT  TTT  TAC      2469
Leu  Ser  Gln  Gly  Asn  Asn  Leu  Tyr  Gly  Gly  Pro  Ile  Val  His  Phe  Tyr
          1560                     1565                     1570

GAT  GTC  TCT  ATT  AAG  TAAGATCGGG  ATCTAATATT  AACAGTTTTT  AGAAGCTAAT           2524
Asp  Val  Ser  Ile  Lys
               1575

TCTTGTATAA  TGTCCTTGAT  TATGGAAAAA  CACAATTTTG  TTTGCTAAGA  TGTATATATA           2584

GCTCACTCAT  TAAAAGGCAA  TCAAGCTT                                                   2612
```

( 2 ) INFORMATION FOR SEQ ID NO:32:

( i ) SEQUENCE CHARACTERISTICS:
        ( A ) LENGTH: 789 amino acids
        ( B ) TYPE: amino acid
        ( D ) TOPOLOGY: linear ( i i ) MOLECULE TYPE: protein ( x i ) SEQUENCE DESCRIPTION: SEQ ID NO:32:

```
Met  Asn  Lys  Asn  Asn  Thr  Lys  Leu  Ser  Thr  Arg  Ala  Leu  Pro  Ser  Phe
 1                  5                        10                      15

Ile  Asp  Tyr  Phe  Asn  Gly  Ile  Tyr  Gly  Phe  Ala  Thr  Gly  Ile  Lys  Asp
               20                       25                      30

Ile  Met  Asn  Met  Ile  Phe  Lys  Thr  Asp  Thr  Gly  Gly  Asp  Leu  Thr  Leu
          35                       40                      45

Asp  Glu  Ile  Leu  Lys  Asn  Gln  Gln  Leu  Leu  Asn  Asp  Ile  Ser  Gly  Lys
     50                       55                      60

Leu  Asp  Gly  Val  Asn  Gly  Ser  Leu  Asn  Asp  Leu  Ile  Ala  Gln  Gly  Asn
 65                      70                      75                      80

Leu  Asn  Thr  Glu  Leu  Ser  Lys  Glu  Ile  Leu  Lys  Ile  Ala  Asn  Glu  Gln
                85                       90                      95

Asn  Gln  Val  Leu  Asn  Asp  Val  Asn  Asn  Lys  Leu  Asp  Ala  Ile  Asn  Thr
               100                      105                     110

Met  Leu  Arg  Val  Tyr  Leu  Pro  Lys  Ile  Thr  Ser  Met  Leu  Ser  Asp  Val
          115                      120                     125

Met  Lys  Gln  Asn  Tyr  Ala  Leu  Ser  Leu  Gln  Ile  Glu  Tyr  Leu  Ser  Lys
     130                      135                     140

Gln  Leu  Gln  Glu  Ile  Ser  Asp  Lys  Leu  Asp  Ile  Ile  Asn  Val  Asn  Val
145                      150                      155                     160

Leu  Ile  Asn  Ser  Thr  Leu  Thr  Glu  Ile  Thr  Pro  Ala  Tyr  Gln  Arg  Ile
```

|       |       |       |       | 165   |       |       |       |       | 170   |       |       |       |       | 175   |       |
|-------|-------|-------|-------|-------|-------|-------|-------|-------|-------|-------|-------|-------|-------|-------|-------|
| Lys | Tyr | Val | Asn | Glu | Lys | Phe | Glu | Glu | Leu | Thr | Phe | Ala | Thr | Glu | Thr |
|     |     |     | 180 |     |     |     |     | 185 |     |     |     | 190 |     |     |     |

Lys Tyr Val Asn Glu Lys Phe Glu Glu Leu Thr Phe Ala Thr Glu Thr
                180                     185                    190

Ser Ser Lys Val Lys Lys Asp Gly Ser Pro Ala Asp Ile Arg Asp Glu
            195             200                 205

Leu Thr Glu Leu Thr Glu Leu Ala Lys Ser Val Thr Lys Asn Asp Val
        210             215                 220

Asp Gly Phe Glu Phe Tyr Leu Asn Thr Phe His Asp Val Met Val Gly
225             230                 235                     240

Asn Asn Leu Phe Gly Arg Ser Ala Leu Lys Thr Ala Ser Glu Leu Ile
                245             250                 255

Thr Lys Glu Asn Val Lys Thr Ser Gly Ser Glu Val Gly Asn Val Tyr
            260             265                 270

Asn Phe Leu Ile Val Leu Thr Ala Leu Gln Ala Lys Ala Phe Leu Thr
            275             280                 285

Leu Thr Pro Cys Arg Lys Leu Gly Leu Ala Asp Ile Asp Tyr Thr
        290             295             300

Ser Ile Met Asn Glu His Leu Asn Lys Glu Lys Glu Glu Phe Arg Val
305             310                 315                     320

Asn Ile Leu Pro Thr Leu Ser Asn Thr Phe Ser Asn Pro Asn Tyr Ala
                325             330                 335

Lys Val Lys Gly Ser Asp Glu Asp Ala Lys Met Ile Val Glu Ala Lys
            340             345                 350

Pro Gly His Ala Leu Ile Gly Phe Glu Ile Ser Asn Asp Ser Ile Thr
        355             360                 365

Val Leu Lys Val Tyr Glu Ala Lys Leu Lys Gln Asn Tyr Gln Val Asp
    370             375                 380

Lys Asp Ser Leu Ser Glu Val Ile Tyr Gly Asp Met Asp Lys Leu Leu
385             390                 395                     400

Cys Pro Asp Gln Ser Gly Gln Ile Tyr Tyr Thr Asn Asn Ile Val Phe
                405             410                 415

Pro Asn Glu Tyr Val Ile Thr Lys Ile Asp Phe Thr Lys Lys Met Lys
            420             425                 430

Thr Leu Arg Tyr Glu Val Thr Ala Asn Phe Tyr Asp Ser Ser Thr Gly
        435             440                 445

Glu Ile Asp Leu Asn Lys Lys Lys Val Glu Ser Ser Glu Ala Glu Tyr
450             455                 460

Arg Thr Leu Ser Ala Asn Asp Asp Gly Val Tyr Met Pro Leu Gly Val
465             470                 475                     480

Ile Ser Glu Thr Phe Leu Thr Pro Ile Asn Gly Phe Gly Leu Gln Ala
                485             490                 495

Asp Glu Asn Ser Arg Leu Ile Thr Leu Thr Cys Lys Ser Tyr Leu Arg
            500             505                 510

Glu Leu Leu Leu Ala Thr Asp Leu Ser Asn Lys Glu Thr Lys Leu Ile
        515             520                 525

Val Pro Pro Ser Gly Phe Ile Ser Asn Ile Val Glu Asn Gly Ser Ile
    530             535                 540

Glu Glu Asp Asn Leu Glu Pro Trp Lys Ala Asn Asn Lys Asn Ala Tyr
545             550                 555                     560

Val Asp His Thr Gly Gly Val Asn Gly Thr Lys Ala Leu Tyr Val His
                565             570                 575

Lys Asp Gly Gly Ile Ser Gln Phe Ile Gly Asp Lys Leu Lys Pro Lys
            580             585                 590

|     |     |     |     |     |     |     |     |     |     |     |     |     |     |     |
| --- | --- | --- | --- | --- | --- | --- | --- | --- | --- | --- | --- | --- | --- | --- |
| Thr | Glu | Tyr 595 | Val | Ile | Gln | Tyr | Thr 600 | Val | Lys | Gly | Lys | Pro 605 | Ser | Ile | His |
| Leu | Lys 610 | Asp | Glu | Asn | Thr | Gly 615 | Tyr | Ile | His | Tyr | Glu 620 | Asp | Thr | Asn | Asn |
| Asn 625 | Leu | Glu | Asp | Tyr | Gln 630 | Thr | Ile | Asn | Lys | Arg 635 | Phe | Thr | Thr | Gly | Thr 640 |
| Asp | Leu | Lys | Gly | Val 645 | Tyr | Leu | Ile | Leu | Lys 650 | Ser | Gln | Asn | Gly | Asp 655 | Glu |
| Ala | Trp | Gly | Asp 660 | Asn | Phe | Ile | Ile | Leu 665 | Glu | Ile | Ser | Pro | Ser 670 | Glu | Lys |
| Leu | Leu | Ser 675 | Pro | Glu | Leu | Ile | Asn 680 | Thr | Asn | Asn | Trp | Thr 685 | Ser | Thr | Gly |
| Ser | Thr 690 | Asn | Ile | Ser | Gly | Asn 695 | Thr | Leu | Thr | Leu | Tyr 700 | Gln | Gly | Gly | Arg |
| Gly 705 | Ile | Leu | Lys | Gln | Asn 710 | Leu | Gln | Leu | Asp | Ser 715 | Phe | Ser | Thr | Tyr | Arg 720 |
| Val | Tyr | Phe | Ser | Val 725 | Ser | Gly | Asp | Ala | Asn 730 | Val | Arg | Ile | Arg | Asn 735 | Ser |
| Arg | Glu | Val | Leu 740 | Phe | Glu | Lys | Arg | Tyr 745 | Met | Ser | Gly | Ala | Lys 750 | Asp | Val |
| Ser | Glu | Met 755 | Phe | Thr | Thr | Lys | Phe 760 | Glu | Lys | Asp | Asn | Phe 765 | Tyr | Ile | Glu |
| Leu | Ser | Gln 770 | Gly | Asn | Asn | Leu | Tyr 775 | Gly | Gly | Pro | Ile | Val 780 | His | Phe | Tyr |
| Asp 785 | Val | Ser | Ile | Lys |     |     |     |     |     |     |     |     |     |     |     |

( 2 ) INFORMATION FOR SEQ ID NO:33:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "forward primer used to make pCIB5526"

( i i i ) HYPOTHETICAL: NO ( x i ) SEQUENCE DESCRIPTION: SEQ ID NO:33:

GGATCCACCA TGAAGACCAA CCAGATCAGC    30

( 2 ) INFORMATION FOR SEQ ID NO:34:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "reverse primer used to make pCIB5526"

( i i i ) HYPOTHETICAL: NO ( x i ) SEQUENCE DESCRIPTION: SEQ ID NO:34:

AAGCTTCAGC TCCTT    15

( 2 ) INFORMATION FOR SEQ ID NO:35:

( i ) SEQUENCE CHARACTERISTICS:
  ( A ) LENGTH: 2576 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "Synthetic DNA"

( i i i ) HYPOTHETICAL: NO ( i x ) FEATURE:
  ( A ) NAME/KEY: CDS
  ( B ) LOCATION: 9..2564
  ( D ) OTHER INFORMATION: /note= "Maize optimized sequence encoding VIP1A(a) with the Bacillus secretion signal removed as contained in pCIB5526"

( x i ) SEQUENCE DESCRIPTION: SEQ ID NO:35:

```
GATCCACC ATG AAG ACC AAC CAG ATC AGC ACC ACC CAG AAG AAC CAG CAG      50
         Met Lys Thr Asn Gln Ile Ser Thr Thr Gln Lys Asn Gln Gln
                     825                 830                 835

AAG GAG ATG GAC CGC AAG GGC CTG CTG GGC TAC TAC TTC AAG GGC AAG       98
Lys Glu Met Asp Arg Lys Gly Leu Leu Gly Tyr Tyr Phe Lys Gly Lys
                840                 845                 850

GAC TTC AGC AAC CTG ACC ATG TTC GCC CCC ACG CGT GAC AGC ACC CTG      146
Asp Phe Ser Asn Leu Thr Met Phe Ala Pro Thr Arg Asp Ser Thr Leu
            855                 860                 865

ATC TAC GAC CAG CAG ACC GCC AAC AAG CTG CTG GAC AAG AAG CAG CAG      194
Ile Tyr Asp Gln Gln Thr Ala Asn Lys Leu Leu Asp Lys Lys Gln Gln
        870                 875                 880

GAG TAC CAG AGC ATC CGC TGG ATC GGC CTG ATC CAG AGC AAG GAG ACC      242
Glu Tyr Gln Ser Ile Arg Trp Ile Gly Leu Ile Gln Ser Lys Glu Thr
    885                 890                 895

GGC GAC TTC ACC TTC AAC CTG AGC GAG GAC GAG CAG GCC ATC ATC GAG      290
Gly Asp Phe Thr Phe Asn Leu Ser Glu Asp Glu Gln Ala Ile Ile Glu
900                 905                 910                 915

ATC AAC GGC AAG ATC ATC AGC AAC AAG GGC AAG GAG AAG CAG GTG GTG      338
Ile Asn Gly Lys Ile Ile Ser Asn Lys Gly Lys Glu Lys Gln Val Val
                920                 925                 930

CAC CTG GAG AAG GGC AAG CTG GTG CCC ATC AAG ATC GAG TAC CAG AGC      386
His Leu Glu Lys Gly Lys Leu Val Pro Ile Lys Ile Glu Tyr Gln Ser
            935                 940                 945

GAC ACC AAG TTC AAC ATC GAC AGC AAG ACC TTC AAG GAG CTG AAG CTT      434
Asp Thr Lys Phe Asn Ile Asp Ser Lys Thr Phe Lys Glu Leu Lys Leu
        950                 955                 960

TTC AAG ATC GAC AGC CAG AAC CAG CCC CAG CAG GTG CAG CAG GAC GAG      482
Phe Lys Ile Asp Ser Gln Asn Gln Pro Gln Gln Val Gln Gln Asp Glu
    965                 970                 975

CTG CGC AAC CCC GAG TTC AAC AAG AAG GAG AGC CAG GAG TTC CTG GCC      530
Leu Arg Asn Pro Glu Phe Asn Lys Lys Glu Ser Gln Glu Phe Leu Ala
980                 985                 990                 995

AAG CCC AGC AAG ATC AAC CTG TTC ACC CAG CAG ATG AAG CGC GAG ATC      578
Lys Pro Ser Lys Ile Asn Leu Phe Thr Gln Gln Met Lys Arg Glu Ile
                1000                1005                1010

GAC GAG GAC ACC GAC ACC GAC GGC GAC AGC ATC CCC GAC CTG TGG GAG      626
Asp Glu Asp Thr Asp Thr Asp Gly Asp Ser Ile Pro Asp Leu Trp Glu
            1015                1020                1025

GAG AAC GGC TAC ACC ATC CAG AAC CGC ATC GCC GTG AAG TGG GAC GAC      674
Glu Asn Gly Tyr Thr Ile Gln Asn Arg Ile Ala Val Lys Trp Asp Asp
        1030                1035                1040

AGC CTG GCT AGC AAG GGC TAC ACC AAG TTC GTG AGC AAC CCC CTG GAG      722
Ser Leu Ala Ser Lys Gly Tyr Thr Lys Phe Val Ser Asn Pro Leu Glu
    1045                1050                1055
```

```
AGC CAC ACC GTG GGC GAC CCC TAC ACC GAC TAC GAG AAG GCC GCC CGC     770
Ser His Thr Val Gly Asp Pro Tyr Thr Asp Tyr Glu Lys Ala Ala Arg
1060              1065              1070              1075

GAC CTG GAC CTG AGC AAC GCC AAG GAG ACC TTC AAC CCC CTG GTG GCC     818
Asp Leu Asp Leu Ser Asn Ala Lys Glu Thr Phe Asn Pro Leu Val Ala
         1080              1085              1090

GCC TTC CCC AGC GTG AAC GTG AGC ATG GAG AAG GTG ATC CTG AGC CCC     866
Ala Phe Pro Ser Val Asn Val Ser Met Glu Lys Val Ile Leu Ser Pro
     1095              1100              1105

AAC GAG AAC CTG AGC AAC AGC GTG GAG AGC CAC TCG AGC ACC AAC TGG     914
Asn Glu Asn Leu Ser Asn Ser Val Glu Ser His Ser Ser Thr Asn Trp
1110              1115              1120

AGC TAC ACC AAC ACC GAG GGC GCC AGC GTG GAG GCC GGC ATC GGT CCC     962
Ser Tyr Thr Asn Thr Glu Gly Ala Ser Val Glu Ala Gly Ile Gly Pro
         1125              1130              1135

AAG GGC ATC AGC TTC GGC GTG AGC GTG AAC TAC CAG CAC AGC GAG ACC    1010
Lys Gly Ile Ser Phe Gly Val Ser Val Asn Tyr Gln His Ser Glu Thr
1140              1145              1150              1155

GTG GCC CAG GAG TGG GGC ACC AGC ACC GGC AAC ACC AGC CAG TTC AAC    1058
Val Ala Gln Glu Trp Gly Thr Ser Thr Gly Asn Thr Ser Gln Phe Asn
         1160              1165              1170

ACC GCC AGC GCC GGC TAC CTG AAC GCC AAC GTG CGC TAC AAC AAC GTG    1106
Thr Ala Ser Ala Gly Tyr Leu Asn Ala Asn Val Arg Tyr Asn Asn Val
     1175              1180              1185

GGC ACC GGC GCC ATC TAC GAC GTG AAG CCC ACC ACC AGC TTC GTG CTG    1154
Gly Thr Gly Ala Ile Tyr Asp Val Lys Pro Thr Thr Ser Phe Val Leu
         1190              1195              1200

AAC AAC GAC ACC ATC GCC ACC ATC ACC GCC AAG TCG AAT TCC ACC GCC    1202
Asn Asn Asp Thr Ile Ala Thr Ile Thr Ala Lys Ser Asn Ser Thr Ala
     1205              1210              1215

CTG AAC ATC AGC CCC GGC GAG AGC TAC CCC AAG AAG GGC CAG AAC GGC    1250
Leu Asn Ile Ser Pro Gly Glu Ser Tyr Pro Lys Lys Gly Gln Asn Gly
1220              1225              1230              1235

ATC GCC ATC ACC AGC ATG GAC GAC TTC AAC AGC CAC CCC ATC ACC CTG    1298
Ile Ala Ile Thr Ser Met Asp Asp Phe Asn Ser His Pro Ile Thr Leu
         1240              1245              1250

AAC AAG AAG CAG GTG GAC AAC CTG CTG AAC AAC AAG CCC ATG ATG CTG    1346
Asn Lys Lys Gln Val Asp Asn Leu Leu Asn Asn Lys Pro Met Met Leu
     1255              1260              1265

GAG ACC AAC CAG ACC GAC GGC GTC TAC AAG ATC AAG GAC ACC CAC GGC    1394
Glu Thr Asn Gln Thr Asp Gly Val Tyr Lys Ile Lys Asp Thr His Gly
         1270              1275              1280

AAC ATC GTG ACG GGC GGC GAG TGG AAC GGC GTG ATC CAG CAG ATC AAG    1442
Asn Ile Val Thr Gly Gly Glu Trp Asn Gly Val Ile Gln Gln Ile Lys
     1285              1290              1295

GCC AAG ACC GCC AGC ATC ATC GTC GAC GAC GGC GAG CGC GTG GCC GAG    1490
Ala Lys Thr Ala Ser Ile Ile Val Asp Asp Gly Glu Arg Val Ala Glu
1300              1305              1310              1315

AAG CGC GTG GCC GCC AAG GAC TAC GAG AAC CCC GAG GAC AAG ACC CCC    1538
Lys Arg Val Ala Ala Lys Asp Tyr Glu Asn Pro Glu Asp Lys Thr Pro
         1320              1325              1330

AGC CTG ACC CTG AAG GAC GCC CTG AAG CTG AGC TAC CCC GAC GAG ATC    1586
Ser Leu Thr Leu Lys Asp Ala Leu Lys Leu Ser Tyr Pro Asp Glu Ile
         1335              1340              1345

AAG GAG ATC GAG GGC TTG CTG TAC TAC AAG AAC AAG CCC ATC TAC GAG    1634
Lys Glu Ile Glu Gly Leu Leu Tyr Tyr Lys Asn Lys Pro Ile Tyr Glu
1350              1355              1360

AGC AGC GTG ATG ACC TAT CTA GAC GAG AAC ACC GCC AAG GAG GTG ACC    1682
Ser Ser Val Met Thr Tyr Leu Asp Glu Asn Thr Ala Lys Glu Val Thr
         1365              1370              1375
```

| | | | | | | | | | | | | | | | |
|---|---|---|---|---|---|---|---|---|---|---|---|---|---|---|---|
| AAG | CAG | CTG | AAC | GAC | ACC | ACC | GGC | AAG | TTC | AAG | GAC | GTG | AGC | CAC | CTG | 1730
| Lys | Gln | Leu | Asn | Asp | Thr | Thr | Gly | Lys | Phe | Lys | Asp | Val | Ser | His | Leu |
| 1380 | | | | 1385 | | | | | 1390 | | | | | | 1395 |

| TAC | GAC | GTG | AAG | CTG | ACC | CCC | AAG | ATG | AAC | GTG | ACC | ATC | AAG | CTG | AGC | 1778
|---|---|---|---|---|---|---|---|---|---|---|---|---|---|---|---|
| Tyr | Asp | Val | Lys | Leu | Thr | Pro | Lys | Met | Asn | Val | Thr | Ile | Lys | Leu | Ser |
| | | | | 1400 | | | | 1405 | | | | | | 1410 | |

| ATC | CTG | TAC | GAC | AAC | GCC | GAG | AGC | AAC | GAC | AAC | AGC | ATC | GGC | AAG | TGG | 1826
|---|---|---|---|---|---|---|---|---|---|---|---|---|---|---|---|
| Ile | Leu | Tyr | Asp | Asn | Ala | Glu | Ser | Asn | Asp | Asn | Ser | Ile | Gly | Lys | Trp |
| | | | 1415 | | | | | 1420 | | | | | 1425 | | |

| ACC | AAC | ACC | AAC | ATC | GTG | AGC | GGC | GGC | AAC | AAC | GGC | AAG | AAG | CAG | TAC | 1874
|---|---|---|---|---|---|---|---|---|---|---|---|---|---|---|---|
| Thr | Asn | Thr | Asn | Ile | Val | Ser | Gly | Gly | Asn | Asn | Gly | Lys | Lys | Gln | Tyr |
| | | 1430 | | | | | 1435 | | | | | 1440 | | | |

| AGC | AGC | AAC | AAC | CCC | GAC | GCC | AAC | CTG | ACC | CTG | AAC | ACC | GAC | GCC | CAG | 1922
|---|---|---|---|---|---|---|---|---|---|---|---|---|---|---|---|
| Ser | Ser | Asn | Asn | Pro | Asp | Ala | Asn | Leu | Thr | Leu | Asn | Thr | Asp | Ala | Gln |
| | 1445 | | | | | 1450 | | | | | 1455 | | | | |

| GAG | AAG | CTG | AAC | AAG | AAC | CGC | GAC | TAC | TAC | ATC | AGC | CTG | TAC | ATG | AAG | 1970
|---|---|---|---|---|---|---|---|---|---|---|---|---|---|---|---|
| Glu | Lys | Leu | Asn | Lys | Asn | Arg | Asp | Tyr | Tyr | Ile | Ser | Leu | Tyr | Met | Lys |
| 1460 | | | | | 1465 | | | | | 1470 | | | | | 1475 |

| AGC | GAG | AAG | AAC | ACC | CAG | TGC | GAG | ATC | ACC | ATC | GAC | GGC | GAG | ATA | TAC | 2018
|---|---|---|---|---|---|---|---|---|---|---|---|---|---|---|---|
| Ser | Glu | Lys | Asn | Thr | Gln | Cys | Glu | Ile | Thr | Ile | Asp | Gly | Glu | Ile | Tyr |
| | | | | 1480 | | | | | 1485 | | | | | 1490 | |

| CCC | ATC | ACC | ACC | AAG | ACC | GTG | AAC | GTG | AAC | AAG | GAC | AAC | TAC | AAG | CGC | 2066
|---|---|---|---|---|---|---|---|---|---|---|---|---|---|---|---|
| Pro | Ile | Thr | Thr | Lys | Thr | Val | Asn | Val | Asn | Lys | Asp | Asn | Tyr | Lys | Arg |
| | | | 1495 | | | | | 1500 | | | | | 1505 | | |

| CTG | GAC | ATC | ATC | GCC | CAC | AAC | ATC | AAG | AGC | AAC | CCC | ATC | AGC | AGC | CTG | 2114
|---|---|---|---|---|---|---|---|---|---|---|---|---|---|---|---|
| Leu | Asp | Ile | Ile | Ala | His | Asn | Ile | Lys | Ser | Asn | Pro | Ile | Ser | Ser | Leu |
| | | 1510 | | | | | 1515 | | | | | 1520 | | | |

| CAC | ATC | AAG | ACC | AAC | GAC | GAG | ATC | ACC | CTG | TTC | TGG | GAC | GAC | ATA | TCG | 2162
|---|---|---|---|---|---|---|---|---|---|---|---|---|---|---|---|
| His | Ile | Lys | Thr | Asn | Asp | Glu | Ile | Thr | Leu | Phe | Trp | Asp | Asp | Ile | Ser |
| | 1525 | | | | | 1530 | | | | | 1535 | | | | |

| ATT | ACC | GAC | GTC | GCC | AGC | ATC | AAG | CCC | GAG | AAC | CTG | ACC | GAC | AGC | GAG | 2210
|---|---|---|---|---|---|---|---|---|---|---|---|---|---|---|---|
| Ile | Thr | Asp | Val | Ala | Ser | Ile | Lys | Pro | Glu | Asn | Leu | Thr | Asp | Ser | Glu |
| 1540 | | | | | 1545 | | | | | 1550 | | | | | 1555 |

| ATC | AAG | CAG | ATA | TAC | AGT | CGC | TAC | GGC | ATC | AAG | CTG | GAG | GAC | GGC | ATC | 2258
|---|---|---|---|---|---|---|---|---|---|---|---|---|---|---|---|
| Ile | Lys | Gln | Ile | Tyr | Ser | Arg | Tyr | Gly | Ile | Lys | Leu | Glu | Asp | Gly | Ile |
| | | | | 1560 | | | | | 1565 | | | | | 1570 | |

| CTG | ATC | GAC | AAG | AAA | GGC | GGC | ATC | CAC | TAC | GGC | GAG | TTC | ATC | AAC | GAG | 2306
|---|---|---|---|---|---|---|---|---|---|---|---|---|---|---|---|
| Leu | Ile | Asp | Lys | Lys | Gly | Gly | Ile | His | Tyr | Gly | Glu | Phe | Ile | Asn | Glu |
| | | | 1575 | | | | | 1580 | | | | | 1585 | | |

| GCC | AGC | TTC | AAC | ATC | GAG | CCC | CTG | CAG | AAC | TAC | GTG | ACC | AAG | TAC | GAG | 2354
|---|---|---|---|---|---|---|---|---|---|---|---|---|---|---|---|
| Ala | Ser | Phe | Asn | Ile | Glu | Pro | Leu | Gln | Asn | Tyr | Val | Thr | Lys | Tyr | Glu |
| | | 1590 | | | | | 1595 | | | | | 1600 | | | |

| GTG | ACC | TAC | AGC | AGC | GAG | CTG | GGC | CCC | AAC | GTG | AGC | GAC | ACC | CTG | GAG | 2402
|---|---|---|---|---|---|---|---|---|---|---|---|---|---|---|---|
| Val | Thr | Tyr | Ser | Ser | Glu | Leu | Gly | Pro | Asn | Val | Ser | Asp | Thr | Leu | Glu |
| | 1605 | | | | | 1610 | | | | | 1615 | | | | |

| AGC | GAC | AAG | ATT | TAC | AAG | GAC | GGC | ACC | ATC | AAG | TTC | GAC | TTC | ACC | AAG | 2450
|---|---|---|---|---|---|---|---|---|---|---|---|---|---|---|---|
| Ser | Asp | Lys | Ile | Tyr | Lys | Asp | Gly | Thr | Ile | Lys | Phe | Asp | Phe | Thr | Lys |
| 1620 | | | | 1625 | | | | | 1630 | | | | | 1635 | |

| TAC | AGC | AAG | AAC | GAG | CAG | GGC | CTG | TTC | TAC | GAC | AGC | GGC | CTG | AAC | TGG | 2498
|---|---|---|---|---|---|---|---|---|---|---|---|---|---|---|---|
| Tyr | Ser | Lys | Asn | Glu | Gln | Gly | Leu | Phe | Tyr | Asp | Ser | Gly | Leu | Asn | Trp |
| | | | | 1640 | | | | | 1645 | | | | | 1650 | |

| GAC | TTC | AAG | ATC | AAC | GCC | ATC | ACC | TAC | GAC | GGC | AAG | GAG | ATG | AAC | GTG | 2546
|---|---|---|---|---|---|---|---|---|---|---|---|---|---|---|---|
| Asp | Phe | Lys | Ile | Asn | Ala | Ile | Thr | Tyr | Asp | Gly | Lys | Glu | Met | Asn | Val |
| | | | 1655 | | | | | 1660 | | | | | 1665 | | |

| TTC | CAC | CGC | TAC | AAC | AAG | TAGATCTGAG | CT | | | | | | | | | 2576
|---|---|---|---|---|---|---|---|
| Phe | His | Arg | Tyr | Asn | Lys | | |
| | | 1670 | | | | | |

( 2 ) INFORMATION FOR SEQ ID NO:36:

( i ) SEQUENCE CHARACTERISTICS:

(A) LENGTH: 852 amino acids
(B) TYPE: amino acid
(D) TOPOLOGY: linear (ii) MOLECULE TYPE: protein (xi) SEQUENCE DESCRIPTION: SEQ ID NO:36:

```
Met Lys Thr Asn Gln Ile Ser Thr Thr Gln Lys Asn Gln Gln Lys Glu
 1               5                  10                  15
Met Asp Arg Lys Gly Leu Leu Gly Tyr Tyr Phe Lys Gly Lys Asp Phe
                20                  25                  30
Ser Asn Leu Thr Met Phe Ala Pro Thr Arg Asp Ser Thr Leu Ile Tyr
                35                  40                  45
Asp Gln Gln Thr Ala Asn Lys Leu Leu Asp Lys Lys Gln Gln Glu Tyr
            50                  55                  60
Gln Ser Ile Arg Trp Ile Gly Leu Ile Gln Ser Lys Glu Thr Gly Asp
 65                  70                  75                  80
Phe Thr Phe Asn Leu Ser Glu Asp Glu Gln Ala Ile Ile Glu Ile Asn
                    85                  90                  95
Gly Lys Ile Ile Ser Asn Lys Gly Lys Glu Lys Gln Val Val His Leu
                100                 105                 110
Glu Lys Gly Lys Leu Val Pro Ile Lys Ile Glu Tyr Gln Ser Asp Thr
                115                 120                 125
Lys Phe Asn Ile Asp Ser Lys Thr Phe Lys Glu Leu Lys Leu Phe Lys
            130                 135                 140
Ile Asp Ser Gln Asn Gln Pro Gln Gln Val Gln Gln Asp Glu Leu Arg
145                 150                 155                 160
Asn Pro Glu Phe Asn Lys Lys Glu Ser Gln Glu Phe Leu Ala Lys Pro
                    165                 170                 175
Ser Lys Ile Asn Leu Phe Thr Gln Gln Met Lys Arg Glu Ile Asp Glu
                180                 185                 190
Asp Thr Asp Thr Asp Gly Asp Ser Ile Pro Asp Leu Trp Glu Glu Asn
            195                 200                 205
Gly Tyr Thr Ile Gln Asn Arg Ile Ala Val Lys Trp Asp Asp Ser Leu
            210                 215                 220
Ala Ser Lys Gly Tyr Thr Lys Phe Val Ser Asn Pro Leu Glu Ser His
225                 230                 235                 240
Thr Val Gly Asp Pro Tyr Thr Asp Tyr Glu Lys Ala Ala Arg Asp Leu
                245                 250                 255
Asp Leu Ser Asn Ala Lys Glu Thr Phe Asn Pro Leu Val Ala Ala Phe
                260                 265                 270
Pro Ser Val Asn Val Ser Met Glu Lys Val Ile Leu Ser Pro Asn Glu
                275                 280                 285
Asn Leu Ser Asn Ser Val Glu Ser His Ser Ser Thr Asn Trp Ser Tyr
            290                 295                 300
Thr Asn Thr Glu Gly Ala Ser Val Glu Ala Gly Ile Gly Pro Lys Gly
305                 310                 315                 320
Ile Ser Phe Gly Val Ser Val Asn Tyr Gln His Ser Glu Thr Val Ala
                325                 330                 335
Gln Glu Trp Gly Thr Ser Thr Gly Asn Thr Ser Gln Phe Asn Thr Ala
                340                 345                 350
Ser Ala Gly Tyr Leu Asn Ala Asn Val Arg Tyr Asn Asn Val Gly Thr
                355                 360                 365
Gly Ala Ile Tyr Asp Val Lys Pro Thr Thr Ser Phe Val Leu Asn Asn
            370                 375                 380
```

| | | | | | | | | | | | | | | |
|---|---|---|---|---|---|---|---|---|---|---|---|---|---|---|
| Asp | Thr | Ile | Ala | Thr | Ile | Thr | Ala | Lys | Ser | Asn | Ser | Thr | Ala | Leu | Asn |
| 385 | | | | | 390 | | | | 395 | | | | | | 400 |
| Ile | Ser | Pro | Gly | Glu | Ser | Tyr | Pro | Lys | Lys | Gly | Gln | Asn | Gly | Ile | Ala |
| | | | | 405 | | | | | 410 | | | | | 415 | |
| Ile | Thr | Ser | Met | Asp | Asp | Phe | Asn | Ser | His | Pro | Ile | Thr | Leu | Asn | Lys |
| | | | 420 | | | | | 425 | | | | | 430 | | |
| Lys | Gln | Val | Asp | Asn | Leu | Leu | Asn | Asn | Lys | Pro | Met | Met | Leu | Glu | Thr |
| | | 435 | | | | | 440 | | | | | 445 | | | |
| Asn | Gln | Thr | Asp | Gly | Val | Tyr | Lys | Ile | Lys | Asp | Thr | His | Gly | Asn | Ile |
| | 450 | | | | | 455 | | | | | 460 | | | | |
| Val | Thr | Gly | Gly | Glu | Trp | Asn | Gly | Val | Ile | Gln | Gln | Ile | Lys | Ala | Lys |
| 465 | | | | | 470 | | | | 475 | | | | | | 480 |
| Thr | Ala | Ser | Ile | Ile | Val | Asp | Asp | Gly | Glu | Arg | Val | Ala | Glu | Lys | Arg |
| | | | | 485 | | | | | 490 | | | | | 495 | |
| Val | Ala | Ala | Lys | Asp | Tyr | Glu | Asn | Pro | Glu | Asp | Lys | Thr | Pro | Ser | Leu |
| | | | 500 | | | | | 505 | | | | | 510 | | |
| Thr | Leu | Lys | Asp | Ala | Leu | Lys | Leu | Ser | Tyr | Pro | Asp | Glu | Ile | Lys | Glu |
| | | 515 | | | | | 520 | | | | | 525 | | | |
| Ile | Glu | Gly | Leu | Leu | Tyr | Tyr | Lys | Asn | Lys | Pro | Ile | Tyr | Glu | Ser | Ser |
| | 530 | | | | | 535 | | | | | 540 | | | | |
| Val | Met | Thr | Tyr | Leu | Asp | Glu | Asn | Thr | Ala | Lys | Glu | Val | Thr | Lys | Gln |
| 545 | | | | | 550 | | | | 555 | | | | | | 560 |
| Leu | Asn | Asp | Thr | Thr | Gly | Lys | Phe | Lys | Asp | Val | Ser | His | Leu | Tyr | Asp |
| | | | | 565 | | | | | 570 | | | | | 575 | |
| Val | Lys | Leu | Thr | Pro | Lys | Met | Asn | Val | Thr | Ile | Lys | Leu | Ser | Ile | Leu |
| | | | 580 | | | | | 585 | | | | | 590 | | |
| Tyr | Asp | Asn | Ala | Glu | Ser | Asn | Asp | Asn | Ser | Ile | Gly | Lys | Trp | Thr | Asn |
| | | 595 | | | | | 600 | | | | | 605 | | | |
| Thr | Asn | Ile | Val | Ser | Gly | Gly | Asn | Asn | Gly | Lys | Lys | Gln | Tyr | Ser | Ser |
| 610 | | | | | 615 | | | | | | 620 | | | | |
| Asn | Asn | Pro | Asp | Ala | Asn | Leu | Thr | Leu | Asn | Thr | Asp | Ala | Gln | Glu | Lys |
| 625 | | | | | 630 | | | | | 635 | | | | | 640 |
| Leu | Asn | Lys | Asn | Arg | Asp | Tyr | Tyr | Ile | Ser | Leu | Tyr | Met | Lys | Ser | Glu |
| | | | | 645 | | | | | 650 | | | | | 655 | |
| Lys | Asn | Thr | Gln | Cys | Glu | Ile | Thr | Ile | Asp | Gly | Glu | Ile | Tyr | Pro | Ile |
| | | | 660 | | | | | 665 | | | | | 670 | | |
| Thr | Thr | Lys | Thr | Val | Asn | Val | Asn | Lys | Asp | Asn | Tyr | Lys | Arg | Leu | Asp |
| | | 675 | | | | | 680 | | | | | 685 | | | |
| Ile | Ile | Ala | His | Asn | Ile | Lys | Ser | Asn | Pro | Ile | Ser | Ser | Leu | His | Ile |
| | 690 | | | | | 695 | | | | | 700 | | | | |
| Lys | Thr | Asn | Asp | Glu | Ile | Thr | Leu | Phe | Trp | Asp | Asp | Ile | Ser | Ile | Thr |
| 705 | | | | | 710 | | | | 715 | | | | | | 720 |
| Asp | Val | Ala | Ser | Ile | Lys | Pro | Glu | Asn | Leu | Thr | Asp | Ser | Glu | Ile | Lys |
| | | | | 725 | | | | | 730 | | | | | 735 | |
| Gln | Ile | Tyr | Ser | Arg | Tyr | Gly | Ile | Lys | Leu | Glu | Asp | Gly | Ile | Leu | Ile |
| | | | 740 | | | | | 745 | | | | | 750 | | |
| Asp | Lys | Lys | Gly | Gly | Ile | His | Tyr | Gly | Glu | Phe | Ile | Asn | Glu | Ala | Ser |
| | | 755 | | | | | 760 | | | | | 765 | | | |
| Phe | Asn | Ile | Glu | Pro | Leu | Gln | Asn | Tyr | Val | Thr | Lys | Tyr | Glu | Val | Thr |
| | 770 | | | | | 775 | | | | | 780 | | | | |
| Tyr | Ser | Ser | Glu | Leu | Gly | Pro | Asn | Val | Ser | Asp | Thr | Leu | Glu | Ser | Asp |
| 785 | | | | | 790 | | | | | 795 | | | | | 800 |
| Lys | Ile | Tyr | Lys | Asp | Gly | Thr | Ile | Lys | Phe | Asp | Phe | Thr | Lys | Tyr | Ser |
| | | | | 805 | | | | | 810 | | | | | 815 | |

|     |     |     |     |     |     |     |     |     |     |     |     |     |     |
|-----|-----|-----|-----|-----|-----|-----|-----|-----|-----|-----|-----|-----|-----|
| Lys | Asn | Glu | Gln | Gly | Leu | Phe | Tyr | Asp | Ser | Gly | Leu | Asn | Trp Asp Phe |
|     |     |     | 820 |     |     |     |     | 825 |     |     |     |     | 830 |

Lys Ile Asn Ala Ile Thr Tyr Asp Gly Lys Glu Met Asn Val Phe His
         835                   840                  845

Arg Tyr Asn Lys
     850

( 2 ) INFORMATION FOR SEQ ID NO:37:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "forward primer used to make
            pCIB5527"

( i i i ) HYPOTHETICAL: NO ( x i ) SEQUENCE DESCRIPTION: SEQ ID NO:37:

GGATCCACCA TGCTGCAGAA CCTGAAGATC AC                                32

( 2 ) INFORMATION FOR SEQ ID NO:38:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "reverse primer used to make
            pCIB5527"

( i i i ) HYPOTHETICAL: NO ( x i ) SEQUENCE DESCRIPTION: SEQ ID NO:38:

AAGCTTCCAC TCCTTCTC                                                  18

( 2 ) INFORMATION FOR SEQ ID NO:39:

( i ) SEQUENCE CHARACTERISTICS:
        ( A ) LENGTH: 1241 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i x ) FEATURE:
        ( A ) NAME/KEY: CDS
        ( B ) LOCATION: 9..1238
        ( D ) OTHER INFORMATION: /note= "Maize optimized DNA
            sequence encoding VIP2A(a) with the Bacillus secretion
            signal removed as contained in pCIB5527"

( x i ) SEQUENCE DESCRIPTION: SEQ ID NO:39:

GATCCACC ATG CTG CAG AAC CTG AAG ATC ACC GAC AAG GTG GAG GAC TTC    50
         Met Leu Gln Asn Leu Lys Ile Thr Asp Lys Val Glu Asp Phe
              855                 860                 865

AAG GAG GAC AAG GAG AAG GCC AAG GAG TGG GGC AAG GAG AAG GAG AAG    98
Lys Glu Asp Lys Glu Lys Ala Lys Glu Trp Gly Lys Glu Lys Glu Lys
         870                 875                 880

GAG TGG AAG CTT ACC GCC ACC GAG AAG GGC AAG ATG AAC AAC TTC CTG    146

|     |     |     |     |     |     |     |     |     |     |     |     |     |     |     |     |
|---|---|---|---|---|---|---|---|---|---|---|---|---|---|---|---|
| Glu | Trp | Lys | Leu | Thr | Ala | Thr | Glu | Lys | Gly | Lys | Met | Asn | Asn | Phe | Leu |
|     |     | 885 |     |     |     |     | 890 |     |     |     | 895 |     |     |     |     |

| GAC | AAC | AAG | AAC | GAC | ATC | AAG | ACC | AAC | TAC | AAG | GAG | ATC | ACC | TTC | AGC | 194 |
|---|---|---|---|---|---|---|---|---|---|---|---|---|---|---|---|---|
| Asp | Asn | Lys | Asn | Asp | Ile | Lys | Thr | Asn | Tyr | Lys | Glu | Ile | Thr | Phe | Ser |     |
|     | 900 |     |     |     | 905 |     |     |     |     |     | 910 |     |     |     |     |     |

| ATA | GCC | GGC | AGC | TTC | GAG | GAC | GAG | ATC | AAG | GAC | CTG | AAG | GAG | ATC | GAC | 242 |
|---|---|---|---|---|---|---|---|---|---|---|---|---|---|---|---|---|
| Ile | Ala | Gly | Ser | Phe | Glu | Asp | Glu | Ile | Lys | Asp | Leu | Lys | Glu | Ile | Asp |     |
| 915 |     |     |     | 920 |     |     |     |     | 925 |     |     |     |     |     | 930 |     |

| AAG | ATG | TTC | GAC | AAG | ACC | AAC | CTG | AGC | AAC | AGC | ATC | ATC | ACC | TAC | AAG | 290 |
|---|---|---|---|---|---|---|---|---|---|---|---|---|---|---|---|---|
| Lys | Met | Phe | Asp | Lys | Thr | Asn | Leu | Ser | Asn | Ser | Ile | Ile | Thr | Tyr | Lys |     |
|     |     |     |     | 935 |     |     |     |     | 940 |     |     |     |     | 945 |     |     |

| AAC | GTG | GAG | CCC | ACC | ACC | ATC | GGC | TTC | AAC | AAG | AGC | CTG | ACC | GAG | GGC | 338 |
|---|---|---|---|---|---|---|---|---|---|---|---|---|---|---|---|---|
| Asn | Val | Glu | Pro | Thr | Thr | Ile | Gly | Phe | Asn | Lys | Ser | Leu | Thr | Glu | Gly |     |
|     |     |     | 950 |     |     |     |     | 955 |     |     |     |     | 960 |     |     |     |

| AAC | ACC | ATC | AAC | AGC | GAC | GCC | ATG | GCC | CAG | TTC | AAG | GAG | CAG | TTC | CTG | 386 |
|---|---|---|---|---|---|---|---|---|---|---|---|---|---|---|---|---|
| Asn | Thr | Ile | Asn | Ser | Asp | Ala | Met | Ala | Gln | Phe | Lys | Glu | Gln | Phe | Leu |     |
|     |     | 965 |     |     |     |     | 970 |     |     |     |     | 975 |     |     |     |     |

| GAC | CGC | GAC | ATC | AAG | TTC | GAC | AGC | TAC | CTG | GAC | ACC | CAC | CTG | ACC | GCC | 434 |
|---|---|---|---|---|---|---|---|---|---|---|---|---|---|---|---|---|
| Asp | Arg | Asp | Ile | Lys | Phe | Asp | Ser | Tyr | Leu | Asp | Thr | His | Leu | Thr | Ala |     |
|     | 980 |     |     |     |     | 985 |     |     |     |     | 990 |     |     |     |     |     |

| CAG | CAG | GTG | AGC | AGC | AAG | GAG | CGC | GTG | ATC | CTG | AAG | GTG | ACC | GTC | CCC | 482 |
|---|---|---|---|---|---|---|---|---|---|---|---|---|---|---|---|---|
| Gln | Gln | Val | Ser | Ser | Lys | Glu | Arg | Val | Ile | Leu | Lys | Val | Thr | Val | Pro |     |
| 995 |     |     |     |     | 1000 |     |     |     |     | 1005 |     |     |     |     | 1010 |     |

| AGC | GGC | AAG | GGC | AGC | ACC | ACC | CCC | ACC | AAG | GCC | GGC | GTG | ATC | CTG | AAC | 530 |
|---|---|---|---|---|---|---|---|---|---|---|---|---|---|---|---|---|
| Ser | Gly | Lys | Gly | Ser | Thr | Thr | Pro | Thr | Lys | Ala | Gly | Val | Ile | Leu | Asn |     |
|     |     |     |     | 1015 |     |     |     |     | 1020 |     |     |     |     | 1025 |     |     |

| AAC | AGC | GAG | TAC | AAG | ATG | CTG | ATC | GAC | AAC | GGC | TAC | ATG | GTG | CAC | GTG | 578 |
|---|---|---|---|---|---|---|---|---|---|---|---|---|---|---|---|---|
| Asn | Ser | Glu | Tyr | Lys | Met | Leu | Ile | Asp | Asn | Gly | Tyr | Met | Val | His | Val |     |
|     |     |     |     | 1030 |     |     |     |     | 1035 |     |     |     |     | 1040 |     |     |

| GAC | AAG | GTG | AGC | AAG | GTG | GTG | AAG | AAG | GGC | GTG | GAG | TGC | CTC | CAG | ATC | 626 |
|---|---|---|---|---|---|---|---|---|---|---|---|---|---|---|---|---|
| Asp | Lys | Val | Ser | Lys | Val | Val | Lys | Lys | Gly | Val | Glu | Cys | Leu | Gln | Ile |     |
|     |     |     | 1045 |     |     |     |     | 1050 |     |     |     |     | 1055 |     |     |     |

| GAG | GGC | ACC | CTG | AAG | AAG | AGT | CTA | GAC | TTC | AAG | AAC | GAC | ATC | AAC | GCC | 674 |
|---|---|---|---|---|---|---|---|---|---|---|---|---|---|---|---|---|
| Glu | Gly | Thr | Leu | Lys | Lys | Ser | Leu | Asp | Phe | Lys | Asn | Asp | Ile | Asn | Ala |     |
|     | 1060 |     |     |     |     | 1065 |     |     |     |     | 1070 |     |     |     |     |     |

| GAG | GCC | CAC | AGC | TGG | GGC | ATG | AAG | AAC | TAC | GAG | GAG | TGG | GCC | AAG | GAC | 722 |
|---|---|---|---|---|---|---|---|---|---|---|---|---|---|---|---|---|
| Glu | Ala | His | Ser | Trp | Gly | Met | Lys | Asn | Tyr | Glu | Glu | Trp | Ala | Lys | Asp |     |
| 1075 |     |     |     |     | 1080 |     |     |     |     | 1085 |     |     |     |     | 1090 |     |

| CTG | ACC | GAC | AGC | CAG | CGC | GAG | GCC | CTG | GAC | GGC | TAC | GCC | CGC | CAG | GAC | 770 |
|---|---|---|---|---|---|---|---|---|---|---|---|---|---|---|---|---|
| Leu | Thr | Asp | Ser | Gln | Arg | Glu | Ala | Leu | Asp | Gly | Tyr | Ala | Arg | Gln | Asp |     |
|     |     |     |     | 1095 |     |     |     |     | 1100 |     |     |     |     | 1105 |     |     |

| TAC | AAG | GAG | ATC | AAC | AAC | TAC | CTG | CGC | AAC | CAG | GGC | GGC | AGC | GGC | AAC | 818 |
|---|---|---|---|---|---|---|---|---|---|---|---|---|---|---|---|---|
| Tyr | Lys | Glu | Ile | Asn | Asn | Tyr | Leu | Arg | Asn | Gln | Gly | Gly | Ser | Gly | Asn |     |
|     |     |     |     | 1110 |     |     |     |     | 1115 |     |     |     |     | 1120 |     |     |

| GAG | AAG | CTG | GAC | GCC | CAG | ATC | AAG | AAC | ATC | AGC | GAC | GCC | CTG | GGC | AAG | 866 |
|---|---|---|---|---|---|---|---|---|---|---|---|---|---|---|---|---|
| Glu | Lys | Leu | Asp | Ala | Gln | Ile | Lys | Asn | Ile | Ser | Asp | Ala | Leu | Gly | Lys |     |
|     |     |     |     | 1125 |     |     |     |     | 1130 |     |     |     |     | 1135 |     |     |

| AAG | CCC | ATC | CCC | GAG | AAC | ATC | ACC | GTG | TAC | CGC | TGG | TGC | GGC | ATG | CCC | 914 |
|---|---|---|---|---|---|---|---|---|---|---|---|---|---|---|---|---|
| Lys | Pro | Ile | Pro | Glu | Asn | Ile | Thr | Val | Tyr | Arg | Trp | Cys | Gly | Met | Pro |     |
|     |     |     | 1140 |     |     |     |     | 1145 |     |     |     |     | 1150 |     |     |     |

| GAG | TTC | GGC | TAC | CAG | ATC | AGC | GAC | CCC | CTG | CCC | AGC | CTG | AAG | GAC | TTC | 962 |
|---|---|---|---|---|---|---|---|---|---|---|---|---|---|---|---|---|
| Glu | Phe | Gly | Tyr | Gln | Ile | Ser | Asp | Pro | Leu | Pro | Ser | Leu | Lys | Asp | Phe |     |
| 1155 |     |     |     |     | 1160 |     |     |     |     | 1165 |     |     |     |     | 1170 |     |

| GAG | GAG | CAG | TTC | CTG | AAC | ACC | ATC | AAG | GAG | GAC | AAG | GGC | TAC | ATG | AGC | 1010 |
|---|---|---|---|---|---|---|---|---|---|---|---|---|---|---|---|---|
| Glu | Glu | Gln | Phe | Leu | Asn | Thr | Ile | Lys | Glu | Asp | Lys | Gly | Tyr | Met | Ser |     |
|     |     |     |     | 1175 |     |     |     |     | 1180 |     |     |     |     | 1185 |     |     |

| ACC | AGC | CTG | AGC | AGC | GAG | CGC | CTG | GCC | GCC | TTC | GGC | AGC | CGC | AAG | ATC | 1058 |
|---|---|---|---|---|---|---|---|---|---|---|---|---|---|---|---|---|
| Thr | Ser | Leu | Ser | Ser | Glu | Arg | Leu | Ala | Ala | Phe | Gly | Ser | Arg | Lys | Ile |     |
|     |     |     | 1190 |     |     |     |     | 1195 |     |     |     |     | 1200 |     |     |     |

| ATC | CTG | CGC | CTG | CAG | GTG | CCC | AAG | GGC | AGC | ACT | GGT | GCC | TAC | CTG | AGC | 1106 |

| | | | | | | | | | | | | | | |
|---|---|---|---|---|---|---|---|---|---|---|---|---|---|---|
| Ile | Leu | Arg | Leu | Gln | Val | Pro | Lys | Gly | Ser | Thr | Gly | Ala | Tyr | Leu | Ser |
| | | | 1205 | | | | 1210 | | | | | 1215 | | | |

| GCC | ATC | GGC | GGC | TTC | GCC | AGC | GAG | AAG | GAG | ATC | CTG | CTG | GAT | AAG | GAC | 1154 |
|-----|-----|-----|-----|-----|-----|-----|-----|-----|-----|-----|-----|-----|-----|-----|-----|------|
| Ala | Ile | Gly | Gly | Phe | Ala | Ser | Glu | Lys | Glu | Ile | Leu | Leu | Asp | Lys | Asp | |
| 1220 | | | | | 1225 | | | | 1230 | | | | | | | |

| AGC | AAG | TAC | CAC | ATC | GAC | AAG | GTG | ACC | GAG | GTG | ATC | ATC | AAG | GGC | GTG | 1202 |
|-----|-----|-----|-----|-----|-----|-----|-----|-----|-----|-----|-----|-----|-----|-----|-----|------|
| Ser | Lys | Tyr | His | Ile | Asp | Lys | Val | Thr | Glu | Val | Ile | Ile | Lys | Gly | Val | |
| 1235 | | | | 1240 | | | | | 1245 | | | | | | 1250 | |

| AAG | CGC | TAC | GTG | GTG | GAC | GCC | ACC | CTG | CTG | ACC | AAC | TAG | 1241 |
|-----|-----|-----|-----|-----|-----|-----|-----|-----|-----|-----|-----|-----|------|
| Lys | Arg | Tyr | Val | Val | Asp | Ala | Thr | Leu | Leu | Thr | Asn | | |
| | | | | 1255 | | | | 1260 | | | | | |

( 2 ) INFORMATION FOR SEQ ID NO:40:

( i ) SEQUENCE CHARACTERISTICS:
        ( A ) LENGTH: 410 amino acids
        ( B ) TYPE: amino acid
        ( D ) TOPOLOGY: linear ( i i ) MOLECULE TYPE: protein ( x i ) SEQUENCE DESCRIPTION: SEQ ID NO:40:

| Met | Leu | Gln | Asn | Leu | Lys | Ile | Thr | Asp | Lys | Val | Glu | Asp | Phe | Lys | Glu |
|-----|-----|-----|-----|-----|-----|-----|-----|-----|-----|-----|-----|-----|-----|-----|-----|
| 1 | | | | 5 | | | | | 10 | | | | | 15 | |
| Asp | Lys | Glu | Lys | Ala | Lys | Glu | Trp | Gly | Lys | Glu | Lys | Glu | Lys | Glu | Trp |
| | | | 20 | | | | | 25 | | | | | 30 | | |
| Lys | Leu | Thr | Ala | Thr | Glu | Lys | Gly | Lys | Met | Asn | Asn | Phe | Leu | Asp | Asn |
| | | | 35 | | | | | 40 | | | | | 45 | | |
| Lys | Asn | Asp | Ile | Lys | Thr | Asn | Tyr | Lys | Glu | Ile | Thr | Phe | Ser | Ile | Ala |
| | | 50 | | | | | 55 | | | | | 60 | | | |
| Gly | Ser | Phe | Glu | Asp | Glu | Ile | Lys | Asp | Leu | Lys | Glu | Ile | Asp | Lys | Met |
| 65 | | | | | 70 | | | | | 75 | | | | | 80 |
| Phe | Asp | Lys | Thr | Asn | Leu | Ser | Asn | Ser | Ile | Ile | Thr | Tyr | Lys | Asn | Val |
| | | | | 85 | | | | | 90 | | | | | 95 | |
| Glu | Pro | Thr | Thr | Ile | Gly | Phe | Asn | Lys | Ser | Leu | Thr | Glu | Gly | Asn | Thr |
| | | | 100 | | | | | 105 | | | | | 110 | | |
| Ile | Asn | Ser | Asp | Ala | Met | Ala | Gln | Phe | Lys | Glu | Gln | Phe | Leu | Asp | Arg |
| | | | 115 | | | | | 120 | | | | | 125 | | |
| Asp | Ile | Lys | Phe | Asp | Ser | Tyr | Leu | Asp | Thr | His | Leu | Thr | Ala | Gln | Gln |
| | | 130 | | | | | 135 | | | | | 140 | | | |
| Val | Ser | Ser | Lys | Glu | Arg | Val | Ile | Leu | Lys | Val | Thr | Val | Pro | Ser | Gly |
| 145 | | | | | 150 | | | | | 155 | | | | | 160 |
| Lys | Gly | Ser | Thr | Thr | Pro | Thr | Lys | Ala | Gly | Val | Ile | Leu | Asn | Asn | Ser |
| | | | | 165 | | | | | 170 | | | | | 175 | |
| Glu | Tyr | Lys | Met | Leu | Ile | Asp | Asn | Gly | Tyr | Met | Val | His | Val | Asp | Lys |
| | | | 180 | | | | | 185 | | | | | 190 | | |
| Val | Ser | Lys | Val | Val | Lys | Lys | Gly | Val | Glu | Cys | Leu | Gln | Ile | Glu | Gly |
| | | 195 | | | | | 200 | | | | | 205 | | | |
| Thr | Leu | Lys | Lys | Ser | Leu | Asp | Phe | Lys | Asn | Asp | Ile | Asn | Ala | Glu | Ala |
| | | 210 | | | | | 215 | | | | | 220 | | | |
| His | Ser | Trp | Gly | Met | Lys | Asn | Tyr | Glu | Glu | Trp | Ala | Lys | Asp | Leu | Thr |
| 225 | | | | | 230 | | | | | 235 | | | | | 240 |
| Asp | Ser | Gln | Arg | Glu | Ala | Leu | Asp | Gly | Tyr | Ala | Arg | Gln | Asp | Tyr | Lys |
| | | | | 245 | | | | | 250 | | | | | 255 | |
| Glu | Ile | Asn | Asn | Tyr | Leu | Arg | Asn | Gln | Gly | Gly | Ser | Gly | Asn | Glu | Lys |
| | | | 260 | | | | | 265 | | | | | 270 | | |
| Leu | Asp | Ala | Gln | Ile | Lys | Asn | Ile | Ser | Asp | Ala | Leu | Gly | Lys | Lys | Pro |
| | | | 275 | | | | | 280 | | | | | 285 | | |

| Ile | Pro | Glu | Asn | Ile | Thr | Val | Tyr | Arg | Trp | Cys | Gly | Met | Pro | Glu | Phe |
|-----|-----|-----|-----|-----|-----|-----|-----|-----|-----|-----|-----|-----|-----|-----|-----|
|     | 290 |     |     |     |     | 295 |     |     |     |     | 300 |     |     |     |     |

| Gly | Tyr | Gln | Ile | Ser | Asp | Pro | Leu | Pro | Ser | Leu | Lys | Asp | Phe | Glu | Glu |
|-----|-----|-----|-----|-----|-----|-----|-----|-----|-----|-----|-----|-----|-----|-----|-----|
| 305 |     |     |     |     | 310 |     |     |     |     | 315 |     |     |     |     | 320 |

| Gln | Phe | Leu | Asn | Thr | Ile | Lys | Glu | Asp | Lys | Gly | Tyr | Met | Ser | Thr | Ser |
|-----|-----|-----|-----|-----|-----|-----|-----|-----|-----|-----|-----|-----|-----|-----|-----|
|     |     |     |     | 325 |     |     |     |     | 330 |     |     |     |     | 335 |     |

| Leu | Ser | Ser | Glu | Arg | Leu | Ala | Ala | Phe | Gly | Ser | Arg | Lys | Ile | Ile | Leu |
|-----|-----|-----|-----|-----|-----|-----|-----|-----|-----|-----|-----|-----|-----|-----|-----|
|     |     |     | 340 |     |     |     |     | 345 |     |     |     |     | 350 |     |     |

| Arg | Leu | Gln | Val | Pro | Lys | Gly | Ser | Thr | Gly | Ala | Tyr | Leu | Ser | Ala | Ile |
|-----|-----|-----|-----|-----|-----|-----|-----|-----|-----|-----|-----|-----|-----|-----|-----|
|     |     | 355 |     |     |     |     | 360 |     |     |     |     | 365 |     |     |     |

| Gly | Gly | Phe | Ala | Ser | Glu | Lys | Glu | Ile | Leu | Leu | Asp | Lys | Asp | Ser | Lys |
|-----|-----|-----|-----|-----|-----|-----|-----|-----|-----|-----|-----|-----|-----|-----|-----|
|     | 370 |     |     |     |     | 375 |     |     |     |     | 380 |     |     |     |     |

| Tyr | His | Ile | Asp | Lys | Val | Thr | Glu | Val | Ile | Ile | Lys | Gly | Val | Lys | Arg |
|-----|-----|-----|-----|-----|-----|-----|-----|-----|-----|-----|-----|-----|-----|-----|-----|
| 385 |     |     |     |     | 390 |     |     |     |     | 395 |     |     |     |     | 400 |

| Tyr | Val | Val | Asp | Ala | Thr | Leu | Leu | Thr | Asn |
|-----|-----|-----|-----|-----|-----|-----|-----|-----|-----|
|     |     |     |     | 405 |     |     |     |     | 410 |

( 2 ) INFORMATION FOR SEQ ID NO:41:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide encoding
            eukaryotic secretion signal used to construct pCIB5527"

( i i i ) HYPOTHETICAL: NO ( x i ) SEQUENCE DESCRIPTION: SEQ ID NO:41:

| GGATCCACCA | TGGGCTGGAG | CTGGATCTTC | CTGTTCCTGC | TGAGCGGCGC | CGCGGGCGTG | 60 |
|---|---|---|---|---|---|---|
| CACTGCCTGC | AG | | | | | 72 |

( 2 ) INFORMATION FOR SEQ ID NO:42:

( i ) SEQUENCE CHARACTERISTICS:
        ( A ) LENGTH: 1241 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i x ) FEATURE:
        ( A ) NAME/KEY: CDS
        ( B ) LOCATION: 9..1238
        ( D ) OTHER INFORMATION: /note= "Maize optimized DNA
            sequence encoding VIP2A(a) with the Bacillus secretion
            signal removed and the eukaryotic secretion signal inserted as contained in pCIB5528"

( x i ) SEQUENCE DESCRIPTION: SEQ ID NO:42:

GATCCACC ATG CTG CAG AAC CTG AAG ATC ACC GAC AAG GTG GAG GAC TTC 50
Met Leu Gln Asn Leu Lys Ile Thr Asp Lys Val Glu Asp Phe
415 420

AAG GAG GAC AAG GAG AAG GCC AAG GAG TGG GGC AAG GAG AAG GAG AAG 98
Lys Glu Asp Lys Glu Lys Ala Lys Glu Trp Gly Lys Glu Lys Glu Lys
425 430 435 440

GAG TGG AAG CTT ACC GCC ACC GAG AAG GGC AAG ATG AAC AAC TTC CTG 146
Glu Trp Lys Leu Thr Ala Thr Glu Lys Gly Lys Met Asn Asn Phe Leu

-continued

|     |     |     |     | 445 |     |     |     |     | 450 |     |     |     |     | 455 |     |     |      |
|-----|-----|-----|-----|-----|-----|-----|-----|-----|-----|-----|-----|-----|-----|-----|-----|-----|------|
| GAC | AAC | AAG | AAC | GAC | ATC | AAG | ACC | AAC | TAC | AAG | GAG | ATC | ACC | TTC | AGC |     | 194  |
| Asp | Asn | Lys | Asn | Asp | Ile | Lys | Thr | Asn | Tyr | Lys | Glu | Ile | Thr | Phe | Ser |     |      |
|     |     |     | 460 |     |     |     | 465 |     |     |     | 470 |     |     |     |     |     |      |
| ATA | GCC | GGC | AGC | TTC | GAG | GAC | GAG | ATC | AAG | GAC | CTG | AAG | GAG | ATC | GAC |     | 242  |
| Ile | Ala | Gly | Ser | Phe | Glu | Asp | Glu | Ile | Lys | Asp | Leu | Lys | Glu | Ile | Asp |     |      |
|     |     |     | 475 |     |     |     | 480 |     |     |     | 485 |     |     |     |     |     |      |
| AAG | ATG | TTC | GAC | AAG | ACC | AAC | CTG | AGC | AAC | AGC | ATC | ACC | TAC | AAG |     |     | 290  |
| Lys | Met | Phe | Asp | Lys | Thr | Asn | Leu | Ser | Asn | Ser | Ile | Thr | Tyr | Lys |     |     |      |
|     | 490 |     |     |     |     | 495 |     |     |     | 500 |     |     |     |     |     |     |      |
| AAC | GTG | GAG | CCC | ACC | ACC | ATC | GGC | TTC | AAC | AAG | AGC | CTG | ACC | GAG | GGC |     | 338  |
| Asn | Val | Glu | Pro | Thr | Thr | Ile | Gly | Phe | Asn | Lys | Ser | Leu | Thr | Glu | Gly |     |      |
| 505 |     |     |     |     | 510 |     |     |     | 515 |     |     |     |     | 520 |     |     |      |
| AAC | ACC | ATC | AAC | AGC | GAC | GCC | ATG | GCC | CAG | TTC | AAG | GAG | CAG | TTC | CTG |     | 386  |
| Asn | Thr | Ile | Asn | Ser | Asp | Ala | Met | Ala | Gln | Phe | Lys | Glu | Gln | Phe | Leu |     |      |
|     |     |     |     | 525 |     |     |     |     | 530 |     |     |     |     | 535 |     |     |      |
| GAC | CGC | GAC | ATC | AAG | TTC | GAC | AGC | TAC | CTG | GAC | ACC | CAC | CTG | ACC | GCC |     | 434  |
| Asp | Arg | Asp | Ile | Lys | Phe | Asp | Ser | Tyr | Leu | Asp | Thr | His | Leu | Thr | Ala |     |      |
|     |     |     | 540 |     |     |     | 545 |     |     |     | 550 |     |     |     |     |     |      |
| CAG | CAG | GTG | AGC | AGC | AAG | GAG | CGC | GTG | ATC | CTG | AAG | GTG | ACC | GTC | CCC |     | 482  |
| Gln | Gln | Val | Ser | Ser | Lys | Glu | Arg | Val | Ile | Leu | Lys | Val | Thr | Val | Pro |     |      |
|     |     | 555 |     |     |     | 560 |     |     |     |     | 565 |     |     |     |     |     |      |
| AGC | GGC | AAG | GGC | AGC | ACC | ACC | CCC | ACC | AAG | GCC | GGC | GTG | ATC | CTG | AAC |     | 530  |
| Ser | Gly | Lys | Gly | Ser | Thr | Thr | Pro | Thr | Lys | Ala | Gly | Val | Ile | Leu | Asn |     |      |
|     | 570 |     |     |     |     | 575 |     |     |     |     | 580 |     |     |     |     |     |      |
| AAC | AGC | GAG | TAC | AAG | ATG | CTG | ATC | GAC | AAC | GGC | TAC | ATG | GTG | CAC | GTG |     | 578  |
| Asn | Ser | Glu | Tyr | Lys | Met | Leu | Ile | Asp | Asn | Gly | Tyr | Met | Val | His | Val |     |      |
| 585 |     |     |     |     | 590 |     |     |     | 595 |     |     |     |     | 600 |     |     |      |
| GAC | AAG | GTG | AGC | AAG | GTG | GTG | AAG | AAG | GGC | GTG | GAG | TGC | CTC | CAG | ATC |     | 626  |
| Asp | Lys | Val | Ser | Lys | Val | Val | Lys | Lys | Gly | Val | Glu | Cys | Leu | Gln | Ile |     |      |
|     |     |     |     | 605 |     |     |     | 610 |     |     |     |     | 615 |     |     |     |      |
| GAG | GGC | ACC | CTG | AAG | AAG | AGT | CTA | GAC | TTC | AAG | AAC | GAC | ATC | AAC | GCC |     | 674  |
| Glu | Gly | Thr | Leu | Lys | Lys | Ser | Leu | Asp | Phe | Lys | Asn | Asp | Ile | Asn | Ala |     |      |
|     |     |     | 620 |     |     |     |     | 625 |     |     |     | 630 |     |     |     |     |      |
| GAG | GCC | CAC | AGC | TGG | GGC | ATG | AAG | AAC | TAC | GAG | GAG | TGG | GCC | AAG | GAC |     | 722  |
| Glu | Ala | His | Ser | Trp | Gly | Met | Lys | Asn | Tyr | Glu | Glu | Trp | Ala | Lys | Asp |     |      |
|     |     | 635 |     |     |     | 640 |     |     |     |     | 645 |     |     |     |     |     |      |
| CTG | ACC | GAC | AGC | CAG | CGC | GAG | GCC | CTG | GAC | GGC | TAC | GCC | CGC | CAG | GAC |     | 770  |
| Leu | Thr | Asp | Ser | Gln | Arg | Glu | Ala | Leu | Asp | Gly | Tyr | Ala | Arg | Gln | Asp |     |      |
|     | 650 |     |     |     | 655 |     |     |     |     | 660 |     |     |     |     |     |     |      |
| TAC | AAG | GAG | ATC | AAC | AAC | TAC | CTG | CGC | AAC | CAG | GGC | GGC | AGC | GGC | AAC |     | 818  |
| Tyr | Lys | Glu | Ile | Asn | Asn | Tyr | Leu | Arg | Asn | Gln | Gly | Gly | Ser | Gly | Asn |     |      |
| 665 |     |     |     |     | 670 |     |     |     | 675 |     |     |     |     | 680 |     |     |      |
| GAG | AAG | CTG | GAC | GCC | CAG | ATC | AAG | AAC | ATC | AGC | GAC | GCC | CTG | GGC | AAG |     | 866  |
| Glu | Lys | Leu | Asp | Ala | Gln | Ile | Lys | Asn | Ile | Ser | Asp | Ala | Leu | Gly | Lys |     |      |
|     |     |     |     | 685 |     |     |     |     | 690 |     |     |     |     | 695 |     |     |      |
| AAG | CCC | ATC | CCC | GAG | AAC | ATC | ACC | GTG | TAC | CGC | TGG | TGC | GGC | ATG | CCC |     | 914  |
| Lys | Pro | Ile | Pro | Glu | Asn | Ile | Thr | Val | Tyr | Arg | Trp | Cys | Gly | Met | Pro |     |      |
|     |     |     | 700 |     |     |     |     | 705 |     |     |     |     | 710 |     |     |     |      |
| GAG | TTC | GGC | TAC | CAG | ATC | AGC | GAC | CCC | CTG | CCC | AGC | CTG | AAG | GAC | TTC |     | 962  |
| Glu | Phe | Gly | Tyr | Gln | Ile | Ser | Asp | Pro | Leu | Pro | Ser | Leu | Lys | Asp | Phe |     |      |
|     |     |     | 715 |     |     |     |     | 720 |     |     |     | 725 |     |     |     |     |      |
| GAG | GAG | CAG | TTC | CTG | AAC | ACC | ATC | AAG | GAG | GAC | AAG | GGC | TAC | ATG | AGC |     | 1010 |
| Glu | Glu | Gln | Phe | Leu | Asn | Thr | Ile | Lys | Glu | Asp | Lys | Gly | Tyr | Met | Ser |     |      |
|     | 730 |     |     |     |     | 735 |     |     |     |     | 740 |     |     |     |     |     |      |
| ACC | AGC | CTG | AGC | AGC | GAG | CGC | CTG | GCC | GCC | TTC | GGC | AGC | CGC | AAG | ATC |     | 1058 |
| Thr | Ser | Leu | Ser | Ser | Glu | Arg | Leu | Ala | Ala | Phe | Gly | Ser | Arg | Lys | Ile |     |      |
| 745 |     |     |     |     | 750 |     |     |     | 755 |     |     |     |     | 760 |     |     |      |
| ATC | CTG | CGC | CTG | CAG | GTG | CCC | AAG | GGC | AGC | ACT | GGT | GCC | TAC | CTG | AGC |     | 1106 |
| Ile | Leu | Arg | Leu | Gln | Val | Pro | Lys | Gly | Ser | Thr | Gly | Ala | Tyr | Leu | Ser |     |      |

|   |   |   |   |   | 765 |   |   |   |   | 770 |   |   |   |   | 775 |   |   |      |
|---|---|---|---|---|-----|---|---|---|---|-----|---|---|---|---|-----|---|---|------|
| GCC | ATC | GGC | GGC | TTC | GCC | AGC | GAG | AAG | GAG | ATC | CTG | CTG | GAT | AAG | GAC | | | 1154 |
| Ala | Ile | Gly | Gly<br>780 | Phe | Ala | Ser | Glu | Lys<br>785 | Glu | Ile | Leu | Leu | Asp<br>790 | Lys | Asp | | | |
| AGC | AAG | TAC | CAC | ATC | GAC | AAG | GTG | ACC | GAG | GTG | ATC | ATC | AAG | GGC | GTG | | | 1202 |
| Ser | Lys | Tyr<br>795 | His | Ile | Asp | Lys | Val<br>800 | Thr | Glu | Val | Ile | Ile<br>805 | Lys | Gly | Val | | | |
| AAG | CGC | TAC | GTG | GTG | GAC | GCC | ACC | CTG | CTG | ACC | AAC | TAG | | | | | | 1241 |
| Lys | Arg<br>810 | Tyr | Val | Val | Asp | Ala<br>815 | Thr | Leu | Leu | Thr | Asn<br>820 | | | | | | | |

( 2 ) INFORMATION FOR SEQ ID NO:43:

( i ) SEQUENCE CHARACTERISTICS:
        ( A ) LENGTH: 410 amino acids
        ( B ) TYPE: amino acid
        ( D ) TOPOLOGY: linear ( i i ) MOLECULE TYPE: protein ( x i ) SEQUENCE DESCRIPTION: SEQ ID NO:43:

| Met<br>1 | Leu | Gln | Asn | Leu<br>5 | Lys | Ile | Thr | Asp | Lys<br>10 | Val | Glu | Asp | Phe | Lys<br>15 | Glu |
|---|---|---|---|---|---|---|---|---|---|---|---|---|---|---|---|
| Asp | Lys | Glu | Lys<br>20 | Ala | Lys | Glu | Trp | Gly<br>25 | Lys | Glu | Lys | Glu | Lys<br>30 | Glu | Trp |
| Lys | Leu | Thr<br>35 | Ala | Thr | Glu | Lys | Gly<br>40 | Lys | Met | Asn | Asn | Phe<br>45 | Leu | Asp | Asn |
| Lys | Asn<br>50 | Asp | Ile | Lys | Thr | Asn<br>55 | Tyr | Lys | Glu | Ile | Thr<br>60 | Phe | Ser | Ile | Ala |
| Gly<br>65 | Ser | Phe | Glu | Asp | Glu<br>70 | Ile | Lys | Asp | Leu | Lys<br>75 | Glu | Ile | Asp | Lys | Met<br>80 |
| Phe | Asp | Lys | Thr | Asn<br>85 | Leu | Ser | Asn | Ser | Ile<br>90 | Ile | Thr | Tyr | Lys | Asn<br>95 | Val |
| Glu | Pro | Thr | Thr<br>100 | Ile | Gly | Phe | Asn | Lys<br>105 | Ser | Leu | Thr | Glu | Gly<br>110 | Asn | Thr |
| Ile | Asn | Ser<br>115 | Asp | Ala | Met | Ala | Gln<br>120 | Phe | Lys | Glu | Gln | Phe<br>125 | Leu | Asp | Arg |
| Asp | Ile<br>130 | Lys | Phe | Asp | Ser | Tyr<br>135 | Leu | Asp | Thr | His | Leu<br>140 | Thr | Ala | Gln | Gln |
| Val<br>145 | Ser | Ser | Lys | Glu | Arg<br>150 | Val | Ile | Leu | Lys | Val<br>155 | Thr | Val | Pro | Ser | Gly<br>160 |
| Lys | Gly | Ser | Thr | Thr<br>165 | Pro | Thr | Lys | Ala | Gly<br>170 | Val | Ile | Leu | Asn | Asn<br>175 | Ser |
| Glu | Tyr | Lys | Met<br>180 | Leu | Ile | Asp | Asn | Gly<br>185 | Tyr | Met | Val | His | Val<br>190 | Asp | Lys |
| Val | Ser | Lys<br>195 | Val | Val | Lys | Lys | Gly<br>200 | Val | Glu | Cys | Leu | Gln<br>205 | Ile | Glu | Gly |
| Thr | Leu<br>210 | Lys | Lys | Ser | Leu | Asp<br>215 | Phe | Lys | Asn | Asp | Ile<br>220 | Asn | Ala | Glu | Ala |
| His<br>225 | Ser | Trp | Gly | Met | Lys<br>230 | Asn | Tyr | Glu | Glu | Trp<br>235 | Ala | Lys | Asp | Leu | Thr<br>240 |
| Asp | Ser | Gln | Arg | Glu<br>245 | Ala | Leu | Asp | Gly | Tyr<br>250 | Ala | Arg | Gln | Asp | Tyr<br>255 | Lys |
| Glu | Ile | Asn | Asn<br>260 | Tyr | Leu | Arg | Asn | Gln<br>265 | Gly | Gly | Ser | Gly | Asn<br>270 | Glu | Lys |
| Leu | Asp | Ala<br>275 | Gln | Ile | Lys | Asn | Ile<br>280 | Ser | Asp | Ala | Leu | Gly<br>285 | Lys | Lys | Pro |

| Ile | Pro | Glu | Asn | Ile | Thr | Val | Tyr | Arg | Trp | Cys | Gly | Met | Pro | Glu | Phe |
| | 290 | | | | 295 | | | | | 300 | | | | | |

| Gly | Tyr | Gln | Ile | Ser | Asp | Pro | Leu | Pro | Ser | Leu | Lys | Asp | Phe | Glu | Glu |
| 305 | | | | | 310 | | | | | 315 | | | | | 320 |

| Gln | Phe | Leu | Asn | Thr | Ile | Lys | Glu | Asp | Lys | Gly | Tyr | Met | Ser | Thr | Ser |
| | | | | 325 | | | | | 330 | | | | | 335 | |

| Leu | Ser | Ser | Glu | Arg | Leu | Ala | Ala | Phe | Gly | Ser | Arg | Lys | Ile | Ile | Leu |
| | | | | 340 | | | | | 345 | | | | | 350 | |

| Arg | Leu | Gln | Val | Pro | Lys | Gly | Ser | Thr | Gly | Ala | Tyr | Leu | Ser | Ala | Ile |
| | | 355 | | | | | 360 | | | | | 365 | | | |

| Gly | Gly | Phe | Ala | Ser | Glu | Lys | Glu | Ile | Leu | Leu | Asp | Lys | Asp | Ser | Lys |
| | 370 | | | | | 375 | | | | | 380 | | | | |

| Tyr | His | Ile | Asp | Lys | Val | Thr | Glu | Val | Ile | Ile | Lys | Gly | Val | Lys | Arg |
| 385 | | | | | 390 | | | | | 395 | | | | | 400 |

| Tyr | Val | Val | Asp | Ala | Thr | Leu | Leu | Thr | Asn |
| | | | | 405 | | | | | 410 |

( 2 ) INFORMATION FOR SEQ ID NO:44:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide encoding
            vacuolar targetting peptide used to construct pCIB5533"

( i i i ) HYPOTHETICAL: NO ( x i ) SEQUENCE DESCRIPTION: SEQ ID NO:44:

```
CCGCGGGCGT GCACTGCCTC AGCAGCAGCA GCTTCGCCGA CAGCAACCCC ATCCGCGTGA        60
CCGACCGCGC CGCCAGCACC CTGCAG                                            86
```

( 2 ) INFORMATION FOR SEQ ID NO:45:

( i ) SEQUENCE CHARACTERISTICS:
        ( A ) LENGTH: 1358 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i x ) FEATURE:
        ( A ) NAME/KEY: CDS
        ( B ) LOCATION: 9..1355
        ( D ) OTHER INFORMATION: /note= "Maize optimized VIP2A(a)
            with the Bacillus secretion signal removed and the
            vacuolar targetting signal inserted as contained in
            pCIB5533"

( x i ) SEQUENCE DESCRIPTION: SEQ ID NO:45:

| GATCCACC | ATG | GGC | TGG | AGC | TGG | ATC | TTC | CTG | TTC | CTG | CTG | AGC | GGC | GCC | 50 |
| | Met | Gly | Trp | Ser | Trp | Ile | Phe | Leu | Phe | Leu | Leu | Ser | Gly | Ala | |
| | | | | | 415 | | | | | 420 | | | | | |

| GCG | GGC | GTG | CAC | TGC | CTC | AGC | AGC | AGC | AGC | TTC | GCC | GAC | AGC | AAC | CCC | 98 |
| Ala | Gly | Val | His | Cys | Leu | Ser | Ser | Ser | Ser | Phe | Ala | Asp | Ser | Asn | Pro | |
| 425 | | | | | 430 | | | | | 435 | | | | | 440 | |

| ATC | CGC | GTG | ACC | GAC | CGC | GCC | GCC | AGC | ACC | CTG | CAG | AAC | CTG | AAG | ATC | 146 |
| Ile | Arg | Val | Thr | Asp | Arg | Ala | Ala | Ser | Thr | Leu | Gln | Asn | Leu | Lys | Ile | |
| | | | | 445 | | | | | 450 | | | | | 455 | | |

| | | | | | | | | | | | | | | | | |
|---|---|---|---|---|---|---|---|---|---|---|---|---|---|---|---|---|
| ACC | GAC | AAG | GTG | GAG | GAC | TTC | AAG | GAG | GAC | AAG | GAG | AAG | GCC | AAG | GAG | 194 |
| Thr | Asp | Lys | Val | Glu | Asp | Phe | Lys | Glu | Asp | Lys | Glu | Lys | Ala | Lys | Glu | |
| | | | 460 | | | | 465 | | | | | 470 | | | | |
| TGG | GGC | AAG | GAG | AAG | GAG | AAG | GAG | TGG | AAG | CTT | ACC | GCC | ACC | GAG | AAG | 242 |
| Trp | Gly | Lys | Glu | Lys | Glu | Lys | Glu | Trp | Lys | Leu | Thr | Ala | Thr | Glu | Lys | |
| | | 475 | | | | | 480 | | | | | 485 | | | | |
| GGC | AAG | ATG | AAC | AAC | TTC | CTG | GAC | AAC | AAG | AAC | GAC | ATC | AAG | ACC | AAC | 290 |
| Gly | Lys | Met | Asn | Asn | Phe | Leu | Asp | Asn | Lys | Asn | Asp | Ile | Lys | Thr | Asn | |
| | 490 | | | | | 495 | | | | | 500 | | | | | |
| TAC | AAG | GAG | ATC | ACC | TTC | AGC | ATA | GCC | GGC | AGC | TTC | GAG | GAC | GAG | ATC | 338 |
| Tyr | Lys | Glu | Ile | Thr | Phe | Ser | Ile | Ala | Gly | Ser | Phe | Glu | Asp | Glu | Ile | |
| 505 | | | | | 510 | | | | | 515 | | | | | 520 | |
| AAG | GAC | CTG | AAG | GAG | ATC | GAC | AAG | ATG | TTC | GAC | AAG | ACC | AAC | CTG | AGC | 386 |
| Lys | Asp | Leu | Lys | Glu | Ile | Asp | Lys | Met | Phe | Asp | Lys | Thr | Asn | Leu | Ser | |
| | | | | 525 | | | | | 530 | | | | | 535 | | |
| AAC | AGC | ATC | ATC | ACC | TAC | AAG | AAC | GTG | GAG | CCC | ACC | ACC | ATC | GGC | TTC | 434 |
| Asn | Ser | Ile | Ile | Thr | Tyr | Lys | Asn | Val | Glu | Pro | Thr | Thr | Ile | Gly | Phe | |
| | | | 540 | | | | | 545 | | | | | 550 | | | |
| AAC | AAG | AGC | CTG | ACC | GAG | GGC | AAC | ACC | ATC | AAC | AGC | GAC | GCC | ATG | GCC | 482 |
| Asn | Lys | Ser | Leu | Thr | Glu | Gly | Asn | Thr | Ile | Asn | Ser | Asp | Ala | Met | Ala | |
| | | 555 | | | | | 560 | | | | | 565 | | | | |
| CAG | TTC | AAG | GAG | CAG | TTC | CTG | GAC | CGC | GAC | ATC | AAG | TTC | GAC | AGC | TAC | 530 |
| Gln | Phe | Lys | Glu | Gln | Phe | Leu | Asp | Arg | Asp | Ile | Lys | Phe | Asp | Ser | Tyr | |
| | 570 | | | | | 575 | | | | | 580 | | | | | |
| CTG | GAC | ACC | CAC | CTG | ACC | GCC | CAG | CAG | GTG | AGC | AGC | AAG | GAG | CGC | GTG | 578 |
| Leu | Asp | Thr | His | Leu | Thr | Ala | Gln | Gln | Val | Ser | Ser | Lys | Glu | Arg | Val | |
| 585 | | | | | 590 | | | | | 595 | | | | | 600 | |
| ATC | CTG | AAG | GTG | ACC | GTC | CCC | AGC | GGC | AAG | GGC | AGC | ACC | ACC | CCC | ACC | 626 |
| Ile | Leu | Lys | Val | Thr | Val | Pro | Ser | Gly | Lys | Gly | Ser | Thr | Thr | Pro | Thr | |
| | | | | 605 | | | | | 610 | | | | | 615 | | |
| AAG | GCC | GGC | GTG | ATC | CTG | AAC | AAC | AGC | GAG | TAC | AAG | ATG | CTG | ATC | GAC | 674 |
| Lys | Ala | Gly | Val | Ile | Leu | Asn | Asn | Ser | Glu | Tyr | Lys | Met | Leu | Ile | Asp | |
| | | | 620 | | | | | 625 | | | | | 630 | | | |
| AAC | GGC | TAC | ATG | GTG | CAC | GTG | GAC | AAG | GTG | AGC | AAG | GTG | GTG | AAG | AAG | 722 |
| Asn | Gly | Tyr | Met | Val | His | Val | Asp | Lys | Val | Ser | Lys | Val | Val | Lys | Lys | |
| | | 635 | | | | | 640 | | | | | 645 | | | | |
| GGC | GTG | GAG | TGC | CTC | CAG | ATC | GAG | GGC | ACC | CTG | AAG | AAG | AGT | CTA | GAC | 770 |
| Gly | Val | Glu | Cys | Leu | Gln | Ile | Glu | Gly | Thr | Leu | Lys | Lys | Ser | Leu | Asp | |
| | 650 | | | | | 655 | | | | | 660 | | | | | |
| TTC | AAG | AAC | GAC | ATC | AAC | GCC | GAG | GCC | CAC | AGC | TGG | GGC | ATG | AAG | AAC | 818 |
| Phe | Lys | Asn | Asp | Ile | Asn | Ala | Glu | Ala | His | Ser | Trp | Gly | Met | Lys | Asn | |
| 665 | | | | | 670 | | | | | 675 | | | | | 680 | |
| TAC | GAG | GAG | TGG | GCC | AAG | GAC | CTG | ACC | GAC | AGC | CAG | CGC | GAG | GCC | CTG | 866 |
| Tyr | Glu | Glu | Trp | Ala | Lys | Asp | Leu | Thr | Asp | Ser | Gln | Arg | Glu | Ala | Leu | |
| | | | | 685 | | | | | 690 | | | | | 695 | | |
| GAC | GGC | TAC | GCC | CGC | CAG | GAC | TAC | AAG | GAG | ATC | AAC | AAC | TAC | CTG | CGC | 914 |
| Asp | Gly | Tyr | Ala | Arg | Gln | Asp | Tyr | Lys | Glu | Ile | Asn | Asn | Tyr | Leu | Arg | |
| | | | 700 | | | | | 705 | | | | | 710 | | | |
| AAC | CAG | GGC | GGC | AGC | GGC | AAC | GAG | AAG | CTG | GAC | GCC | CAG | ATC | AAG | AAC | 962 |
| Asn | Gln | Gly | Gly | Ser | Gly | Asn | Glu | Lys | Leu | Asp | Ala | Gln | Ile | Lys | Asn | |
| | | 715 | | | | | 720 | | | | | 725 | | | | |
| ATC | AGC | GAC | GCC | CTG | GGC | AAG | AAG | CCC | ATC | CCC | GAG | AAC | ATC | ACC | GTG | 1010 |
| Ile | Ser | Asp | Ala | Leu | Gly | Lys | Lys | Pro | Ile | Pro | Glu | Asn | Ile | Thr | Val | |
| | 730 | | | | | 735 | | | | | 740 | | | | | |
| TAC | CGC | TGG | TGC | GGC | ATG | CCC | GAG | TTC | GGC | TAC | CAG | ATC | AGC | GAC | CCC | 1058 |
| Tyr | Arg | Trp | Cys | Gly | Met | Pro | Glu | Phe | Gly | Tyr | Gln | Ile | Ser | Asp | Pro | |
| 745 | | | | | 750 | | | | | 755 | | | | | 760 | |
| CTG | CCC | AGC | CTG | AAG | GAC | TTC | GAG | GAG | CAG | TTC | CTG | AAC | ACC | ATC | AAG | 1106 |
| Leu | Pro | Ser | Leu | Lys | Asp | Phe | Glu | Glu | Gln | Phe | Leu | Asn | Thr | Ile | Lys | |
| | | | | 765 | | | | | 770 | | | | | 775 | | |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| GAG | GAC | AAG | GGC | TAC | ATG | AGC | ACC | AGC | CTG | AGC | AGC | GAG | CGC | CTG | GCC | 1154 |
| Glu | Asp | Lys | Gly | Tyr | Met | Ser | Thr | Ser | Leu | Ser | Ser | Glu | Arg | Leu | Ala |      |
|     |     |     | 780 |     |     |     | 785 |     |     |     |     | 790 |     |     |     |      |
| GCC | TTC | GGC | AGC | CGC | AAG | ATC | ATC | CTG | CGC | CTG | CAG | GTG | CCC | AAG | GGC | 1202 |
| Ala | Phe | Gly | Ser | Arg | Lys | Ile | Ile | Leu | Arg | Leu | Gln | Val | Pro | Lys | Gly |      |
|     |     | 795 |     |     |     |     | 800 |     |     |     |     | 805 |     |     |     |      |
| AGC | ACT | GGT | GCC | TAC | CTG | AGC | GCC | ATC | GGC | GGC | TTC | GCC | AGC | GAG | AAG | 1250 |
| Ser | Thr | Gly | Ala | Tyr | Leu | Ser | Ala | Ile | Gly | Gly | Phe | Ala | Ser | Glu | Lys |      |
|     |     | 810 |     |     |     |     | 815 |     |     |     |     | 820 |     |     |     |      |
| GAG | ATC | CTG | CTG | GAT | AAG | GAC | AGC | AAG | TAC | CAC | ATC | GAC | AAG | GTG | ACC | 1298 |
| Glu | Ile | Leu | Leu | Asp | Lys | Asp | Ser | Lys | Tyr | His | Ile | Asp | Lys | Val | Thr |      |
| 825 |     |     |     |     | 830 |     |     |     |     | 835 |     |     |     |     | 840 |      |
| GAG | GTG | ATC | ATC | AAG | GGC | GTG | AAG | CGC | TAC | GTG | GTG | GAC | GCC | ACC | CTG | 1346 |
| Glu | Val | Ile | Ile | Lys | Gly | Val | Lys | Arg | Tyr | Val | Val | Asp | Ala | Thr | Leu |      |
|     |     |     |     | 845 |     |     |     |     | 850 |     |     |     |     | 855 |     |      |
| CTG | ACC | AAC | TAG |     |     |     |     |     |     |     |     |     |     |     |     | 1358 |
| Leu | Thr | Asn |     |     |     |     |     |     |     |     |     |     |     |     |     |      |

( 2 ) INFORMATION FOR SEQ ID NO:46:

( i ) SEQUENCE CHARACTERISTICS:
        ( A ) LENGTH: 449 amino acids
        ( B ) TYPE: amino acid
        ( D ) TOPOLOGY: linear ( i i ) MOLECULE TYPE: protein ( x i ) SEQUENCE DESCRIPTION: SEQ ID NO:46:

|     |     |     |     |     |     |     |     |     |     |     |     |     |     |     |     |
| --- | --- | --- | --- | --- | --- | --- | --- | --- | --- | --- | --- | --- | --- | --- | --- |
| Met | Gly | Trp | Ser | Trp | Ile | Phe | Leu | Phe | Leu | Leu | Ser | Gly | Ala | Ala | Gly |
| 1   |     |     |     | 5   |     |     |     |     | 10  |     |     |     |     | 15  |     |
| Val | His | Cys | Leu | Ser | Ser | Ser | Ser | Phe | Ala | Asp | Ser | Asn | Pro | Ile | Arg |
|     |     |     | 20  |     |     |     |     | 25  |     |     |     |     | 30  |     |     |
| Val | Thr | Asp | Arg | Ala | Ala | Ser | Thr | Leu | Gln | Asn | Leu | Lys | Ile | Thr | Asp |
|     |     | 35  |     |     |     |     | 40  |     |     |     |     | 45  |     |     |     |
| Lys | Val | Glu | Asp | Phe | Lys | Glu | Asp | Lys | Glu | Lys | Ala | Lys | Glu | Trp | Gly |
|     | 50  |     |     |     |     | 55  |     |     |     |     | 60  |     |     |     |     |
| Lys | Glu | Lys | Glu | Lys | Glu | Trp | Lys | Leu | Thr | Ala | Thr | Glu | Lys | Gly | Lys |
| 65  |     |     |     |     | 70  |     |     |     |     | 75  |     |     |     |     | 80  |
| Met | Asn | Asn | Phe | Leu | Asp | Asn | Lys | Asn | Asp | Ile | Lys | Thr | Asn | Tyr | Lys |
|     |     |     |     | 85  |     |     |     |     | 90  |     |     |     |     | 95  |     |
| Glu | Ile | Thr | Phe | Ser | Ile | Ala | Gly | Ser | Phe | Glu | Asp | Glu | Ile | Lys | Asp |
|     |     |     | 100 |     |     |     |     | 105 |     |     |     |     | 110 |     |     |
| Leu | Lys | Glu | Ile | Asp | Lys | Met | Phe | Asp | Lys | Thr | Asn | Leu | Ser | Asn | Ser |
|     |     | 115 |     |     |     |     | 120 |     |     |     |     | 125 |     |     |     |
| Ile | Ile | Thr | Tyr | Lys | Asn | Val | Glu | Pro | Thr | Thr | Ile | Gly | Phe | Asn | Lys |
|     | 130 |     |     |     |     | 135 |     |     |     |     | 140 |     |     |     |     |
| Ser | Leu | Thr | Glu | Gly | Asn | Thr | Ile | Asn | Ser | Asp | Ala | Met | Ala | Gln | Phe |
| 145 |     |     |     |     | 150 |     |     |     |     | 155 |     |     |     |     | 160 |
| Lys | Glu | Gln | Phe | Leu | Asp | Arg | Asp | Ile | Lys | Phe | Asp | Ser | Tyr | Leu | Asp |
|     |     |     |     | 165 |     |     |     |     | 170 |     |     |     |     | 175 |     |
| Thr | His | Leu | Thr | Ala | Gln | Gln | Val | Ser | Ser | Lys | Glu | Arg | Val | Ile | Leu |
|     |     |     | 180 |     |     |     |     | 185 |     |     |     |     | 190 |     |     |
| Lys | Val | Thr | Val | Pro | Ser | Gly | Lys | Gly | Ser | Thr | Thr | Pro | Thr | Lys | Ala |
|     |     | 195 |     |     |     |     | 200 |     |     |     |     | 205 |     |     |     |
| Gly | Val | Ile | Leu | Asn | Asn | Ser | Glu | Tyr | Lys | Met | Leu | Ile | Asp | Asn | Gly |
|     | 210 |     |     |     |     | 215 |     |     |     |     | 220 |     |     |     |     |
| Tyr | Met | Val | His | Val | Asp | Lys | Val | Ser | Lys | Val | Val | Lys | Lys | Gly | Val |
| 225 |     |     |     |     | 230 |     |     |     |     | 235 |     |     |     |     | 240 |

| Glu | Cys | Leu | Gln | Ile<br>245 | Glu | Gly | Thr | Leu | Lys<br>250 | Lys | Ser | Leu | Asp | Phe<br>255 | Lys |

| Asn | Asp | Ile | Asn<br>260 | Ala | Glu | Ala | His | Ser<br>265 | Trp | Gly | Met | Lys | Asn<br>270 | Tyr | Glu |

| Glu | Trp | Ala<br>275 | Lys | Asp | Leu | Thr | Asp<br>280 | Ser | Gln | Arg | Glu | Ala<br>285 | Leu | Asp | Gly |

| Tyr | Ala<br>290 | Arg | Gln | Asp | Tyr | Lys<br>295 | Glu | Ile | Asn | Asn | Tyr<br>300 | Leu | Arg | Asn | Gln |

| Gly<br>305 | Gly | Ser | Gly | Asn | Glu<br>310 | Lys | Leu | Asp | Ala | Gln<br>315 | Ile | Lys | Asn | Ile | Ser<br>320 |

| Asp | Ala | Leu | Gly | Lys<br>325 | Lys | Pro | Ile | Pro | Glu<br>330 | Asn | Ile | Thr | Val | Tyr<br>335 | Arg |

| Trp | Cys | Gly | Met<br>340 | Pro | Glu | Phe | Gly | Tyr<br>345 | Gln | Ile | Ser | Asp | Pro<br>350 | Leu | Pro |

| Ser | Leu | Lys<br>355 | Asp | Phe | Glu | Glu | Gln<br>360 | Phe | Leu | Asn | Thr | Ile<br>365 | Lys | Glu | Asp |

| Lys | Gly<br>370 | Tyr | Met | Ser | Thr | Ser<br>375 | Leu | Ser | Ser | Glu | Arg<br>380 | Leu | Ala | Ala | Phe |

| Gly<br>385 | Ser | Arg | Lys | Ile | Ile<br>390 | Leu | Arg | Leu | Gln | Val<br>395 | Pro | Lys | Gly | Ser | Thr<br>400 |

| Gly | Ala | Tyr | Leu | Ser<br>405 | Ala | Ile | Gly | Gly | Phe<br>410 | Ala | Ser | Glu | Lys | Glu<br>415 | Ile |

| Leu | Leu | Asp | Lys<br>420 | Asp | Ser | Lys | Tyr | His<br>425 | Ile | Asp | Lys | Val | Thr<br>430 | Glu | Val |

| Ile | Ile | Lys<br>435 | Gly | Val | Lys | Arg | Tyr<br>440 | Val | Val | Asp | Ala | Thr<br>445 | Leu | Leu | Thr |

Asn ( 2 ) INFORMATION FOR SEQ ID NO:47:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i x ) FEATURE:
        ( A ) NAME/KEY: Peptide
        ( B ) LOCATION: 1..16
        ( D ) OTHER INFORMATION: /note= "linker peptide for fusion
            of VIP1A(a) and VIP2A(a) used to construct pCIB5533"

( x i ) SEQUENCE DESCRIPTION: SEQ ID NO:47:

|

( x i ) SEQUENCE DESCRIPTION: SEQ ID NO:48:

```
CCCGGGCCTT CTACTCCCCC AACTCCCTCT CCTAGCACGC CTCCGACACC TAGCGATATC        60

GGATCC                                                                   66
```

( 2 ) INFORMATION FOR SEQ ID NO:49:

( i ) SEQUENCE CHARACTERISTICS:
        ( A ) LENGTH: 4031 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i x ) FEATURE:
        ( A ) NAME/KEY: CDS
        ( B ) LOCATION: 6..4019
        ( D ) OTHER INFORMATION: /note= "Maize optimized DNA
            sequence encoding a VIP2A(a) - VIP1A(a) fusion protein as
            contained in pCIB5531"

( x i ) SEQUENCE DESCRIPTION: SEQ ID NO:49:

```
GATCC ATG AAG CGC ATG GAG GGC AAG CTG TTC ATG GTG AGC AAG AAG      47
      Met Lys Arg Met Glu Gly Lys Leu Phe Met Val Ser Lys Lys
      450                 455                 460

CTC CAG GTG GTG ACC AAG ACC GTG CTG CTG AGC ACC GTG TTC AGC ATC    95
Leu Gln Val Val Thr Lys Thr Val Leu Leu Ser Thr Val Phe Ser Ile
    465                 470                 475

AGC CTG CTG AAC AAC GAG GTG ATC AAG GCC GAG CAG CTG AAC ATC AAC   143
Ser Leu Leu Asn Asn Glu Val Ile Lys Ala Glu Gln Leu Asn Ile Asn
480                 485                 490                 495

AGC CAG AGC AAG TAC ACC AAC CTC CAG AAC CTG AAG ATC ACC GAC AAG   191
Ser Gln Ser Lys Tyr Thr Asn Leu Gln Asn Leu Lys Ile Thr Asp Lys
                500                 505                 510

GTG GAG GAC TTC AAG GAG GAC AAG GAG AAG GCC AAG GAG TGG GGC AAG   239
Val Glu Asp Phe Lys Glu Asp Lys Glu Lys Ala Lys Glu Trp Gly Lys
            515                 520                 525

GAG AAG GAG AAG GAG TGG AAG CTT ACC GCC ACC GAG AAG GGC AAG ATG   287
Glu Lys Glu Lys Glu Trp Lys Leu Thr Ala Thr Glu Lys Gly Lys Met
        530                 535                 540

AAC AAC TTC CTG GAC AAC AAG AAC GAC ATC AAG ACC AAC TAC AAG GAG   335
Asn Asn Phe Leu Asp Asn Lys Asn Asp Ile Lys Thr Asn Tyr Lys Glu
    545                 550                 555

ATC ACC TTC AGC ATA GCC GGC AGC TTC GAG GAC GAG ATC AAG GAC CTG   383
Ile Thr Phe Ser Ile Ala Gly Ser Phe Glu Asp Glu Ile Lys Asp Leu
560                 565                 570                 575

AAG GAG ATC GAC AAG ATG TTC GAC AAG ACC AAC CTG AGC AAC AGC ATC   431
Lys Glu Ile Asp Lys Met Phe Asp Lys Thr Asn Leu Ser Asn Ser Ile
                580                 585                 590

ATC ACC TAC AAG AAC GTG GAG CCC ACC ACC ATC GGC TTC AAC AAG AGC   479
Ile Thr Tyr Lys Asn Val Glu Pro Thr Thr Ile Gly Phe Asn Lys Ser
            595                 600                 605

CTG ACC GAG GGC AAC ACC ATC AAC AGC GAC GCC ATG GCC CAG TTC AAG   527
Leu Thr Glu Gly Asn Thr Ile Asn Ser Asp Ala Met Ala Gln Phe Lys
        610                 615                 620

GAG CAG TTC CTG GAC CGC GAC ATC AAG TTC GAC AGC TAC CTG GAC ACC   575
Glu Gln Phe Leu Asp Arg Asp Ile Lys Phe Asp Ser Tyr Leu Asp Thr
    625                 630                 635

CAC CTG ACC GCC CAG CAG GTG AGC AGC AAG GAG CGC GTG ATC CTG AAG   623
His Leu Thr Ala Gln Gln Val Ser Ser Lys Glu Arg Val Ile Leu Lys
```

```
640                         645                         650                              655
GTG  ACC  GTC  CCC  AGC  GGC  AAG  GGC  AGC  ACC  ACC  CCC  ACC  AAG  GCC  GGC        671
Val  Thr  Val  Pro  Ser  Gly  Lys  Gly  Ser  Thr  Thr  Pro  Thr  Lys  Ala  Gly
               660                         665                              670

GTG  ATC  CTG  AAC  AAC  AGC  GAG  TAC  AAG  ATG  CTG  ATC  GAC  AAC  GGC  TAC        719
Val  Ile  Leu  Asn  Asn  Ser  Glu  Tyr  Lys  Met  Leu  Ile  Asp  Asn  Gly  Tyr
               675                         680                         685

ATG  GTG  CAC  GTG  GAC  AAG  GTG  AGC  AAG  GTG  GTG  AAG  AAG  GGC  GTG  GAG        767
Met  Val  His  Val  Asp  Lys  Val  Ser  Lys  Val  Val  Lys  Lys  Gly  Val  Glu
               690                         695                         700

TGC  CTC  CAG  ATC  GAG  GGC  ACC  CTG  AAG  AAG  AGT  CTA  GAC  TTC  AAG  AAC        815
Cys  Leu  Gln  Ile  Glu  Gly  Thr  Leu  Lys  Lys  Ser  Leu  Asp  Phe  Lys  Asn
     705                         710                         715

GAC  ATC  AAC  GCC  GAG  GCC  CAC  AGC  TGG  GGC  ATG  AAG  AAC  TAC  GAG  GAG        863
Asp  Ile  Asn  Ala  Glu  Ala  His  Ser  Trp  Gly  Met  Lys  Asn  Tyr  Glu  Glu
720                         725                         730                         735

TGG  GCC  AAG  GAC  CTG  ACC  GAC  AGC  CAG  CGC  GAG  GCC  CTG  GAC  GGC  TAC        911
Trp  Ala  Lys  Asp  Leu  Thr  Asp  Ser  Gln  Arg  Glu  Ala  Leu  Asp  Gly  Tyr
               740                         745                         750

GCC  CGC  CAG  GAC  TAC  AAG  GAG  ATC  AAC  AAC  TAC  CTG  CGC  AAC  CAG  GGC        959
Ala  Arg  Gln  Asp  Tyr  Lys  Glu  Ile  Asn  Asn  Tyr  Leu  Arg  Asn  Gln  Gly
               755                         760                         765

GGC  AGC  GGC  AAC  GAG  AAG  CTG  GAC  GCC  CAG  ATC  AAG  AAC  ATC  AGC  GAC       1007
Gly  Ser  Gly  Asn  Glu  Lys  Leu  Asp  Ala  Gln  Ile  Lys  Asn  Ile  Ser  Asp
               770                         775                         780

GCC  CTG  GGC  AAG  AAG  CCC  ATC  CCC  GAG  AAC  ATC  ACC  GTG  TAC  CGC  TGG       1055
Ala  Leu  Gly  Lys  Lys  Pro  Ile  Pro  Glu  Asn  Ile  Thr  Val  Tyr  Arg  Trp
               785                         790                         795

TGC  GGC  ATG  CCC  GAG  TTC  GGC  TAC  CAG  ATC  AGC  GAC  CCC  CTG  CCC  AGC       1103
Cys  Gly  Met  Pro  Glu  Phe  Gly  Tyr  Gln  Ile  Ser  Asp  Pro  Leu  Pro  Ser
800                         805                         810                         815

CTG  AAG  GAC  TTC  GAG  GAG  CAG  TTC  CTG  AAC  ACC  ATC  AAG  GAG  GAC  AAG       1151
Leu  Lys  Asp  Phe  Glu  Glu  Gln  Phe  Leu  Asn  Thr  Ile  Lys  Glu  Asp  Lys
               820                         825                         830

GGC  TAC  ATG  AGC  ACC  AGC  CTG  AGC  AGC  GAG  CGC  CTG  GCC  GCC  TTC  GGC       1199
Gly  Tyr  Met  Ser  Thr  Ser  Leu  Ser  Ser  Glu  Arg  Leu  Ala  Ala  Phe  Gly
               835                         840                         845

AGC  CGC  AAG  ATC  ATC  CTG  CGC  CTG  CAG  GTG  CCC  AAG  GGC  AGC  ACT  GGT       1247
Ser  Arg  Lys  Ile  Ile  Leu  Arg  Leu  Gln  Val  Pro  Lys  Gly  Ser  Thr  Gly
          850                         855                         860

GCC  TAC  CTG  AGC  GCC  ATC  GGC  GGC  TTC  GCC  AGC  GAG  AAG  GAG  ATC  CTG       1295
Ala  Tyr  Leu  Ser  Ala  Ile  Gly  Gly  Phe  Ala  Ser  Glu  Lys  Glu  Ile  Leu
     865                         870                         875

CTG  GAT  AAG  GAC  AGC  AAG  TAC  CAC  ATC  GAC  AAG  GTG  ACC  GAG  GTG  ATC       1343
Leu  Asp  Lys  Asp  Ser  Lys  Tyr  His  Ile  Asp  Lys  Val  Thr  Glu  Val  Ile
880                         885                         890                         895

ATC  AAG  GGC  GTG  AAG  CGC  TAC  GTG  GTG  GAC  GCC  ACC  CTG  CTG  ACC  AAC       1391
Ile  Lys  Gly  Val  Lys  Arg  Tyr  Val  Val  Asp  Ala  Thr  Leu  Leu  Thr  Asn
               900                         905                         910

TCC  CGG  GGG  CCT  TCT  ACT  CCC  CCA  ACT  CCC  TCT  CCT  AGC  ACG  CCT  CCG       1439
Ser  Arg  Gly  Pro  Ser  Thr  Pro  Pro  Thr  Pro  Ser  Pro  Ser  Thr  Pro  Pro
               915                         920                         925

ACA  CCT  AGC  GAT  ATC  GGA  TCC  ACC  ATG  AAG  ACC  AAC  CAG  ATC  AGC  ACC       1487
Thr  Pro  Ser  Asp  Ile  Gly  Ser  Thr  Met  Lys  Thr  Asn  Gln  Ile  Ser  Thr
               930                         935                         940

ACC  CAG  AAG  AAC  CAG  CAG  AAG  GAG  ATG  GAC  CGC  AAG  GGC  CTG  CTG  GGC       1535
Thr  Gln  Lys  Asn  Gln  Gln  Lys  Glu  Met  Asp  Arg  Lys  Gly  Leu  Leu  Gly
     945                         950                         955

TAC  TAC  TTC  AAG  GGC  AAG  GAC  TTC  AGC  AAC  CTG  ACC  ATG  TTC  GCC  CCC       1583
Tyr  Tyr  Phe  Lys  Gly  Lys  Asp  Phe  Ser  Asn  Leu  Thr  Met  Phe  Ala  Pro
```

-continued

```
  960                      965                      970                      975
ACG CGT GAC AGC ACC CTG ATC TAC GAC CAG CAG ACC GCC AAC AAG CTG          1631
Thr Arg Asp Ser Thr Leu Ile Tyr Asp Gln Gln Thr Ala Asn Lys Leu
                980                      985                      990

CTG GAC AAG AAG CAG CAG GAG TAC CAG AGC ATC CGC TGG ATC GGC CTG          1679
Leu Asp Lys Lys Gln Gln Glu Tyr Gln Ser Ile Arg Trp Ile Gly Leu
            995                     1000                     1005

ATC CAG AGC AAG GAG ACC GGC GAC TTC ACC TTC AAC CTG AGC GAG GAC          1727
Ile Gln Ser Lys Glu Thr Gly Asp Phe Thr Phe Asn Leu Ser Glu Asp
        1010                     1015                     1020

GAG CAG GCC ATC ATC GAG ATC AAC GGC AAG ATC ATC AGC AAC AAG GGC          1775
Glu Gln Ala Ile Ile Glu Ile Asn Gly Lys Ile Ile Ser Asn Lys Gly
    1025                     1030                     1035

AAG GAG AAG CAG GTG GTG CAC CTG GAG AAG GGC AAG CTG GTG CCC ATC          1823
Lys Glu Lys Gln Val Val His Leu Glu Lys Gly Lys Leu Val Pro Ile
1040                     1045                     1050                     1055

AAG ATC GAG TAC CAG AGC GAC ACC AAG TTC AAC ATC GAC AGC AAG ACC          1871
Lys Ile Glu Tyr Gln Ser Asp Thr Lys Phe Asn Ile Asp Ser Lys Thr
                    1060                     1065                     1070

TTC AAG GAG CTG AAG CTT TTC AAG ATC GAC AGC CAG AAC CAG CCC CAG          1919
Phe Lys Glu Leu Lys Leu Phe Lys Ile Asp Ser Gln Asn Gln Pro Gln
                1075                     1080                     1085

CAG GTG CAG CAG GAC GAG CTG CGC AAC CCC GAG TTC AAC AAG AAG GAG          1967
Gln Val Gln Gln Asp Glu Leu Arg Asn Pro Glu Phe Asn Lys Lys Glu
            1090                     1095                     1100

AGC CAG GAG TTC CTG GCC AAG CCC AGC AAG ATC AAC CTG TTC ACC CAG          2015
Ser Gln Glu Phe Leu Ala Lys Pro Ser Lys Ile Asn Leu Phe Thr Gln
        1105                     1110                     1115

CAG ATG AAG CGC GAG ATC GAC GAG GAC ACC GAC ACC GAC GGC GAC AGC          2063
Gln Met Lys Arg Glu Ile Asp Glu Asp Thr Asp Thr Asp Gly Asp Ser
1120                     1125                     1130                     1135

ATC CCC GAC CTG TGG GAG GAG AAC GGC TAC ACC ATC CAG AAC CGC ATC          2111
Ile Pro Asp Leu Trp Glu Glu Asn Gly Tyr Thr Ile Gln Asn Arg Ile
                    1140                     1145                     1150

GCC GTG AAG TGG GAC GAC AGC CTG GCT AGC AAG GGC TAC ACC AAG TTC          2159
Ala Val Lys Trp Asp Asp Ser Leu Ala Ser Lys Gly Tyr Thr Lys Phe
                1155                     1160                     1165

GTG AGC AAC CCC CTG GAG AGC CAC ACC GTG GGC GAC CCC TAC ACC GAC          2207
Val Ser Asn Pro Leu Glu Ser His Thr Val Gly Asp Pro Tyr Thr Asp
            1170                     1175                     1180

TAC GAG AAG GCC GCC CGC GAC CTG GAC CTG AGC AAC GCC AAG GAG ACC          2255
Tyr Glu Lys Ala Ala Arg Asp Leu Asp Leu Ser Asn Ala Lys Glu Thr
        1185                     1190                     1195

TTC AAC CCC CTG GTG GCC GCC TTC CCC AGC GTG AAC GTG AGC ATG GAG          2303
Phe Asn Pro Leu Val Ala Ala Phe Pro Ser Val Asn Val Ser Met Glu
1200                     1205                     1210                     1215

AAG GTG ATC CTG AGC CCC AAC GAG AAC CTG AGC AAC AGC GTG GAG AGC          2351
Lys Val Ile Leu Ser Pro Asn Glu Asn Leu Ser Asn Ser Val Glu Ser
                    1220                     1225                     1230

CAC TCG AGC ACC AAC TGG AGC TAC ACC AAC ACC GAG GGC GCC AGC GTG          2399
His Ser Ser Thr Asn Trp Ser Tyr Thr Asn Thr Glu Gly Ala Ser Val
                1235                     1240                     1245

GAG GCC GGC ATC GGT CCC AAG GGC ATC AGC TTC GGC GTG AGC GTG AAC          2447
Glu Ala Gly Ile Gly Pro Lys Gly Ile Ser Phe Gly Val Ser Val Asn
            1250                     1255                     1260

TAC CAG CAC AGC GAG ACC GTG GCC CAG GAG TGG GGC ACC AGC ACC GGC          2495
Tyr Gln His Ser Glu Thr Val Ala Gln Glu Trp Gly Thr Ser Thr Gly
        1265                     1270                     1275

AAC ACC AGC CAG TTC AAC ACC GCC AGC GCC GGC TAC CTG AAC GCC AAC          2543
Asn Thr Ser Gln Phe Asn Thr Ala Ser Ala Gly Tyr Leu Asn Ala Asn
```

```
                                        -continued
1280                    1285                    1290                    1295

GTG  CGC  TAC  AAC  AAC  GTG  GGC  ACC  GGC  GCC  ATC  TAC  GAC  GTG  AAG  CCC       2591
Val  Arg  Tyr  Asn  Asn  Val  Gly  Thr  Gly  Ala  Ile  Tyr  Asp  Val  Lys  Pro
               1300                    1305                    1310

ACC  ACC  AGC  TTC  GTG  CTG  AAC  AAC  GAC  ACC  ATC  GCC  ACC  ATC  ACC  GCC       2639
Thr  Thr  Ser  Phe  Val  Leu  Asn  Asn  Asp  Thr  Ile  Ala  Thr  Ile  Thr  Ala
               1315                    1320                    1325

AAG  TCG  AAT  TCC  ACC  GCC  CTG  AAC  ATC  AGC  CCC  GGC  GAG  AGC  TAC  CCC       2687
Lys  Ser  Asn  Ser  Thr  Ala  Leu  Asn  Ile  Ser  Pro  Gly  Glu  Ser  Tyr  Pro
               1330                    1335                    1340

AAG  AAG  GGC  CAG  AAC  GGC  ATC  GCC  ATC  ACC  AGC  ATG  GAC  GAC  TTC  AAC       2735
Lys  Lys  Gly  Gln  Asn  Gly  Ile  Ala  Ile  Thr  Ser  Met  Asp  Asp  Phe  Asn
               1345                    1350                    1355

AGC  CAC  CCC  ATC  ACC  CTG  AAC  AAG  AAG  CAG  GTG  GAC  AAC  CTG  CTG  AAC       2783
Ser  His  Pro  Ile  Thr  Leu  Asn  Lys  Lys  Gln  Val  Asp  Asn  Leu  Leu  Asn
1360                    1365                    1370                    1375

AAC  AAG  CCC  ATG  ATG  CTG  GAG  ACC  AAC  CAG  ACC  GAC  GGC  GTC  TAC  AAG       2831
Asn  Lys  Pro  Met  Met  Leu  Glu  Thr  Asn  Gln  Thr  Asp  Gly  Val  Tyr  Lys
               1380                    1385                    1390

ATC  AAG  GAC  ACC  CAC  GGC  AAC  ATC  GTG  ACG  GGC  GGC  GAG  TGG  AAC  GGC       2879
Ile  Lys  Asp  Thr  His  Gly  Asn  Ile  Val  Thr  Gly  Gly  Glu  Trp  Asn  Gly
               1395                    1400                    1405

GTG  ATC  CAG  CAG  ATC  AAG  GCC  AAG  ACC  GCC  AGC  ATC  ATC  GTC  GAC  GAC       2927
Val  Ile  Gln  Gln  Ile  Lys  Ala  Lys  Thr  Ala  Ser  Ile  Ile  Val  Asp  Asp
               1410                    1415                    1420

GGC  GAG  CGC  GTG  GCC  GAG  AAG  CGC  GTG  GCC  GCC  AAG  GAC  TAC  GAG  AAC       2975
Gly  Glu  Arg  Val  Ala  Glu  Lys  Arg  Val  Ala  Ala  Lys  Asp  Tyr  Glu  Asn
               1425                    1430                    1435

CCC  GAG  GAC  AAG  ACC  CCC  AGC  CTG  ACC  CTG  AAG  GAC  GCC  CTG  AAG  CTG       3023
Pro  Glu  Asp  Lys  Thr  Pro  Ser  Leu  Thr  Leu  Lys  Asp  Ala  Leu  Lys  Leu
1440                    1445                    1450                    1455

AGC  TAC  CCC  GAC  GAG  ATC  AAG  GAG  ATC  GAG  GGC  TTG  CTG  TAC  TAC  AAG       3071
Ser  Tyr  Pro  Asp  Glu  Ile  Lys  Glu  Ile  Glu  Gly  Leu  Leu  Tyr  Tyr  Lys
               1460                    1465                    1470

AAC  AAG  CCC  ATC  TAC  GAG  AGC  AGC  GTG  ATG  ACC  TAT  CTA  GAC  GAG  AAC       3119
Asn  Lys  Pro  Ile  Tyr  Glu  Ser  Ser  Val  Met  Thr  Tyr  Leu  Asp  Glu  Asn
               1475                    1480                    1485

ACC  GCC  AAG  GAG  GTG  ACC  AAG  CAG  CTG  AAC  GAC  ACC  ACC  GGC  AAG  TTC       3167
Thr  Ala  Lys  Glu  Val  Thr  Lys  Gln  Leu  Asn  Asp  Thr  Thr  Gly  Lys  Phe
               1490                    1495                    1500

AAG  GAC  GTG  AGC  CAC  CTG  TAC  GAC  GTG  AAG  CTG  ACC  CCC  AAG  ATG  AAC       3215
Lys  Asp  Val  Ser  His  Leu  Tyr  Asp  Val  Lys  Leu  Thr  Pro  Lys  Met  Asn
               1505                    1510                    1515

GTG  ACC  ATC  AAG  CTG  AGC  ATC  CTG  TAC  GAC  AAC  GCC  GAG  AGC  AAC  GAC       3263
Val  Thr  Ile  Lys  Leu  Ser  Ile  Leu  Tyr  Asp  Asn  Ala  Glu  Ser  Asn  Asp
1520                    1525                    1530                    1535

AAC  AGC  ATC  GGC  AAG  TGG  ACC  AAC  ACC  AAC  ATC  GTG  AGC  GGC  GGC  AAC       3311
Asn  Ser  Ile  Gly  Lys  Trp  Thr  Asn  Thr  Asn  Ile  Val  Ser  Gly  Gly  Asn
               1540                    1545                    1550

AAC  GGC  AAG  AAG  CAG  TAC  AGC  AGC  AAC  AAC  CCC  GAC  GCC  AAC  CTG  ACC       3359
Asn  Gly  Lys  Lys  Gln  Tyr  Ser  Ser  Asn  Asn  Pro  Asp  Ala  Asn  Leu  Thr
               1555                    1560                    1565

CTG  AAC  ACC  GAC  GCC  CAG  GAG  AAG  CTG  AAC  AAG  AAC  CGC  GAC  TAC  TAC       3407
Leu  Asn  Thr  Asp  Ala  Gln  Glu  Lys  Leu  Asn  Lys  Asn  Arg  Asp  Tyr  Tyr
               1570                    1575                    1580

ATC  AGC  CTG  TAC  ATG  AAG  AGC  GAG  AAG  AAC  ACC  CAG  TGC  GAG  ATC  ACC       3455
Ile  Ser  Leu  Tyr  Met  Lys  Ser  Glu  Lys  Asn  Thr  Gln  Cys  Glu  Ile  Thr
               1585                    1590                    1595

ATC  GAC  GGC  GAG  ATA  TAC  CCC  ATC  ACC  ACC  AAG  ACC  GTG  AAC  GTG  AAC       3503
Ile  Asp  Gly  Glu  Ile  Tyr  Pro  Ile  Thr  Thr  Lys  Thr  Val  Asn  Val  Asn
```

-continued

|  |  |  |  |  |  |  |  |  |  |  |  |  |  |  |  |
|---|---|---|---|---|---|---|---|---|---|---|---|---|---|---|---|
| 1600 | | | | 1605 | | | | 1610 | | | | 1615 | | | |
| AAG | GAC | AAC | TAC | AAG | CGC | CTG | GAC | ATC | ATC | GCC | CAC | AAC | ATC | AAG | AGC | 3551 |
| Lys | Asp | Asn | Tyr | Lys | Arg | Leu | Asp | Ile | Ile | Ala | His | Asn | Ile | Lys | Ser |  |
|  |  |  | 1620 |  |  |  |  | 1625 |  |  |  |  |  | 1630 |  |  |
| AAC | CCC | ATC | AGC | AGC | CTG | CAC | ATC | AAG | ACC | AAC | GAC | GAG | ATC | ACC | CTG | 3599 |
| Asn | Pro | Ile | Ser | Ser | Leu | His | Ile | Lys | Thr | Asn | Asp | Glu | Ile | Thr | Leu |  |
|  |  |  | 1635 |  |  |  |  | 1640 |  |  |  |  |  | 1645 |  |  |
| TTC | TGG | GAC | GAC | ATA | TCG | ATT | ACC | GAC | GTC | GCC | AGC | ATC | AAG | CCC | GAG | 3647 |
| Phe | Trp | Asp | Asp | Ile | Ser | Ile | Thr | Asp | Val | Ala | Ser | Ile | Lys | Pro | Glu |  |
|  |  |  | 1650 |  |  |  |  | 1655 |  |  |  |  |  | 1660 |  |  |
| AAC | CTG | ACC | GAC | AGC | GAG | ATC | AAG | CAG | ATA | TAC | AGT | CGC | TAC | GGC | ATC | 3695 |
| Asn | Leu | Thr | Asp | Ser | Glu | Ile | Lys | Gln | Ile | Tyr | Ser | Arg | Tyr | Gly | Ile |  |
|  |  |  | 1665 |  |  |  |  | 1670 |  |  |  |  |  | 1675 |  |  |
| AAG | CTG | GAG | GAC | GGC | ATC | CTG | ATC | GAC | AAG | AAA | GGC | GGC | ATC | CAC | TAC | 3743 |
| Lys | Leu | Glu | Asp | Gly | Ile | Leu | Ile | Asp | Lys | Lys | Gly | Gly | Ile | His | Tyr |  |
| 1680 |  |  |  |  |  |  | 1685 |  |  |  |  | 1690 |  |  |  | 1695 |
| GGC | GAG | TTC | ATC | AAC | GAG | GCC | AGC | TTC | AAC | ATC | GAG | CCC | CTG | CAG | AAC | 3791 |
| Gly | Glu | Phe | Ile | Asn | Glu | Ala | Ser | Phe | Asn | Ile | Glu | Pro | Leu | Gln | Asn |  |
|  |  |  |  |  | 1700 |  |  |  |  | 1705 |  |  |  |  | 1710 |  |
| TAC | GTG | ACC | AAG | TAC | GAG | GTG | ACC | TAC | AGC | AGC | GAG | CTG | GGC | CCC | AAC | 3839 |
| Tyr | Val | Thr | Lys | Tyr | Glu | Val | Thr | Tyr | Ser | Ser | Glu | Leu | Gly | Pro | Asn |  |
|  |  |  |  | 1715 |  |  |  |  | 1720 |  |  |  |  | 1725 |  |  |
| GTG | AGC | GAC | ACC | CTG | GAG | AGC | GAC | AAG | ATT | TAC | AAG | GAC | GGC | ACC | ATC | 3887 |
| Val | Ser | Asp | Thr | Leu | Glu | Ser | Asp | Lys | Ile | Tyr | Lys | Asp | Gly | Thr | Ile |  |
|  |  |  | 1730 |  |  |  |  | 1735 |  |  |  |  |  | 1740 |  |  |
| AAG | TTC | GAC | TTC | ACC | AAG | TAC | AGC | AAG | AAC | GAG | CAG | GGC | CTG | TTC | TAC | 3935 |
| Lys | Phe | Asp | Phe | Thr | Lys | Tyr | Ser | Lys | Asn | Glu | Gln | Gly | Leu | Phe | Tyr |  |
|  |  |  | 1745 |  |  |  |  | 1750 |  |  |  |  |  | 1755 |  |  |
| GAC | AGC | GGC | CTG | AAC | TGG | GAC | TTC | AAG | ATC | AAC | GCC | ATC | ACC | TAC | GAC | 3983 |
| Asp | Ser | Gly | Leu | Asn | Trp | Asp | Phe | Lys | Ile | Asn | Ala | Ile | Thr | Tyr | Asp |  |
| 1760 |  |  |  |  |  |  | 1765 |  |  |  |  | 1770 |  |  |  | 1775 |
| GGC | AAG | GAG | ATG | AAC | GTG | TTC | CAC | CGC | TAC | AAC | AAG | TAGATCTGAG | | | | 4029 |
| Gly | Lys | Glu | Met | Asn | Val | Phe | His | Arg | Tyr | Asn | Lys |  |  |  |  |  |
|  |  |  |  | 1780 |  |  |  |  | 1785 |  |  |  |  |  |  |  |
| CT | | | | | | | | | | | | | | | | 4031 |

(2) INFORMATION FOR SEQ ID NO:50:

(i) SEQUENCE CHARACTERISTICS:
        (A) LENGTH: 1338 amino acids
        (B) TYPE: amino acid
        (D) TOPOLOGY: linear (ii) MOLECULE TYPE: protein (xi) SEQUENCE DESCRIPTION: SEQ ID NO:50:

| Met | Lys | Arg | Met | Glu | Gly | Lys | Leu | Phe | Met | Val | Ser | Lys | Lys | Leu | Gln |
|---|---|---|---|---|---|---|---|---|---|---|---|---|---|---|---|
| 1 | | | | 5 | | | | | 10 | | | | | 15 | |
| Val | Val | Thr | Lys | Thr | Val | Leu | Leu | Ser | Thr | Val | Phe | Ser | Ile | Ser | Leu |
|  |  |  | 20 |  |  |  |  | 25 |  |  |  |  | 30 |  |  |
| Leu | Asn | Asn | Glu | Val | Ile | Lys | Ala | Glu | Gln | Leu | Asn | Ile | Asn | Ser | Gln |
|  |  | 35 |  |  |  |  | 40 |  |  |  |  | 45 |  |  |  |
| Ser | Lys | Tyr | Thr | Asn | Leu | Gln | Asn | Leu | Lys | Ile | Thr | Asp | Lys | Val | Glu |
|  | 50 |  |  |  |  | 55 |  |  |  |  | 60 |  |  |  |  |
| Asp | Phe | Lys | Glu | Asp | Lys | Glu | Lys | Ala | Lys | Glu | Trp | Gly | Lys | Glu | Lys |
| 65 |  |  |  |  | 70 |  |  |  |  | 75 |  |  |  |  | 80 |
| Glu | Lys | Glu | Trp | Lys | Leu | Thr | Ala | Thr | Glu | Lys | Gly | Lys | Met | Asn | Asn |
|  |  |  |  | 85 |  |  |  |  | 90 |  |  |  |  | 95 |  |
| Phe | Leu | Asp | Asn | Lys | Asn | Asp | Ile | Lys | Thr | Asn | Tyr | Lys | Glu | Ile | Thr |
|  |  |  | 100 |  |  |  |  | 105 |  |  |  |  | 110 |  |  |

-continued

```
Phe  Ser  Ile  Ala  Gly  Ser  Phe  Glu  Asp  Glu  Ile  Lys  Asp  Leu  Lys  Glu
          115                 120                 125
Ile  Asp  Lys  Met  Phe  Asp  Lys  Thr  Asn  Leu  Ser  Asn  Ser  Ile  Ile  Thr
          130                 135                 140
Tyr  Lys  Asn  Val  Glu  Pro  Thr  Thr  Ile  Gly  Phe  Asn  Lys  Ser  Leu  Thr
145                           150                 155                      160
Glu  Gly  Asn  Thr  Ile  Asn  Ser  Asp  Ala  Met  Ala  Gln  Phe  Lys  Glu  Gln
                    165                      170                 175
Phe  Leu  Asp  Arg  Asp  Ile  Lys  Phe  Asp  Ser  Tyr  Leu  Asp  Thr  His  Leu
                    180                 185                      190
Thr  Ala  Gln  Gln  Val  Ser  Ser  Lys  Glu  Arg  Val  Ile  Leu  Lys  Val  Thr
                    195                 200                      205
Val  Pro  Ser  Gly  Lys  Gly  Ser  Thr  Thr  Pro  Thr  Lys  Ala  Gly  Val  Ile
          210                 215                      220
Leu  Asn  Asn  Ser  Glu  Tyr  Lys  Met  Leu  Ile  Asp  Asn  Gly  Tyr  Met  Val
225                           230                 235                      240
His  Val  Asp  Lys  Val  Ser  Lys  Val  Val  Lys  Lys  Gly  Val  Glu  Cys  Leu
                    245                 250                      255
Gln  Ile  Glu  Gly  Thr  Leu  Lys  Lys  Ser  Leu  Asp  Phe  Lys  Asn  Asp  Ile
                    260                 265                      270
Asn  Ala  Glu  Ala  His  Ser  Trp  Gly  Met  Lys  Asn  Tyr  Glu  Glu  Trp  Ala
                    275                 280                      285
Lys  Asp  Leu  Thr  Asp  Ser  Gln  Arg  Glu  Ala  Leu  Asp  Gly  Tyr  Ala  Arg
          290                 295                      300
Gln  Asp  Tyr  Lys  Glu  Ile  Asn  Asn  Tyr  Leu  Arg  Asn  Gln  Gly  Gly  Ser
305                           310                 315                      320
Gly  Asn  Glu  Lys  Leu  Asp  Ala  Gln  Ile  Lys  Asn  Ile  Ser  Asp  Ala  Leu
                    325                 330                      335
Gly  Lys  Lys  Pro  Ile  Pro  Glu  Asn  Ile  Thr  Val  Tyr  Arg  Trp  Cys  Gly
                    340                 345                      350
Met  Pro  Glu  Phe  Gly  Tyr  Gln  Ile  Ser  Asp  Pro  Leu  Pro  Ser  Leu  Lys
          355                 360                      365
Asp  Phe  Glu  Glu  Gln  Phe  Leu  Asn  Thr  Ile  Lys  Glu  Asp  Lys  Gly  Tyr
          370                 375                      380
Met  Ser  Thr  Ser  Leu  Ser  Ser  Glu  Arg  Leu  Ala  Ala  Phe  Gly  Ser  Arg
385                           390                 395                      400
Lys  Ile  Ile  Leu  Arg  Leu  Gln  Val  Pro  Lys  Gly  Ser  Thr  Gly  Ala  Tyr
                    405                 410                      415
Leu  Ser  Ala  Ile  Gly  Gly  Phe  Ala  Ser  Glu  Lys  Glu  Ile  Leu  Leu  Asp
                    420                 425                      430
Lys  Asp  Ser  Lys  Tyr  His  Ile  Asp  Lys  Val  Thr  Glu  Val  Ile  Ile  Lys
                    435                 440                      445
Gly  Val  Lys  Arg  Tyr  Val  Val  Asp  Ala  Thr  Leu  Leu  Thr  Asn  Ser  Arg
          450                 455                      460
Gly  Pro  Ser  Thr  Pro  Pro  Thr  Pro  Ser  Pro  Ser  Thr  Pro  Pro  Thr  Pro
465                           470                 475                      480
Ser  Asp  Ile  Gly  Ser  Thr  Met  Lys  Thr  Asn  Gln  Ile  Ser  Thr  Thr  Gln
                    485                 490                      495
Lys  Asn  Gln  Gln  Lys  Glu  Met  Asp  Arg  Lys  Gly  Leu  Leu  Gly  Tyr  Tyr
               500                 505                 510
Phe  Lys  Gly  Lys  Asp  Phe  Ser  Asn  Leu  Thr  Met  Phe  Ala  Pro  Thr  Arg
          515                 520                      525
Asp  Ser  Thr  Leu  Ile  Tyr  Asp  Gln  Gln  Thr  Ala  Asn  Lys  Leu  Leu  Asp
```

|  |  |  |  |  | 530 |  |  |  |  | 535 |  |  |  |  | 540 |  |
|---|---|---|---|---|---|---|---|---|---|---|---|---|---|---|---|---|
| Lys 545 | Lys | Gln | Gln | Glu | Tyr 550 | Gln | Ser | Ile | Arg | Trp 555 | Ile | Gly | Leu | Ile | Gln 560 |
| Ser | Lys | Glu | Thr | Gly 565 | Asp | Phe | Thr | Phe | Asn 570 | Leu | Ser | Glu | Asp | Glu 575 | Gln |
| Ala | Ile | Ile | Glu 580 | Ile | Asn | Gly | Lys | Ile 585 | Ile | Ser | Asn | Lys | Gly 590 | Lys | Glu |
| Lys | Gln | Val 595 | Val | His | Leu | Glu 600 | Lys | Gly | Lys | Leu | Val 605 | Pro | Ile | Lys | Ile |
| Glu | Tyr 610 | Gln | Ser | Asp | Thr | Lys 615 | Phe | Asn | Ile | Asp | Ser 620 | Lys | Thr | Phe | Lys |
| Glu 625 | Leu | Lys | Leu | Phe | Lys 630 | Ile | Asp | Ser | Gln | Asn 635 | Gln | Pro | Gln | Gln | Val 640 |
| Gln | Gln | Asp | Glu | Leu 645 | Arg | Asn | Pro | Glu | Phe 650 | Asn | Lys | Lys | Glu | Ser 655 | Gln |
| Glu | Phe | Leu | Ala 660 | Lys | Pro | Ser | Lys | Ile 665 | Asn | Leu | Phe | Thr | Gln 670 | Gln | Met |
| Lys | Arg | Glu 675 | Ile | Asp | Glu | Asp | Thr 680 | Asp | Thr | Asp | Gly | Asp 685 | Ser | Ile | Pro |
| Asp | Leu 690 | Trp | Glu | Glu | Asn | Gly 695 | Tyr | Thr | Ile | Gln | Asn 700 | Arg | Ile | Ala | Val |
| Lys 705 | Trp | Asp | Asp | Ser | Leu 710 | Ala | Ser | Lys | Gly | Tyr 715 | Thr | Lys | Phe | Val | Ser 720 |
| Asn | Pro | Leu | Glu | Ser 725 | His | Thr | Val | Gly | Asp 730 | Pro | Tyr | Thr | Asp | Tyr 735 | Glu |
| Lys | Ala | Ala | Arg 740 | Asp | Leu | Asp | Leu | Ser 745 | Asn | Ala | Lys | Glu | Thr 750 | Phe | Asn |
| Pro | Leu | Val 755 | Ala | Ala | Phe | Pro | Ser 760 | Val | Asn | Val | Ser | Met 765 | Glu | Lys | Val |
| Ile | Leu | Ser 770 | Pro | Asn | Glu | Asn 775 | Leu | Ser | Asn | Ser | Val 780 | Glu | Ser | His | Ser |
| Ser 785 | Thr | Asn | Trp | Ser | Tyr 790 | Thr | Asn | Thr | Glu | Gly 795 | Ala | Ser | Val | Glu | Ala 800 |
| Gly | Ile | Gly | Pro | Lys 805 | Gly | Ile | Ser | Phe | Gly 810 | Val | Ser | Val | Asn | Tyr 815 | Gln |
| His | Ser | Glu | Thr 820 | Val | Ala | Gln | Glu | Trp 825 | Gly | Thr | Ser | Thr | Gly 830 | Asn | Thr |
| Ser | Gln | Phe 835 | Asn | Thr | Ala | Ser | Ala 840 | Gly | Tyr | Leu | Asn | Ala 845 | Asn | Val | Arg |
| Tyr | Asn 850 | Asn | Val | Gly | Thr | Gly 855 | Ala | Ile | Tyr | Asp | Val 860 | Lys | Pro | Thr | Thr |
| Ser 865 | Phe | Val | Leu | Asn | Asn 870 | Asp | Thr | Ile | Ala | Thr 875 | Ile | Thr | Ala | Lys | Ser 880 |
| Asn | Ser | Thr | Ala | Leu 885 | Asn | Ile | Ser | Pro | Gly 890 | Glu | Ser | Tyr | Pro | Lys 895 | Lys |
| Gly | Gln | Asn | Gly 900 | Ile | Ala | Ile | Thr | Ser 905 | Met | Asp | Asp | Phe | Asn 910 | Ser | His |
| Pro | Ile | Thr 915 | Leu | Asn | Lys | Lys | Gln 920 | Val | Asp | Asn | Leu | Leu 925 | Asn | Asn | Lys |
| Pro | Met 930 | Met | Leu | Glu | Thr | Asn 935 | Gln | Thr | Asp | Gly | Val 940 | Tyr | Lys | Ile | Lys |
| Asp 945 | Thr | His | Gly | Asn | Ile 950 | Val | Thr | Gly | Gly | Glu 955 | Trp | Asn | Gly | Val | Ile 960 |

-continued

```
Gln  Gln  Ile  Lys  Ala  Lys  Thr  Ala  Ser  Ile  Ile  Val  Asp  Asp  Gly  Glu
               965                 970                      975

Arg  Val  Ala  Glu  Lys  Arg  Val  Ala  Ala  Lys  Asp  Tyr  Glu  Asn  Pro  Glu
               980                 985                      990

Asp  Lys  Thr  Pro  Ser  Leu  Thr  Leu  Lys  Asp  Ala  Leu  Lys  Leu  Ser  Tyr
          995                 1000                     1005

Pro  Asp  Glu  Ile  Lys  Glu  Ile  Glu  Gly  Leu  Leu  Tyr  Tyr  Lys  Asn  Lys
     1010                1015                     1020

Pro  Ile  Tyr  Glu  Ser  Ser  Val  Met  Thr  Tyr  Leu  Asp  Glu  Asn  Thr  Ala
1025                1030                     1035                          1040

Lys  Glu  Val  Thr  Lys  Gln  Leu  Asn  Asp  Thr  Thr  Gly  Lys  Phe  Lys  Asp
               1045                1050                     1055

Val  Ser  His  Leu  Tyr  Asp  Val  Lys  Leu  Thr  Pro  Lys  Met  Asn  Val  Thr
               1060                1065                     1070

Ile  Lys  Leu  Ser  Ile  Leu  Tyr  Asp  Asn  Ala  Glu  Ser  Asn  Asp  Asn  Ser
               1075                1080                     1085

Ile  Gly  Lys  Trp  Thr  Asn  Thr  Asn  Ile  Val  Ser  Gly  Gly  Asn  Asn  Gly
          1090                1095                     1100

Lys  Lys  Gln  Tyr  Ser  Ser  Asn  Asn  Pro  Asp  Ala  Asn  Leu  Thr  Leu  Asn
1105                     1110                1115                          1120

Thr  Asp  Ala  Gln  Glu  Lys  Leu  Asn  Lys  Asn  Arg  Asp  Tyr  Tyr  Ile  Ser
                    1125                1130                     1135

Leu  Tyr  Met  Lys  Ser  Glu  Lys  Asn  Thr  Gln  Cys  Glu  Ile  Thr  Ile  Asp
               1140                1145                     1150

Gly  Glu  Ile  Tyr  Pro  Ile  Thr  Thr  Lys  Thr  Val  Asn  Val  Asn  Lys  Asp
          1155                1160                     1165

Asn  Tyr  Lys  Arg  Leu  Asp  Ile  Ile  Ala  His  Asn  Ile  Lys  Ser  Asn  Pro
     1170                1175                     1180

Ile  Ser  Ser  Leu  His  Ile  Lys  Thr  Asn  Asp  Glu  Ile  Thr  Leu  Phe  Trp
1185                     1190                1195                          1200

Asp  Asp  Ile  Ser  Ile  Thr  Asp  Val  Ala  Ser  Ile  Lys  Pro  Glu  Asn  Leu
               1205                1210                     1215

Thr  Asp  Ser  Glu  Ile  Lys  Gln  Ile  Tyr  Ser  Arg  Tyr  Gly  Ile  Lys  Leu
               1220                1225                     1230

Glu  Asp  Gly  Ile  Leu  Ile  Asp  Lys  Lys  Gly  Gly  Ile  His  Tyr  Gly  Glu
          1235                1240                     1245

Phe  Ile  Asn  Glu  Ala  Ser  Phe  Asn  Ile  Glu  Pro  Leu  Gln  Asn  Tyr  Val
     1250                1255                     1260

Thr  Lys  Tyr  Glu  Val  Thr  Tyr  Ser  Ser  Glu  Leu  Gly  Pro  Asn  Val  Ser
1265                1270                     1275                          1280

Asp  Thr  Leu  Glu  Ser  Asp  Lys  Ile  Tyr  Lys  Asp  Gly  Thr  Ile  Lys  Phe
                    1285                1290                     1295

Asp  Phe  Thr  Lys  Tyr  Ser  Lys  Asn  Glu  Gln  Gly  Leu  Phe  Tyr  Asp  Ser
               1300                1305                     1310

Gly  Leu  Asn  Trp  Asp  Phe  Lys  Ile  Asn  Ala  Ile  Thr  Tyr  Asp  Gly  Lys
          1315                1320                     1325

Glu  Met  Asn  Val  Phe  His  Arg  Tyr  Asn  Lys
          1330                1335
```

( 2 ) INFORMATION FOR SEQ ID NO:51:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear (i i) MOLECULE TYPE: peptide (i i i) HYPOTHETICAL: NO (x i) SEQUENCE DESCRIPTION: SEQ ID NO:51:

Lys Asp Glu Leu
1

(2) INFORMATION FOR SEQ ID NO:52:

(i) SEQUENCE CHARACTERISTICS:
(A) LENGTH: 4 amino acids
(B) TYPE: amino acid
(C) STRANDEDNESS: single
(D) TOPOLOGY: linear (i i) MOLECULE TYPE: peptide (i i i) HYPOTHETICAL: NO (x i) SEQUENCE DESCRIPTION: SEQ ID NO:52:

His Asp Glu Leu
1

What is claimed is:

1. An isolated insecticidal protein produced during bacterial vegetative growth, comprising a pesticidal protein and an auxiliary protein, wherein said auxiliary protein activates said pesticidal protein by forming an oligomeric protein with said pesticidal protein.

2. An isolated insecticidal protein produced during bacterial vegetative growth, comprising a pesticidal protein and an auxiliary protein, wherein said auxiliary protein enhances the insecticidal activity of said pesticidal protein by forming an oligomeric protein with said pesticidal protein.

3. The insecticidal protein of claims 1 or 2 wherein said pesticidal protein is selected from the group consisting of VIP1A(*a*) and VIP1A(*b*).

4. The VIP1 protein of claim 3 which is VIP1A(*a*).

5. The VIP1 protein of claim 3 which is VIP1A(*b*).

6. The insecticidal protein of claims 1 or 2 where said auxiliary protein is selected from the group consisting of VIP2A(*a*) and VIP2A(*b*).

7. The VIP2 protein of claim 6 which is VIP2A(*a*).

8. The VIP2 protein of claim 6 which is VIP2A(*b*).

9. The insecticidal protein of claims 1 or 2 wherein said insecticidal protein is a binary toxin.

* * * * *